(12) United States Patent
Kiuchi et al.

(10) Patent No.: US 8,809,304 B2
(45) Date of Patent: Aug. 19, 2014

(54) AMINE COMPOUND AND USE THEREOF FOR MEDICAL PURPOSES

(75) Inventors: Masatoshi Kiuchi, Osaka (JP); Kaoru Marukawa, Osaka (JP); Nobutaka Kobayashi, Osaka (JP); Kunio Sugahara, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 1267 days.

(21) Appl. No.: 12/086,419

(22) PCT Filed: Dec. 15, 2006

(86) PCT No.: PCT/JP2006/325016
§ 371 (c)(1),
(2), (4) Date: Jul. 31, 2008

(87) PCT Pub. No.: WO2007/069712
PCT Pub. Date: Jun. 21, 2007

(65) Prior Publication Data
US 2009/0137530 A1    May 28, 2009

(30) Foreign Application Priority Data
Dec. 15, 2005  (JP) .................................. 2005-361363

(51) Int. Cl.
| | | |
|---|---|---|
| *C07C 215/00* | (2006.01) | |
| *A01N 57/00* | (2006.01) | |
| *A61K 31/66* | (2006.01) | |
| *A01N 57/10* | (2006.01) | |
| *A01N 37/00* | (2006.01) | |
| *A61K 31/185* | (2006.01) | |
| *C07D 319/06* | (2006.01) | |
| *C07F 9/09* | (2006.01) | |
| *C07F 9/40* | (2006.01) | |
| *C07F 9/6527* | (2006.01) | |
| *C07C 323/32* | (2006.01) | |
| *C07F 9/653* | (2006.01) | |
| *C07C 323/43* | (2006.01) | |
| *C07C 255/54* | (2006.01) | |
| *C07C 217/64* | (2006.01) | |

(52) U.S. Cl.
CPC ............ *C07C 255/54* (2013.01); *C07D 319/06* (2013.01); *C07F 9/091* (2013.01); *C07F 9/4056* (2013.01); *C07F 9/6527* (2013.01); *C07F 9/09* (2013.01); *C07C 323/32* (2013.01); *C07F 9/653* (2013.01); *C07C 323/43* (2013.01); *C07C 217/64* (2013.01)
USPC ............ 514/114; 564/355; 514/109; 514/576

(58) Field of Classification Search
None
See application file for complete search history.

(56) References Cited

U.S. PATENT DOCUMENTS 5,948,820 A * 9/1999 Fujita et al. .................... 514/653
6,187,821 B1 * 2/2001 Fujita et al. .................... 514/653

FOREIGN PATENT DOCUMENTS

| EP | 0627406 A1 | 12/1994 |
|---|---|---|
| EP | 0778263 A1 | 6/1997 |
| EP | 1 782 804 A1 | 5/2007 |
| RU | 2 217 136 C2 | 11/2003 |
| RU | 2003 136 730 A | 5/2010 |
| WO | WO-94/08943 A1 | 4/1994 |
| WO | WO-96/06068 A1 | 4/1994 |
| WO | WO 98/22100 A2 | 5/1998 |
| WO | WO-98/45429 A2 | 10/1998 |
| WO | WO-02/076995 A2 | 10/2002 |
| WO | WO 02/100148 A2 | 12/2002 |
| WO | WO-2004/024673 A1 | 3/2004 |
| WO | WO-2004/096752 A1 | 11/2004 |
| WO | WO-2004/110421 A1 | 12/2004 |
| WO | WO-2004/110979 A2 | 12/2004 |
| WO | WO 2006/011554 A1 | 2/2006 |

OTHER PUBLICATIONS

Morissette et al. Advanced Drug Delivery Reviews 2004, 56, 275-300.*
Vippagunta et al. Advanced Drug Delivery Reviews 2001, 48, 3-26.*
Page et al. "Understanding Autoimmune Disease—A review article for the layman", 2012, 18 pages.*

(Continued)

*Primary Examiner* — Clinton Brooks
(74) *Attorney, Agent, or Firm* — Birch, Stewart, Kolasch & Birch, LLP

(57) ABSTRACT

A novel amine compound represented by the following formula (I), which is superior in immunosuppressive action, rejection suppressive action and the like, and shows reduced side effects such as bradycardia and the like, or a pharmaceutically acceptable acid addition salt thereof, or hydrates thereof, or solvate, as well as a pharmaceutical composition containing this compound and a pharmaceutically acceptable carrier.

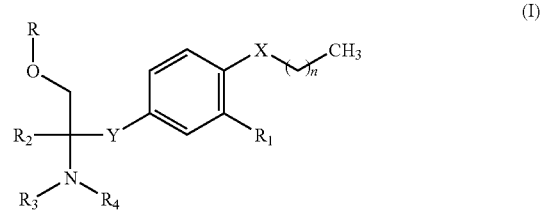

(I)

wherein R is a hydrogen atom or $P(=O)(OH)_2$, X is an oxygen atom or a sulfur atom, Y is $CH_2CH_2$ or $CH=CH$, $R_1$ is cyano or alkyl having a carbon number of 1 to 4 and substituted by a halogen atom(s), $R_2$ is alkyl having a carbon number of 1 to 4 and optionally substituted by a hydroxyl group(s) or a halogen atom(s), $R_3$ and $R_4$ may be the same or different and each is a hydrogen atom or alkyl having a carbon number of 1 to 4, and n is 5-8.

13 Claims, No Drawings

(56) References Cited

OTHER PUBLICATIONS

Supplementary European Search Report for EP Application No. 06834759.0 mailed Feb. 24, 2009.
Mandala et al., Science, vol. 296, pp. 346-349, Apr. 12, 2002.
Matloublan et al., Nature, vol. 427, pp. 355-360, Jan. 22, 2004.
Australian Office Action dated Jun. 15, 2011, for Australian Application No. 2006325931.
Decision of Grant dated Apr. 19, 2011 for corresponding Russian Application No. 2008128875.

* cited by examiner

AMINE COMPOUND AND USE THEREOF FOR MEDICAL PURPOSES

TECHNICAL FIELD

The present invention relates to amine compounds and use thereof as pharmaceutical agents.

BACKGROUND ART

In recent years, calcineurin inhibitors such as cyclosporine and FK506 are used to suppress rejection of patients who underwent organ transplantation. However, a certain kind of calcineurin inhibitor such as cyclosporine sometimes causes adverse side effects such as renal toxicity, liver toxicity, neurotoxicity and the like. Therefore, the development of a safer and highly effective pharmaceutical agent is ongoing to suppress rejection of transplant patients.

Patent references 1-3 disclose 2-aminopropane-1,3-diol compounds are useful as suppressants of (acute or chronic) rejection in organ or bone marrow transplantation, as well as therapeutic drugs for various autoimmune diseases such as psoriasis, Behcet's disease and the like and rheumatism diseases.

One of these compounds, 2-amino-2-[2-(4-octylphenyl)ethyl]propane-1,3-diol hydrochloride (hereinafter to be sometimes referred to as FTY720) is currently under clinical development as a suppressant of rejection in renal transplantation. FTY720 is rapidly converted to phospho-FTY720 (hereinafter to be sometimes referred to as FTY720-P, e.g., 2-amino-2-phosphoryloxymethyl-4-(4-octylphenyl)butanol) by sphingosine kinase in vivo. FTY720-P acts as an agonist of 4 kinds of S1P receptors (other than S1P2) out of 5 kinds of sphingosine-1-phosphate (hereinafter to be sometimes referred to as S1P) receptors (hereinafter to be sometimes referred to as S1P1-5, respectively) (non-patent reference 1).

Recently, it has been suggested that S1P1 in S1P receptors is essential for the emigration of mature lymphocytes from thymus and secondary lymphoid tissues. FTY720-P acts as an S1P1 agonist to down-regulate S1P1 on lymphocytes. As a result, the emigration of mature lymphocytes from thymus and secondary lymphoid tissues is inhibited and circulating mature lymphocytes in blood are sequestered in the secondary lymphoid tissues, whereby the immunosuppressive action is exhibited (non-patent reference 2).

On the other hand, conventional 2-aminopropane-1,3-diol compounds are feared to show transient bradycardia expression as side effects, and to solve this problem, a number of novel compounds obtained by modifying the chemical structures of 2-aminopropane-1,3-diol compounds have been reported. Among those, as a compound having a substituent on the benzene ring of FTY720, patent reference 4 discloses an aminopropanol derivative as an S1P receptor modulator with a phosphoric group, and patent references 5 and 6 both disclose aminopropanol derivatives as S1P receptor modulators. However, a trihaloalkyl group, for example, a trifluoromethyl group, is not disclosed as a substituent on the benzene ring therein. In effect, the level of safety as a pharmaceutical product has not reached a satisfactory level as the situation stands.

patent reference 1: WO94/08943
patent reference 2: WO96/06068
patent reference 3: WO98/45429
patent reference 4: WO02/076995
patent reference 5: WO2004/096752
patent reference 6: WO2004/110979
non-patent reference 1: Science, 2002, vol. 296, pages 346-349
non-patent reference 2: Nature, 2004, vol. 427, pages 355-360

DISCLOSURE OF THE INVENTION

Problems to be Solved by the Invention

An object of the present invention is to provide a novel amine compound superior in the immunosuppressive action, rejection suppressive action and the like, which shows reduced side effects such as bradycardia and the like.

Means of Solving the Problems

The present inventors have conducted further studies in view of the above-mentioned situation and found that an amine compound having the below-mentioned particular structural formula can achieve the object, which resulted in the completion of the present invention.

Accordingly, the gist of the present invention is as follows.

1. A compound represented by the following formula (I)

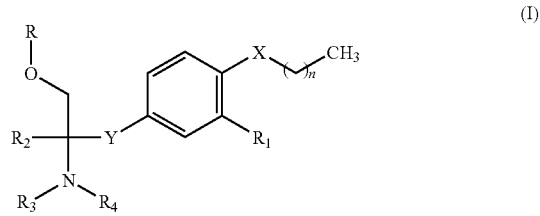

wherein R is a hydrogen atom or $P(=O)(OH)_2$, X is an oxygen atom or a sulfur atom, Y is $CH_2CH_2$ or $CH=CH$, $R_1$ is cyano or alkyl having a carbon number of 1 to 4 and substituted by a halogen atom(s), $R_2$ is alkyl having a carbon number of 1 to 4 and optionally substituted by a hydroxyl group(s) or a halogen atom(s), $R_3$ and $R_4$ may be the same or different and each is a hydrogen atom or alkyl having a carbon number of 1 to 4, and n is 5-8, or a pharmaceutically acceptable acid addition salt thereof, or a hydrate thereof, or a solvate thereof.

2. The compound of the above-mentioned 1, wherein $R_3$ and $R_4$ are each a hydrogen atom, or a pharmaceutically acceptable acid addition salt thereof, or a hydrate thereof, or a solvate thereof.

3. The compound of 1 or 2, having the following formula (Ia) or (Ib)

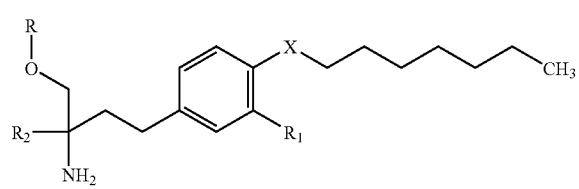

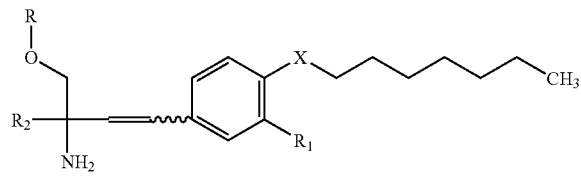

wherein R is hydrogen or P(=O)(OH)$_2$, X is an oxygen atom or a sulfur atom, R$_1$ is cyano or alkyl having a carbon number of 1 to 4 and substituted by a halogen atom(s), R$_2$ is alkyl having a carbon number of 1 to 4 and optionally substituted by a hydroxyl group(s) or a halogen atom(s), or a pharmaceutically acceptable acid addition salt thereof, or a hydrate thereof, or a solvate thereof.
4. The compound of any of 1 to 3, wherein X is an oxygen atom, or a pharmaceutically acceptable acid addition salt thereof, or a hydrate thereof, or a solvate thereof.
5. The compound of any of 1 to 4, wherein Y is CH$_2$CH$_2$, or a pharmaceutically acceptable acid addition salt thereof, or a hydrate thereof, or a solvate thereof.
6. The compound of any of 1 to 5, wherein R$_1$ is methyl substituted by a halogen atom(s), or a pharmaceutically acceptable acid addition salt thereof, or a hydrate thereof, or a solvate thereof.
7. The compound of any of 1 to 6, wherein R$_1$ is trifluoromethyl, or a pharmaceutically acceptable acid addition salt thereof, or a hydrate thereof, or a solvate thereof.
8. The compound of any of 1 to 7, wherein R$_2$ is methyl optionally substituted by a hydroxyl group(s), or a pharmaceutically acceptable acid addition salt thereof, or a hydrate thereof, or a solvate thereof.
9. The compound of any of 1 to 8, wherein R$_2$ is hydroxymethyl, or a pharmaceutically acceptable acid addition salt thereof, or a hydrate thereof, or a solvate thereof.
10. The compound of any of 1 to 9, wherein R is a hydrogen atom, or a pharmaceutically acceptable acid addition salt thereof, or a hydrate thereof, or a solvate thereof.
11. The compound of any of 1 to 4, wherein the compound of the formula (I) is any of the following a-e, or a pharmaceutically acceptable acid addition salt thereof, or a hydrate thereof, or a solvate thereof.
 a. 2-amino-2-[2-(4-heptyloxy-3-trifluoromethylphenyl)ethyl]propane-1,3-diol, or a pharmaceutically acceptable acid addition salt thereof, or a hydrate thereof, or a solvate thereof
 b. (E)-2-amino-2-[2-(4-heptyloxy-3-trifluoromethylphenyl)vinyl]propane-1,3-diol, or a pharmaceutically acceptable acid addition salt thereof, or a hydrate thereof, or a solvate thereof
 c. 2-amino-4-(4-heptyloxy-3-trifluoromethylphenyl)-2-methylbutanol, or a pharmaceutically acceptable acid addition salt thereof, or a hydrate thereof, or a solvate thereof
 d. (R)-2-amino-4-(4-heptyloxy-3-trifluoromethylphenyl)-2-methylbutanol, or a pharmaceutically acceptable acid addition salt thereof, or a hydrate thereof, or a solvate thereof
 e. 2-amino-2-[2-(3-cyano-4-heptyloxyphenyl)ethyl]propane-1,3-diol, or a pharmaceutically acceptable acid addition salt thereof, or a hydrate thereof, or a solvate thereof.
12. The compound of any of 1 to 4, wherein the compound of the formula (I) is any of the following f-j, or a pharmaceutically acceptable acid addition salt thereof, or a hydrate thereof, or a solvate thereof.
 f. 2-amino-4-(4-heptyloxy-3-trifluoromethylphenyl)-2-(phosphoryloxymethyl)butanol, or a pharmaceutically acceptable acid addition salt thereof, or a hydrate thereof, or a solvate thereof
 g. (E)-2-amino-4-(4-heptyloxy-3-trifluoromethylphenyl)-2-(phosphoryloxymethyl)-3-buten-1-ol, or a pharmaceutically acceptable acid addition salt thereof, or a hydrate thereof, or a solvate thereof
 h. phosphoric acid mono[2-amino-4-(4-heptyloxy-3-trifluoromethylphenyl)-2-methylbutyl]ester, or a pharmaceutically acceptable acid addition salt thereof, or a hydrate thereof, or a solvate thereof
 i. (R)-phosphoric acid mono[2-amino-4-(4-heptyloxy-3-trifluoromethylphenyl)-2-methylbutyl]ester, or a pharmaceutically acceptable acid addition salt thereof, or a hydrate thereof, or a solvate thereof
 j. 2-amino-4-(3-cyano-4-heptyloxyphenyl)-2-(phosphoryloxymethyl)butanol, or a pharmaceutically acceptable acid addition salt thereof, or a hydrate thereof, or a solvate thereof
13. 2-Amino-2-[2-(4-heptyloxy-3-trifluoromethylphenyl)ethyl]propane-1,3-diol, or a hydrochloride thereof.
14. A pharmaceutical composition comprising the compound of any of 1 to 13 and a pharmaceutically acceptable carrier.
15. The pharmaceutical composition of 14, which is used for the treatment or prophylaxis of autoimmune diseases; prophylaxis or suppression of resistance or acute rejection or chronic rejection of organ or tissue transplantation; treatment or prophylaxis of graft-versus-host (GvH) disease due to bone marrow transplantation; or treatment or prophylaxis of allergic diseases.
16. The pharmaceutical composition of 14, wherein the autoimmune disease is rheumatoid arthritis, multiple sclerosis, encephalomyelitis, systemic lupus erythematosus, lupus nephritis, nephrotic syndrome, psoriasis or Type I diabetes mellitus.
17. The pharmaceutical composition of 14, wherein the allergic disease is atopic dermatitis, allergic rhinitis or asthma.

Effect of the Invention

According to the present invention, a novel compound having a superior peripheral blood lymphocyte decreasing action, and reduced side effects such as bradycardia and the like can be provided.

BEST MODE FOR CARRYING OUT THE INVENTION

The present invention is explained in detail in the following.

The compound of the present invention is a compound represented by the following formula (I)

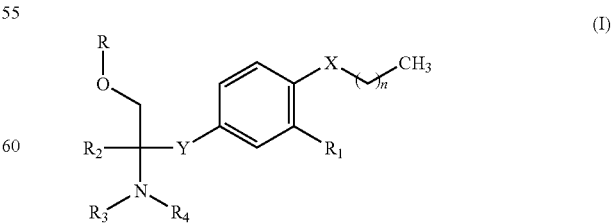

wherein R is a hydrogen atom or P(=O)(OH)$_2$, X is an oxygen atom or a sulfur atom, Y is CH$_2$CH$_2$ or CH=CH, R$_1$ is cyano or alkyl having a carbon number of 1 to 4 and substituted by a halogen atom(s), $R_2$ is alkyl having a carbon number of 1 to 4 and optionally substituted by a hydroxyl group(s) or a halogen atom(s), $R_3$ and $R_4$ may be the same or different and each is a hydrogen atom or alkyl having a carbon number of 1 to 4, and n is 5-8, or a pharmaceutically acceptable acid addition salt or a metal salt thereof, or a hydrate thereof, or a solvate thereof.

In the present invention, the halogen atom is a fluorine atom, a chlorine atom, a bromine atom or an iodine atom, wherein a fluorine atom is a preferable example.

The alkyl having a carbon number of 1 to 4 means a straight chain or branched chain alkyl having a carbon number of 1 to 4. Examples thereof include methyl, ethyl, n-propyl, isopropyl, n-butyl, isobutyl, secondary butyl, tertiary butyl (hereinafter "tertiary" is sometimes indicated as t- or tert-) and the like. Preferable examples include methyl, ethyl, n-propyl and isopropyl, and more preferable examples include methyl and ethyl.

Preferable examples of R in the above-mentioned formula (I) include a hydrogen atom.

Preferable examples of X include an oxygen atom, and preferable examples of Y include $CH_2CH_2$.

Preferable example of n is 6 or 7, and more preferable example is 6.

Preferable examples of $R_1$ include fluoromethyl, difluoromethyl, trifluoromethyl, 2,2,2-trifluoroethyl and cyano, and more preferable examples include trifluoromethyl and cyano, and still more preferable example is trifluoromethyl.

Preferable examples of $R_2$ include methyl, ethyl, hydroxymethyl, hydroxyethyl, fluoromethyl, chloromethyl, fluoroethyl, difluoroethyl, trifluoroethyl and trichloroethyl, more preferable examples include methyl, ethyl, hydroxymethyl, 2-hydroxyethyl and 2-fluoroethyl, still more preferable examples include methyl and hydroxymethyl, and hydroxymethyl is most preferable.

Preferable examples of $R_3$ and $R_4$ include a hydrogen atom, methyl and ethyl, which may be the same or different, more preferable examples include a hydrogen atom and methyl, and a hydrogen atom is most preferable.

Examples of the pharmaceutically acceptable acid addition salt of the compound of the present invention include inorganic acid salt, organic acid salt, alkali metal salt, alkaline earth metal salt and the like. The compound of the present invention encompasses the above-mentioned compound of the formula (I) and a pharmaceutically acceptable acid addition salt thereof, and also a geometric isomer, an optically active form, a hydrate and a solvate thereof.

Specific examples of the compound of the present invention include the following.

2-amino-2-[[2-(4-heptyloxy-3-trifluoromethylphenyl)ethyl]]propane-1,3-diol, and a hydrochloride thereof, (E)-2-amino-2-[2-(4-heptyloxy-3-trifluoromethylphenyl)vinyl]propane-1,3-diol, and a hydrochloride thereof, (R)-2-amino-4-(4-heptyloxy-3-trifluoromethylphenyl)-2-methylbutanol, and a hydrochloride thereof.

Of the compounds of the present invention, a preferable compound is 2-amino-2-[2-(4-heptyloxy-3-trifluoromethylphenyl)ethyl]propane-1,3-diol or a hydrochloride thereof.

The synthesis method of the compound of the present invention is, for example, the following.

1) Of the compounds of the present invention, compound (I-1) represented by the formula (Ia) wherein R is a hydrogen atom, X is an oxygen atom and $R_1$ is alkyl having a carbon number of 1 to 4 and substituted by a halogen atom(s) is synthesized by the following scheme (II).

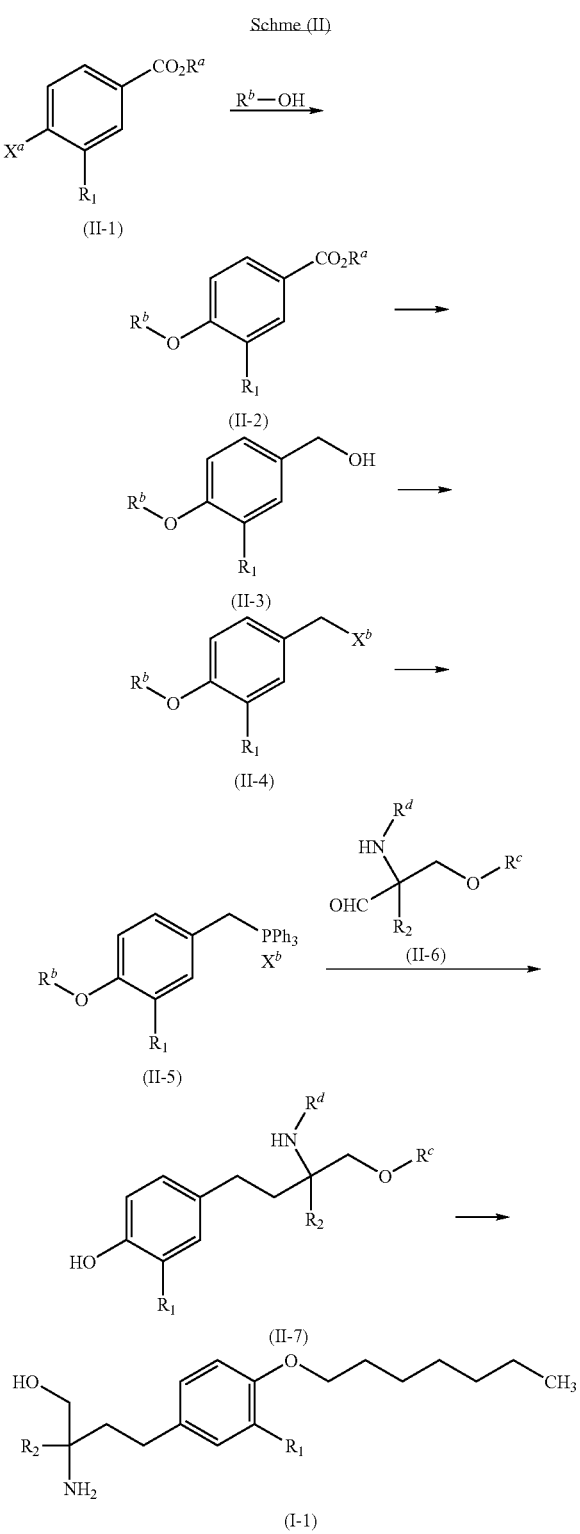

wherein $R^a$, $R^b$, $R^c$ and $R^d$ are protecting groups, $X^a$ and $X^b$ are leaving groups, $R_1$ is alkyl having a carbon number of 1 to 4 and substituted by a halogen atom(s), and $R_2$ is alkyl having a carbon number of 1 to 4 and optionally substituted by a hydroxyl group(s) or a halogen atom(s).

$R^a$ in the formula is a hydrogen atom or a various protecting carboxyl group. For example, alkyl (specifically methyl, ethyl and the like), aralkyl (benzyl and the like), the same substituent as for $R^b$ and the like can be mentioned. $R^b$ in the formula is not particularly limited as long as it protects a phenolic hydroxyl group. For example, alkyl (specifically methyl, heptyl and the like), aralkyl (benzyl and the like) and the like can be mentioned. When heptyl is used as $R^b$, the inventive compound (I-1) can be obtained without removal of $R^b$. $R^c$ in the formula is not particularly limited as long as it protects a hydroxyl group. For example, acyl (preferably one having a carbon number of about 2-4, specifically acetyl and the like), trialkylsilyl (specifically trimethylsilyl and the like), benzyl and a substituent forming acetal compound (specifically methoxymethyl, tetrahydropyranyl and the like) can be mentioned. When $R_2$ has a hydroxyl group, its protecting groups $R^e$ ($R^e$ is specifically similar to $R^c$) and $R^c$ can also be bonded to form cyclic acetal. The protecting group shown by $R^d$ in the formula is not particularly limited as long as it protects an amino group. For example, acyl (preferably one having a carbon number of about 2-4, specifically acetyl and the like), a carbamate group (specifically t-butyloxycarbonyl, benzyloxycarbonyl and the like) and the like can be mentioned. The leaving group for $X^a$ is not particularly limited as long as it is dissociated during a substitution reaction by alkoxide ion ($R^b$—$O^-$). For example, a halogen atom (specifically a fluorine atom and the like), toluenesulfonyloxy and the like can be mentioned. The leaving group for $X^b$ is not particularly limited as long as it is dissociated during a condensation of intermediate (II-4) and triphenylphosphine, and does not inhibit the subsequent Wittig reaction. For example, a halogen atom (specifically iodine atom, bromine atom, chlorine atom and the like), methanesulfonyloxy, toluenesulfonyloxy and the like can be mentioned.

In the first step, intermediate (II-2) is obtained by condensing benzoic acid derivative (II-1) having the leaving group $X^a$ at the 4-position with alcohol $R^b$—OH to introduce an oxygen functional group having the protecting group $R^b$ at the 4-position. This step can be performed in a polar solvent such as N,N-dimethylformamide, dimethyl sulfoxide and the like or an ether solvent such as tetrahydrofuran and the like in the presence of a base. As the base, an inorganic base such as sodium hydride, potassium hydroxide and the like or an organic base such as 1,8-diazabicyclo[5.4.0]undec-7-en and the like can be used. The reaction is performed, for example, under ice-cooling to about 100° C. for about 10 min to 10 hr. After the reaction, the object product can be obtained by extraction, washing, drying, solvent removal and the like by a general method and, where necessary, purification by distillation, silica gel column chromatography, recrystallization and the like.

In the second step, intermediate (II-3) having a hydroxyl group is obtained by reducing the carboxyl group of intermediate (II-2). The reagent to be used for the reduction is not particularly limited as long as it is generally used. Examples thereof include alkali metals such as sodium and the like, alkaline earth metals, metal hydrides such as diisobutylaluminum hydride and the like, metal hydrogen complex compounds such as lithium aluminum hydride, sodium borohydride and the like, boron compounds such as diborane and the like, catalytic hydrogenation using a homogeneous type or heterogeneous type catalyst, and the like. As the reaction conditions, temperature and time appropriate for the reducing reagent to be used are selected. Specific examples thereof include reduction using diborane, lithium aluminum hydride or lithium borohydride in an ether solvent such as tetrahydrofuran and the like from −30° C. to the refluxing temperature for 10 min to 12 hr, reduction using sodium borohydride or calcium borohydride in an alcohol solvent such as ethanol and the like or in a mixed solvent of an alcohol solvent and an ether solvent such as tetrahydrofuran and the like under ice-cooling to the refluxing temperature for 30 min to 24 hr, and the like. After the reaction, the object product can be obtained by quenching reaction, extraction, washing, drying, solvent removal and the like by a general method and, where necessary, purification by distillation, silica gel column chromatography, recrystallization and the like.

In the third step, the hydroxyl group of intermediate (II-3) is converted into leaving group $X^b$. The reagent is not particularly limited as long as it is a reagent capable of converting an alcoholic hydroxyl group into $X^b$. Examples of the reagent used when $X^b$ is a halogen atom include N-chlorosuccinimide, N-bromosuccinimide, carbon tetrachloride and a combination of them and a reaction aid such as triphenylphosphine, a base and the like, inorganic acids such as hydrochloric acid, hydrobromic acid, hydroiodic acid, phosphorus tribromide, phosphorus pentabromide, phosphorus trichloride, phosphorus pentachloride, iodine, bromine, chlorine, halogenated thionyl and the like. The reaction is performed, for example, in an organic solvent such as a halogen solvent (e.g., methylene chloride and the like), an ether solvent (e.g., tetrahydrofuran and the like) and the like from −30° C. to 130° C. for 10 min to 6 hr. When an inorganic acid is used, the reaction can be performed in an aqueous solution or a two-layer system of an organic solvent such as toluene and the like and water.

Examples of the reagent used when $X^b$ is sulfonyloxy include a combination of a sulfonyl chloride such as methanesulfonyl chloride, toluene sulfonyl chloride and the like, an organic base such as triethylamine, pyridine and the like. The reaction is performed, for example, in an organic solvent such as a halogen solvent (e.g., methylene chloride and the like), an ether solvent (e.g., tetrahydrofuran and the like) and the like from −30° C. to 50° C. for about 5 min to 3 hr. After the reaction, the object product can be obtained by quenching reaction, extraction, washing, drying, solvent removal and the like by a general method and, where necessary, purification by distillation, silica gel column chromatography, recrystallization and the like.

In the fourth step, phosphonium salt (II-5) is obtained by reacting intermediate (II-4) having leaving group $X^b$ with triphenylphosphine. The reaction is performed, for example, in an inactive solvent such as diethyl ether, benzene, toluene and the like from room temperature to the refluxing temperature for about 30 min to 12 hr. After the reaction, the object product can be obtained by solvent evaporation, cooling and addition of poorly soluble solvent such as diisopropyl ether, hexane and the like, as necessary, after which collection of the precipitated solid by filtration.

In the fifth step, phenolic intermediate (II-7) is obtained by condensing phosphonium salt (II-5) with aldehyde (II-6) separately synthesized using Wittig reaction, reducing the obtained olefin compound, and removing the protecting group $R^b$. The conditions of the Wittig reaction are those generally used for Wittig reaction. For example, the reaction is performed using a base such as potassium t-butoxide and the like in an ether solvent such as tetrahydrofuran and the like from −30° C. to the refluxing temperature for about 30 min to 12 hr. After the reaction, the object product can be obtained by quenching reaction, extraction, washing, drying, solvent removal and the like by a general method and, where necessary, purification by silica gel column chromatography, recrystallization and the like. The reagent to be used the subsequent reduction of a double bond is not limited as long as it is used for general olefin reduction. Examples thereof include catalytic hydrogenation using a heterogeneous catalyst such as palladium carbon, Raney-nickel and the like, a homogeneous catalyst such as rhodium complex (chlorotris (triphenylphosphine)rhodium(I) and the like) and the like. The reaction is performed, for example, in an alcohol solvent such as ethanol and the like, an ether solvent such as dioxane and the like, or a hydrocarbon solvent such as toluene and the like, under 1 to 20 atm of hydrogen pressure, under ice-cooling to the refluxing temperature from 30 min to 1 week. An acid such as acetic acid and the like or a base such as triethylamine and the like can be added to the reaction mixture depending on the reaction speed, stability of compound and the like. After the reaction, the object product can be obtained by filtration, extraction, washing, drying, solvent removal and the like by a general method and, where necessary, purification by silica gel column chromatography, recrystallization and the like. The conditions of the subsequent removal of the protecting group $R^b$ are not particularly limited as long as they are used for the removal of $R^b$. For example, when $R^b$ is methyl, a method of using a Lewis acid such as boron tribromide and the like in methylene chloride solvent can be used. When $R^b$ is acyl such as acetyl and the like, a method of using an inorganic base such as sodium hydroxide and the like in a mixed solvent of an alcohol solvent and water can be used. When $R^b$ is an ether type protecting group such as methoxymethyl, tetrahydropyranyl, t-butyl and the like, a method of using an acid such as hydrochloric acid, trifluoroacetic acid and the like can be used. When $R^b$ is a protecting group which can be removed by catalytic hydrogenation (e.g., benzyl, substituted benzyl, benzyloxymethyl and the like), the deprotection of $R^b$ can be performed simultaneously with the aforementioned reduction of the double bond. When $R^b$ is heptyl, the removal of $R^b$ is not necessary, and the alkylation of phenol in the next step can also be omitted.

In the sixth step, the compound of the present invention (I-1) is obtained by alkylating the phenolic hydroxyl group of intermediate (II-7), and removing $R^c$ and $R^d$, and the protecting group $R^e$ ($R^e$ is as defined above) which protects the hydroxyl group(s) when $R_2$ has such the hydroxyl group(s). Examples of the reagent to be used for alkylation of the phenolic hydroxyl group that intermediate (II-7) has include a combination of an alkylating agent such as heptyl halide and the like and an inorganic base such as potassium carbonate, sodium hydride and the like. The reaction is performed, for example, in a polar solvent such as N,N-dimethylformamide and the like, or in an ether solvent such as tetrahydrofuran and the like, under ice-cooling to 80° C. for about 30 min to 12 hr. For alkylation of the phenolic hydroxyl group that intermediate (II-7) has, Mitsunobu reaction of condensing heptyl alcohol and using a phosphine compound such as triphenylphosphine and the like and an azocarboxylic acid derivative such as diisopropyl azodicarboxylate and the like can be used. The reaction is performed, for example, in an ether solvent such as tetrahydrofuran and the like, under ice-cooling to −50° C. for about 10 min to 6 hr. After the reaction, the object product can be obtained by extraction, washing, drying, solvent removal and the like by a general method and, where necessary, purification by silica gel column chromatography, recrystallization and the like. The subsequent deprotection is not particularly limited as long as it is used for general removal of protecting groups, and all protecting groups can be removed at once or stepwisely. For example, when $R^c$ and $R^e$ are bonded to form a cyclic acetal, and $R^d$ is t-butyloxycarbonyl, they can be simultaneously deprotected by using an acid. Examples of the acid therefor include inorganic acids such as hydrochloric acid and the like, trifluoroacetic acid and the like. The reaction is performed, for example, in an alcohol solvent such as ethanol and the like, an ether solvent such as tetrahydrofuran and the like, water or a mixed solvent thereof, under ice-cooling to 80° C. for about 10 min-12 hr. After the reaction, the object product can be obtained by extraction, washing, drying, solvent removal and the like by a general method and, where necessary, purification by silica gel column chromatography, recrystallization and the like.

2) Of the compounds of the present invention, compound (I-1), i.e., a compound wherein, in the formula (Ia), R is a hydrogen atom, X is an oxygen atom and $R_1$ is alkyl having a carbon number of 1 to 4 and substituted by a halogen atom(s) is also synthesized using intermediate (III-1) which is synthesized by the following scheme (III) from intermediate (II-2, $R^a$ is H) in the scheme (II) or a known compound represented by the formula (III-2).

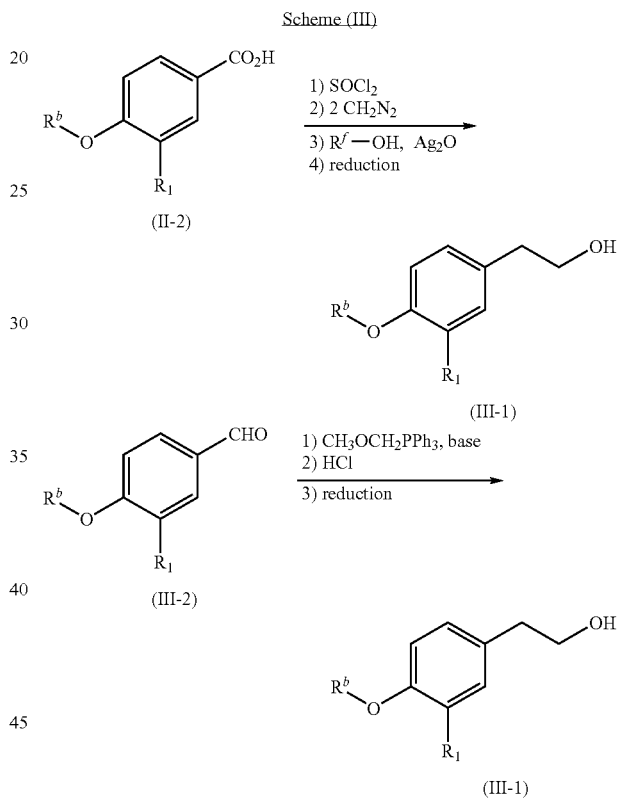

wherein $R^b$ is a protecting group, $R^f$—OH is an alcohol used for a solvolysis reaction, and $R_1$ is alkyl having a carbon number of 1 to 4 and substituted by a halogen atom(s).

$R^b$ is as defined in the formula scheme (II). Examples of $R^f$ include methyl, ethyl, benzyl and the like. For the synthesis from compound (II-2) in the above-mentioned scheme, a general reaction conditions for Arndt-Eistert reaction can be used. In addition, for the reduction of the obtained ester, the reagent and conditions used for the second step in the scheme (II) can be used. For the synthesis from compound (III-2) in the above-mentioned scheme, the conditions for general Wittig reaction can be used. For the subsequent acid treatment, an inorganic acid such as hydrochloric acid and the like is used in water or an mixed solvent of an organic solvent such as tetrahydrofuran and the like and water. For the subsequent reduction, a reduction using a metal hydrogen complex compound such as lithium aluminum hydride, sodium borohydride and the like, a catalytic hydrogenation using a heterogeneous catalyst such as palladium carbon, Raney-nickel and the like or a homogeneous catalyst such as rhodium complex (chlorotris(triphenylphosphine)rhodium(I) and the like) and the like can be performed, or these may be sequentially performed continuously. The obtained alcoholic intermediate (III-1) in the scheme can be converted into the compound of the present invention by a known method (for example, Journal of Medicinal Chemistry vol. 43 (2000) 2946-2961).

3) Compound (I-2), i.e., a compound wherein, the formula (Ia), R is a hydrogen atom, X is an oxygen atom and $R_1$ is trifluoromethyl or cyano is synthesized by the following scheme (IV).

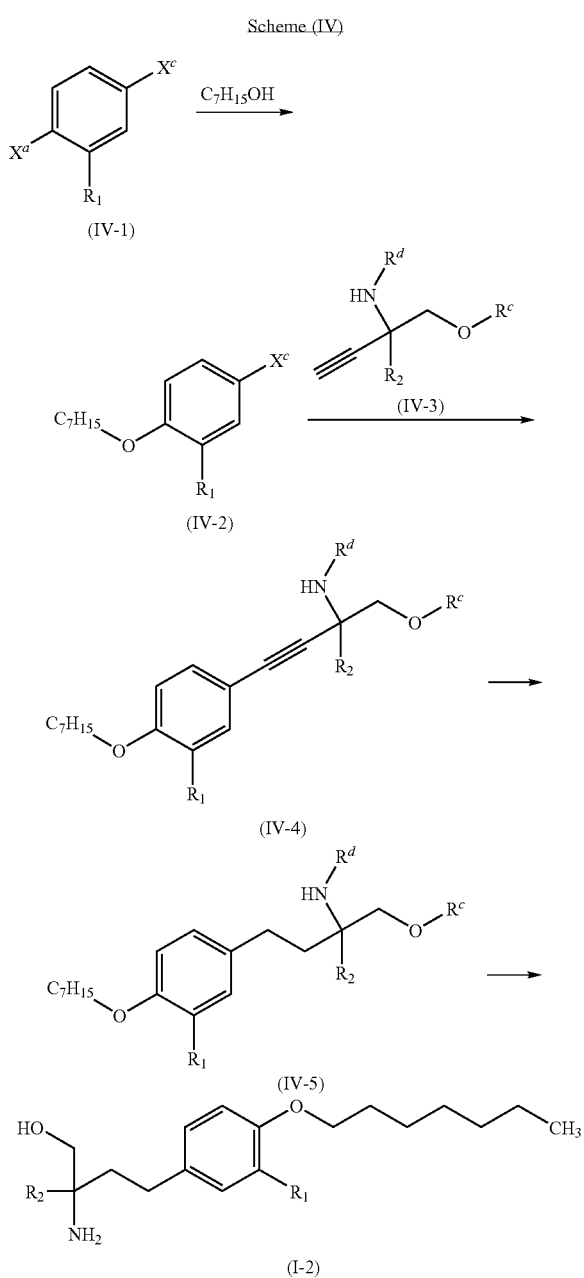

wherein $R^c$, $R^d$ is a protecting group, $X^a$ and $X^c$ are leaving groups, $R_1$ is trifluoromethyl or cyano, and $R_2$ is as defined above $R^c$, $R^d$ and $X^a$ in the formula are as defined above. The leaving group for $X^c$ is not particularly limited as long as it is activated by a catalyst and dissociated during a Sonogashira reaction. Examples thereof include a halogen atom (preferably an iodine atom, a bromine atom and the like), trifluoromethanesulfonyloxy and the like.

In the first step, intermediate (IV-2) is obtained by condensing compound (IV-1) having the leaving group Xa with heptyl alcohol. This step can be performed in a polar solvent such as N,N-dimethylformamide and dimethylsulfoxide, or in an ether solvent such as tetrahydrofuran and the like, in the presence of a base. Examples of the base include inorganic bases such as sodium hydride, potassium hydroxide and the like and organic bases such as 1,8-diazabicyclo[5.4.0]undec-7-en and the like. The reaction is performed, for example, under ice-cooling to about 100° C. for about 10 min to 10 hr. After the reaction, the object product can be obtained by extraction, washing, drying, solvent removal and the like by a general method and, where necessary, purification by distillation, silica gel column chromatography, recrystallization and the like.

In the second step, intermediate (IV-4) having a triple bond is obtained by condensing intermediate (IV-2) with intermediate (IV-3) which is synthesized from intermediate (II-6) by a known method (for example, Tetrahedron vol. 57 (2001) 6531-6538, Chemical & Pharmaceutical Bulletin vol. 53 (2005) 100-102), under Sonogashira reaction condition. Examples of the catalyst include palladium compound such as tetrakis(triphenylphosphine)palladium(0), tris(dibenzylideneacetone)dipalladium(0), dichlorobis(acetonitrile)palladium(II) and the like. To promote the reaction, an organic base such as triethylamine and the like, an inorganic base such as ammonia and the like, a copper compound such as copper iodide, copper bromide and the like, a phosphine compound such as 2-dicyclohexylphosphino-2',4',6'-triisopropylbiphenyl and the like, and the like can be added. The reaction is performed, for example, in an ether solvent such as tetrahydrofuran, dioxane and the like, a polar solvent such as acetonitrile, dimethylformamide and the like, or a hydrocarbon solvent such as benzene and the like, under ice-cooling to the refluxing temperature for about 30 min to 24 hr. After the reaction, the object product can be obtained by extraction, washing, drying, solvent removal and the like by a general method and, where necessary, purification by silica gel column chromatography, recrystallization and the like.

In the third step, intermediate (IV-5) is obtained by reducing the triple bond of intermediate (IV-4). The reagent to be used is not limited as long as it is used for general reduction of unsaturated carbon bond. For example, catalytic hydrogenation using a heterogeneous catalyst such as palladium carbon, Raney-nickel, palladium carbon-ethylenediamine complex and the like, or a homogeneous catalyst such as rhodium complex (chlorotris(triphenylphosphine)rhodium(I) and the like) and the like can be used. The reaction is performed, for example, in an alcohol solvent such as ethanol and the like, an ether solvent such as dioxane and the like, or a hydrocarbon solvent such as toluene and the like, under 1-20 atm of hydrogen pressure, under ice-cooling to the refluxing temperature for 30 min to 1 week. An acid such as acetic acid and the like or a base such as triethylamine and the like can be added to the reaction mixture depending on the reaction speed, stability of compound and the like. After the reaction, the object product can be obtained by filtration, extraction, washing, drying, solvent removal and the like by a general method and, where necessary, purification by silica gel column chromatography, recrystallization and the like.

In the fourth step, intermediate (IV-5) is deprotected to give the compound of the present invention (1-2). Removal of $R^c$ and $R^d$, and the protecting group $R^e$ ($R^e$ is as defined above) which protects the hydroxyl group(s) when $R_2$ has such the hydroxyl group(s), is not particularly limited as long as it is used for general removal of protecting groups, and all protecting groups can be removed at once or stepwise. For example, when $R^c$ and $R^e$ are bonded to form cyclic acetal, and $R^d$ is t-butyloxycarbonyl, cyclic acetal is deprotected by a catalytic amount of an acid, and then stronger acidic conditions are employed, whereby $R^d$ can be removed. The conditions employed for the deprotection of acetal are, for example, an alcohol solvent such as methanol and the like or a mixed solution of an alcohol solvent and other organic solvent, a catalytic amount of hydrochloric acid or toluenesulfonic acid, under ice-cooling-80° C. for about 30 min-12 hr. On the other hand, the removal conditions of $R^d$ performed after acetal deprotection are, for example, not less than equivalent amount of an inorganic acid such as hydrochloric acid and the like, trifluoroacetic acid and the like, in an alcohol solvent such as ethanol and the like, an ether solvent such as tetrahydrofuran and the like, water, or a mixed solvent thereof, under ice-cooling-80° C. for about 10 min-12 hr. After the reaction, the object product can be obtained by extraction, washing, drying, solvent removal and the like by a general method and, where necessary, purification by silica gel column chromatography, recrystallization and the like.

4) A compound (I-3) represented by the formula (Ia) wherein R is a hydrogen atom, X is a sulfur atom, and $R_1$ is alkyl having a carbon number of 1 to 4 and substituted by a halogen atom(s) is synthesized by the following scheme (V).

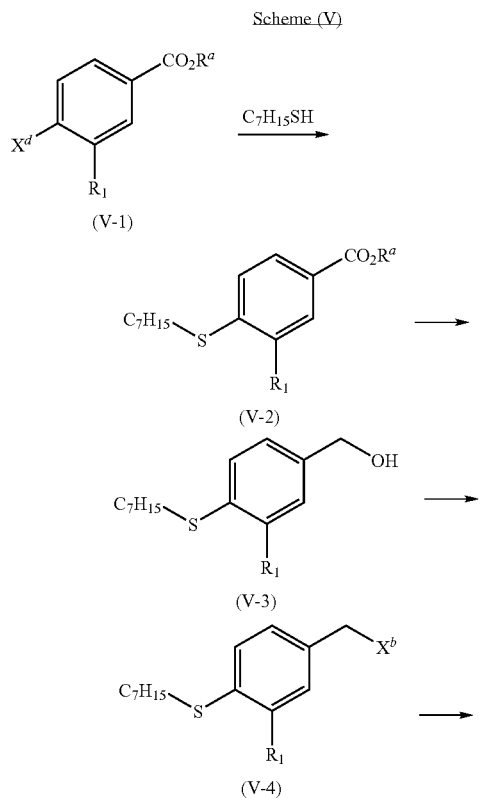

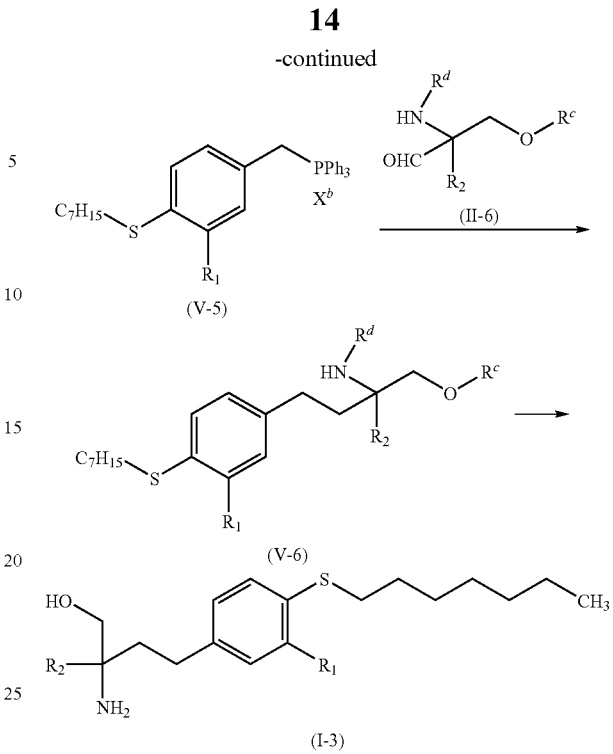

wherein $R^a$, $R^c$ and $R^d$ are protecting groups, $X^b$ and $X^d$ are leaving groups, $R_1$ is alkyl having a carbon number of 1 to 4 and substituted by a halogen atom(s), and $R_2$ is as defined above.

$R^a$, $R^c$, $R^d$ and $X^b$ in the formula are as defined above. The leaving group for $X^d$ is not particularly limited as long as it is dissociated during a substitution reaction by a heptylthio ion ($C_7H_{15}S^-$). For example, a halogen atom (specifically a fluorine atom and the like), toluenesulfonyloxy and the like can be mentioned.

In the first step, benzoic acid derivative (V-1) having a leaving group $X^d$ at the 4-position is condensed with heptylthiol to introduce heptylthio into the 4-position, whereby intermediate (V-2) is obtained. This step can be performed in a polar solvent such as N,N-dimethylformamide and dimethyl sulfoxide, an ether solvent such as tetrahydrofuran and the like in the presence of a base. As the base, an inorganic base such as potassium carbonate, sodium hydroxide and the like or an organic base such as triethylamine, 1,8-diazabicyclo[5.4.0]undec-7-en and the like can be used. The reaction conditions are, for example, about −30-80° C. for about 10 min-10 hr. After the reaction, the object product can be obtained by extraction, washing, drying, solvent removal and the like by a general method and, where necessary, purification by distillation, silica gel column chromatography, recrystallization and the like.

In the second step, the carboxyl group of intermediate (V-2) is reduced to give intermediate (V-3) having a hydroxyl group. The reagent to be used for the reduction is not particularly limited as long as it is generally used. Examples thereof include alkali metals such as sodium and the like, alkaline earth metals, metal hydrides such as diisobutylaluminum hydride and the like, metal hydrogen complex compounds such as lithium aluminum hydride, sodium borohydride and the like, boron compounds such as diborane and the like, catalytic hydrogenation using a catalyst of the homogeneous system or heterogeneous system and the like. As the reaction conditions, temperature and time appropriate for the reducing reagent to be used are selected. Specific examples thereof include reduction using diborane, lithium aluminum hydride or lithium borohydride in an ether solvent such as tetrahydrofuran and the like from −30° C. to the refluxing temperature for 10 min to 12 hr, reduction using sodium borohydride or calcium borohydride in an alcohol solvent such as ethanol and the like or in a mixed solvent of an alcohol solvent and an ether solvent such as tetrahydrofuran and the like under ice-cooling to the refluxing temperature for 30 min to 24 hr, and the like. After the reaction, the object product can be obtained by quenching reaction, extraction, washing, drying, solvent removal and the like by a general method and, where necessary, purification by distillation, silica gel column chromatography, recrystallization and the like.

In the third step, the hydroxyl group of intermediate (V-3) is converted into leaving group $X^b$. The reagent is not particularly limited as long as it is a reagent capable of converting an alcoholic hydroxyl group into $X^b$. Examples of the reagent used when $X^b$ is a halogen atom include N-chlorosuccinimide, N-bromosuccinimide, carbon tetrachloride and a combination of them and a reaction aid such as triphenylphosphine, a base and the like, inorganic acids such as hydrochloric acid, hydrobromic acid, hydroiodic acid, phosphorus tribromide, phosphorus pentabromide, phosphorus trichloride, phosphorus pentachloride, iodine, bromine, chlorine, halogenated thionyl and the like. The reaction is performed, for example, in an organic solvent such as a halogen solvent (e.g., methylene chloride and the like), an ether solvent (e.g., tetrahydrofuran and the like) and the like from −30° C. to 130° C. for 10 min to 6 hr. When an inorganic acid is used, the reaction can be performed in an aqueous solution or a two-layer system of an organic solvent such as toluene and the like and water. Examples of the reagent used when $X^b$ is sulfonyloxy include a combination of sulfonyl chloride (e.g., methanesulfonyl chloride, toluene sulfonyl chloride and the like) and an organic base (e.g., triethylamine, pyridine and the like). The reaction conditions are, for example, an organic solvent such as a halogen solvent (e.g., methylene chloride and the like), an ether solvent (e.g., tetrahydrofuran and the like), and the like at −30° C.-50° C. for about 5 min-3 hr. After the reaction, the object product can be obtained by quenching reaction, extraction, washing, drying, solvent removal and the like by a general method and, where necessary, purification by distillation, silica gel column chromatography, recrystallization and the like.

In the fourth step, phosphonium salt (V-5) is obtained by reacting intermediate (V-4) having leaving group $X^b$ with triphenylphosphine. The reaction is performed, for example, in an inactive solvent such as diethyl ether, benzene, toluene and the like from room temperature to the refluxing temperature for about 30 min to 6 hr. After the reaction, the object product can be obtained by solvent evaporation, cooling and addition of poorly soluble solvent such as diisopropyl ether, hexane and the like, as necessary, after which collection of the precipitated solid by filtration.

In the fifth step, intermediate (V-6) is obtained by condensing phosphonium salt (V-5) with aldehyde (II-6) separately synthesized using Wittig reaction, and reducing the obtained olefin compound. The conditions of the Wittig reaction are those generally used for Wittig reaction. For example, the reaction is performed using a base such as potassium t-butoxide and the like in an ether solvent such as tetrahydrofuran and the like from −30° C. to the refluxing temperature for about 30 min to 12 hr. After the reaction, the object product can be obtained by quenching reaction, extraction, washing, drying, solvent removal and the like by a general method and, where necessary, purification by silica gel column chromatography, recrystallization and the like. The reagent to be used the subsequent reduction of a double bond is not limited as long as it is used for general olefin reduction. Examples thereof include catalytic hydrogenation using a heterogeneous catalyst such as palladium carbon, Raney-nickel and the like, homogeneous catalysts such as rhodium complex (chlorotris(triphenylphosphine)rhodium(I) and the like) and the like. The reaction is performed, for example, in an alcohol solvent such as ethanol and the like, an ether solvent such as dioxane and the like, or a hydrocarbon solvent such as toluene and the like, under 1 to 20 atm of hydrogen pressure, under ice-cooling to the refluxing temperature from 30 min to 1 week. An acid such as acetic acid and the like or a base such as triethylamine and the like can be added to the reaction mixture depending on the reaction speed, stability of compound and the like. After the reaction, the object product can be obtained by filtration, extraction, washing, drying, solvent removal and the like by a general method and, where necessary, purification by silica gel column chromatography, recrystallization and the like.

In the sixth step, the compound of the present invention (I-3) is obtained by removing intermediate (V-6) possessing $R^c$ and $R^d$, and the protecting group $R^e$ ($R^e$ is as defined above) which protects the hydroxyl group(s) when $R_2$ has such the hydroxyl group(s). The deprotection of intermediate (V-6) is not particularly limited as long as it is used for general removal of protecting groups, and all protecting groups can be removed at once or stepwisely. For example, when $R^c$ and $R^e$ are bonded to form a cyclic acetal, and $R^d$ is t-butyloxycarbonyl, they can be simultaneously removed by using an acid. Examples of the acid therefor include inorganic acids such as hydrochloric acid and the like, trifluoroacetic acid and the like. The reaction is performed, for example, in an alcohol solvent such as ethanol and the like, an ether solvent such as tetrahydrofuran and the like, water or a mixed solvent thereof, under ice-cooling to 80° C. for about 10 min-12 hr. After the reaction, the object product can be obtained by extraction, washing, drying, solvent removal and the like by a general method and, where necessary, purification by silica gel column chromatography, recrystallization and the like.

5) A compound (I-4) represented by the formula (Ia) wherein R is a hydrogen atom, X is a sulfur atom, and $R_1$ is cyano or alkyl having a carbon number of 1 to 4 and substituted by a halogen atom(s) is synthesized by the following scheme (VI).

Scheme (VI)

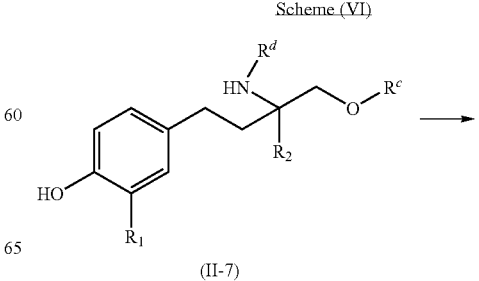

(II-7)

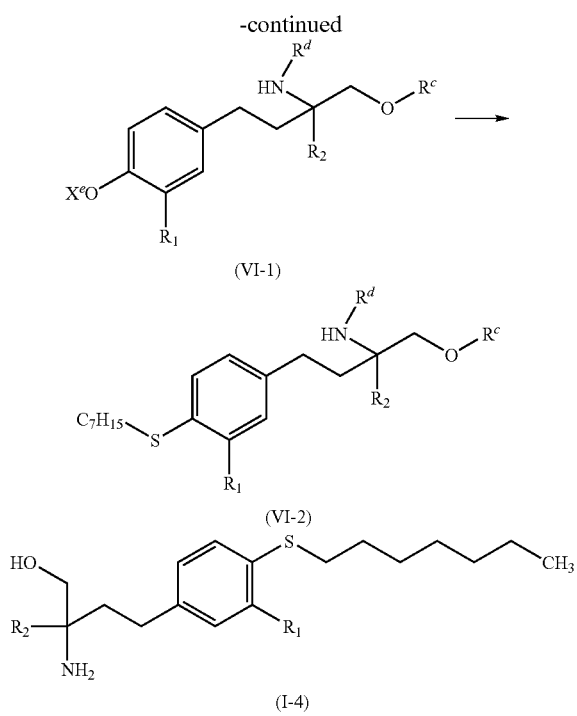

wherein $R^c$, $R^d$ is a protecting group, $X^e$ is an hydroxyl-activating group, $R_1$ is cyano or alkyl having a carbon number of 1 to 4 and substituted by a halogen atom(s), and $R_2$ is as defined above.

$R^c$ and $R^d$ in the formula are as defined above. As the hydroxyl-activating group for $X^e$, sulfonyl groups such as trifluoromethanesulfonyl, toluenesulfonyl and the like can be mentioned.

In the first step, intermediate (VI-1) is obtained by introducing an activating group into the phenolic hydroxyl group of intermediate (II-7) in scheme (II). This step can be performed in a halogen solvent such as methylene chloride and chloroform or an ether solvent such as tetrahydrofuran and the like in the presence of a base. As a reagent for this reaction, activated sulfonic acid derivatives such as trifluoromethanesulfonic acid anhydride, 1-(trifluoromethanesulfonyl)imidazole, toluene sulfonyl chloride are used. This reaction can also be performed by using sulfonic acid and a condensation agent in combination. As the base, an organic base such as triethylamine, pyridine, lutidine and the like is used. The reaction conditions are, for example, −50-50° C. for about 5 min-3 hr. After the reaction, the object product can be obtained by extraction, washing, drying, solvent removal and the like by a general method and, where necessary, purification by silica gel column chromatography, recrystallization and the like.

In the second step, intermediate (VI-1) is condensed with heptylthiol to give intermediate (VI-2). This step can be performed in an ether solvent such as dioxane and the like or a hydrocarbon solvent such as toluene and the like, in the presence of a palladium catalyst. Examples of the palladium catalyst include palladium(II) acetate, tris(dibenzylideneacetone)dipalladium(0) and the like. In addition, a phosphine compound or a base can be added as a reaction aid for this reaction. Examples of the phosphine compound include triphenylphosphine, 4,5-bis(diphenylphosphino)-9,9-dimethylxanthene and the like. On the other hand, as the base, inorganic base such as cesium carbonate and the like, and an organic base such as N,N-diisopropylethylamine and the like can be mentioned. The reaction conditions are, for example, room temperature-refluxing temperature for about 30 min-24 hr. After the reaction, the object product can be obtained by extraction, washing, drying, solvent removal and the like by a general method and, where necessary, purification by silica gel column chromatography, recrystallization and the like.

In the third step, the compound of the present invention (I-4) is obtained by removing intermediate (VI-2) possessing $R^c$ and $R^d$, and the protecting group $R^e$ ($R^e$ is as defined above) which protects the hydroxyl group(s) when $R_2$ has such the hydroxyl group(s). Deprotection of intermediate (VI-2) is not particularly limited as long as it is used for general removal of protecting groups, and all protecting groups can be removed at once or stepwisely. For example, when $R^c$ is a protecting group that can be removed by an acid such as methoxymethyl and the like and $R^d$ is t-butyloxycarbonyl, they can be removed simultaneously by an acid. Examples of the acid therefor include an inorganic acid such as hydrochloric acid and the like, trifluoroacetic acid and the like. The reaction conditions are, for example, an alcohol solvent such as ethanol and the like, an ether solvent such as tetrahydrofuran and the like, water, or a mixed solvent thereof, under ice-cooling-80° C. for about 10 min-12 hr. After the reaction, the object product can be obtained by extraction, washing, drying, solvent removal and the like by a general method and, where necessary, purification by silica gel column chromatography, recrystallization and the like.

6) Of the compounds of the present invention, a compound (I-5) represented by the formula (Ia) wherein R is P(=O)(OH)$_2$ is synthesized by the following scheme (VII).

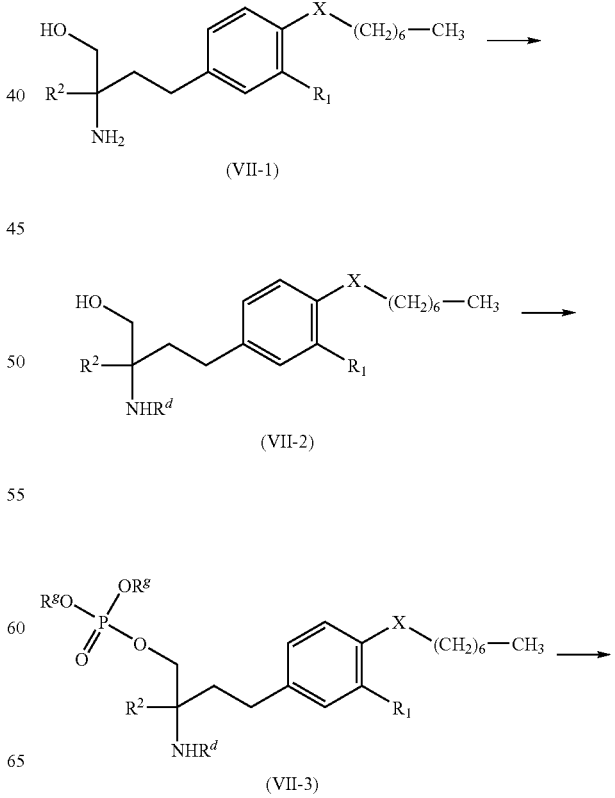

-continued

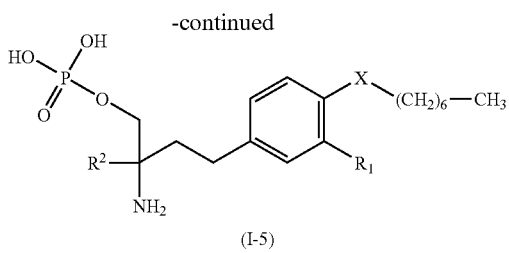

(I-5)

wherein X is an oxygen atom or a sulfur atom, $R^d$ and $R^g$ are protecting groups, $R_1$ is cyano or alkyl having a carbon number of 1 to 4 and substituted by a halogen atom(s), and $R_2$ is as defined above.

$R^d$ in the formula are as defined above. The protecting group for $R^g$ in the formula is not particularly limited as long as it protects a phosphoric acid group. For example, alkyl (preferably having a carbon number of about 1-6, specifically t-butyl and the like), benzyl, phenyl and the like can be mentioned.

In the first step, amino group-protected form (VII-2) is synthesized by protecting the amino group of compound (VII-1) wherein R is a hydrogen atom, from the compounds of the present invention. This step can be performed by a general amino group protection reaction. Specifically, when acyl, alkyloxycarbonyl, benzyloxycarbonyl and the like is used as a protecting group ($R^d$), this step can be performed in alcohol such as methanol and the like, or a two-layer system or mixture of water and an organic solvent such as ethyl acetate, chloroform and the like. Examples of the reagent to be used include acid chloride such as acetyl chloride, benzyloxycarbonyl chloride and the like, or acid anhydride such as acetic anhydride, di-t-butyl dicarbonate and the like. An organic base such as triethylamine and the like or an inorganic base such as sodium bicarbonate and the like can be added as a reaction promoter for this reaction. The reaction conditions are, for example, under ice-cooling-50° C. for about 30 min-24 hr. After the reaction, the object product can be obtained by extraction, washing, drying, solvent removal and the like by a general method and, where necessary, purification by silica gel column chromatography, recrystallization and the like.

In the second step, phosphorylated form (VII-3) is synthesized by reacting amino group-protected form (VII-2) with a phosphorylation reagent (e.g., phosphorus chloride, phosphorylamidite and oxidant, pyrophosphoric acid tetrabenzyl ester and the like). When pyrophosphoric acid tetrabenzyl ester is used as a phosphorylation reagent, this step can be performed under nonaqueous conditions preferably in an organic solvent such as toluene, dichloromethane, a mixed solvent thereof and the like using an additive (e.g., silver oxide, tetra-n-hexyl ammonium iodide and the like). The reaction conditions are, for example, under ice-cooling-50° C. for about 5-24 hr. After the reaction, the object product can be obtained by filtration, extraction, washing, drying, solvent removal and the like by a general method and, where necessary, purification by silica gel column chromatography, recrystallization and the like. For this reaction, a general phosphorylation reagent (phosphorus chloride and base, phosphoramidite and oxidant and the like) may be reacted according to a known method.

In the third step, the compound of the present invention (I-5) is prepared from a phosphorylated form (VII-3). This step can be performed by general deprotection. Specifically, the step can be performed by hydrogenolysis, an acid such as hydrochloric acid, trifluoroacetic acid and the like, or a Lewis acid such as trimethylsilyl bromide and the like. When hydrogenolysis is used for this reaction, this step is performed, for example, in an alcohol solvent such as methanol and the like using a catalyst such as palladium carbon and the like udder a hydrogen atmosphere. The reaction conditions are, for example, room temperature-60° C. for about 1-24 hr. The object product can be obtained by filtration, concentration and the like of the reaction mixture by a general method and, where necessary, purification by silica gel column chromatography, recrystallization and the like. The reaction conditions when an acid is used for this reaction are, for example, an alcohol solvent such as ethanol and the like or a mixed solvent thereof with water at room temperature-100° C. for about 30 min-12 hr.

7) Of the compounds of the present invention, a compound (I-1a) represented by the formula (I) wherein R is a hydrogen atom, X is an oxygen atom, Y is $CH_2CH_2$, $R_1$ is cyano or alkyl having a carbon number of 1 to 4 and substituted by a halogen atom(s), and $R_3$ and $R_4$ are hydrogen atoms is synthesized by the following scheme (VIII).

Scheme (VIII)

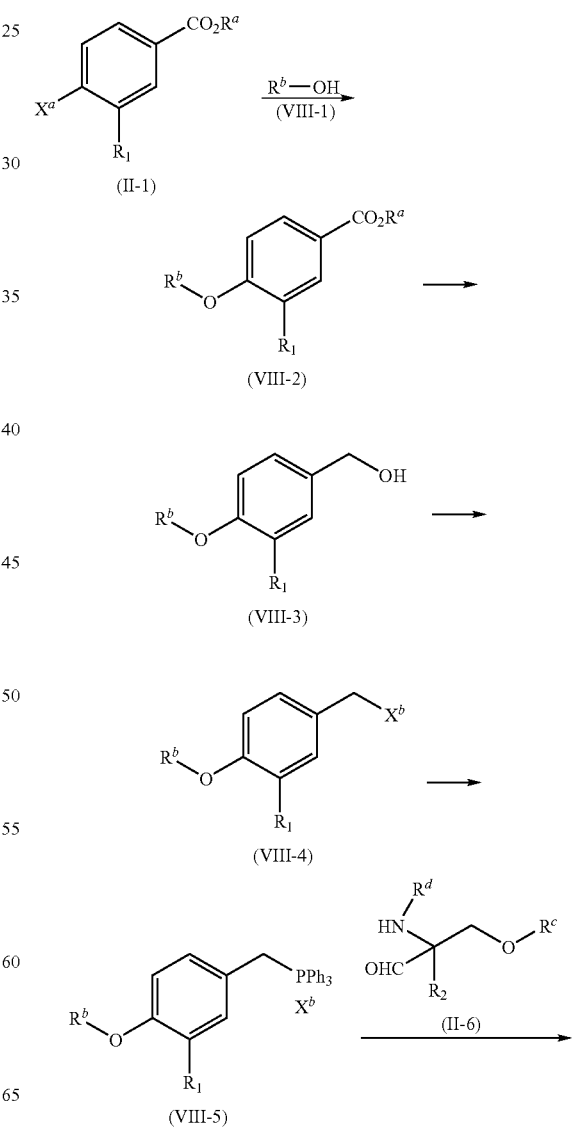

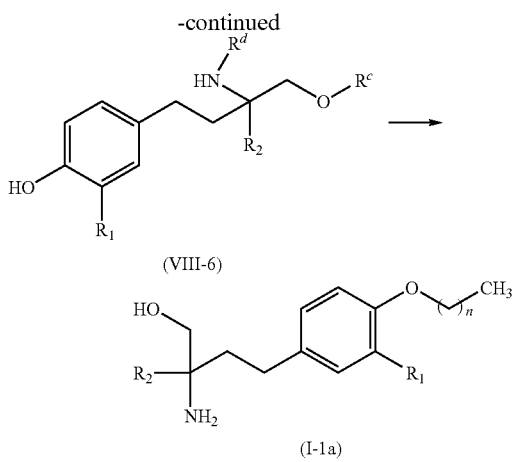

(VIII-6)

(I-1a)

wherein n is 5-8, $R^a$ is a hydrogen atom or a protecting group, $R^b$, $R^c$ and $R^d$ are protecting groups, $X^a$ and $X^b$ are leaving groups, $R_1$ is cyano or alkyl having a carbon number of 1 to 4 and substituted by a halogen atom(s), and $R_2$ is as defined above.

$R^a$ in the formula is not particularly limited as long as it protects a hydrogen atom or a carboxyl group. For example, alkyl (specifically methyl, ethyl and the like), aralkyl (benzyl and the like), the same substituent as for $R^b$ and the like can be mentioned. $R^b$ in the formula is not particularly limited as long as it protects a phenolic hydroxyl group. For example, alkyl (specifically methyl, ethyl and the like), aralkyl (benzyl and the like) and the like can be mentioned. When —$(CH_2)_n$ $CH_3$ (n is as defined above), which is a partial structure of inventive compound (I-1a) is used as $R^b$, the inventive compound (I-1a) can be obtained without removal of $R^b$. $R^c$ in the formula is not particularly limited as long as it protects a hydroxyl group. For example, acyl (preferably one having a carbon number of about 2-4, specifically acetyl and the like), trialkylsilyl (specifically trimethylsilyl and the like), benzyl and a substituent forming acetal compound (specifically methoxymethyl, tetrahydropyranyl and the like) can be mentioned. When $R_2$ has a hydroxyl group, its protecting groups $R^e$ ($R^e$ is specifically similar to $R^c$) and $R^c$ can also be bonded to form cyclic acetal. The protecting group shown by $R^d$ in the formula is not particularly limited as long as it protects an amino group. For example, acyl (preferably one having a carbon number of about 2-4, specifically acetyl and the like), carbamate (specifically t-butyloxycarbonyl, benzyloxycarbonyl and the like) and the like can be mentioned. The leaving group for $X^a$ is not particularly limited as long as it is dissociated during a substitution reaction by alkoxide ion ($R^b$—$O^-$). For example, a halogen atom (specifically a fluorine atom and the like), toluenesulfonyloxy and the like can be mentioned. The leaving group for $X^b$ is not particularly limited as long as it is dissociated during a condensation of intermediate (VIII-4) and triphenylphosphine, and does not inhibit the subsequent Wittig reaction. For example, a halogen atom (specifically an iodine atom, a bromine atom, a chlorine atom and the like), methanesulfonyloxy, toluenesulfonyloxy and the like can be mentioned.

In the first step, intermediate (VIII-2) is obtained by condensing benzoic acid derivative (II-1) having the leaving group $X^a$ at the 4-position with alcohol (VIII-1) to introduce an oxygen functional group having the protecting group $R^b$ at the 4-position. This step can be performed in a polar solvent such as N,N-dimethylformamide, dimethyl sulfoxide and the like or an ether solvent such as tetrahydrofuran and the like in the presence of a base. As the base, an inorganic base such as sodium hydride, potassium hydroxide and the like or an organic base such as 1,8-diazabicyclo[5.4.0]undec-7-en and the like can be used. The reaction is performed, for example, under ice-cooling to about 100° C. for about 10 min to 10 hr. After the reaction, the object product can be obtained by extraction, washing, drying, solvent removal and the like by a general method and, where necessary, purification by distillation, silica gel column chromatography, recrystallization and the like.

In the second step, intermediate (VIII-3) having a hydroxyl group is obtained by reducing the carboxyl group of intermediate (VIII-2). The reagent to be used for the reduction is not particularly limited as long as it is generally used. Examples thereof include alkali metals such as sodium and the like or alkaline earth metals, metal hydrides such as diisobutylaluminum hydride and the like, metal hydrogen complex compounds such as lithium aluminum hydride, sodium borohydride and the like, boron compounds such as diborane and the like, catalytic hydrogenation using a homogeneous type or heterogeneous type catalyst, and the like. As the reaction conditions, temperature and time appropriate for the reducing reagent to be used are selected. Specific examples thereof include reduction using diborane, lithium aluminum hydride or lithium borohydride in an ether solvent such as tetrahydrofuran and the like from −30° C. to the refluxing temperature for 10 min to 12 hr, reduction using sodium borohydride or calcium borohydride in an alcohol solvent such as ethanol and the like or in a mixed solvent of an alcohol solvent and an ether solvent such as tetrahydrofuran and the like under ice-cooling to the refluxing temperature for 30 min to 24 hr, and the like. After the reaction, the object product can be obtained by quenching reaction, extraction, washing, drying, solvent removal and the like by a general method and, where necessary, purification by distillation, silica gel column chromatography, recrystallization and the like.

In the third step, the hydroxyl group of intermediate (VIII-3) is converted into leaving group $X^b$. The reagent is not particularly limited as long as it is a reagent capable of converting an alcoholic hydroxyl group into $X^b$. Examples of the reagent used when $X^b$ is a halogen atom include N-chlorosuccinimide, N-bromosuccinimide, carbon tetrachloride and a combination of them and a reaction aid such as triphenylphosphine, a base and the like, inorganic acids such as hydrochloric acid, hydrobromic acid, hydroiodic acid, phosphorus tribromide, phosphorus pentabromide, phosphorus trichloride, phosphorus pentachloride, iodine, bromine, chlorine, halogenated thionyl and the like. The reaction is performed, for example, in an organic solvent such as a halogen solvent (e.g., methylene chloride and the like), an ether solvent (e.g., tetrahydrofuran and the like) and the like from −30° C. to 130° C. for 10 min to 6 hr. When an inorganic acid is used, the reaction can be performed in an aqueous solution or a two-layer system of an organic solvent such as toluene and the like and water. Examples of the reagent used when $X^b$ is sulfonyloxy include a combination of sulfonyl chloride (e.g., methanesulfonyl chloride, toluene sulfonyl chloride and the like) and an organic base (e.g., triethylamine, pyridine and the like). The reaction conditions are, for example, an organic solvent such as a halogen solvent (e.g., methylene chloride and the like), an ether solvent (e.g., tetrahydrofuran and the like), and the like at −30° C.-50° C. for about 5 min-3 hr. After the reaction, the object product can be obtained by quenching reaction, extraction, washing, drying, solvent removal and the like by a general method and, where necessary, purification by distillation, silica gel column chromatography, recrystallization and the like.

In the fourth step, phosphonium salt (VIII-5) is obtained by reacting intermediate (VIII-4) having leaving group $X^b$ with triphenylphosphine. The reaction is performed, for example, in an inactive solvent such as diethyl ether, benzene, toluene and the like from room temperature to the refluxing temperature for about 30 min to 12 hr. After the reaction, the object product can be obtained by solvent evaporation, cooling and addition of poorly soluble solvent such as diisopropyl ether, hexane and the like, as necessary, after which collection of the precipitated solid by filtration.

In the fifth step, phenolic intermediate (VIII-6) is obtained by condensing phosphonium salt (VIII-5) with aldehyde (II-6) separately synthesized using Wittig reaction, reducing the obtained olefin compound, and removing the protecting group $R^b$. The conditions of the Wittig reaction are those generally used for Wittig reaction. For example, the reaction is performed using a base such as potassium t-butoxide and the like in an ether solvent such as tetrahydrofuran and the like from –30° C. to the refluxing temperature for about 30 min to 12 hr. After the reaction, the object product can be obtained by quenching reaction, extraction, washing, drying, solvent removal and the like by a general method and, where necessary, purification by silica gel column chromatography, recrystallization and the like. The reagent to be used the subsequent reduction of a double bond is not limited as long as it is used for general olefin reduction. Examples thereof include catalytic hydrogenation using a heterogeneous catalyst such as palladium carbon, Raney-nickel and the like, or a homogeneous catalysts such as rhodium complex (chlorotris(triphenylphosphine)rhodium(I) and the like) and the like. The reaction is performed, for example, in an alcohol solvent such as ethanol and the like, an ether solvent such as dioxane and the like, or a hydrocarbon solvent such as toluene and the like, under 1 to 20 atm of hydrogen pressure, under ice-cooling to the refluxing temperature from 30 min to 1 week. An acid such as acetic acid and the like or a base such as triethylamine and the like can be added to the reaction mixture depending on the reaction speed, stability of compound and the like. After the reaction, the object product can be obtained by filtration, extraction, washing, drying, solvent removal and the like by a general method and, where necessary, purification by silica gel column chromatography, recrystallization and the like. The conditions of the subsequent removal of the protecting group $R^b$ are not particularly limited as long as they are used for the removal of $R^b$. For example, when $R^b$ is methyl, a method of using a Lewis acid such as boron tribromide and the like in methylene chloride solvent can be used. When $R^b$ is acyl such as acetyl and the like, a method of using an inorganic base such as sodium hydroxide and the like in a mixed solvent of an alcohol solvent and water can be used. When $R^b$ is an ether type protecting group such as methoxymethyl, tetrahydropyranyl, t-butyl and the like, a method of using an acid such as hydrochloric acid, trifluoroacetic acid and the like can be used. When $R^b$ is a protecting group which can be removed by catalytic hydrogenation (e.g., benzyl, substituted benzyl, benzyloxymethyl and the like), the removal of $R^b$ can be performed simultaneously with the aforementioned reduction of the double bond. When —$(CH_2)_nCH_3$ (n is as defined above), which is a partial structure of inventive compound (I-1a), is used as $R^b$, the removal of $R^b$ is not necessary, and the alkylation of phenol in the next step can also be omitted.

In the sixth step, the compound of the present invention (I-1a) is obtained by alkylating the phenolic hydroxyl group of intermediate (VIII-6), and removing $R^c$ and $R^d$, and the protecting group $R^e$ ($R^e$ is as defined above) which protects the hydroxyl group(s) when $R_2$ has such the hydroxyl group(s). Examples of the reagent to be used for alkylation of the phenolic hydroxyl group that intermediate (VIII-6) has include a combination of an alkylating agent such as heptyl halide and the like and an inorganic base such as potassium carbonate, sodium hydride and the like. The reaction is performed, for example, in a polar solvent such as N,N-dimethylformamide and the like, or in an ether solvent such as tetrahydrofuran and the like, under ice-cooling to 80° C. for about 30 min to 12 hr. For alkylation of the phenolic hydroxyl group that intermediate (VIII-6) has, Mitsunobu reaction of condensing heptyl alcohol etc. and using a phosphine compound such as triphenylphosphine and the like and an azocarboxylic acid derivative such as diisopropyl azodicarboxylate and the like can be used. The reaction is performed, for example, in an ether solvent such as tetrahydrofuran and the like, under ice-cooling-50° C. for about 10 min to 6 hr. After the reaction, the object product can be obtained by extraction, washing, drying, solvent removal and the like by a general method and, where necessary, purification by silica gel column chromatography, recrystallization and the like. The subsequent deprotection is not particularly limited as long as it is used for general removal of protecting groups, and all protecting groups can be removed at once or stepwisely. For example, when $R^c$ and $R^e$ are bonded to form a cyclic acetal, and $R^d$ is t-butyloxycarbonyl, they can be simultaneously removed by using an acid. Examples of the acid therefor include inorganic acids such as hydrochloric acid and the like, trifluoroacetic acid and the like. The reaction is performed, for example, in an alcohol solvent such as ethanol and the like, an ether solvent such as tetrahydrofuran and the like, water or a mixed solvent thereof, under ice-cooling to 80° C. for about 10 min-12 hr. After the reaction, the object product can be obtained by extraction, washing, drying, solvent removal and the like by a general method and, where necessary, purification by silica gel column chromatography, recrystallization and the like.

8) Of the compounds of the present invention, a compound (I-1a) represented by the formula (I) wherein R is a hydrogen atom, X is an oxygen atom, Y is $CH_2CH_2$, $R_1$ is cyano or alkyl having a carbon number of 1 to 4 and substituted by a halogen atom(s), and $R_3$ and $R_4$ are hydrogen atoms can also be synthesized using an intermediate (VIII-2, $R^a$ is H) in scheme (VIII) or intermediate (IX-1) synthesized from a compound represented by the formula (IX-2) by the following scheme (IX).

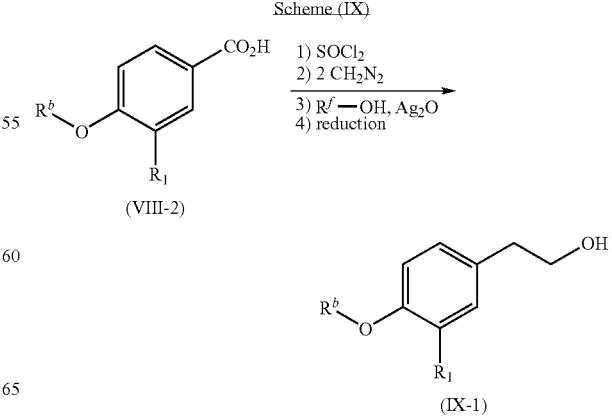

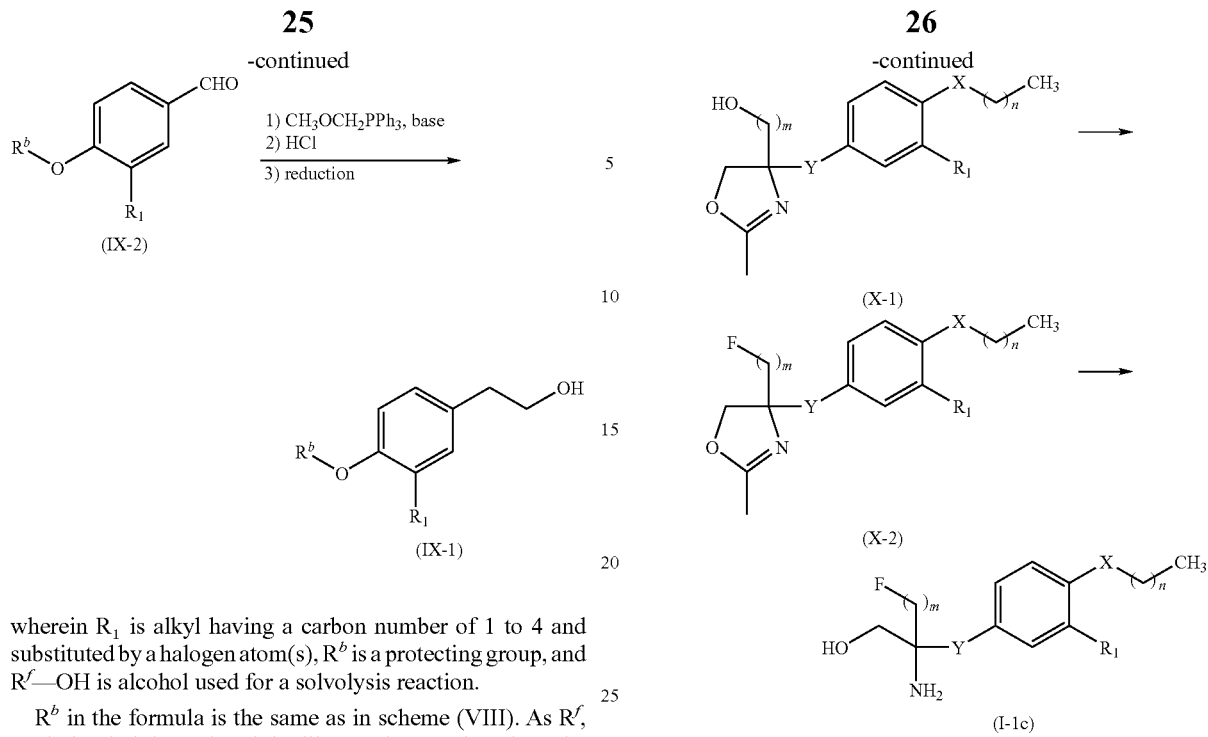

wherein $R_1$ is alkyl having a carbon number of 1 to 4 and substituted by a halogen atom(s), $R^b$ is a protecting group, and $R^f$—OH is alcohol used for a solvolysis reaction.

$R^b$ in the formula is the same as in scheme (VIII). As $R^f$, methyl, ethyl, benzyl and the like can be mentioned. In the above-mentioned scheme, for synthesis from compound (VIII-2), general reaction conditions of Arndt-Eistert reaction are used. For reduction of the ester group obtained thereby, the reagent and conditions used in the second step of scheme (VIII) can be mentioned. In the above-mentioned scheme, for synthesis from compound (IX-2), the conditions for general Wittig reaction are used. For acid treatment thereafter, an inorganic acid such as hydrochloric acid and the like is used in water or a mixed solvent of an organic solvent such as tetrahydrofuran and the like and water. For the subsequent reduction, a metal hydrogen complex compound such as lithium aluminum hydride, sodium borohydride and the like, catalytic hydrogenation using heterogeneous catalyst such as palladium carbon, Raney-nickel and the like or homogeneous catalyst such as rhodium complex (chlorotris(triphenylphosphine)rhodium(I) and the like) and the like may be performed, or these may be sequentially performed continuously. The alcoholic intermediate (IX-1) obtained in this scheme can be converted into the compound of the present invention by a known method (for example, Journal of Medicinal Chemistry vol. 43 (2000) 2946-2961).

9) Of the compounds of the present invention, compound (I-1c) represented by the formula (I) wherein R is a hydrogen atom, $R_1$ is cyano or alkyl having a carbon number of 1 to 4 and substituted by a halogen atom(s), $R_2$ is ω-fluoroalkyl, and $R_3$ and $R_4$ are hydrogen atoms can also be synthesized by the following scheme.

Scheme (X)

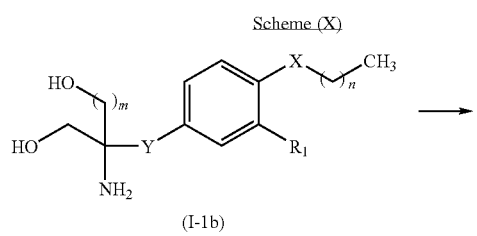

wherein m is an integer of 1-4, X is an oxygen atom or a sulfur atom, Y is $CH_2CH_2$ or $CH=CH$, $R_1$ is cyano or alkyl having a carbon number of 1 to 4 and substituted by a halogen atom(s), and n is as defined above.

In the first step, oxazoline form (X-1) is synthesized by protecting compound (I-1b) of the formula (I) wherein R is a hydrogen atom, and $R_2$ is ω-hydroxyalkyl. This step can be performed by reaction in a polar solvent such as acetonitrile, N,N-dimethylformamide and the like, a halogen solvent such as methylene chloride and the like, or a hydrocarbon solvent such as toluene and the like using orthoacetic acid ester as a reagent. To promote the reaction, a base such as N,N-diisopropylethylamine and the like, or an acid such as p-toluenesulfonic acid and the like can be added. The reaction conditions are, for example, room temperature-refluxing temperature for about 30 min-12 hr. After the reaction, the object product can be obtained by extraction, washing, drying, solvent removal and the like by a general method and, where necessary, purification by silica gel column chromatography, recrystallization and the like.

In the second step, fluoride form (X-2) is synthesized by fluorination of the hydroxyl group of compound (X-1). Examples of the fluorinating agent include (diethylamino)sulfur trifluoride (DAST), 2,2-difluoro-1,3-dimethylimidazolidine (DFI) and the like. This step can be performed by reaction in a halogen solvent such as methylene chloride and the like, or a hydrocarbon solvent such as hexane and the like. The reaction conditions are, for example, −78° C.-room temperature for about 30 min-12 hr. After the reaction, the object product can be obtained by extraction, washing, drying, solvent removal and the like by a general method and, where necessary, purification by silica gel column chromatography, recrystallization and the like. This step can also be performed by a method including converting the hydroxyl group of compound (X-1) to the corresponding sulfonate form, and then reacting same with fluoride ion. For example, when p-toluenesulfonyl fluoride and tetrabutylammonium fluoride (TBAF) are used, reaction is performed in an ether solvent such as tetrahydrofuran and the like at room temperature-80°

C. for about 1 hr-24 hr. In this reaction, a dehydrating agent such as molecular sieves and the like can be added. After the reaction, the object product can be obtained by extraction, washing, drying, solvent removal and the like by a general method and, where necessary, purification by silica gel column chromatography, recrystallization and the like.

In the third step, compound (X-2) is deprotected to give the compound of the present invention (I-1c). This step can be performed by general deprotection. Specifically, it can be performed using an acid such as hydrochloric acid, trifluoroacetic acid and the like. The reaction conditions are, for example, an alcohol solvent such as ethanol and the like or a mixed solvent thereof with water at room temperature-100° C. for about 30 min-12 hr. The object product can be obtained by filtration, concentration and the like of the reaction mixture by a general method and, where necessary, purification by silica gel column chromatography, recrystallization and the like.

10) A compound (I-2a) represented by the formula (I), wherein R is a hydrogen atom, X is an oxygen atom, Y is $CH_2CH_2$, $R_1$ is trifluoromethyl or cyano, and $R_3$ and $R_4$ are hydrogen atoms is synthesized by the following scheme (XI).

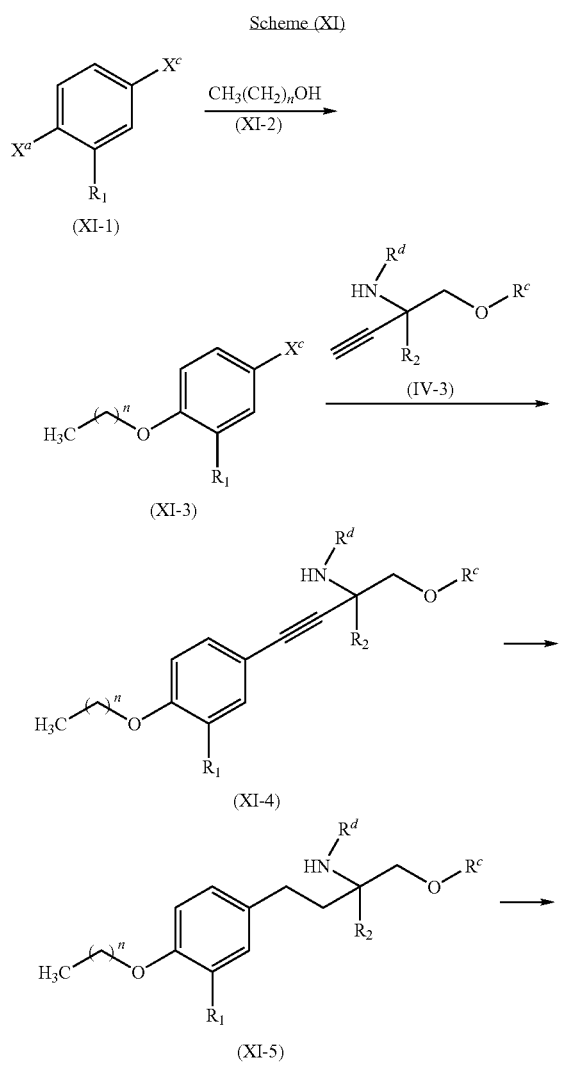

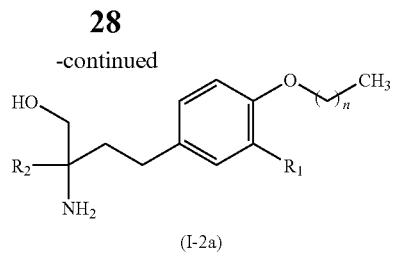

wherein $R_1$ is trifluoromethyl or cyano, $R^c$ and $R^d$ are protecting groups, $X^a$ and $X^c$ are leaving groups, and $R_2$, and n is as defined above.

$R^c$, $R^d$, $X^a$ in the formula are as defined above. The leaving group for $X^c$ is not particularly limited as long as it is activated by a catalyst and dissociated during a Sonogashira reaction. For example, a halogen atom (preferably an iodine atom, a bromine atom and the like), trifluoromethanesulfonyloxy and the like can be mentioned.

In the first step, intermediate (XI-3) is obtained by condensing compound (XI-1) having the leaving group $X^a$ with alcohol (XI-2). This step can be performed in a polar solvent such as N,N-dimethylformamide, dimethyl sulfoxide and the like or an ether solvent such as tetrahydrofuran and the like in the presence of a base. As the base, an inorganic base such as sodium hydride, potassium hydroxide and the like or an organic base such as 1,8-diazabicyclo[5.4.0]undec-7-en and the like can be used. The reaction is performed, for example, under ice-cooling to about 100° C. for about 10 min to 10 hr. After the reaction, the object product can be obtained by extraction, washing, drying, solvent removal and the like by a general method and, where necessary, purification by distillation, silica gel column chromatography, recrystallization and the like.

In the second step, intermediate (XI-4) having a triple bond is obtained by condensing intermediate (XI-3) with intermediate (IV-3) by the Sonogashira reaction. Examples of the catalyst include palladium compound such as tetrakis(triphenylphosphine)palladium(0), tris(dibenzylideneacetone)dipalladium(0), dichlorobis(acetonitrile)palladium(II) and the like. To promote the reaction, an organic base such as triethylamine and the like, an inorganic base such as ammonia and the like, a copper compound such as copper iodide, copper bromide and the like, a phosphine compound such as 2-dicyclohexylphosphino-2',4',6'-triisopropylbiphenyl and the like, and the like can be added. The reaction is performed, for example, in an ether solvent such as tetrahydrofuran, dioxane and the like, a polar solvent such as acetonitrile, dimethylformamide and the like, or a hydrocarbon solvent such as benzene and the like, under ice-cooling to the refluxing temperature for about 30 min to 24 hr. After the reaction, the object product can be obtained by extraction, washing, drying, solvent removal and the like by a general method and, where necessary, purification by silica gel column chromatography, recrystallization and the like.

In the third step, intermediate (XI-5) is obtained by reducing the triple bond of intermediate (XI-4). The reagent to be used is not limited as long as it is used for general reduction of unsaturated carbon bond. For example, catalytic hydrogenation using a heterogeneous catalyst such as palladium carbon, Raney-nickel, palladium carbon-ethylenediamine complex and the like, homogeneous catalyst such as rhodium complex (chlorotris(triphenylphosphine)rhodium(I) and the like) and the like can be mentioned. The reaction conditions are, for example, an alcohol solvent such as ethanol and the like, an ether solvent such as dioxane and the like, or a hydrocarbon solvent such as toluene and the like at 1-20 atm of hydrogen pressure under ice-cooling-refluxing for 30 min-1 week. An acid such as acetic acid and the like or a base such as triethylamine and the like can be added to the reaction mixture depending on the reaction speed, stability of compound and the like. After the reaction, the object product can be obtained by filtration, extraction, washing, drying, solvent removal and the like by a general method and, where necessary, purification by silica gel column chromatography, recrystallization and the like.

In the fourth step, intermediate (XI-5) is deprotected to give the compound of the present invention (I-2a). Removal of $R^c$ and $R^d$, and protecting group $R^e$ ($R^e$ is as defined above) which protects the hydroxyl group(s) when $R_2$ has such the hydroxyl group(s), is not particularly limited as long as it is used for general removal of protecting groups, and all protecting groups can be removed at once or stepwisely. For example, when $R^c$ and $R^e$ are bonded to form cyclic acetal, and $R^d$ is t-butyloxycarbonyl group, cyclic acetal is deprotected by a catalytic amount of an acid, and then stronger acidic conditions are employed, whereby $R^d$ can be removed. The conditions employed for the deprotection of acetal are, for example, an alcohol solvent such as methanol and the like or a mixed solution of an alcohol solvent and other organic solvent, a catalytic amount of hydrochloric acid or toluenesulfonic acid, under ice-cooling-80° C. for about 30 min-12 hr. On the other hand, the removal conditions of $R^d$ performed after acetal deprotection are, for example, not less than equivalent amount of an inorganic acid such as hydrochloric acid and the like, trifluoroacetic acid and the like, in an alcohol solvent such as ethanol and the like, an ether solvent such as tetrahydrofuran and the like, water, or a mixed solvent thereof, under ice-cooling-80° C. for about 10 min-12 hr. After the reaction, the object product can be obtained by extraction, washing, drying, solvent removal and the like by a general method and, where necessary, purification by silica gel column chromatography, recrystallization and the like.

11) A compound (I-3a) represented by the formula (I) wherein R is a hydrogen atom, X is a sulfur atom, Y is $CH_2CH_2$, $R_1$ is alkyl having a carbon number of 1 to 4 and substituted by a halogen atom(s), and $R_3$ and $R_4$ are hydrogen atoms is synthesized by the following scheme (XII).

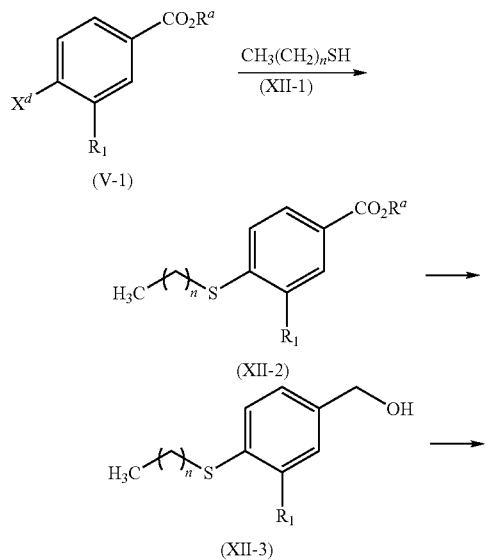

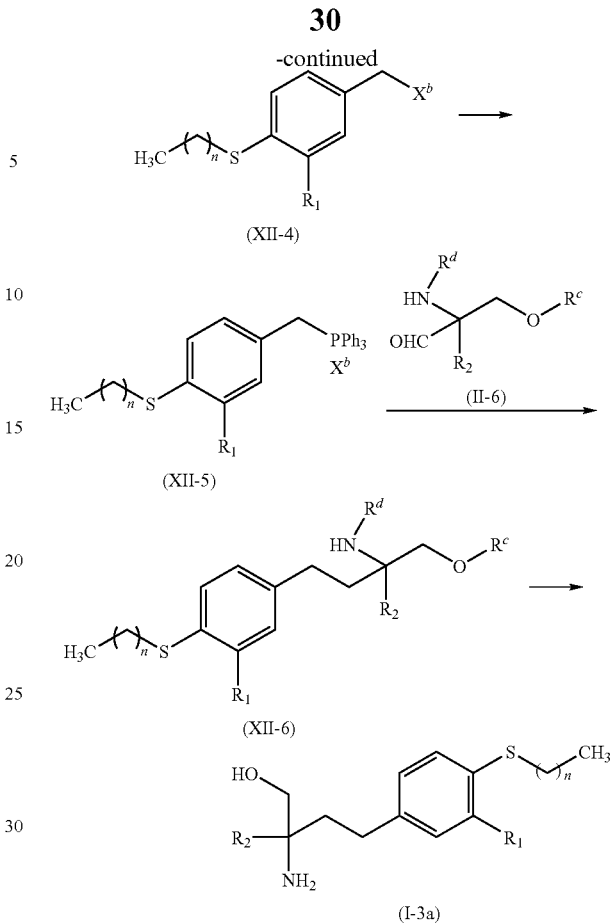

wherein $R_1$ is alkyl having a carbon number of 1 to 4 and substituted by a halogen atom(s), $R^a$ is a hydrogen atom or a protecting group, $R^c$ and $R^d$ are protecting groups, $X^b$ and $X^d$ are leaving groups and $R_2$ and n are as defined above.

$R^a$, $R^c$, $R^d$, $X^b$ and $X^d$ in the formula are as defined above. The leaving group for $X^d$ is not particularly limited as long as it is dissociated during a substitution reaction by an alkylthio ion $(CH_3(CH_2)_nS^-)$. For example, a halogen atom (specifically fluorine atom and the like), toluenesulfonyloxy and the like can be mentioned.

In the first step, intermediate (XII-2) is obtained by condensing benzoic acid derivative (V-1) having the leaving group $X^a$ at the 4-position with thiol (XII-1) to introduce alkylthio into the 4-position. This step can be performed in a polar solvent such as N,N-dimethylformamide, dimethyl sulfoxide and the like or an ether solvent such as tetrahydrofuran and the like in the presence of a base. As the base, an inorganic base such as potassium carbonate, sodium hydroxide and the like or an organic base such as triethylamine, 1,8-diazabicyclo[5.4.0]undec-7-en and the like can be used. The reaction is performed, for example, −30-80° C. for about 10 min to 10 hr. After the reaction, the object product can be obtained by extraction, washing, drying, solvent removal and the like by a general method and, where necessary, purification by distillation, silica gel column chromatography, recrystallization and the like.

In the second step, intermediate (XII-3) having a hydroxyl group is obtained by reducing the carboxyl group of intermediate (XII-2). The reagent to be used for the reduction is not particularly limited as long as it is generally used. Examples thereof include alkali metals such as sodium and the like or alkaline earth metals, metal hydrides such as diisobutylaluminum hydride and the like, metal hydrogen complex compounds such as lithium aluminum hydride, sodium borohydride and the like, boron compounds such as diborane and the like, catalytic hydrogenation using a homogeneous type or heterogeneous type catalyst, and the like. As the reaction conditions, temperature and time appropriate for the reducing reagent to be used are selected. Specific examples thereof include reduction using diborane, lithium aluminum hydride or lithium borohydride in an ether solvent such as tetrahydrofuran and the like from −30° C. to the refluxing temperature for 10 min to 12 hr, reduction using sodium borohydride or calcium borohydride in an alcohol solvent such as ethanol and the like or in a mixed solvent of an alcohol solvent and an ether solvent such as tetrahydrofuran and the like under ice-cooling to the refluxing temperature for 30 min to 24 hr, and the like. After the reaction, the object product can be obtained by quenching reaction, extraction, washing, drying, solvent removal and the like by a general method and, where necessary, purification by distillation, silica gel column chromatography, recrystallization and the like.

In the third step, the hydroxyl group of intermediate (XII-3) is converted into leaving group $X^b$. The reagent is not particularly limited as long as it is a reagent capable of converting an alcoholic hydroxyl group into $X^b$. Examples of the reagent used when $X^b$ is a halogen atom include N-chlorosuccinimide, N-bromosuccinimide, carbon tetrachloride and a combination of them and a reaction aid such as triphenylphosphine, a base and the like, inorganic acids such as hydrochloric acid, hydrobromic acid, hydroiodic acid, phosphorus tribromide, phosphorus pentabromide, phosphorus trichloride, phosphorus pentachloride, iodine, bromine, chlorine, halogenated thionyl and the like. The reaction is performed, for example, in an organic solvent such as a halogen solvent (e.g., methylene chloride and the like), an ether solvent (e.g., tetrahydrofuran and the like) and the like from −30° C. to 130° C. for 10 min to 6 hr. When an inorganic acid is used, the reaction can be performed in an aqueous solution or a two-layer system of an organic solvent such as toluene and the like and water. Examples of the reagent used when $X^b$ is sulfonyloxy include a combination of sulfonyl chloride (e.g., methanesulfonyl chloride, toluene sulfonyl chloride and the like) and an organic base (e.g., triethylamine, pyridine and the like). The reaction conditions are, for example, an organic solvent such as a halogen solvent (e.g., methylene chloride and the like), an ether solvent (e.g., tetrahydrofuran and the like), and the like at −30° C.-50° C. for about 5 min-3 hr. After the reaction, the object product can be obtained by quenching reaction, extraction, washing, drying, solvent removal and the like by a general method and, where necessary, purification by distillation, silica gel column chromatography, recrystallization and the like.

In the fourth step, phosphonium salt (XII-5) is obtained by reacting intermediate (XII-4) having leaving group $X^b$ with triphenylphosphine. The reaction is performed, for example, in an inactive solvent such as diethyl ether, benzene, toluene and the like from room temperature to the refluxing temperature for about 30 min to 6 hr. After the reaction, the object product can be obtained by solvent evaporation, cooling and addition of poorly soluble solvent such as diisopropyl ether, hexane and the like, as necessary, after which collection of the precipitated solid by filtration.

In the fifth step, intermediate (XII-6) is obtained by condensing phosphonium salt (XII-5) with aldehyde (II-6) separately synthesized using Wittig reaction, and reducing the obtained olefin compound. The conditions of the Wittig reaction are those generally used for Wittig reaction. For example, the reaction is performed using a base such as potassium t-butoxide and the like in an ether solvent such as tetrahydrofuran and the like from −30° C. to the refluxing temperature for about 30 min to 12 hr. After the reaction, the object product can be obtained by quenching reaction, extraction, washing, drying, solvent removal and the like by a general method and, where necessary, purification by silica gel column chromatography, recrystallization and the like. The reagent to be used the subsequent reduction of a double bond is not limited as long as it is used for general olefin reduction. Examples thereof include catalytic hydrogenation using a heterogeneous catalyst such as palladium carbon, Raney-nickel and the like, a homogeneous catalyst such as rhodium complex (chlorotris(triphenylphosphine)rhodium(I) and the like) and the like. The reaction is performed, for example, in an alcohol solvent such as ethanol and the like, an ether solvent such as dioxane and the like, or a hydrocarbon solvent such as toluene and the like, under 1 to 20 atm of hydrogen pressure, under ice-cooling to the refluxing temperature from 30 min to 1 week. An acid such as acetic acid and the like or a base such as triethylamine and the like can be added to the reaction mixture depending on the reaction speed, stability of compound and the like. After the reaction, the object product can be obtained by filtration, extraction, washing, drying, solvent removal and the like by a general method and, where necessary, purification by silica gel column chromatography, recrystallization and the like.

In the sixth step, the compound of the present invention (I-3a) is obtained by removing intermediate (XII-6) possessing $R^c$ and $R^d$, and the protecting group $R^e$ ($R^e$ is as defined above) which protects the hydroxyl group(s) when $R_2$ has such the hydroxyl group(s). The deprotection of intermediate (XII-6) is not particularly limited as long as it is used for general removal of protecting groups, and all protecting groups can be removed at once or stepwisely. For example, when $R^c$ and $R^e$ are bonded to form a cyclic acetal, and $R^d$ is t-butyloxycarbonyl, they can be simultaneously removed by using an acid. Examples of the acid therefor include inorganic acids such as hydrochloric acid and the like, trifluoroacetic acid and the like. The reaction is performed, for example, in an alcohol solvent such as ethanol and the like, an ether solvent such as tetrahydrofuran and the like, water or a mixed solvent thereof, under ice-cooling to 80° C. for about 10 min to -12 hr. After the reaction, the object product can be obtained by extraction, washing, drying, solvent removal and the like by a general method and, where necessary, purification by silica gel column chromatography, recrystallization and the like.

12) A compound (I-4a) represented by the formula (I) wherein R is a hydrogen atom, X is a sulfur atom, $R_1$ is cyano or alkyl having a carbon number of 1 to 4 and substituted by a halogen atom(s), and $R_3$ and $R_4$ are hydrogen atoms is synthesized by the following scheme (XIII).

Scheme (XIII)

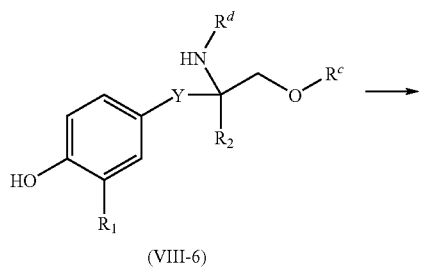

(VIII-6)

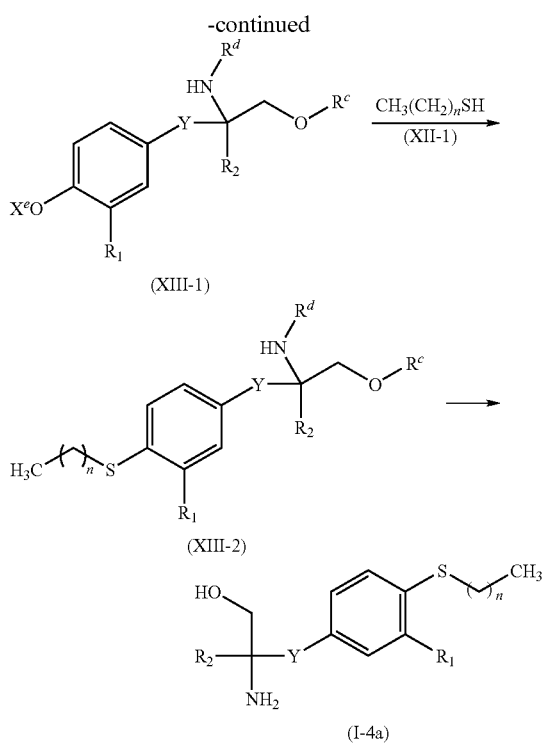

wherein $R_1$ is cyano or alkyl having a carbon number of 1 to 4 and substituted by a halogen atom(s), $R^c$ and $R^d$ are protecting groups, $X^e$ is an hydroxyl-activating group, Y is $CH_2CH_2$ or $CH=CH$, and $R_2$ and n are as defined above.

$R^c$, $R^d$ in the formula are as defined above. As the hydroxyl-activating group for $X^e$, sulfonyl such as trifluoromethanesulfonyl, toluenesulfonyl and the like can be mentioned.

In the first step, intermediate (XIII-1) is obtained by introducing an activating group into the phenolic hydroxyl group of intermediate (VIII-6) in scheme (VIII). This step can be performed in a halogen solvent such as methylene chloride and chloroform, an ether solvent such as tetrahydrofuran and the like in the presence of a base. As a reagent for this reaction, activated sulfonic acid derivatives such as trifluoromethanesulfonic acid anhydride, 1-(trifluoromethanesulfonyl)imidazole, chloride toluenesulfonyl are used. This reaction can also be performed by using sulfonic acid and a condensation agent in combination. As the base, an organic base such as triethylamine, pyridine, lutidine and the like is used. The reaction conditions are, for example, −50-50° C. for about 5 min-3 hr. After the reaction, the object product can be obtained by extraction, washing, drying, solvent removal and the like by a general method and, where necessary, purification by silica gel column chromatography, recrystallization and the like.

In the second step, intermediate (XIII-2) is obtained by condensation of intermediate (XIII-1) and thiol (XII-1). This step can be performed in an ether solvent such as dioxane and the like or a hydrocarbon solvent such as toluene and the like in the presence of a palladium catalyst. Examples of the palladium catalyst include palladium(II) acetate, tris(dibenzylideneacetone)dipalladium(0) and the like. In addition, a phosphine compound or a base can be added as a reaction aid for this reaction. Examples of the phosphine compound include triphenylphosphine, 4,5-bis(diphenylphosphino)-9,9-dimethylxanthene and the like. On the other hand, as the base, inorganic base such as cesium carbonate and the like, organic base such as N,N-diisopropylethylamine and the like can be mentioned. The reaction conditions are, for example, room temperature-refluxing temperature for about 30 min-24 hr. After the reaction, the object product can be obtained by extraction, washing, drying, solvent removal and the like by a general method and, where necessary, purification by silica gel column chromatography, recrystallization and the like.

In the third step, the compound of the present invention (I-4a) is obtained by removing intermediate (XIII-2) possessing $R^c$ and $R^d$, and protecting group $R^e$ ($R^e$ is as defined above) which protects the hydroxyl group(s) when $R_2$ has such the hydroxyl group(s). The deprotection of intermediate (XIII-2) is not particularly limited as long as it is used for general removal of protecting groups, and all protecting groups can be removed at once or stepwisely. For example, when $R^c$ is a protecting group that can be removed by an acid such as methoxymethyl and the like and $R^d$ is t-butyloxycarbonyl, they can be removed simultaneously by an acid. Examples of the acid therefor include an inorganic acid such as hydrochloric acid and the like and trifluoroacetic acid and the like. The reaction conditions are, for example, an alcohol solvent such as ethanol and the like, an ether solvent such as tetrahydrofuran and the like, water or a mixed solvent thereof under ice-cooling-80° C. for about 10 min-12 hr. After the reaction, the object product can be obtained by extraction, washing, drying, solvent removal and the like by a general method and, where necessary, purification by silica gel column chromatography, recrystallization and the like.

13) Of the compounds of the present invention, a compound (I-5a) represented by the formula (I) wherein R is a hydrogen atom, Y is $CH_2CH_2$, $R_1$ is alkyl having a carbon number of 1 to 4 and substituted by a halogen atom(s), $R_2$ is hydroxymethyl, and $R_3$ and $R_4$ are hydrogen atoms can also be synthesized by the following scheme (XIV).

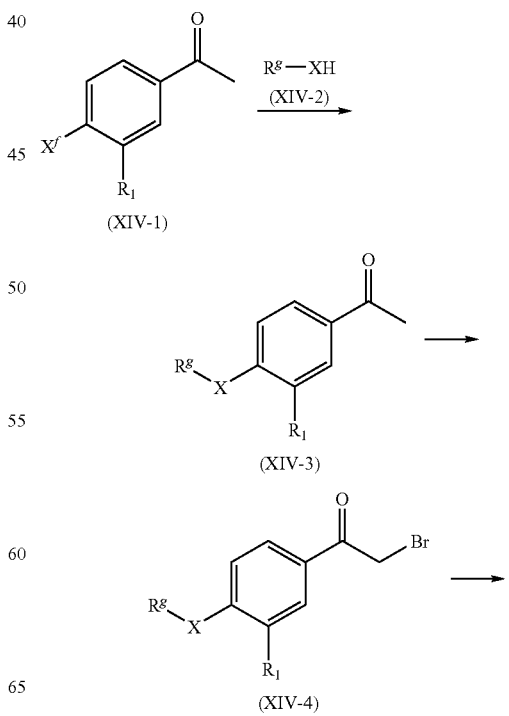

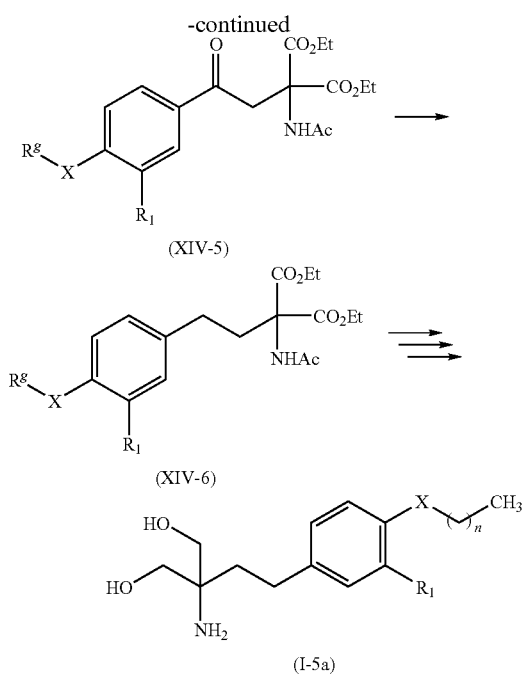

wherein $R_1$ is alkyl having a carbon number of 1 to 4 and substituted by a halogen atom(s), X is an oxygen atom or a sulfur atom, $X^f$ is a leaving group, $R^g$ is a protecting group or —$(CH_2)_n CH_3$, $R_2$ is hydroxymethyl, and n is as defined above.

The leaving group for $X^f$ is not particularly limited as long as it is dissociated during a substitution reaction by an alkoxide or thiol anion. For example, a halogen atom (specifically a fluorine atom and the like), toluenesulfonyloxy and the like can be mentioned. When $R^g$ in the formula is a protecting group, $R^g$ is not particularly limited as long as it protects a phenol group or a thiol group. Examples of $R^g$ when X is an oxygen atom include alkyl (methyl and the like), aralkyl (benzyl and the like), protecting group forming acetal (methoxymethyl, ethoxyethyl and the like) and the like. When X is a sulfur atom, alkyl (methyl and the like), aralkyl (4-methoxybenzyl and the like), a protecting group forming thioacetal (methoxymethyl, phenylthiomethyl, acetamidomethyl and the like) and the like can be mentioned.

In the first step, intermediate (XIV-3) is obtained by condensation of acetophenone (XIV-1) having leaving group $X^f$ at the 4-position and alcohol or thiol (XIV-2). This step can be performed in a polar solvent such as N,N-dimethylformamide, dimethyl sulfoxide and the like or an ether solvent such as tetrahydrofuran and the like in the presence of a base. As the base, an inorganic base such as sodium hydride, potassium hydroxide and the like or an organic base such as 1,8-diazabicyclo[5.4.0]undec-7-en and the like can be used. The reaction conditions are, for example, under ice-cooling-about 100° C. for about 10 min-10 hr. After the reaction, the object product can be obtained by extraction, washing, drying, solvent removal and the like by a general method and, where necessary, purification by distillation, silica gel column chromatography, recrystallization and the like.

In the second step, phenacyl bromide form (XIV-4) is obtained by bromination of acetyl group of intermediate (XIV-3). This step can be performed in a solvent such as a halogen solvent such as chloroform and the like, an ether solvent such as dioxane and the like, an alcohol solvent such as ethanol and the like or acetic acid and the like. As a bromination reagent, bromine, pyridinium tribromide, phenyltrimethylammonium tribromide and the like can be mentioned. The reaction conditions are, for example, under ice-cooling-about 60° C. for about 30 min-10 hr. After the reaction, the object product can be obtained by extraction, washing, drying, solvent removal and the like by a general method and, where necessary, purification by silica gel column chromatography, recrystallization and the like.

In the third step, intermediate (XIV-5) is obtained by condensation of intermediate (XIV-4) and diethyl acetamidomalonate. This step can be performed in a polar solvent such as N,N-dimethylformamide, dimethyl sulfoxide and the like or an ether solvent such as tetrahydrofuran and the like in the presence of a base. As the base, inorganic bases such as sodium hydride, potassium hydroxide, potassium t-butoxide and the like can be used. The reaction conditions are, for example, under ice-cooling-about 50° C. for about 10 min-5 hr. After the reaction, the object product can be obtained by quenching reaction, extraction, washing, drying, solvent removal and the like by a general method and, where necessary, purification by silica gel column chromatography, recrystallization and the like.

In the fourth step, intermediate (XIV-6) is obtained by reducing the carbonyl group of intermediate (XIV-5) to methylene. As the reducing agent, a combination of trialkylsilane and trifluoroacetic acid, a combination of trialkylsilane and titanium tetrachloride and the like can be used in a halogen solvent such as 1,2-dichloroethane and the like, or without solvent. The reaction conditions are, for example, under ice-cooling-refluxing for about 1-48 hr. After the reaction, the object product can be obtained by extraction, washing, drying, solvent removal and the like by a general method and, where necessary, purification by silica gel column chromatography, recrystallization and the like.

The obtained intermediate can be led to the compound of the present invention (I-5a) by a known method (for example, Journal of Medicinal Chemistry vol. 43 (2000) 2946-2961).

14) Of the compounds of the present invention, a compound (I-6a) represented by the formula (I) wherein one of $R_3$ and $R_4$ or both of $R_3$ and $R_4$ is(are) alkyl having a carbon number of 1 to 4 is synthesized by the following scheme (XV).

Scheme (XV)

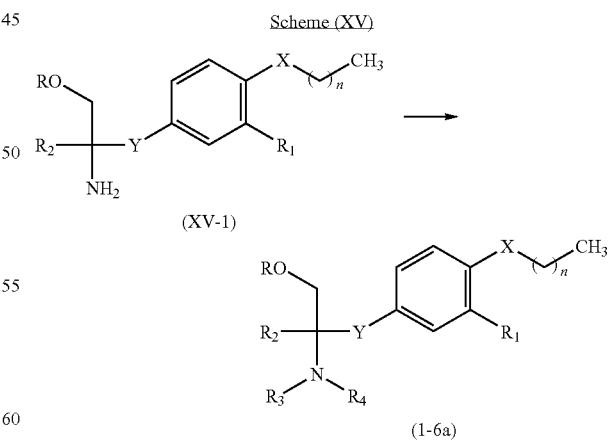

wherein R is a hydrogen atom or $P(=O)(OH)_2$, X is an oxygen atom or a sulfur atom, $R_1$ is cyano or alkyl having a carbon number of 1 to 4 and substituted by a halogen atom(s), $R_2$ is alkyl having a carbon number of 1 to 4 and optionally substituted by a hydroxyl group(s) or a halogen atom(s), one or both of $R_3$ and $R_4$ are alkyl having a carbon number of 1 to 4, Y is $CH_2CH_2$ or $CH=CH$; and n is as defined above.

In this step, the compound of the present invention (I-6a) is synthesized by alkylation of the amino group of compound (XV-1) having a primary amino group, from the compounds of the present invention. For this synthesis, reductive amination reaction or alkylation reaction of amine using alkyl halide and base can be used. When reductive amination reaction is used, the object product is obtained by reacting aldehyde having the same carbon number as that of $R_3$ or $R_4$ with compound (XV-1) in an alcohol solvent such as ethanol and the like or a halogen solvent such as dichloroethane and the like using a reducing agent such as sodium borohydride, sodium cyanoborohydride, sodium triacetoxyborohydride and the like. The reduction can also be performed using hydrogen and a catalyst such as Raney-nickel, platinum oxide and the like. For this reaction, generation of Schiff base and reduction reaction may also be sequentially performed. An acid such as acetic acid and the like can be added as a reaction promoter for the reductive amination reaction. The reaction conditions are, for example, under ice-cooling-about 50° C. for about 30 min-10 hr. After the reaction, the object product can be obtained by quenching reaction, extraction, washing, drying, solvent removal and the like by a general method and, where necessary, purification by silica gel column chromatography, recrystallization and the like. When $R_3$ and $R_4$ are methyl, methylation reaction of Eschweiler-Clarke can also be performed using a reducing agent such as formic acid and formaldehyde, or formaldehyde and sodium cyanoborohydride and the like.

15) Of the compounds of the present invention, a compound (I-7a) represented by the formula (I) wherein R is a hydrogen atom, Y is $CH=CH$, $R_1$ is cyano or alkyl having a carbon number of 1 to 4 and substituted by a halogen atom(s), and $R_3$ and $R_4$ are hydrogen atoms is synthesized by the following scheme (XVI).

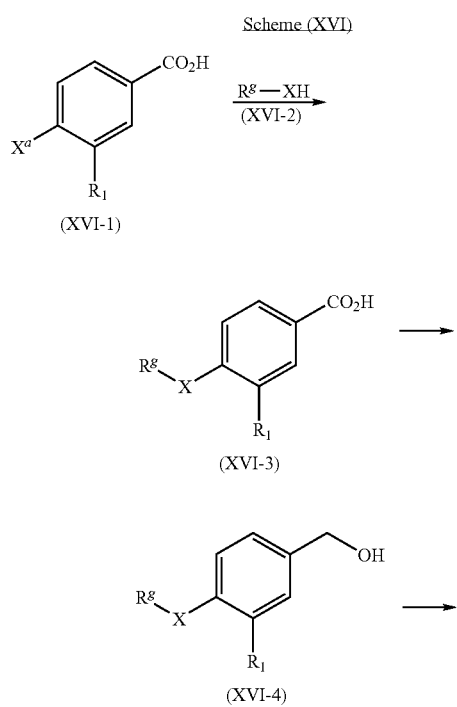

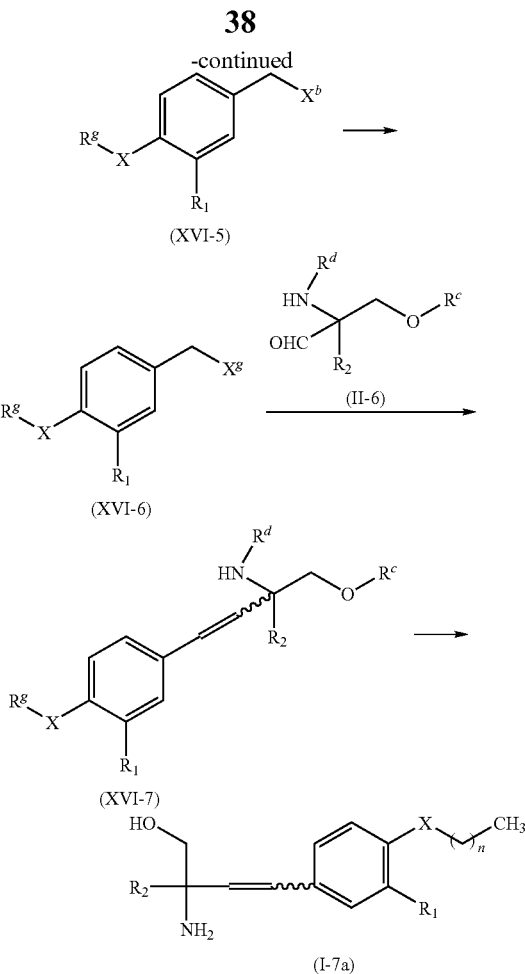

wherein X is an oxygen atom or a sulfur atom, $R_1$ is cyano or alkyl having a carbon number of 1 to 4 and substituted by a halogen atom(s), $R_2$ is alkyl having a carbon number of 1 to 4 and optionally substituted by a hydroxyl group(s) or a halogen atom(s), $R^c$ and $R^d$ are protecting groups, $R^g$ is a protecting group or $-(CH_2)_nCH_3$, $X^a$ and $X^b$ are leaving groups, $X^g$ is a leaving group containing phosphorus, and n is as defined above.

$R^c$ in the formula is not particularly limited as long as it protects a hydroxyl group. For example, acyl (preferably having a carbon number of about 2-4, specifically acetyl and the like), trialkylsilyl (specifically trimethylsilyl and the like), benzyl and substituent forming an acetal compound (specifically methoxymethyl, tetrahydropyranyl and the like) can be mentioned. When $R_2$ has a hydroxyl group, its protecting groups $R^e$ ($R^e$ is specifically similar to $R^c$) and $R^c$ can also be bonded to form cyclic acetal. The protecting group shown by $R^d$ in the formula is not particularly limited as long as it protects an amino group. For example, acyl (preferably one having a carbon number of about 2-4, specifically acetyl and the like), carbamate (specifically t-butyloxycarbonyl, benzyloxycarbonyl and the like) and the like can be mentioned. When $R^g$ in the formula is a protecting group, $R^g$ is not particularly limited as long as it protects a phenol group or a thiol group. Examples of $R^g$ when X is an oxygen atom include alkyl (methyl and the like), aralkyl (4-methoxybenzyl and the like), protecting group forming acetal (methoxymethyl, ethoxyethyl and the like) and the like. When X is a sulfur atom, alkyl (methyl and the like), aralkyl (4-methoxybenzyl and the like), a protecting group forming thioacetal (methoxymethyl, phenylthiomethyl, acetamidomethyl and the like) and the like can be mentioned. The leaving group for $X^a$ is not particularly limited as long as it is dissociated during a substitution reaction by an alkoxide ion ($R^g$—$O^-$) or thiolate ($R^g$—$S^-$). For example, a halogen atom (specifically a fluorine atom and the like), toluenesulfonyloxy and the like can be mentioned. The leaving group for $X^b$ is not particularly limited as long as it is dissociated during a reaction between an intermediate (XVI-5) and a phosphorus compound and does not inhibit the subsequent reaction with aldehyde (II-6). For example, a halogen atom (specifically an iodine atom, a bromine atom, a chlorine atom and the like), methanesulfonyloxy, toluenesulfonyloxy and the like can be mentioned. Examples of the leaving group containing phosphorus for $X^g$ include $P(C_6H_5)_3$ and $P(O)(OR^h)_2$ ($R^h$, is alkyl having a carbon number of 1 to 4).

In the first step, intermediate (XVI-3) is obtained by condensing benzoic acid (XVI-1) having the leaving group $X^a$ at the 4-position with alcohol or thiol (XVI-2). This step can be performed in a polar solvent such as N,N-dimethylformamide, dimethyl sulfoxide and the like or an ether solvent such as tetrahydrofuran and the like in the presence of a base. As the base, an inorganic base such as sodium hydride, potassium hydroxide, potassium carbonate and the like or an organic base such as alkoxide (e.g., potassium t-butoxide and the like), 1,8-diazabicyclo[5.4.0]undec-7-en and the like can be used. The reaction is performed, for example, under ice-cooling to about 80° C. for about 30 min to 24 hr. After the reaction, the object product can be obtained by extraction, washing, drying, solvent removal and the like by a general method and, where necessary, purification by silica gel column chromatography, recrystallization and the like.

In the second step, intermediate (XVI-4) having a hydroxyl group is obtained by reducing the carboxyl group of intermediate (XVI-3) The reagent to be used for the reduction is not particularly limited as long as it is generally used. Examples thereof include alkali metals such as sodium and the like, alkaline earth metals, metal hydrides such as diisobutylaluminum hydride and the like, metal hydrogen complex compounds such as lithium aluminum hydride, sodium bis(2-methoxyethoxy)aluminum hydride and the like, boron compounds such as diborane and the like, catalytic hydrogenation using a homogeneous type or heterogeneous type catalyst, and the like. As the reaction conditions, temperature and time appropriate for the reducing reagent to be used are selected. Specific examples thereof include reduction using diborane, lithium aluminum hydride in an ether solvent such as tetrahydrofuran and the like from –30° C. to the refluxing temperature for 10 min to 12 hr, reduction using sodium bis(2-methoxyethoxy)aluminum hydride in an inactive solvent such as toluene and the like, under ice-cooling-50° C. for about 30 min-24 hr, and the like. After the reaction, the object product can be obtained by quenching reaction, extraction, washing, drying, solvent removal and the like by a general method and, where necessary, purification by distillation, silica gel column chromatography, recrystallization and the like.

In the third step, the hydroxyl group of intermediate (XVI-4) is converted into leaving group $X^b$. The reagent is not particularly limited as long as it is a reagent capable of converting an alcoholic hydroxyl group into $X^b$. Examples of the reagent used when $X^b$ is a halogen atom include N-chlorosuccinimide, N-bromosuccinimide, carbon tetrachloride and a combination of them and triphenylphosphine, a base and the like, inorganic acids such as hydrochloric acid, hydrobromic acid, hydroiodic acid, phosphorus tribromide, phosphorus pentabromide, phosphorus trichloride, phosphorus pentachloride, iodine, bromine, chlorine, halogenated thionyl, α-haloenamine and the like. The reaction is performed, for example, in an organic solvent such as a halogen solvent (e.g., methylene chloride and the like), an ether solvent (e.g., tetrahydrofuran and the like) and the like from –30° C. to 130° C. for 10 min to 6 hr. When an inorganic acid is used, the reaction can be performed in an aqueous solution or a two-layer system of an organic solvent such as toluene and the like and water. Examples of the reagent used when $X^b$ is sulfonyloxy include a combination of sulfonyl chloride (e.g., methanesulfonyl chloride, toluene sulfonyl chloride and the like) and an organic base (e.g., triethylamine, pyridine and the like). The reaction conditions are, for example, an organic solvent such as a halogen solvent (e.g., methylene chloride and the like), an ether solvent (e.g., tetrahydrofuran and the like), and the like at –30° C.-50° C. for about 5 min-3 hr. After the reaction, the object product can be obtained by quenching reaction, extraction, washing, drying, solvent removal and the like by a general method and, where necessary, purification by silica gel column chromatography, recrystallization and the like.

In the fourth step, intermediate (XVI-6) having a leaving group $X^g$ containing phosphorus is obtained by reacting intermediate (XVI-5) having a leaving group $X^b$ with a phosphorus compound. When $X^g$ is $P(C_6H_5)_3$, intermediate (XVI-6) can be obtained by reacting intermediate (XVI-5) with triphenylphosphine. The reaction conditions are, for example, an inactive solvent such as diethyl ether, benzene, toluene and the like at room temperature-refluxing temperature for about 30 min-12 hr. After the reaction, the object product can be obtained by solvent evaporation, cooling and addition of poorly soluble solvent such as diisopropyl ether, hexane and the like, as necessary, after which collection of the precipitated solid by filtration. When $X^g$ is $P(O)(OR^h)_2$ ($R^h$ is as defined above), intermediate (XVI-6) can be obtained by Arbuzov reaction by reacting intermediate (XVI-5) with triethyl phosphite. The reaction conditions are, for example, without solvent or inactive solvent such as xylene and the like at 100° C.-170° C. for about 30 min-12 hr. After the reaction, the object product can be obtained by evaporation or distillation of excess triethyl phosphate.

In the fifth step, intermediate (XVI-6) containing phosphorus and separately synthesized aldehyde (II-6) are condensed to give olefin form (XVI-7). When $X^g$ is $P(C_6H_5)_3$, the conditions for general Wittig reaction are used. For example, reaction is performed in an ether solvent such as tetrahydrofuran and the like, using a base such as sodium hydride, potassium t-butoxide and the like at –30° C.-refluxing temperature for about 30 min-12 hr. A Z form may be preferentially obtained by reaction in an aprotic polar solvent under salt-free conditions, or an E form may also be preferentially obtained by an improved method of Schlosser. After the reaction, the object product can be obtained by quenching reaction, extraction, washing, drying, solvent removal and the like by a general method and, where necessary, purification by silica gel column chromatography, recrystallization and the like. When $X^g$ is $P(O)(OR^h)_2$ ($R^h$ is as defined above), the conditions of general Horner-Wadsworth-Emmons reaction are used. For example, reaction is performed in a hydrocarbon solvent such as benzene and the like, or an ether solvent such as tetrahydrofuran and the like using a base such as sodium hydride, potassium t-butoxide, lithium hexamethyldisilazane and the like at –20° C.-refluxing temperature for about 30 min-12 hr. An olefin can be preferentially obtained as an E form. After the reaction, the object product can be obtained by quenching reaction, extraction, washing, drying, solvent removal and the like by a general method and, where necessary, purification by silica gel column chromatography, recrystallization and the like.

In the sixth step, the compound of the present invention (I-7a) is obtained by removing intermediate (XVI-7) possessing $R^c$ and $R^d$, and the protecting group $R^e$ ($R^e$ is as defined above) which protects the hydroxyl group(s) when $R_2$ has such the hydroxyl group(s). The conditions are not particularly limited as long as they are used for general removal of protecting groups, and all protecting groups can be removed at once or stepwisely. For example, when $R^c$ is a protecting group that forms an acetal, and $R^d$ is t-butyloxycarbonyl, they can be simultaneously removed by using an acid. Examples of the acid therefor include inorganic acids such as hydrochloric acid and the like, trifluoroacetic acid and the like. The reaction is performed, for example, in an alcohol solvent such as ethanol and the like, an ether solvent such as tetrahydrofuran and the like, water or a mixed solvent thereof, under ice-cooling to 80° C. for about 10 min to 12 hr. After the reaction, the object product can be obtained by extraction, washing, drying, solvent removal and the like by a general method and, where necessary, purification by silica gel column chromatography, recrystallization and the like. When $R^g$ is a protecting group, prior to removal of protecting groups $R^c$ and $R^d$, removal of $R^g$ and alkylation of phenol or thiol obtained thereby can be performed. The conditions to be employed for removal of $R^g$ are not particularly limited as long as they are used for general removal of protecting groups. For example, when $R^g$ is 4-methoxybenzyl, oxidization reaction by 2,3-dichloro-5,6-dicyano-1,4-benzoquinone (DDQ) and the like are employed, when $R^g$ is allyl, a reaction using a palladium compound as a catalyst can be employed. Examples of the reagent to be used for alkylation of the phenolic hydroxyl group or thiol group that the obtained compound have include a combination of an alkylating agent such as alkyl halide and the like and an inorganic base such as potassium carbonate, sodium hydride and the like. The reaction conditions are, for example, a polar solvent such as N,N-dimethylformamide and the like, an ether solvent such as tetrahydrofuran and the like, under ice-cooling-80° C. for about 10 min-12 hr. In addition, for alkylation of a phenolic hydroxyl group, the Mitsunobu reaction can also be used.

16) A compound (I-8a) represented by the formula (I) wherein R is a hydrogen atom and $R_1$ is difluoromethyl can also be synthesized by the following scheme (XVII).

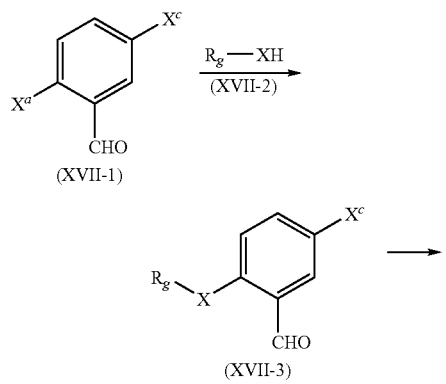

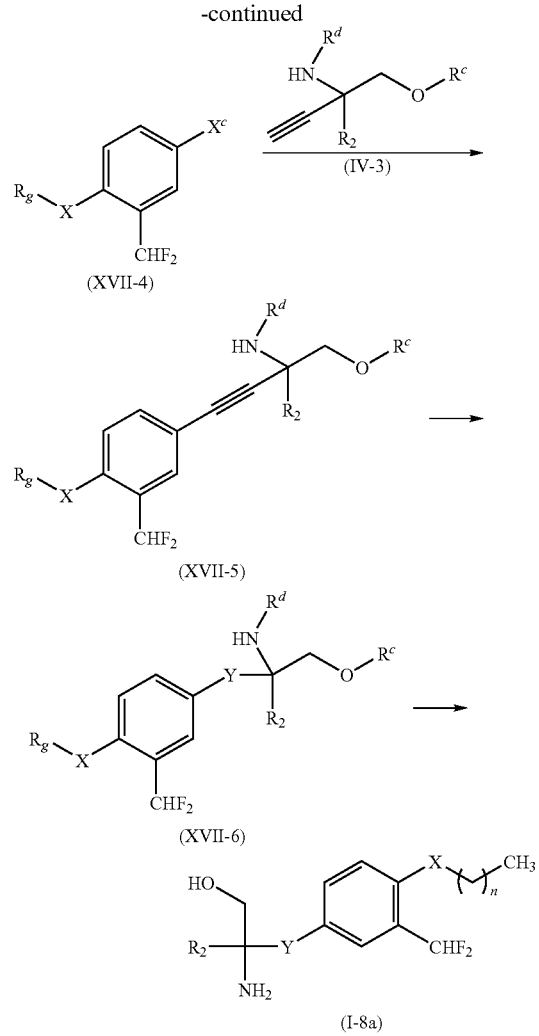

wherein X is an oxygen atom or a sulfur atom, Y is $CH_2CH_2$ or $CH=CH$, $R_2$ is alkyl having a carbon number of 1 to 4 and optionally substituted by a hydroxyl group(s) or a halogen atom(s), $R^c$ and $R^d$ are protecting groups, $R_g$ is a protecting group or $—(CH_2)_nCH_3$, $X^a$ and $X^c$ are leaving groups, and n is as defined above.

$R^c$, $R^d$, $R^g$, $X^a$ and $X^c$ are specifically as defined above.

In the first step, intermediate (XVII-3) is obtained by condensing starting material (XVII-1) having the leaving group $X^a$ with alcohol or thiol (XVII-2). This step can be performed in a polar solvent such as N,N-dimethylformamide, dimethyl sulfoxide and the like or an ether solvent such as tetrahydrofuran and the like in the presence of a base. As the base, an inorganic base such as sodium hydride, potassium hydroxide, potassium carbonate and the like or an organic base such as alkoxide such as potassium t-butoxide and the like, 1,8-diazabicyclo[5.4.0]undec-7-en and the like can be used. The reaction is performed, for example, under ice-cooling to about 80° C. for about 30 min to 24 hr. After the reaction, the object product can be obtained by extraction, washing, drying, solvent removal and the like by a general method and, where necessary, purification by silica gel column chromatography, recrystallization and the like. In addition, compound (XVII-1) wherein the leaving group $X^a$ is a phenolic hydroxyl group or thiol can also be used as the starting material. In this case, the first step is alkylation of a phenolic hydroxyl group or thiol. Examples of the reagent to be used for alkylation include a combination of an alkylating agent such as alkyl halide and the like and an inorganic base such as potassium carbonate, sodium hydride and the like. The reaction conditions are, for example, a polar solvent such as N,N-dimethylformamide and the like or an ether solvent such as tetrahydrofuran and the like, under ice-cooling-80° C. for about 10 min-12 hr. For alkylation of phenolic hydroxyl group, moreover, Mitsunobu reaction can be used.

In the second step, intermediate (XVII-4) having difluoromethyl is obtained by fluorination of the formyl group of intermediate (XVII-3). This step can be performed in a halogen solvent such as methylene chloride and the like using a fluorinating agent such as (diethylamino)sulfur trifluoride (DAST), xenon difluoride and the like. For this fluorination reaction, an oxidant such as N-iodosuccinimide and the like can be reacted in the presence of fluorinate ion such as tetrabutylammonium fluoride and the like, instead of using a single fluorinating agent. The reaction conditions are, for example, under ice-cooling-about 50° C. for about 1-24 hr. After the reaction, the object product can be obtained by extraction, washing, drying, solvent removal and the like by a general method and, where necessary, purification by distillation, silica gel column chromatography, recrystallization and the like.

In the third step, intermediate (XVII-5) having a triple bond is obtained by condensing intermediate (XVII-4) with intermediate (IV-3) by the Sonogashira reaction. Examples of the catalyst include palladium compound such as tetrakis(triphenylphosphine)palladium(0), tris(dibenzylideneacetone)dipalladium(0), dichlorobis(acetonitrile)palladium(II) and the like. To promote the reaction, an organic base such as triethylamine and the like, an inorganic base such as ammonia and the like, a copper compound such as copper iodide, copper bromide and the like, a phosphine compound such as 2"-dicyclohexylphosphino-2',4',6'-triisopropylbiphenyl and the like, and the like can be added. The reaction is performed, for example, in an ether solvent such as tetrahydrofuran, dioxane and the like, a polar solvent such as acetonitrile, dimethylformamide and the like, or a hydrocarbon solvent such as benzene and the like, under ice-cooling to the refluxing temperature for about 30 min to 24 hr. After the reaction, the object product can be obtained by extraction, washing, drying, solvent removal and the like by a general method and, where necessary, purification by silica gel column chromatography, recrystallization and the like.

In the fourth step, intermediate (XVII-6) is obtained by reducing the triple bond of intermediate (XVII-5). The reagent to be used when Y is $CH_2CH_2$ is not limited as long as it is used for general reduction of unsaturated carbon bond. For example, catalytic hydrogenation using a heterogeneous catalyst such as palladium carbon, Raney-nickel, palladium carbon-ethylenediamine complex and the like, a homogeneous catalyst rhodium complex (chlorotris(triphenylphosphine)rhodium(I) and the like) and the like can be mentioned. The reaction conditions are, for example, an alcohol solvent such as ethanol and the like, an ether solvent such as dioxane and the like, or a hydrocarbon solvent such as toluene and the like at 1-20 atm of hydrogen pressure under ice-cooling-refluxing temperature for 30 min-1 week. An acid such as acetic acid and the like or a base such as triethylamine and the like can be added to the reaction mixture depending on the reaction speed, stability of compound and the like. After the reaction, the object product can be obtained by filtration, extraction, washing, drying, solvent removal and the like by a general method and, where necessary, purification by silica gel column chromatography, recrystallization and the like. On the other hand, as the reaction used when Y is CH=CH, catalytic hydrogenation in the presence of a catalyst with controlled activity such as Lindlar catalyst, nickel-graphite-ethylenediamine complex, various complex diene compound and phosphine compound and rhodium, and the like can be mentioned. In addition, a reduction reaction using a metal hydride such as diisobutylaluminum hydride and the like is also possible. After the reaction, the object product can be obtained by filtration, extraction, washing, drying, solvent removal and the like by a general method and, where necessary, purification by silica gel column chromatography, recrystallization and the like.

In the fifth step, the compound of the present invention (I-8a) is obtained by deprotecting intermediate (XVII-6). Removal of $R^c$ and $R^d$, and protecting group $R^e$ ($R^e$ is as defined above) which protects hydroxyl group(s) when $R_2$ has such the hydroxyl group(s), is not particularly limited as long as it is used for general removal of protecting groups, and all protecting groups can be removed at once or stepwisely. For example, when $R^c$ and $R^e$ are bonded to form cyclic acetal and $R^d$ is t-butyloxycarbonyl, cyclic acetal is deprotected by a catalytic amount of an acid, and then stronger acidic conditions are employed, whereby $R^d$ can be removed. The conditions employed for the deprotection of acetal are, for example, an alcohol solvent such as ethanol and the like, or a mixed solution of an alcohol solvent and other organic solvent, catalytic amount of hydrochloric acid or toluenesulfonic acid under ice-cooling-80° C. for about 30 min-12 hr. On the other hand, the conditions of removal of $R^d$ to be sequentially performed after acetal deprotection are, for example, not less than equivalent amount of an inorganic acid such as hydrochloric acid and the like, trifluoroacetic acid and the like, in an alcohol solvent such as ethanol and the like, an ether solvent such as tetrahydrofuran and the like, water or a mixed solvent thereof under ice-cooling-80° C. for about 10 min-12 hr. After the reaction, the object product can be obtained by extraction, washing, drying, solvent removal and the like by a general method and, where necessary, purification by silica gel column chromatography, recrystallization and the like. When $R^g$ is a protecting group, alkylation of phenol or thiol resulting from removal of $R^g$ can be performed prior to removal of the protecting groups $R^c$ and $R^d$. The conditions to be employed for removal of $R^g$ are not particularly limited as long as they are used for general removal of protecting groups. When, for example, $R^g$ is 4-methoxybenzyl, oxidization reaction by 2,3-dichloro-5,6-dicyano-1,4-benzoquinone (DDQ) and the like can be performed, and when $R^g$ is allyl, a reaction using a palladium compound as a catalyst can be performed. Examples of the reagent to be used for the alkylation of the phenolic hydroxyl group or thiol group of the obtained compound include a combination of an alkylating agent such as alkyl halide and the like and an inorganic base such as potassium carbonate, sodium hydride and the like. The reaction conditions are, for example, a polar solvent such as N,N-dimethylformamide and the like or an ether solvent such as tetrahydrofuran and the like under ice-cooling-80° C. for about 10 min-12 hr. For alkylation of the phenolic hydroxyl group, Mitsunobu reaction can also be used.

17) A compound (I-9a) represented by the formula (I) wherein R is a hydrogen atom, and $R_1$ is fluoromethyl can also be synthesized by the following scheme (XVIII).

Scheme (XVIII)

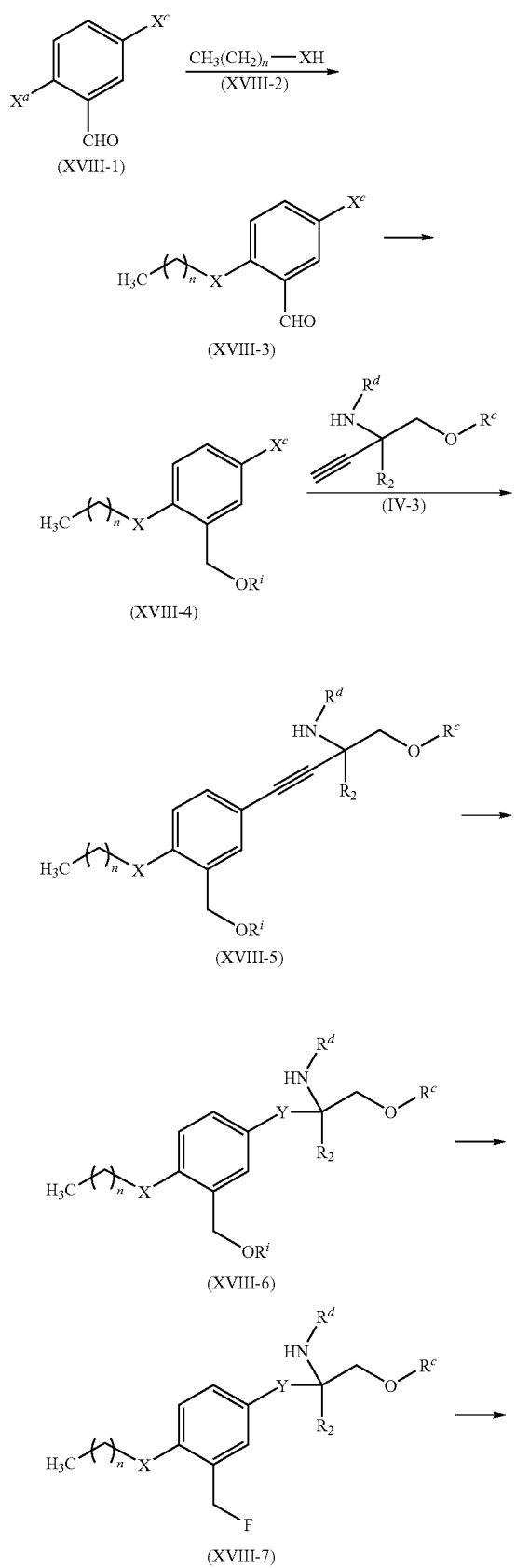

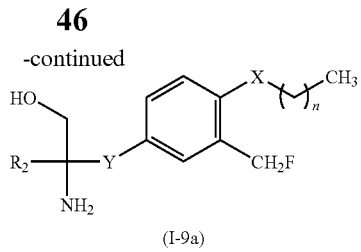

(I-9a)

wherein X is an oxygen atom or a sulfur atom, Y is $CH_2CH_2$ or CH=CH, $R_2$ is alkyl having a carbon number of 1 to 4 and optionally substituted by a hydroxyl group(s) or a halogen atom(s), $R^c$, $R^d$ and $R^i$ are protecting groups, $X^a$ and $X^c$ are leaving groups, and n is as defined above.

Specific examples of $R^c$, $R^d$, $X^a$ and $X^c$ in the formula are as those mentioned above. The protecting group for $R^i$ is not particularly limited as long as it protects hydroxyl group in the formula. For example, trialkylsilyl (specifically t-butyldimethylsilyl and the like) can be mentioned.

In the first step, intermediate (XVIII-3) is obtained by condensing starting material (XVIII-1) having the leaving group $X^a$ with alcohol or thiol (XVIII-2). This step can be performed in a polar solvent such as N,N-dimethylformamide, dimethyl sulfoxide and the like or an ether solvent such as tetrahydrofuran and the like in the presence of a base. As the base, an inorganic base such as sodium hydride, potassium hydroxide, potassium carbonate and the like or an organic base such as alkoxide (e.g., potassium t-butoxide and the like), 1,8-diazabicyclo[5.4.0]undec-7-en and the like can be used. The reaction is performed, for example, under ice-cooling to about 80° C. for about 30 min to 24 hr. After the reaction, the object product can be obtained by extraction, washing, drying, solvent removal and the like by a general method and, where necessary, purification by silica gel column chromatography, recrystallization and the like. In addition, compound (XVIII-1) wherein the leaving group $X^a$ is a phenolic hydroxyl group or thiol can also be used as the starting material. In this case, the first step is alkylation of a phenolic hydroxyl group or thiol. Examples of the reagent to be used for alkylation include a combination of an alkylating agent such as alkyl halide and the like and an inorganic base such as potassium carbonate, sodium hydride and the like. The reaction conditions are, for example, a polar solvent such as N,N-dimethylformamide and the like or an ether solvent such as tetrahydrofuran and the like, under ice-cooling-80° C. for about 10 min-12 hr. For alkylation of phenolic hydroxyl group, moreover, Mitsunobu reaction can be used.

In the second step, the formyl group of intermediate (XVIII-3) is reduced to give hydroxymethyl, and protecting group $R^i$ is introduced thereinto. The reagent to be used for the reduction of the formyl group is not particularly limited as long as it is generally used. Examples thereof include metal hydride such as diisobutylaluminum hydride and the like, metal hydrogen complex compound such as lithium aluminum hydride, sodium borohydride and the like, catalytic hydrogenation using homogeneous system or heterogeneous system catalyst and the like. As the reaction conditions, temperature and time appropriate for the reducing reagent to be used are selected. Specifically, reduction by lithium aluminum hydride or lithium borohydride, which is performed in an ether solvent such as tetrahydrofuran and the like at −30° C.-room temperature for about 10 min-3 hr, reduction by sodium borohydride or calcium borohydride, which is performed in an alcohol solvent such as ethanol and the like or a mixed solvent of an alcohol solvent and an ether solvent such as tetrahydrofuran and the like under ice-cooling-room temperature for about 10 min-3 hr and the like can be mentioned. After the reaction, the object product can be obtained by quenching reaction, extraction, washing, drying, solvent removal and the like by a general method and, where necessary, purification by distillation, silica gel column chromatography, recrystallization and the like. For introduction of the protecting group $R^i$, general introduction reaction of protecting groups is used. When a trialkylsilyl group is used for $R^i$, a silylation agent such as t-butyldimethylchlorosilane and the like is used as a reagent, and a base such as imidazole, triethylamine and the like can be added as a reaction promoter. After the reaction, the object product can be obtained by quenching reaction, extraction, washing, drying, solvent removal and the like by a general method and, where necessary, purification by distillation, silica gel column chromatography, recrystallization and the like.

In the third step, intermediate (XVIII-5) having a triple bond is obtained by condensing intermediate (XVIII-4) with intermediate (IV-3) by the Sonogashira reaction. Examples of the catalyst include palladium compound such as tetrakis(triphenylphosphine)palladium(0), tris(dibenzylideneacetone)dipalladium(0), dichlorobis(acetonitrile)palladium(II) and the like. To promote the reaction, an organic base such as triethylamine and the like, an inorganic base such as ammonia and the like, a copper compound such as copper iodide, copper bromide and the like, a phosphine compound such as 2-dicyclohexylphosphino-2',4',6'-triisopropylbiphenyl and the like, and the like can be added. The reaction is performed, for example, in an ether solvent such as tetrahydrofuran, dioxane and the like, a polar solvent such as acetonitrile, dimethylformamide and the like, or a hydrocarbon solvent such as benzene and the like, under ice-cooling to the refluxing temperature for about 30 min to 24 hr. After the reaction, the object product can be obtained by extraction, washing, drying, solvent removal and the like by a general method and, where necessary, purification by silica gel column chromatography, recrystallization and the like.

In the fourth step, intermediate (XVIII-6) is obtained by reducing the triple bond of intermediate (XVIII-5). When Y is $CH_2CH_2$, the reagent to be used is not limited as long as it is used for general reduction of unsaturated carbon bond. For example, catalytic hydrogenation using s heterogeneous catalyst such as palladium carbon, Raney-nickel, palladium carbon-ethylenediamine complex and the like or a homogeneous catalyst such as rhodium complex (chlorotris(triphenylphosphine)rhodium(I) and the like) and the like can be mentioned. The reaction conditions are, for example, an alcohol solvent such as ethanol and the like, an ether solvent such as dioxane and the like, or a hydrocarbon solvent such as toluene and the like at 1-20 atm of hydrogen pressure under ice-cooling-refluxing temperature for 30 min-1 week. An acid such as acetic acid and the like or a base such as triethylamine and the like can be added to the reaction mixture depending on the reaction speed, stability of compound and the like. After the reaction, the object product can be obtained by filtration, extraction, washing, drying, solvent removal and the like by a general method and, where necessary, purification by silica gel column chromatography, recrystallization and the like. On the other hand, as a reaction used when Y is CH=CH, catalytic hydrogenation in the presence of a catalyst having controlled activity such as Lindlar catalyst, nickel-graphite-ethylenediamine complex, various complexes of diene and phosphine and rhodium and the like can be mentioned. In addition, reduction reaction by metal hydride such as diisobutylaluminum hydride and the like can also be used. After the reaction, the object product can be obtained by filtration, extraction, washing, drying, solvent removal and the like by a general method and, where necessary, purification by silica gel column chromatography, recrystallization and the like.

In the fifth step, fluoride form (XVIII-7) is synthesized by removing $R^i$ of compound (XVIII-6), and fluorination of the hydroxyl group of the obtained compound. The protecting group $R^i$ can be removed by general deprotection. Examples of the reagent to be used when $R^i$ is trialkylsilyl include fluorine compounds such as tetrabutylammonium fluoride and the like. The conditions of the reaction are, for example, in an ether solvent such as tetrahydrofuran and the like, ice-cooling-refluxing temperature for about 30 min-24 hr. After the reaction, the object product can be obtained by extraction, washing, drying, solvent removal and the like by a general method and, where necessary, purification by distillation, silica gel column chromatography, recrystallization and the like. As the reagent to be used for successive fluorination, (diethylamino)sulfur trifluoride (DAST), 2,2-difluoro-1,3-dimethylimidazolidine (DFI) and the like can be mentioned. In this step, the reaction can be performed in a halogen solvent such as methylene chloride and the like or a hydrocarbon solvent such as hexane and the like. The reaction conditions are, for example, −78° C.-room temperature for about 30 min-12 hr. After the reaction, the object product can be obtained by extraction, washing, drying, solvent removal and the like by a general method and, where necessary, purification by silica gel column chromatography, recrystallization and the like. This step can also be performed by a method including converting the hydroxyl group to the corresponding sulfonate form, and reacting same with fluoride ion. For example, when p-toluenesulfonyl fluoride and tetrabutylammonium fluoride (TBAF) are used, reaction is performed in an ether solvent such as tetrahydrofuran and the like at room temperature-80° C. for about 1 hr-24 hr. In this reaction, a dehydrating agent such as molecular sieves and the like can be added. After the reaction, the object product can be obtained by extraction, washing, drying, solvent removal and the like by a general method and, where necessary, purification by silica gel column chromatography, recrystallization and the like. When $R^i$ is trialkylsilyl, fluorination can be performed without removal of $R^i$.

In the sixth step, the compound of the present invention (I-9a) is obtained by deprotecting intermediate (XVIII-7). Removal of $R^c$ and $R^d$, and protecting group $R^e$ ($R^e$ is as defined above) which protects the hydroxyl group(s) when $R_2$ have such the hydroxyl group(s), is not particularly limited as long as it is used for general removal of protecting groups, and all protecting groups can be removed at once or stepwisely. For example, when $R^c$ and $R^e$ are bonded to form cyclic acetal and $R^d$ is t-butyloxycarbonyl, cyclic acetal is deprotected by a catalytic amount of an acid, and then stronger acidic conditions are employed, whereby $R^d$ can be removed. The conditions employed for the deprotection of acetal are, for example, an alcohol solvent such as methanol and the like or a mixed solution of an alcohol solvent and other organic solvent using a catalytic amount of hydrochloric acid or toluenesulfonic acid under ice-cooling-80° C. for about 30 min-12 hr. On the other hand, the conditions of removal of $R^d$ to follow acetal deprotection are, for example, not less than equivalent amount of an inorganic acid such as hydrochloric acid and the like, trifluoroacetic acid and the like in an alcohol solvent such as ethanol and the like, an ether solvent such as tetrahydrofuran and the like, water or a mixed solvent thereof under ice-cooling-room temperature for about 10 min-5 hr. After the reaction, the object product can be obtained by extraction, washing, drying, solvent removal and the like by a general method and, where necessary, purification by silica gel column chromatography, recrystallization and the like. In addition, a solvent having low solubility such as diisopropyl ether and the like may be added to the reaction solution and the precipitated object product may be collected by filtration.

18) Of the compounds of the present invention, a compound (I-10a) represented by the formula (I) wherein R is P(=O)(OH)$_2$, and R$_3$ and R$_4$ are hydrogen atoms is synthesized by the following scheme (XIX).

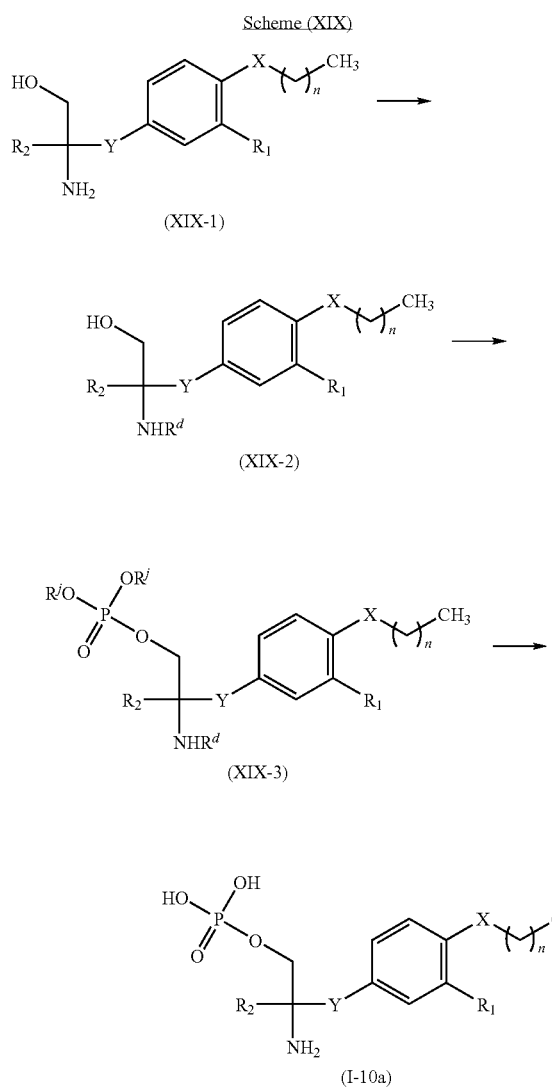

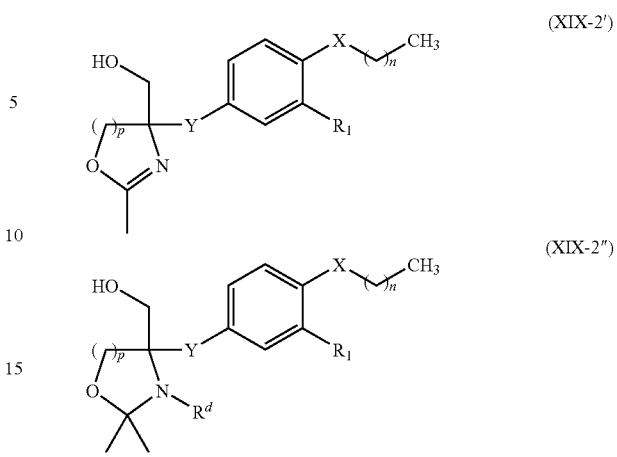

wherein p is 1 or 2, and other symbols are as defined for scheme (XIX), whereby amino group and hydroxyl group are protected.

The protecting group for R$^j$ in the formula is not particularly limited as long as it protects phosphoric acid group. For example, alkyl (preferably having a carbon number of about 1-6, specifically t-butyl and the like), benzyl, phenyl and the like can be mentioned.

In the first step, amino group-protected form (XIX-2) is synthesized by protecting the amino group of compound (XIX-1) wherein R is a hydrogen atom, from the compounds of the present invention. This step can be performed by a general amino group protection reaction. Specifically, when acyl, alkyloxycarbonyl, benzyloxycarbonyl and the like are used as protecting group (R$^d$), this step can be performed in alcohol such as methanol and the like, or a two-layer system or mixture of water and an organic solvent such as ethyl acetate, chloroform and the like. Examples of the reagent to be used include acid chloride such as acetyl chloride, benzyl oxycarbonyl chloride and the like, acid anhydride such as acetic anhydride, di-t-butyl dicarbonate and the like. An organic base such as triethylamine and the like, an inorganic base such as sodium bicarbonate and the like can be added as a reaction promoter for this reaction. The reaction conditions are, for example, under ice-cooling-50° C. for about 30 min-24 hr. After the reaction, the object product can be obtained by extraction, washing, drying, solvent removal and the like by a general method and, where necessary, purification by silica gel column chromatography, recrystallization and the like. When amino group and hydroxyl group contained in R$_2$ are protected simultaneously as oxazoline of the formula (XIX-2'), this step can be performed by reaction in a polar solvent such as acetonitrile, N,N-dimethylformamide and the like, a halogen solvent such as methylene chloride and the like, or a hydrocarbon solvent such as toluene and the like, using orthoacetic acid ester as a reagent. In addition, for promotion of the reaction, a base such as N,N-diisopropylethylamine and the like, or an acid such as p-toluenesulfonic acid and the like can be added. The reaction conditions are, for example, room temperature-refluxing for about 30 min-12 hr. After the reaction, the object product can be obtained by extraction, washing, drying, solvent removal and the like by a general method and, where necessary, purification by silica gel column chromatography, recrystallization and the like.

wherein X is an oxygen atom or a sulfur atom, Y is CH$_2$CH$_2$ or CH=CH, R$_1$ is cyano or alkyl having a carbon number of 1 to 4 and substituted by a halogen atom(s), R$_2$ is alkyl having a carbon number of 1 to 4 and optionally substituted by a hydroxyl group(s) or a halogen atom(s), R$^d$ and R$^j$ are protecting groups, and n is as defined above.

R$^d$ in the formula is as defined above. When R$_2$ of compound (XIX-2) contains a hydroxyl group, the hydroxyl group may be protected by a protecting group R$^e$ (R$^e$ is as defined above). When R$_2$ is protected hydroxymethyl or hydroxyethyl, its protecting group R$^e$ is bonded to R$^d$ or the nitrogen atom to which R$^d$ is bonded to form the following cyclic compound (XIX-2', XIX-2")

In the second step, phosphorylated form (XIX-3) is synthesized by reacting amino group-protected form (XIX-2) with a phosphorylation reagent (e.g., phosphorus chloride, phosphorylamidite and oxidant, pyrophosphoric acid tetrabenzyl ester and the like). When pyrophosphoric acid tetrabenzyl ester is used as a phosphorylation reagent, this step can be performed under nonaqueous conditions preferably in an organic solvent such as toluene, dichloromethane, a mixed solvent thereof and the like using an additive (e.g., silver oxide, tetra-n-hexyl ammonium iodide and the like). The reaction conditions are, for example, under ice-cooling-50° C. for about 5-24 hr. After the reaction, the object product can be obtained by filtration, extraction, washing, drying, solvent removal and the like by a general method and, where necessary, purification by silica gel column chromatography, recrystallization and the like. For this reaction, a general phosphorylation reagent (phosphorus chloride and base, phosphoramidite and oxidant and the like) can also be reacted by a known method. For example, when phosphoramidite and an oxidant are used, reaction is performed in a halogen solvent such as dichloromethane and the like, an ether solvent such as tetrahydrofuran and the like, a polar solvent such as acetonitrile and the like or a mixed solvent thereof, using phosphoramidite such as di-t-butyl diisopropylphosphoramidite and the like under ice-cooling-50° C. for about 10 min-5 hr. 1H-Tetrazole and the like can be added as a reaction promoter for this reaction. For an oxidization reaction of phosphorus successively performed after the phosphorylation, an organic peroxide such as m-chloroperbenzoic acid, t-butyl hydroperoxide and the like or an inorganic peroxide such as hydrogen peroxide and the like can be used. The reaction is performed under ice-cooling-50° C. for about 3 min-1 hr. After the reaction, the object product can be obtained by extraction, washing, drying, solvent removal and the like by a general method and, where necessary, purification by silica gel column chromatography, recrystallization and the like.

In the third step, the compound of the present invention (I-10a) is prepared from a phosphorylated form (XIX-3). This step can be performed by general deprotection. Specifically, the step can be performed by hydrogenolysis using an acid such as hydrochloric acid, trifluoroacetic acid and the like, a Lewis acid such as trimethylsilyl bromide and the like. When hydrogenolysis is used for this reaction, this step is performed, for example, in an alcohol solvent such as methanol and the like using a catalyst such as palladium carbon and the like udder a hydrogen atmosphere. The reaction conditions are, for example, room temperature-60° C. for about 1-24 hr. The object product can be obtained by filtration, concentration and the like of the reaction mixture by a general method and, where necessary, purification by silica gel column chromatography, recrystallization and the like. The reaction conditions when an acid is used for this reaction are, for example, an alcohol solvent such as ethanol and the like or a mixed solvent thereof with water at room temperature-100° C. for about 30 min-12 hr. After the reaction, the object product can be obtained by adding the reaction mixture to water and collecting the precipitated object product by filtration, or extraction, washing, drying, solvent removal and the like and, where necessary, purification by silica gel column chromatography, recrystallization and the like. Of the compounds of the present invention, a compound of the formula (I) wherein R is $P(=O)(OH)_2$, and one of $R_3$ and $R_4$ is alkyl having a carbon number of 1 to 4 is also synthesized by a method similar to the above-mentioned scheme (XIX). A compound of the formula (I) wherein R is $P(=O)(OH)_2$, and both $R_3$ and $R_4$ are alkyl having a carbon number of 1 to 4 is synthesized by a method similar to scheme (XIX), without using amino-protecting group $R^d$ used in scheme (XIX).

The compound of the present invention can be converted to an acid addition salt as necessary by treatment with an acid in a suitable solvent (water, alcohol, ether and the like). In addition, the obtained compound of the present invention can be converted to a hydrate or solvate by treatment with water, water-containing solvent or other solvent (for example, alcohol etc.).

The compound of the present invention is useful for the treatment or prophylaxis of autoimmune diseases (e.g., rheumatoid arthritis, multiple sclerosis, encephalomyelitis, systemic lupus erythematosus, lupus nephritis, nephrosis syndrome, psoriasis, Type I diabetes mellitus etc.); prophylaxis or suppression of resistance or acute rejection or chronic rejection of transplantation of organ or tissue (e.g., including transplantation and heterogenous transplantation of heart, kidney, liver, lung, bone marrow, cornea, pancreas, small intestine, extremity, muscle, nerve, fatty marrow, duodenum, skin, islet cells of the pancreas and the like) in mammals such as human, dog, cat, bovine, horse, swine, monkey, mouse and the like; graft-versus-host (GvH) disease due to bone marrow transplantation; and the treatment or prophylaxis of allergic diseases (e.g., atopic dermatitis, allergic rhinitis, asthma etc.).

In the present invention, the "prophylaxis" means the act of administering the compound of the present invention or a pharmaceutical composition containing the compound to an individual who has not developed a disease or symptom. In addition, the "treatment" means the act of administering the compound of the present invention or a pharmaceutical composition containing the compound to an individual who has already developed a disease or disorder or symptom. Accordingly, the act of administration to an individual who has already developed a disease or disorder or symptom for the prevention of aggravation of the symptom and the like, prevention of attacks or prevention of recurrence is one embodiment of the "treatment".

When the compound of the present invention is used as a pharmaceutical agent, the compound of the present invention is mixed with a pharmaceutically acceptable carrier (excipient, binder, disintegrant, corrigent, flavor, emulsifier, diluent, solubilizer and the like) and the obtained pharmaceutical composition or preparation (oral preparation, injection and the like) can be orally or parenterally administered. A pharmaceutical composition can be prepared according to a general method.

In the present specification, parenteral includes subcutaneous injection, intravenous injection, intramuscular injection, intraperitoneal injection, drip method or topical administration (transdermal administration, transocular administration, transpulmonic-bronchial administration, transnasal administration, transrectal administration and the like) and the like.

The content of the compound of the present invention that can be combined with a carrier can be varied depending on the individual to be treated and particular dosage form. However, the particular dose of particular patients is determined depending on various factors including age, body weight, general health conditions, sex, diet, administration time, administration method, clearance rate and severity of the particular disease under treatment.

The dose of the compound of the present invention is determined in consideration of the age, body weight, general health conditions, sex, diet, administration time, administration method, clearance rate and severity of the disease of patients under treatment, as well as other factors. The compound of the present invention does not affect the heart rate and can be used safely. Its daily dose varies depending on the condition and body weight of patients, the kind of compound, administration route and the like. For example, for parenteral administration, it is administered subcutaneously, intravenously, intramuscularly, transdermally, transocularly, transpulmonically or bronchially, transnasally or rectally at about 0.01-50 mg/patient/day, and for oral administration, it is administered at about 0.01-150 mg/patient/day.

EXAMPLES

The present invention is explained in more detail in the following by referring to Examples, which are not to be construed as limitative.

Reference Example 1

(2,2-Dimethyl-5-formyl-1,3-dioxan-5-yl)carbamic Acid t-butyl Ester (1-1) Synthesis of (2,2-dimethyl-5-hydroxymethyl-1, 3-dioxan-5-yl)carbamic Acid t-butyl Ester (Reference Example Compound 1-1)

Tris(hydroxymethyl)aminomethane hydrochloride (2 g) was dissolved in N,N-dimethylformamide (50 ml), 2,2-dimethoxypropane (7.8 ml) and p-toluenesulfonic acid monohydrate (229 mg) were added, and the mixture was stirred at room temperature for 15 hr. To the mixed solution were added triethylamine (9.5 ml), methanol (20 ml) and di-t-butyl dicarbonate (4.17 g), and the mixture was stirred at room temperature for 12 hr. Water was added to the reaction mixture, and the mixture was extracted with ethyl acetate, washed with water and saturated brine and dried over anhydrous magnesium sulfate. The solvent was evaporated under reduced pressure to give the object product (3.11 g) as a colorless solid.
$^1$H-NMR (CDCl$_3$) δ (ppm): 1.44 (3H, s), 1.46 (12H, s), 3.73 (2H, d, J=6.4 Hz), 3.80 (2H, d, J=11.6 Hz), 3.84 (2H, d, J=11.6 Hz), 4.20 (1H, brs), 5.32 (1H, brs).

(1-2) Synthesis of (2,2-dimethyl-5-formyl-1,3-dioxan-5-yl)carbamic Acid t-butyl Ester (Reference Example compound 1-2)

The compound (2.96 g) of Reference Example compound 1-1 was dissolved in dimethyl sulfoxide (50 ml), triethylamine (11 ml) and sulfur trioxide-pyridine complex (5.4 g) were added, and the mixture was stirred at room temperature for 2 hr. Water was added to the reaction mixture, and the mixture was extracted with ethyl acetate, washed with water and saturated brine, and dried over anhydrous magnesium sulfate. The solvent was evaporated under reduced pressure and the residue was washed with diethyl ether to give the object product (2.4 g) as a colorless powder.
$^1$H-NMR (CDCl$_3$) δ (ppm): 1.46 (15H, s), 3.96 (2H, d, J=11.7 Hz), 4.07 (2H, d, J=11.7 Hz), 5.54 (1H, brs), 9.64 (1H, s).

Reference Example 2

(4-Benzyloxy-3-trifluoromethylbenzyl)triphenylphosphonium Chloride (2-1) Synthesis of 4-fluoro-3-trifluoromethylbenzoic Acid Benzyl Ester (Reference Example Compound 2-1)

4-Fluoro-3-trifluoromethylbenzoic acid (100 g) was dissolved in N,N-dimethylformamide (400 ml), potassium carbonate (199 g) and benzyl bromide (84.0 g) were added under ice-cooling, and the mixture was stirred for 20 min under ice-cooling and at room temperature for 2 hr. Water was added to the reaction mixture, and the mixture was extracted with ethyl acetate, washed with water and saturated brine, and dried over anhydrous magnesium sulfate. The solvent was evaporated under reduced pressure to give the object product (144 g) as a pale-yellow oil.
$^1$H-NMR (CDCl$_3$) δ (ppm): 5.38 (2H, s), 7.27 (1H, t, J=9.3 Hz), 7.35-7.46 (5H, m), 8.27 (1H, m), 8.35 (1H, dd, J=6.8, 1.8 Hz).

(2-2) Synthesis of 4-benzyloxy-3-trifluoromethylbenzoic Acid Benzyl Ester (Reference Example Compound 2-2)

Benzyl alcohol (52.0 g) was dissolved in N,N-dimethylformamide (300 ml), sodium hydride (60%, 20.2 g) was added under ice-cooling, and the mixture was stirred for 50 min under ice-cooling. A solution of Reference Example compound 2-1 (144 g) in N,N-dimethylformamide (400 ml) was added, and the mixture was stirred for 2 hr under ice-cooling. Water was added to the reaction mixture, and the mixture was extracted with ethyl acetate, washed with water and saturated brine, and dried over anhydrous magnesium sulfate. The solvent was evaporated under reduced pressure to give the object product (198 g, a mixture with mineral oil contained in sodium hydride) as a pale-yellow solid.
$^1$H-NMR (CDCl$_3$) δ (ppm): 5.26 (2H, s), 5.35 (2H, s), 7.06 (1H, d, J=8.8 Hz), 7.31-7.45 (10H, m), 8.18 (1H, dd, J=8.8, 2.0 Hz), 8.32 (1H, d, J=2.0 Hz).

(2-3) Synthesis of 4-benzyloxy-3-trifluoromethylbenzyl Alcohol (Reference Example Compound 2-3)

The compound (198 g) obtained in Reference Example compound 2-2 was dissolved in tetrahydrofuran (1000 ml), lithium borohydride (15.7 g) was added, and the mixture was heated under reflux for 3 hr. After once cooling, lithium borohydride (4.0 g) was added, and the mixture was further heated under reflux for 3 hr. The reaction mixture was ice-cooled, water (500 ml) was added to quench the reaction. The reaction mixture was added to water, and the mixture was neutralized with concentrated hydrochloric acid. The mixture was extracted with ethyl acetate, washed with water and saturated brine, and dried over anhydrous magnesium sulfate. The solvent was evaporated under reduced pressure. The impurities (mineral oil and benzyl alcohol) were removed from the obtained mixture by heating under reduced pressure at 135° C. using a vacuum pump. The obtained residue was crystallized from hexane to give the object product (99.2 g) as a white powder.
$^1$H-NMR (CDCl$_3$) δ (ppm): 1.62 (1H, t, J=5.7 Hz), 4.66 (2H, d, J=5.7 Hz), 5.20 (2H, s), 7.02 (1H, d, J=8.5 Hz), 7.30-7.33 (1H, m), 7.38 (2H, t, J=7.4 Hz), 7.44 (2H, d, J=7.4 Hz), 7.46 (1H, dd, J=8.5, 2.0 Hz), 7.61 (1H, d, J=2.0 Hz).

(2-4) Synthesis of 4-benzyloxy-3-trifluoromethylbenzyl Chloride (Reference Example Compound 2-4)

The compound (99.2 g) obtained in Reference Example compound 2-3 was dissolved in methylene chloride (900 ml), triphenylphosphine (102 g) and N-chlorosuccinimide (49.3 g) were added under ice-cooling, and the mixture was stirred under ice-cooling for 40 min, and further at room temperature for 1 hr. The reaction mixture was washed with water and saturated brine, and dried over anhydrous magnesium sulfate. The solvent was evaporated under reduced pressure. Ether (500 ml) was added, triphenylphosphine oxide precipitated first was removed and the residue was purified by silica gel column chromatography (hexane:ethyl acetate=99:1-4:1) to give the object product (99.5 g) as a colorless oil.

$^1$H-NMR (CDCl$_3$) δ (ppm): 4.56 (2H, s), 5.20 (2H, s), 7.01 (1H, d, J=8.6 Hz), 7.31-7.34 (1H, m), 7.39 (2H, t, J=7.4 Hz), 7.43 (2H, d, J=7.4 Hz), 7.48 (1H, dd, J=8.6, 2.0 Hz), 7.62 (1H, d, J=2.0 Hz).

(2-5) (4-Benzyloxy-3-trifluoromethylbenzyl)triphenylphosphonium Chloride (Reference Example Compound 2-5)

The compound (99.0 g) obtained in Reference Example compound 2-4 was dissolved in toluene (450 ml), triphenylphosphine (90.7 g) was added, and the mixture was refluxed for 8 hr. After cooling, the crystals in the reaction mixture were collected by filtration, and washed with ether to give the object compound (132 g) as a white powder. The mother liquor was concentrated, toluene (200 ml) was added, and the above-mentioned operation was performed to give the object compound (31.0 g). Further, the mother liquor was treated in the same manner to give the object compound (12.3 g). The total yield was 176 g.

MS-(ESI) m/z: 527[M$^+$]

$^1$H-NMR (DMSO-d$_6$) δ (ppm): 5.17 (2H, d, J=15.1 Hz), 5.23 (2H, s), 7.02-7.04 (1H, m), 7.26-7.30 (2H, m), 7.31-7.37 (1H, m), 7.38-7.42 (4H, m), 7.65-7.70 (6H, m), 7.72-7.78 (6H, m), 7.90-7.94 (3H, m).

Reference Example 3

5-Bromo-2-heptyloxybenzonitrile (3-1) Synthesis of 5-bromo-2-heptyloxybenzonitrile (Reference Example Compound 3-1)

1-Heptanol (1.55 g) was dissolved in N,N-dimethylformamide (24 ml), and sodium hydride (0.321 g) was added at room temperature. The mixture was stirred for 1 hr, 5-bromo-2-fluorobenzonitrile (2.43 g) was added, and the mixture was further stirred for 50 min. The reaction mixture was poured into water, extracted with ethyl acetate, washed with water and saturated brine, and dried over anhydrous sodium sulfate. The solvent was evaporated under reduced pressure. To consume the starting material, 5-bromo-2-fluorobenzonitrile, the reaction was performed again under the same conditions, and the residue was purified by silica gel column chromatography (hexane:ethyl acetate=50:1-5:1) to give the object product (3.10 g) as a colorless oil.

$^1$H-NMR (CDCl$_3$) δ (ppm): 0.89 (3H, t, J=6.4 Hz), 1.24-1.35 (6H, m), 1.48 (2H, quint, J=7.2 Hz), 1.84 (2H, quint, J=6.4 Hz), 4.04 (2H, t, J=6.4 Hz), 6.84 (1H, d, J=8.8 Hz), 7.59 (1H, dd, J=8.8, 2.4 Hz), 7.65 (1H, d, J=2.4 Hz).

Example 1

2-Amino-2-[2-(4-heptyloxy-3-trifluoromethylphenyl)ethyl]propane-1,3-diol Hydrochloride (1-1) Synthesis of {2,2-dimethyl-5-[2-(4-hydroxy-3-trifluoromethylphenyl)ethyl]-1,3-dioxan-5-yl}carbamic Acid t-butyl Ester (Compound 1-1)

Reference Example compound 2-5 (70.3 g) was dissolved in tetrahydrofuran (500 ml), potassium t-butoxide (13.0 g) was added, and the mixture was stirred for 1 hr. To the mixed solution was added dropwise a solution of the compound (15.0 g) of Reference Example 1 in tetrahydrofuran (100 ml) under ice-cooling, and the mixture was stirred for 2 hr under ice-cooling. Water was added to the reaction mixture, and the mixture was extracted with ethyl acetate, washed with water and saturated brine, and dried over anhydrous magnesium sulfate. The solvent was evaporated under reduced pressure. The residue was purified by silica gel column chromatography (hexane:ethyl acetate=3:1) to give a pale-yellow oil (31.0 g). The geometric isomer ratio of the obtained compound was (E:Z=1:6).

The pale-yellow oil was dissolved in ethyl acetate (200 ml), 10% palladium carbon (3.00 g) was added, and the mixture was stirred at room temperature for 7 hr under a hydrogen atmosphere. The inside of the reaction container was substituted with nitrogen, and the solution was filtrated, and the filtrate was concentrated. The residue was washed with diisopropyl ether to give the object product (22.3 g) as a colorless powder.

$^1$H-NMR (CDCl$_3$) δ (ppm): 1.43 (3H, s), 1.44 (3H, s), 1.47 (9H, s), 1.91-1.98 (2H, m), 2.50-2.56 (2H, m), 3.69 (2H, d, J=11.6 Hz), 3.89 (2H, d, J=11.6 Hz), 5.02 (1H, brs), 5.52 (1H, brs), 6.86 (1H, d, J=8.2 Hz), 7.22 (1H, dd, J=8.2, 1.7 Hz), 7.29 (1H, d, J=1.7 Hz).

(1-2) Synthesis of {2,2-dimethyl-5-[2-(4-heptyloxy-3-trifluoromethylphenyl)ethyl]-1,3-dioxan-5-yl}carbamic Acid t-butyl Ester (Compound 1-2)

Compound 1-1 (510 mg) was dissolved in N,N-dimethylformamide (10 ml), potassium carbonate (506 mg) and n-heptyl bromide (0.235 ml) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (640 mg) as a colorless oil.

$^1$H-NMR (CDCl$_3$) δ (ppm): 0.89 (3H, t, J=6.8 Hz), 1.30-1.37 (6H, m), 1.42-1.50 (2H, m), 1.42 (3H, s), 1.44 (3H, s), 1.47 (9H, s), 1.76-1.82 (2H, m), 1.91-1.98 (2H, m), 2.50-2.57 (2H, m), 3.69 (2H, d, J=11.6 Hz), 3.89 (2H, d, J=11.6 Hz), 4.00 (2H, t, J=6.4 Hz), 4.98 (1H, brs), 6.88 (1H, d, J=8.5 Hz), 7.26-7.29 (1H, m), 7.35 (1H, d, J=1.5 Hz).

(1-3) Synthesis of 2-amino-2-[2-(4-heptyloxy-3-trifluoromethylphenyl)ethyl]propane-1,3-diol Hydrochloride (Compound 1-3)

Compound 1-2 (640 mg) was dissolved in ethanol (15 ml), concentrated hydrochloric acid (3 ml) was added, and the mixture was stirred at 80° C. for 2 hr. The reaction mixture was concentrated, and the residue was washed with diethyl ether to give the object product (492 mg) as white powder.

MS (ESI) m/z: 378[M+H]

$^1$H-NMR (DMSO-d$_6$) δ (ppm): 0.86 (3H, t, J=6.8 Hz), 1.24-1.39 (6H, m), 1.39-1.46 (2H, m), 1.68-1.78 (4H, m), 2.55-2.62 (2H, m), 3.51 (4H, d, J=5.1 Hz), 4.06 (2H, t, J=6.2 Hz), 5.38 (2H, t, J=5.1 Hz), 7.18 (1H, d, J=8.4 Hz), 7.42-7.45 (2H, m), 7.76 (3H, brs).

Example 2

2-Amino-4-(4-heptyloxy-3-trifluoromethylphenyl)-2-(phosphoryloxymethyl)butanol

(2-1) Synthesis of [1,1-bis(hydroxymethyl)-3-(4-heptyloxy-3-trifluoromethylphenyl)propyl]carbamic Acid Benzyl Ester (Compound 2-1)

A two layer mixture of compound 1-3 (290 mg), ethyl acetate (5 ml), saturated aqueous sodium hydrogencarbonate solution (5 ml) and benzyloxycarbonyl chloride (0.129 ml) was stirred at room temperature for 5 hr. The ethyl acetate layer was separated, and the aqueous layer was extracted with ethyl acetate. The separated ethyl acetate layer and the ethyl acetate layer obtained by the extraction were combined, washed with saturated brine, and dried over anhydrous magnesium sulfate. The solvent was evaporated under reduced pressure and the residue was purified by silica gel column chromatography (hexane:ethyl acetate=1:3) to give the object product (230 mg) as a colorless oil.

$^1$H-NMR (CDCl$_3$) δ (ppm): 0.89 (3H, t, J=6.8 Hz), 1.26-1.39 (6H, m), 1.41-1.51 (2H, m), 1.75-1.83 (2H, m), 1.84-1.91 (2H, m), 2.45-2.60 (2H, m), 3.03 (2H, brs), 3.66-3.71 (2H, m), 3.88-3.93 (2H, m), 3.99 (2H, t, J=6.3 Hz), 5.09 (2H, s), 5.31 (1H, brs), 6.87 (1H, d, J=8.5 Hz), 7.22-7.26 (2H, m), 7.31-7.35 (5H, m).

(2-2) Synthesis of [1-(dibenzyl)phosphoryloxymethyl-1-hydroxymethyl-3-(4-heptyloxy-3-trifluoromethylphenyl)propyl]carbamic Acid Benzyl Ester (Compound 2-2)

Compound 2-1 (230 mg), pyrophosphoric acid tetrabenzyl ester (485 mg), silver oxide (208 mg) and tetra-n-hexyl ammonium iodide (433 mg) were added to a mixed solvent of toluene (4 ml), dichloromethane (4 ml) and perfluorohexane (4 ml), and the mixture was stirred at room temperature for 15 hr. Insoluble material was filtered off and the solvent was evaporated under reduced pressure. The residue was purified by preparative HPLC to give the object product (210 mg) as a colorless oil.

MS (ESI) m/z: 772[M+H]

$^1$H-NMR (CD$_3$OD) δ (ppm): 0.91 (3H, t, J=6.4 Hz), 1.29-1.44 (6H, m), 1.45-1.53 (2H, m), 1.74-1.84 (3H, m), 1.85-2.02 (1H, m), 2.49-2.59 (2H, m), 3.59 (1H, d, J=11.2 Hz), 3.69 (1H, d, J=11.2 Hz), 4.02 (2H, t, J=6.2 Hz), 4.15-4.20 (1H, m), 4.26-4.31 (1H, m), 4.99-5.03 (6H, m), 6.98 (1H, d, J=8.5 Hz), 7.22-7.34 (17H, m).

(2-3) Synthesis of 2-amino-4-(4-heptyloxy-3-trifluoromethylphenyl)-2-(phosphoryloxymethyl)butanol (Compound 2-3)

Compound 2-2 (210 mg) was dissolved in methanol (10 ml), 10% palladium carbon (100 mg) was added, and the reaction container was displaced with hydrogen. The mixture was stirred at room temperature for 4 hr, the reaction container was displaced with nitrogen, and the reaction mixture was filtrated. The filtrate was concentrated to give the object product (33.0 mg) as a white powder.

MS (ESI) m/z: 458[M+H]

$^1$H-NMR (CD$_3$OD) δ (ppm): 0.91 (3H, t, J=6.4 Hz), 1.29-1.44 (6H, m), 1.45-1.53 (2H, m), 1.74-1.82 (2H, m), 1.90-1.99 (2H, m), 2.60-2.75 (2H, m), 3.70 (2H, brs), 3.93-3.99 (2H, m), 4.04 (2H, t, J=6.2 Hz), 7.07 (1H, d, J=8.3 Hz), 7.42-7.46 (2H, m).

Example 3

(S)-2-Amino-4-(4-heptyloxy-3-trifluoromethylphenyl)-2-(phosphoryloxymethyl)butanol

(3-1) Synthesis of N-[1,1-bis(hydroxymethyl)-3-(4-heptyloxy-3-trifluoromethylphenyl)propyl]acetamide (Compound 3-1)

To a mixture of compound 1-1 (3.00 g), chloroform (300 ml) and saturated aqueous sodium hydrogencarbonate solution (300 ml) was added acetic anhydride (1.03 ml) 8 times at 10 min intervals with stirring. The mixture was stirred for 1.5 hr from the final addition of acetic anhydride. The organic layer was separated, washed with saturated brine, and dried over anhydrous magnesium sulfate. The solvent was evaporated under reduced pressure to give the object product (2.96 g) as a white solid.

$^1$H-NMR (CDCl$_3$) δ (ppm): 0.89 (3H, t, J=6.7 Hz), 1.30-1.38 (6H, m), 1.46 (2H, quint, J=7.3 Hz), 1.80 (2H, quint, J=6.9 Hz), 1.91-1.96 (2H, m), 2.02 (3H, s), 2.59-2.63 (2H, m), 3.59 (2H, brs), 3.63 (2H, d, J=11.8 Hz), 3.85 (2H, d, J=10.4 Hz), 4.00 (2H, t, J=6.5 Hz), 5.92 (1H, brs), 6.90 (1H, d, J=8.6 Hz), 7.29 (1H, dd, J=2.1, 8.6 Hz), 7.36 (1H, d, J=2.1 Hz).

(3-2) Synthesis of [2-acetamido-4-(4-heptyloxy-3-trifluoromethylphenyl)-2-hydroxymethyl]butyl Acetate (Compound 3-2)

To a solution of compound 3-1 (2.96 g) in dichloromethane (70 ml) were added pyridine (0.742 ml) and acetic anhydride (0.734 ml) under ice-cooling, and the mixture was stirred for 7 hr under ice-cooling. Pyridine (0.371 ml) and acetic anhydride (0.367 ml) were added, and the mixture was stirred for 1 hr under ice-cooling, and further at room temperature for 14 hr. The reaction mixture was diluted with dichloromethane (200 ml), washed successively with 0.1M hydrochloric acid, saturated aqueous sodium hydrogencarbonate solution and saturated brine, and dried over anhydrous magnesium sulfate. The solvent was evaporated under reduced pressure and the residue was purified by silica gel chromatography to give the object product (1.55 g) as a colorless oil.

$^1$H-NMR (CDCl$_3$) δ (ppm): 0.89 (3H, t, J=6.7 Hz), 1.28-1.38 (6H, m), 1.46 (2H, quint, J=7.3 Hz), 1.79 (2H, quint, J=7.0 Hz), 1.84-1.92 (1H, m), 2.01 (3H, s), 2.13 (3H, s), 2.13-2.22 (1H, m), 2.53 (1H, dt, J=5.1, 13.1 Hz), 2.66 (1H, dt, J=4.9, 13.2 Hz), 3.72-3.75 (2H, m), 4.00 (2H, t, J=6.4 Hz), 4.16 (1H, d, J=11.5 Hz), 4.38 (1H, d, J=11.5 Hz), 4.40 (1H, t, J=6.8 Hz), 5.82 (1H, brs), 6.90 (1H, d, J=8.6 Hz), 7.28 (1H, dd, J=1.7, 8.6 Hz), 7.35 (1H, d, J=1.7 Hz).

(3-3) Synthesis of 2-acetamido-2-di(tert-butyl)phosphoryloxymethyl-4-(4-heptyloxy-3-trifluoromethylphenyl)butyl Acetate (Compound 3-3)

To a solution of compound 3-2 (1.55 g) and 1H-tetrazole (0.282 g) in dichloromethane (50 ml) and acetonitrile (50 ml) was added di-t-butyl diisopropylphosphoramidite (1.27 ml) under ice-cooling, and the mixture was stirred for 1.5 hr under ice-cooling. 1H-Tetrazole (0.282 g) and di-t-butyl diisopropylphosphoramidite (1.27 ml) were added, and the mixture was further stirred for 2 hr. To the reaction mixture was added m-chloroperbenzoic acid (25% water-containing, 0.994 g) under ice-cooling, and the mixture was stirred for 20 min. m-Chloroperbenzoic acid (25% water-containing, 0.994 g) was further added, and the mixture was stirred for 10 min. The reaction mixture was diluted with dichloromethane (100 ml), washed successively with saturated aqueous sodium hydrogencarbonate solution and saturated brine, and dried over anhydrous magnesium sulfate. The solvent was evaporated under reduced pressure and the residue was purified by silica gel chromatography to give the object product (1.71 g) as a colorless oil.

$^1$H-NMR (CDCl$_3$) δ (ppm): 0.89 (3H, t, J=6.8 Hz), 1.30-1.38 (6H, m), 1.42-1.50 (2H, m), 1.50 (9H, s), 1.51 (9H, s), 1.79 (2H, quint, J=7.0 Hz), 1.98 (3H, s), 2.02-2.10 (1H, m), 2.07 (3H, s), 2.32-2.40 (1H, m), 2.50-2.65 (2H, m), 4.00 (2H, t, J=6.3 Hz), 4.09 (2H, d, J=8.4 Hz), 4.37 (1H, d, J=11.1 Hz), 4.47 (1H, t, J=11.1 Hz), 6.67 (1H, brs), 6.88 (1H, d, J=8.6 Hz), 7.28 (1H, dd, J=1.5, 8.6 Hz), 7.35 (1H, d, J=1.5 Hz).

(3-4) Synthesis of (S)-2-acetamido-2-di(tert-butyl)phosphoryloxymethyl-4-(4-heptyloxy-3-trifluoromethylphenyl)butyl Acetate (Compound 3-4-1) and (R)-2-acetamido-2-di(tert-butyl)phosphoryloxymethyl-4-(4-heptyloxy-3-trifluoromethylphenyl)butyl Acetate (Compound 3-4-2)

Compound 3-3 (1.47 g) was separated by HPLC using CHIRALPAK (registered trade mark) AD-H (hexane/ethanol/diisopropylamine) to give both enantiomers as colorless oil. The first peak with short retention time was S form (0.55 g, compound 3-4-1), and the second peak with long retention time was R form (0.65 g, compound 3-4-2).

(3-5) Synthesis of (S)-2-amino-4-(4-heptyloxy-3-trifluoromethylphenyl)-2-(phosphoryloxymethyl)butanol (Compound 3-5)

Compound 3-4-1 (0.55 g) was dissolved in ethanol (15 ml) and hydrochloric acid (3 ml), and the mixture was stirred at 50° C. for 3 hr. The reaction mixture was poured into water (150 ml), and the mixture was stood for 7 hr. The precipitated solid was collected by filtration, washed with water and dried to give the object product (0.33 g) as a white powder.

MS (ESI) m/z: 458[M+H]

$^1$H-NMR (CD$_3$OD) δ (ppm): 0.91 (3H, t, J=6.8 Hz), 1.29-1.41 (6H, m), 1.45-1.53 (2H, m), 1.74-1.81 (2H, m), 1.89-1.99 (2H, m), 2.60-2.75 (2H, m), 3.70 (2H, brs), 3.94-4.02 (2H, m), 4.04 (2H, t, J=6.2 Hz), 7.07 (1H, d, J=8.4 Hz), 7.42-7.46 (2H, m).

Example 4

(4-1) Synthesis of (R)-2-amino-4-(4-heptyloxy-3-trifluoromethylphenyl)-2-(phosphoryloxymethyl)butanol (Compound 4-1)

Compound 3-4-2 (0.65 g) was dissolved in ethanol (15 ml) and hydrochloric acid (3 ml), and the mixture was stirred at 50° C. for 2.5 hr. The reaction mixture was poured into water (150 ml), and the mixture was stood for 4 hr. The precipitated solid was collected by filtration, washed with water and dried to give the object product (0.35 g) as a white powder.

MS (ESI) m/z: 458[M+H]

$^1$H-NMR (CD$_3$OD) δ (ppm): 0.91 (3H, t, J=6.8 Hz), 1.29-1.41 (6H, m), 1.45-1.53 (2H, m), 1.74-1.81 (2H, m), 1.90-2.01 (2H, m), 2.61-2.74 (2H, m), 3.69 (1H, d, J=12.0 Hz), 3.70 (1H, d, J=12.0 Hz), 3.93-4.02 (2H, m), 4.04 (2H, t, J=6.2 Hz), 7.07 (1H, d, J=8.4 Hz), 7.42-7.46 (2H, m).

Example 5

2-Amino-2-[2-(3-cyano-4-heptyloxyphenyl)ethyl]propane-1,3-diol Hydrochloride

(5-1) Synthesis of {2,2-dimethyl-5-[2-(3-cyano-4-heptyloxyphenyl)ethyl]-1,3-dioxan-5-yl}carbamic Acid t-butyl Ester (Compound 5-1)

Reference Example compound 3-1 (836 mg), (2,2-dimethyl-5-ethynyl-1,3-dioxan-5-yl)carbamic acid t-butyl ester (482 mg) synthesized by a known method (for example, Tetrahedron vol. 57 (2001) 6531-6538), 2-dicyclohexylphosphino-2',4',6'-triisopropylbiphenyl (54 mg), bis(acetonitrile)palladium(II) dichloride (10 mg), cesium carbonate (919 mg) were stirred in a mixed solvent of acetonitrile (15 ml) and tetrahydrofuran (2 ml) at 70° C. for 4 hr. Water was added to the reaction mixture; and the mixture was extracted with ethyl acetate, washed with saturated brine, and dried over anhydrous sodium sulfate. The solvent was evaporated under reduced pressure. The residue was purified by silica gel column chromatography (hexane:ethyl acetate=4:1) to give [2,2-dimethyl-5-(3-cyano-4-heptyloxyphenyl)ethynyl-1,3-dioxan-5-yl]carbamic acid t-butyl ester as a brown oil (493 mg). The intermediate was dissolved in ethyl acetate (5 ml), Lindlar catalyst (80 mg) was added, and the mixture was stirred overnight under a hydrogen atmosphere. The reaction mixture was filtered and concentrated and the residue was dissolved in ethanol (4 ml), 10% palladium carbon (ethylenediamine poisoning, 40 mg) was added, and the mixture was stirred at room temperature for 2.5 hr under a hydrogen atmosphere. The solution was filtered, and the filtrate was concentrated to give the object product (182 mg).

$^1$H-NMR (CDCl$_3$) δ (ppm): 0.89 (3H, t, J=7.2 Hz), 1.26-1.31 (6H, m), 1.35-1.37 (2H, m), 1.43 (3H, s), 1.44 (3H, s), 1.47 (9H, s), 1.78-1.86 (2H, m), 1.91-1.96 (2H, m), 2.49-2.53 (2H, m), 3.68 (2H, d, J=11.6 Hz), 3.87 (2H, d, J=11.6 Hz), 4.02 (2H, t, J=6.4 Hz), 4.99 (1H, brs), 6.85 (1H, d, J=8.4 Hz), 7.32 (1H, dd, J=8.4, 1.6 Hz), 7.33 (1H, m).

(5-2) Synthesis of 2-amino-2-[2-(3-cyano-4-heptyloxyphenyl)ethyl]propane-1,3-diol Hydrochloride (Compound 5-2)

Compound 5-1 (255 mg) was dissolved in ethanol (2 ml), p-toluenesulfonic acid (19 mg) was added, and the mixture was stirred at room temperature for 4 hr. To the reaction mixture was added saturated aqueous sodium hydrogencarbonate, and the mixture was extracted with ethyl acetate, washed with saturated brine, and dried over anhydrous sodium sulfate. The solvent was evaporated under reduced pressure and the residue was purified by silica gel column chromatography (hexane:ethyl acetate=4:1) to give an oil. To the oil was added dioxane containing hydrogen chloride (4 mol/l), and the mixture was stirred at room temperature for 3 hr. The precipitate was collected by filtration and dried to give the object product (45 mg) as a white powder.

MS (ESI) m/z: 335[M+H]

$^1$H-NMR (DMSO-d$_6$) δ (ppm): 0.86 (3H, t, J=6.8 Hz), 1.26-1.37 (6H, m), 1.38-1.44 (2H, m), 1.69-1.77 (4H, m), 2.55-2.59 (2H, m), 3.50 (4H, d, J=4.4 Hz), 4.09 (2H, t, J=6.4 Hz), 5.38 (2H, t, J=4.4 Hz), 7.18 (1H, d, J=8.8 Hz), 7.49 (1H, dd, J=8.8, 2.0 Hz), 7.55 (1H, d, J=2.0 Hz), 7.82 (3H, brs).

Example 6

2-Amino-4-(3-cyano-4-heptyloxyphenyl)-2-(phosphoryloxymethyl)butanol

(6-1) Synthesis of [3-(3-cyano-4-heptyloxyphenyl)-1-(dibenzyl)phosphoryloxymethyl-1-hydroxymethylpropyl]carbamic t-butyl Ester (Compound 6-1)

Compound 5-1 (340 mg) was dissolved in ethanol (3 ml), p-toluenesulfonic acid monohydrate (0.025 g) was added, and the mixture was stirred at room temperature for 6 hr. Water was added to the reaction mixture, and the mixture was neutralized with saturated aqueous sodium hydrogencarbonate, extracted with ethyl acetate, washed with saturated brine, and dried over anhydrous sodium sulfate. The solvent was evaporated to give acetonide deprotected compound (300 mg) as a colorless oil. The colorless oil (205 mg) was taken and dissolved in a mixed solvent of dichloromethane (2 ml) and toluene (2 ml), perfluorohexane (2 ml), silver oxide (219 mg) and pyrophosphoric acid tetrabenzyl ester (508 mg) were added, and the mixture was stirred at room temperature. 5 min later, tetra-n-hexyl ammonium iodide (454 mg) was added, and the mixture was further stirred for 5 hr. Insoluble material was filtered off, and the solvent was evaporated. The residue was purified by silica gel chromatography and preparative HPLC to give the object product (81.0 mg) as a colorless oil.

$^1$H-NMR (CDCl$_3$) δ (ppm): 0.89 (3H, t, J=6.4 Hz), 1.31-1.36 (6H, m), 1.43 (9H, s), 1.64-1.71 (2H, m), 1.79-1.86 (2H, m), 1.99-2.06 (2H, m), 2.39-2.49 (2H, m), 3.50-3.55 (2H, m), 4.02 (2H, t, J=6.4 Hz), 4.10 (1H, d, J=7.2 Hz), 4.13 (1H, d, J=7.2 Hz), 5.00 (1H, s), 5.03-5.09 (4H, m), 6.82 (1H, d, J=8.4 Hz), 7.26-7.27 (2H, m), 7.32-7.34 (10H, m).

(6-2) Synthesis of 2-amino-4-(3-cyano-4-heptyloxyphenyl)-2-(phosphoryloxymethyl)butanol (Compound 6-2)

Compound 6-1 (81.0 mg) was dissolved in acetonitrile (2 ml), sodium iodide (140 mg) and chlorotrimethylsilane (0.12 ml) were added, and the mixture was stirred at room temperature for 4.5 hr. Water and ethyl acetate were added, and the mixture was ultrasonicated. The resulting solid was collected by filtration. The solid was washed with water and ethyl acetate, and dried to give the object product (35.0 mg) as a pale-yellow powder.

MS (ESI) m/z: 415[M+H]

$^1$H-NMR (CD$_3$OD) δ (ppm): 0.86 (3H, t, J=6.8 Hz), 1.32-1.39 (6H, m), 1.47-1.53 (2H, m), 1.79-1.83 (2H, m), 1.89-1.95 (2H, m), 2.63-2.67 (2H, m), 3.68 (2H, d, J=2.0 Hz), 3.96 (2H, t, J=6.4 Hz), 4.10 (2H, t, J=6.4 Hz), 7.08 (1H, d, J=9.2 Hz), 7.49-7.51 (2H, m).

Example 7

2-Amino-2-[2-(3-cyano-4-octyloxyphenyl)ethyl]propane-1,3-diol Hydrochloride (7-1) Synthesis of 5-bromo-2-octyloxybenzonitrile (Compound 7-1)

Octanol (0.834 g) was dissolved in N,N-dimethylformamide (10 ml), and sodium hydride (60%, 0.256 g) was added. After stirring for 30 min, 5-bromo-2-fluorobenzonitrile (0.640 g) was added, and the mixture was further stirred at 40-50° C. for 1 hr. The reaction mixture was poured into water, and the mixture was extracted with ethyl acetate, washed with water and saturated brine, and dried over anhydrous sodium sulfate. The solvent was evaporated under reduced pressure and the residue was purified by silica gel column chromatography to give the object product (1.042 g) as a colorless oil.

$^1$H-NMR (CDCl$_3$) δ (ppm): 0.88 (3H, t, J=6.8 Hz), 1.24-1.37 (8H, m), 1.44-1.51 (2H, m), 1.80-1.87 (2H, m), 4.04 (2H, t, J=6.4 Hz), 6.83 (1H, d, J=8.8 Hz), 7.59 (1H, dd, J=8.8, 2.4 Hz), 7.64 (1H, d, J=2.4 Hz).

(7-2) Synthesis of {2,2-dimethyl-5-[2-(3-cyano-4-octyloxyphenyl)ethyl]-1,3-dioxan-5-yl}carbamic Acid t-butyl Ester (Compound 7-2)

Compound 7-1 (0.636 g), (2,2-dimethyl-5-ethynyl-1,3-dioxan-5-yl)carbamic acid t-butyl ester (0.571 g), 2-dicyclohexylphosphino-2',4',6'-triisopropylbiphenyl (0.045 g), bis(acetonitrile)palladium(II) dichloride (0.008 g) and cesium carbonate (0.668 g) were stirred in acetonitrile (10 ml) at 70-80° C. for 2 hr. Water was added to the reaction mixture, and the mixture was extracted with ethyl acetate, washed with saturated brine, and dried over anhydrous sodium sulfate. The solvent was evaporated under reduced pressure. The residue was purified by silica gel column chromatography to give [2,2-dimethyl-5-(3-cyano-4-octyloxyphenylethynyl)-1,3-dioxan-5-yl]carbamic acid t-butyl ester as a brown oil. The oil was dissolved in ethyl acetate (6 ml), 10% palladium carbon (about 50% water containing, 0.080 g) was added, and the mixture was stirred at room temperature for 3.5 hr under a hydrogen atmosphere. The solution was filtrated, and the filtrate was concentrated to give the object product (0.610 g) as a pale-yellow powder.

$^1$H-NMR (CDCl$_3$) δ (ppm): 0.88 (3H, t, J=6.8 Hz), 1.27-1.34 (8H, m), 1.41-1.43 (2H, m), 1.42 (3H, s), 1.43 (3H, s), 1.46 (9H, s), 1.78-1.85 (2H, m), 1.92-1.96 (2H, m), 2.49-2.53 (2H, m), 3.67 (2H, d, J=11.6 Hz), 3.86 (2H, d, J=11.6 Hz), 4.02 (2H, t, J=6.4 Hz), 4.97 (1H, s), 6.84 (1H, d, J=8.8 Hz), 7.33 (1H, dd, J=8.8, 2.0 Hz), 7.34 (1H, d, J=2.0 Hz).

(7-3) Synthesis of 2-amino-2-[2-(3-cyano-4-octyloxyphenyl)ethyl]propane-1,3-diol Hydrochloride (Compound 7-3)

Compound 7-2 (0.610 g) was dissolved in a mixed solvent of ethanol (5 ml) and tetrahydrofuran (2 ml), p-toluenesulfonic acid monohydrate (0.043 g) was added, and the mixture was stirred at room temperature for 3.5 hr, and further at 50-60° C. for 2.5 hr. To the reaction mixture was added saturated aqueous sodium hydrogencarbonate, and the mixture was extracted with ethyl acetate, washed with saturated brine, and dried over anhydrous sodium sulfate. The solvent was evaporated under reduced pressure. The residue was purified by silica gel column chromatography to give acetal deprotected compound of Example (6-2) as an oil. To the obtained oil was added dioxane containing hydrogen chloride (4 mol/l, 2 ml), and the mixture was stirred at room temperature for 8 hr. The precipitate was collected by filtration and dried to give the object product (145 mg) as a white powder.

MS (ESI) m/z: 349[M+H]

$^1$H-NMR (DMSO-d$_6$) δ (ppm): 0.86 (3H, t, J=6.8 Hz), 1.26-1.35 (8H, m), 1.40-1.46 (2H, m), 1.69-1.76 (4H, m), 2.54-2.58 (2H, m), 3.49 (4H, d, J=4.4 Hz), 4.09 (2H, t, J=6.4 Hz), 5.39 (2H, brs), 7.18 (1H, d, J=8.8 Hz), 7.49 (1H, d, J=8.8 Hz), 7.54 (1H, s), 7.63 (3H, brs).

Example 8

2-Amino-4-(3-cyano-4-octyloxyphenyl)-2-(phosphoryloxymethyl)butanol (8-1) Synthesis of [3-(3-cyano-4-octyloxyphenyl)1-(dibenzyl)phosphoryloxymethyl-1-hydroxymethyl-propyl]carbamic Acid t-butyl Ester (Compound 8-1)

Compound 7-2 (208 mg) was dissolved in ethanol (2 ml), p-toluenesulfonic acid monohydrate (73.0 mg) was added, and the mixture was stirred at room temperature for 6.5 hr. Water was added to the reaction mixture, and the mixture was neutralized with saturated aqueous sodium hydrogencarbonate, extracted with ethyl acetate, washed with saturated brine, and dried over anhydrous sodium sulfate. The solvent was evaporated and the obtained residue was dissolved in a mixed solvent of dichloromethane (2 ml) and toluene (2 ml), perfluorohexane (2 ml), silver oxide (197 mg) and pyrophosphoric acid tetrabenzyl ester (459 mg) were added, and the mixture was stirred at room temperature. 5 min later, tetra-n-hexyl ammonium iodide (410 mg) was added, and the mixture was further stirred for 17 hr. Insoluble material was filtered off and the solvent was evaporated and purified by silica gel chromatography and preparative HPLC to give the object product (106 mg) as a colorless oil.

$^1$H-NMR (CDCl$_3$) δ (ppm): 0.88 (3H, t, J=6.8 Hz), 1.27-1.34 (6H, m), 1.43 (9H, s), 1.46-1.51 (2H, m), 1.78-1.86 (2H, m), 1.79-1.86 (2H, m), 2.00-2.06 (2H, m), 2.39-2.51 (2H, m), 3.47-3.56 (2H, m), 3.90-3.92 (1H, m), 3.97-4.06 (4H, m), 4.79 (1H, s), 5.03-5.07 (4H, m), 6.84 (1H, d, J=8.0 Hz), 7.26 (1H, d, J=8.0 Hz), 7.34-7.35 (11H, m).

(8-2) Synthesis of 2-amino-4-(3-cyano-4-octyloxyphenyl)-2-(phosphoryloxymethyl)butanol (Compound 8-2)

Compound 8-1 (104 mg) was dissolved in acetonitrile (2 ml), sodium iodide (110 mg) and chlorotrimethylsilane (80.0 mg) were added, and the mixture was stirred at room temperature for 3 hr. Water and ethyl acetate were added, and the mixture was ultrasonicated. The resulting solid was collected by filtration. The solid was washed with water and ethyl acetate, further washed with methanol, and dried to give the object product (26.0 mg) as a white powder.

MS (ESI) m/z: 429[M+H]

$^1$H-NMR (CD$_3$OD) δ (ppm): 0.89 (3H, t, J=6.8 Hz), 1.31-1.35 (8H, m), 1.50-1.52 (2H, m), 1.79-1.83 (2H, m), 1.89-1.92 (2H, m), 2.63-2.67 (2H, m), 3.63-3.67 (2H, m), 3.95-3.97 (2H, m), 4.09 (2H, t, J=6.4 Hz), 7.07 (1H, d, J=9.2 Hz), 7.49-7.50 (2H, m).

Example 9

2-Amino-2-[2-(4-octyloxy-3-trifluoromethylphenyl)ethyl]propane-1,3-diol Hydrochloride (9-1) Synthesis of 4'-methoxy-3'-trifluoromethylacetophenone (Compound 9-1)

To a solution of 4'-fluoro-3'-trifluoromethylacetophenone (25.0 g) in N,N-dimethylformamide (70 ml) was added sodium methoxide (7.21 g) under ice-cooling, and the mixture was stirred for 2 hr under ice-cooling and further at room temperature for 1 hr. The reaction mixture was added to water, and extracted with ethyl acetate. The organic layer was washed with saturated brine, and dried over anhydrous magnesium sulfate. The solvent was evaporated under reduced pressure to give the object product (24.3 g) as a brown solid.

$^1$H-NMR (CDCl$_3$) δ (ppm): 2.59 (3H, s), 3.99 (3H, s), 7.06 (1H, d, J=8.7 Hz), 8.14 (1H, dd, J=2.1, 8.7 Hz), 8.19 (1H, d, J=2.1 Hz).

(9-2) Synthesis of 4'-methoxy-3'-trifluoromethylphenacyl Bromide (Compound 9-2)

To a solution of compound 9-1 (24.3 g) in acetic acid (120 ml) was added pyridinium tribromide (90%, 39.6 g) and the mixture was stirred at 50° C. for 1 hr. The reaction mixture was added to ice water, extracted with ethyl acetate, and the organic layer was washed successively with water, 1M aqueous sodium hydroxide solution, saturated ammonium chloride and saturated brine. The organic layer was dried over anhydrous magnesium sulfate, and the solvent was evaporated under reduced pressure to give the object product (34.2 g) as a brown solid.

$^1$H-NMR (CDCl$_3$) δ (ppm): 4.01 (3H, s), 4.39 (2H, s), 7.09 (1H, d, J=8.7 Hz), 8.18 (1H, dd, J=2.2, 8.7 Hz), 8.23 (1H, d, J=1.9 Hz).

(9-3) Synthesis of 2-acetamido-2-[2-(4-methoxy-3-trifluoromethylphenyl)-2-oxoethyl]malonic Acid Diethyl Ester (Compound 9-3)

To a solution of diethyl 2-acetamidomalonate (20.1 g) in N,N-dimethylformamide (100 ml) was added sodium hydride (60%, 4.07 g) in two portions under ice-cooling, and the mixture was stirred for 30 min. To the solution was added a solution of compound 9-2 (33.0 g) in N,N-dimethylformamide (50 ml) and the mixture was stirred for 2 hr under ice-cooling. The reaction mixture was added to ice water, extracted with ethyl acetate, and the organic layer was washed with saturated brine and dried over anhydrous magnesium sulfate. The solvent was evaporated under reduced pressure. The obtained residue was purified by silica gel chromatography to give the object product (31.8 g) as a brown oil.

$^1$H-NMR (CDCl$_3$) δ (ppm): 1.25 (6H, t, J=7.1 Hz), 1.97 (3H, s), 3.98 (3H, s), 4.22 (2H, s), 4.27 (4H, dq, J=2.4, 7.1 Hz), 7.05 (1H, d, J=8.7 Hz), 7.09 (1H, brs), 8.13 (1H, dd, J=2.2, 8.7 Hz), 8.20 (1H, d, J=2.0 Hz).

(9-4) Synthesis of 2-acetamido-2-[2-(4-methoxy-3-trifluoromethylphenyl)ethyl]malonic Acid Diethyl Ester (Compound 9-4)

To a solution of compound 9-3 (31.5 g) in trifluoroacetic acid (230 ml) was added triethylsilane (116 ml), and the mixture was stirred at 70° C. for 13 hr. The reaction mixture was concentrated under reduced pressure, water was added, and the mixture was extracted with ethyl acetate. The organic layer was washed successively with aqueous sodium hydroxide solution and saturated brine, and dried over anhydrous magnesium sulfate. The solvent was evaporated under reduced pressure. The obtained residue was purified by silica gel chromatography to give a mixture of the title compound and the starting material as a yellow oil. To a solution of the oil in trifluoroacetic acid (230 ml) was added triethylsilane (116 ml), and the mixture was stirred at 70° C. for 12 hr. The reaction mixture was concentrated under reduced pressure, water was added, and the mixture was extracted with ethyl acetate. The organic layer was washed successively with aqueous sodium hydroxide solution and saturated brine, and dried over anhydrous magnesium sulfate. The solvent was evaporated under reduced pressure. Diethyl ether was added to the obtained residue and the precipitated solid was collected by filtration, and dried to give the object product (7.91 g) as a white powder. The mother liquor was concentrated under reduced pressure, and the residue was purified by silica gel chromatography to give the object product (4.29 g). The total yield was 12.2 g.

$^1$H-NMR (CDCl$_3$) δ (ppm): 1.25 (6H, t, J=7.2 Hz), 2.02 (3H, s), 2.44-2.48 (2H, m), 2.62-2.68 (2H, m), 3.87 (3H, s), 4.15-4.27 (4H, m), 6.78 (1H, brs), 6.90 (1H, d, J=8.4 Hz), 7.27 (1H, dd, J=2.0, 8.4 Hz), 7.32 (1H, d, J=2.0 Hz).

(9-5) Synthesis of N-[1,1-bis(hydroxymethyl)-3-(4-methoxy-3-trifluoromethylphenyl)propyl]acetamide (Compound 9-5)

To a solution of compound 9-4 (12.2 g) in ethanol (200 ml) and water (40 ml) was added calcium chloride (6.46 g) and the mixture was dissolved. Sodium borohydride (4.40 g) was added to the mixture in two portions under ice-cooling, and the mixture was stirred for 3 hr under ice-cooling, and further at room temperature for 20 hr. 1M Hydrochloric acid (300 ml) was added to the reaction mixture under ice-cooling, and the mixture was concentrated under reduced pressure, and extracted with ethyl acetate. The organic layer was washed with saturated brine, and dried over anhydrous magnesium sulfate. The solvent was evaporated under reduced pressure to give the object product (9.88 g) as a white foam.

$^1$H-NMR (CDCl$_3$) δ (ppm): 1.92-1.96 (2H, m), 2.02 (3H, s), 2.60-2.64 (2H, m), 3.57 (2H, brs), 3.64 (2H, brd, J=11.6 Hz), 3.85 (2H, brd, J=11.6 Hz), 3.87 (3H, s), 5.94 (1H, brs), 6.92 (1H, d, J=8.5 Hz), 7.32 (1H, dd, J=1.9, 8.5 Hz), 7.37 (1H, d, J=1.9 Hz).

(9-6) Synthesis of [1,1-bis(hydroxymethyl)-3-(4-hydroxy-3-trifluoromethylphenyl)propyl]carbamic Acid t-butyl Ester (Compound 9-6)

To a solution of compound 9-5 (9.70 g) in methylene chloride (90 ml) was added dropwise at −70° C. a 1M solution (116 ml) of boron tribromide in methylene chloride. The mixture was warmed to 0° C. over 1 hr with stirring, and further stirred for 2 hr under ice-cooling. Methanol (200 ml) was gradually added to the reaction mixture under ice-cooling, and the mixture was concentrated under reduced pressure. Concentrated hydrochloric acid (50 ml) was added to a solution of the obtained residue in ethanol (50 ml), and the mixture was stirred at 70° C. for 1 hr. The reaction mixture was concentrated under reduced pressure. To a solution of the obtained residue and N,N-diisopropylethylamine (12.6 ml) in methanol (80 ml) was added di-t-butyl dicarbonate (6.94 g) under ice-cooling, and the mixture was stirred for 2 hr under ice-cooling, and further at room temperature for 4 hr. Saturated aqueous sodium hydrogencarbonate solution (500 ml) was added and the mixture was concentrated under reduced pressure, and extracted with ethyl acetate. The organic layer was washed successively with saturated aqueous sodium hydrogencarbonate solution and saturated brine, and dried over anhydrous magnesium sulfate. The solvent was evaporated under reduced pressure. The obtained residue was purified by silica gel chromatography to give the object product (2.15 g) as a colorless oil.

$^1$H-NMR (CDCl$_3$) δ (ppm): 1.46 (9H, s), 1.84-1.89 (2H, m), 2.57-2.61 (2H, m), 3.26 (2H, brs), 3.66 (2H, dd, J=5.9, 11.4 Hz), 3.87 (2H, dd, J=5.2, 11.4 Hz), 5.04 (1H, brs), 5.58 (1H, brs), 6.87 (1H, d, J=8.4 Hz), 7.23 (1H, dd, J=1.8, 8.4 Hz), 7.30 (1H, d, J=1.8 Hz).

(9-7) Synthesis of [1,1-bis(hydroxymethyl)-3-(4-octyloxy-3-trifluoromethylphenyl)propyl]carbamic Acid t-butyl Ester (Compound 9-7)

Compound 9-6 (360 mg) was dissolved in N,N-dimethylformamide (10 ml), potassium carbonate (263 mg) and 1-bromooctane (0.198 ml) were added, and the mixture was stirred at 80° C. for 6 hr. Water was added to the reaction mixture, and the mixture was extracted with ethyl acetate, washed with water and saturated brine, and dried over anhydrous magnesium sulfate. The solvent was evaporated under reduced pressure to give the object product (490 mg) as a colorless oil.

$^1$H-NMR (CDCl$_3$) δ (ppm): 0.88 (3H, t, J=6.8 Hz), 1.23-1.40 (8H, m), 1.41-1.50 (2H, m), 1.47 (9H, s), 1.75-1.82 (2H, m), 1.83-1.90 (2H, m), 2.57-2.62 (2H, m), 3.28 (2H, brs), 3.63-3.67 (2H, m), 3.85-3.90 (2H, m), 4.00 (2H, t, J=6.4 Hz), 5.02 (1H, brs), 6.89 (1H, d, J=8.5 Hz), 7.27 (1H, dd, J=8.5, 1.9 Hz), 7.36 (1H, d, J=1.9 Hz).

(9-8) Synthesis of 2-amino-2-[2-(4-octyloxy-3-trifluoromethylphenyl)ethyl]propane-1,3-diol Hydrochloride (Compound 9-8)

Compound 9-7 (490 mg) was dissolved in methylene chloride (5 ml), dioxane containing hydrogen chloride (4 mol/l, 5 ml) was added, and the mixture was stirred at room temperature for 12 hr. The reaction mixture was concentrated, and the residue was washed with diethyl ether to give the object product (350 mg) as a white powder.

MS (ESI) m/z: 392[M+H]

$^1$H-NMR (CD$_3$OD) δ (ppm): 0.90 (3H, t, J=6.8 Hz), 1.24-1.41 (8H, m), 1.47-1.53 (2H, m), 1.75-1.81 (2H, m), 1.91-1.97 (2H, m), 2.63-2.70 (2H; m), 3.69 (4H, s), 4.05 (2H, t, J=6.2 Hz), 7.03 (1H, d, J=8.4 Hz), 7.41 (1H, d, J=8.4 Hz), 7.44 (1H, brs).

Example 10

2-Amino-4-(4-octyloxy-3-trifluoromethylphenyl)-2-(phosphoryloxymethyl)butanol (10-1) Synthesis of 4-di(t-butyl)phosphoryloxymethyl-2-methyl-4-[2-(4-octyloxy-3-trifluoromethylphenyl)ethyl]-2-oxazoline (Compound 10-1)

To a solution of compound 9-8 (270 mg) in N,N-dimethylformamide (7 ml) were added N,N-diisopropylethylamine (0.340 ml) and trimethyl orthoacetate (0.121 ml), and the mixture was stirred at 120° C. for 5.5 hr. Water was added to the reaction mixture, and the mixture was extracted with ethyl acetate, washed with water and saturated brine, and dried over anhydrous magnesium sulfate. The solvent was evaporated under reduced pressure to give 280 mg of a brown oil. To a solution of the brown oil (280 mg) in methylene chloride (5 ml) and acetonitrile (2 ml) were added 1H-tetrazole (88 mg) and di-t-butyl diethylphosphoramidite (0.377 ml), and the mixture was stirred at room temperature for 2 hr. The reaction solution was ice-cooled, m-chloroperbenzoic acid (25% water containing product, 335 mg) was added, and the mixture was stirred at room temperature for 30 min. Saturated aqueous sodium hydrogencarbonate solution was added to the reaction mixture, and the mixture was extracted with chloroform. The organic layer was dried over anhydrous magnesium sulfate, and the solvent was evaporated under reduced pressure. The obtained residue was purified by silica gel column chromatography (hexane:ethyl acetate=1:3-ethyl acetate alone) to give the object product (190 mg) as a brown oil.

$^1$H-NMR (CDCl$_3$) δ (ppm): 0.90 (3H, t, J=6.9 Hz), 1.28-1.40 (8H, m), 1.47-1.52 (2H, m), 1.48 (9H, s), 1.49 (9H, s), 1.70-1.90 (4H, m), 2.01 (3H, s), 2.51-2.71 (2H, m), 3.89-3.92 (2H, m), 4.04 (2H, t, J=6.2 Hz), 4.17 (1H, d, J=9.0 Hz), 4.32 (1H, d, J=9.0 Hz), 7.05 (1H, d, J=8.4 Hz), 7.36-7.41 (2H, m).

(10-2) Synthesis of 2-amino-4-(4-octyloxy-3-trifluoromethylphenyl)-2-(phosphoryloxymethyl)butanol (Compound 10-2)

Compound 10-1 (190 mg) was dissolved in ethanol (5 ml), concentrated hydrochloric acid (1 ml) was added, and the mixture was stirred at 50° C. for 3 hr. The solvent was concentrated under reduced pressure, methanol (5 ml), diethyl ether (5 ml) and propyleneoxide (5 ml) were added to the residue. The precipitated powder was collected by filtration, washed with ethyl acetate and diethyl ether to give the object product (137 mg) as a white solid.

MS (ESI) m/z: 472[M+H]

$^1$H-NMR (CD$_3$OD) δ (ppm): 0.90 (3H, t, J=6.4 Hz), 1.25-1.40 (8H, m), 1.45-1.53 (2H, m), 1.76-1.83 (2H, m), 1.93-2.00 (2H, m), 2.63-2.74 (2H, m), 3.70 (2H, brs), 3.96-4.00 (2H, m), 4.04 (2H, t, J=6.2 Hz), 7.07 (1H, d, J=8.3 Hz), 7.42-7.46 (2H, m).

Example 11

2-Amino-2-[2-(4-hexyloxy-3-trifluoromethylphenyl)ethyl]propane-1,3-diol Hydrochloride (11-1) Synthesis of {2,2-dimethyl-5-[2-(4-hexyloxy-3-trifluoromethylphenyl)ethyl]-1,3-dioxan-5-yl}carbamic Acid t-butyl Ester (Compound 11-1)

Compound 1-1 (500 mg) was dissolved in N,N-dimethylformamide (10 ml), potassium carbonate (494 mg) and 1-bromohexane (0.201 ml) were added, and the mixture was stirred at 80° C. for 2 hr. Water was added to the reaction mixture, and the mixture was extracted with ethyl acetate, washed with water and saturated brine, and dried over anhydrous magnesium sulfate. The solvent was evaporated under reduced pressure to give the object product (620 mg) as a colorless oil.

$^1$H-NMR (CDCl$_3$) δ (ppm): 0.90 (3H, t, J=6.9 Hz), 1.30-1.36 (4H, m), 1.41-1.50 (2H, m), 1.43 (3H, s), 1.44 (3H, s), 1.47 (9H, s), 1.76-1.81 (2H, m), 1.91-1.99 (2H, m), 2.51-2.56 (2H, m), 3.69 (2H, d, J=11.7 Hz), 3.89 (2H, d, J=11.7 Hz), 4.00 (2H, t, J=6.4 Hz), 4.98 (1H, brs), 6.88 (1H, d, J=8.5 Hz), 7.26-7.28 (1H, m), 7.35 (1H, d, J=1.6 Hz).

(11-2) Synthesis of 2-amino-2-[2-(4-hexyloxy-3-trifluoromethylphenyl)ethyl]propane-1,3-diol Hydrochloride (Compound 11-2)

Compound 11-1 (620 mg) was dissolved in ethanol (15 ml), concentrated hydrochloric acid (2.5 ml) was added, and the mixture was stirred at 80° C. for 3 hr. The reaction mixture was concentrated, and the residue was washed with diethyl ether to give the object product (465 mg) as a white powder.

MS (ESI) m/z: 364[M+H]

$^1$H-NMR (CD$_3$OD) δ (ppm): 0.91 (3H, t, J=6.9 Hz), 1.32-1.40 (4H, m), 1.47-1.53 (2H, m), 1.73-1.81 (2H, m), 1.90-1.96 (2H, m), 2.62-2.68 (2H, m), 3.68 (4H, d, J=5.1 Hz), 4.04 (2H, t, J=6.2 Hz), 7.07 (1H, d, J=8.4 Hz), 7.41 (1H, dd, J=8.4, 1.9 Hz), 7.45 (1H, d, J=1.9 Hz).

Example 12

2-Amino-4-(4-hexyloxy-3-trifluoromethylphenyl)-2-(phosphoryloxymethyl)butanol (12-1) Synthesis of 4-di(t-butyl)phosphoryloxymethyl-4-[2-(4-hexyloxy-3-trifluoromethylphenyl)ethyl]-2-methyl-2-oxazoline (Compound 12-1)

To a solution of compound 11-2 (380 mg) in N,N-dimethylformamide (10 ml) were added N,N-diisopropylethylamine (0.512 ml) and trimethyl orthoacetate (0.180 ml), and the mixture was stirred at 120° C. for 12 hr. Water was added to the reaction mixture, and the mixture was extracted with ethyl acetate, washed with water and saturated brine, and dried over anhydrous magnesium sulfate. The solvent was evaporated under reduced pressure to give 380 mg of a brown oil. 1H-Tetrazole (133 mg) and di-t-butyl diethylphosphoramidite (0.569 ml) were added to a solution of the brown oil (380 mg) in methylene chloride (5 ml) and acetonitrile (2 ml), and the mixture was stirred at room temperature for 2 hr. The reaction solution was ice-cooled, m-chloroperbenzoic acid (25% water containing product, 504 mg) was added, and the mixture was stirred at room temperature for 1 hr. Saturated aqueous sodium hydrogencarbonate solution was added to the reaction mixture, and the mixture was extracted with chloroform. The organic layer was dried over anhydrous magnesium sulfate, and the solvent was evaporated under reduced pressure. The obtained residue was purified by silica gel column chromatography (hexane:ethyl acetate=1:4-ethyl acetate alone) to give the object product (220 mg) as a yellow oil.

$^1$H-NMR (CDCl$_3$) δ (ppm): 0.93 (3H, t, J=6.9 Hz), 1.30-1.40 (4H, m), 1.47-1.52 (2H, m), 1.48 (9H, s), 1.49 (9H, s), 1.74-1.88 (4H, m), 2.01 (3H, s), 2.51-2.70 (2H, m), 3.87-3.92 (2H, m), 4.04 (2H, t, J=6.2 Hz), 4.18 (1H, d, J=8.9 Hz), 4.32 (1H, d, J=8.9 Hz), 7.05 (1H, d, J=8.4 Hz), 7.37-7.41 (2H, m).

(12-2) Synthesis of 2-amino-4-(4-hexyloxy-3-trifluoromethylphenyl)-2-(phosphoryloxymethyl)butanol (Compound 12-2)

Compound 12-1 (220 mg) was dissolved in ethanol (5 ml), concentrated hydrochloric acid (1 ml) was added, and the mixture was stirred at 50° C. for 3 hr. The solvent was concentrated under reduced pressure, and methanol (5 ml), diethyl ether (5 ml) and propyleneoxide (5 ml) were added to the residue. The precipitated powder was collected by filtration, and washed with ethyl acetate and diethyl ether to give the object product (118 mg) as a white solid.

MS (ESI) m/z: 444[M+H]

$^1$H-NMR (CD$_3$OD) δ (ppm): 0.91 (3H, t, J=6.9 Hz), 1.31-1.40 (4H, m), 1.45-1.54 (2H, m), 1.74-1.82 (2H, m), 1.92-1.98 (2H, m), 2.60-2.75 (2H, m), 3.70 (2H, brs), 3.93-3.99 (2H, m), 4.04 (2H, t, J=6.2 Hz), 7.07 (1H, d, J=8.2 Hz), 7.42-7.46 (2H, m).

Example 13

2-Amino-4-(4-heptyloxy-3-trifluoromethylphenyl)-2-methylbutanol Hydrochloride (13-1) Synthesis of (2-hydroxy-1-hydroxymethyl-1-methyl)ethylcarbamic Acid t-butyl Ester (Compound 13-1)

2-Amino-2-methyl-1,3-propanediol hydrochloride (14.0 g) was dissolved in methanol (200 ml), N,N-diisopropylethylamine (46.3 ml) and di-t-butyl dicarbonate (43.7 g) were added under ice-cooling, and the mixture was stirred for 40 min under ice-cooling and further at room temperature for 27 hr. 1M Aqueous sodium hydroxide solution (100 ml) was added to the reaction mixture under ice-cooling, and the mixture was stirred for 40 min. Methanol was evaporated under reduced pressure. Water was added, and the mixture was extracted with ethyl acetate. The organic layer was washed with saturated brine, and dried over anhydrous magnesium sulfate. The solvent was evaporated under reduced pressure to give the object product (25.3 g) as a white powder.

$^1$H-NMR (CDCl$_3$) δ (ppm): 1.17 (3H, s), 1.44 (9H, s), 3.45 (2H, brs), 3.62 (2H, dd, J=7.1, 11.3 Hz), 3.78 (2H, dd, J=5.4, 11.3 Hz), 4.96 (1H, brs).

(13-2) Synthesis of (1-hydroxymethyl-2-methoxymethoxy-1-methyl)ethylcarbamic Acid t-butyl Ester (Compound 13-2)

To a solution of compound 13-1 (25.3 g) in methylene chloride (300 ml) were added under ice-cooling N,N-diisopropylethylamine (26.8 ml) and methoxymethyl chloride (11.6 ml), and the mixture was stirred for 20 min under ice-cooling and further at room temperature for 22 hr. Water was added to the reaction mixture, and the mixture was extracted with methylene chloride. The organic layer was washed with water and saturated brine, and dried over anhydrous magnesium sulfate. The solvent was evaporated under reduced pressure and the obtained residue was purified by silica gel chromatography to give the object product (14.2 g) as a colorless oil.

$^1$H-NMR (CDCl$_3$) δ (ppm): 1.26 (3H, s), 1.44 (9H, s), 3.38 (3H, s), 3.57 (1H, d, J=9.7 Hz), 3.61 (1H, dd, J=7.8, 11.5 Hz), 3.66 (1H, d, J=9.7 Hz), 3.71 (1H, dd, J=5.0, 11.5 Hz), 3.91 (1H, brs), 4.64 (2H, s), 5.10 (1H, brs).

(13-3) Synthesis of (1-formyl-2-methoxymethoxy-1-methyl)ethylcarbamic Acid t-butyl Ester (Compound 13-3)

To a mixed solution of compound 13-2 (14.2 g) and sodium bromide (5.86 g) in toluene (100 ml), ethyl acetate (100 ml) and water (20 ml) were added 2,2,6,6-tetramethylpiperidine 1-oxyl, free radical (178 mg) under ice-cooling. Then, 10% aqueous sodium hypochlorite solution (46.7 g) and a solution of sodium hydrogencarbonate (13.8 g) in water (150 ml) were added dropwise over 1.5 hr. The solution was further stirred for 1.5 hr under ice-cooling. The organic layer was separated, washed with water and saturated brine, and dried over anhydrous magnesium sulfate. The solvent was evaporated under reduced pressure to give the object product (13.1 g) as a pale-brown oil.

$^1$H-NMR (CDCl$_3$) δ (ppm): 1.39 (3H, s), 1.45 (9H, s), 3.34 (3H, s), 3.75 (2H, s), 4.60 (2H, s), 5.39 (1H, brs), 9.51 (1H, s).

(13-4) Synthesis of [3-(4-hydroxy-3-trifluoromethylphenyl)-1-(methoxymethoxy)methyl-1-methyl]propylcarbamic Acid t-butyl Ester (Compound 13-4)

Reference Example compound 2-5 (21.8 g) was suspended in tetrahydrofuran (200 ml), potassium t-butoxide (4.35 g) was added under ice-cooling, and the mixture was stirred for 1 hr. A solution of compound 13-3 (4.80 g) in tetrahydrofuran (40 ml) was added to the mixed solution, and the mixture was stirred under ice-cooling for 1.5 hr and at room temperature for 1 hr. The reaction mixture was poured into water, and the mixture was extracted with ethyl acetate. The organic layer was washed with saturated brine, and dried over anhydrous magnesium sulfate. The solvent was evaporated under reduced pressure and the obtained residue was purified by silica gel column chromatography to give [3-(4-benzyloxy-3-trifluoromethylphenyl)-1-(methoxymethoxy)methyl-1-methyl]allylcarbamic acid t-butyl ester (8.45 g) as a colorless oil. The geometric isomer ratio of the obtained compound was E:Z=3:7. 10% Palladium carbon (about 50% water containing, 845 mg) was added to a solution of this oil in 1,4-dioxane (150 ml), and the mixture was stirred at room temperature for 24 hr under a hydrogen atmosphere. The reaction mixture was filtered through celite and concentrated to give the object product (6.92 g) as a colorless oil.

$^1$H-NMR (CDCl$_3$) δ (ppm): 1.34 (3H, s), 1.45 (9H, s), 1.88-1.95 (1H, m), 2.00-2.08 (1H, m), 2.52-2.60 (2H, m), 3.38 (3H, s), 3.47 (1H, d, J=9.5 Hz), 3.65 (1H, d, J=9.5 Hz), 4.65 (2H, s), 4.78 (1H, brs), 5.98 (1H, brs), 6.85 (1H, d, J=8.4 Hz), 7.18 (1H, dd, J=1.5, 8.4 Hz), 7.29 (1H, d, J=1.5 Hz).

(13-5) Synthesis of [3-(4-heptyloxy-3-trifluoromethylphenyl)-1-(methoxymethoxy)methyl-1-methyl]propylcarbamic Acid t-butyl Ester (Compound 13-5)

To a solution of compound 13-4 (1.5 g) in N,N-dimethylformamide (15 ml) were added potassium carbonate (1.53 g) and n-heptyl bromide (0.63 ml), and the mixture was stirred at 50° C. for 6 hr. The reaction mixture was added to water, and the mixture was extracted with ethyl acetate. The organic layer was washed with saturated brine and dried over anhydrous magnesium sulfate. The solvent was evaporated under reduced pressure to give the object product (1.69 g) as a colorless oil.

$^1$H-NMR (CDCl$_3$) δ (ppm): 0.89 (3H, t, J=6.8 Hz), 1.29-1.49 (6H, m), 1.34 (3H, s), 1.42-1.50 (2H, m), 1.45 (9H, s), 1.79 (2H, quint, J=6.9 Hz), 1.84-1.95 (1H, m), 2.00-2.08 (1H, m), 2.54-2.61 (2H, m), 3.38 (3H, s), 3.49 (1H, d, J=9.5 Hz), 3.64 (1H, d, J=9.5 Hz), 4.00 (2H, t, J=6.5 Hz), 4.64 (2H, s), 4.72 (1H, brs), 6.88 (1H, d, J=8.5 Hz), 7.27 (1H, dd, J=1.9, 8.5 Hz), 7.35 (1H, d, J=1.9 Hz).

(13-6) Synthesis of 2-amino-4-(4-heptyloxy-3-trifluoromethylphenyl)-2-methylbutanol Hydrochloride (Compound 13-6)

To a solution of compound 13-5 (1.69 g) in ethanol (15 ml) was added concentrated hydrochloric acid (3 ml), and the mixture was stirred at 50° C. for 3 hr. 1M aqueous sodium hydroxide solution (50 ml) and brine (50 ml) were added to the reaction mixture and the mixture was extracted with ethyl acetate. The organic layer was washed with saturated brine, and dried over anhydrous magnesium sulfate. The solvent was evaporated under reduced pressure. The obtained residue was dissolved in ethyl acetate (50 ml), 1M hydrogen chloride ether solution (5 ml) was added, and the solvent was evaporated. Ether was added to the residue and the precipitated solid was filtered and dried under reduced pressure to give the object product (607 mg) as a white powder.

MS (ESI) m/z: 362[M+H]

$^1$H-NMR (DMSO-d$_6$) δ (ppm): 0.86 (3H, t, J=6.4 Hz), 1.20 (3H, s), 1.26-1.35 (6H, m), 1.37-1.43 (2H, m), 1.67-1.83 (4H, m), 2.61 (2H, t, J=8.7 Hz), 3.39 (1H, dd, J=4.6, 11.2 Hz), 3.46 (1H, dd, J=4.6, 11.2 Hz), 4.05 (2H, t, J=6.1 Hz), 5.52 (1H, t, J=4.9 Hz), 7.18 (1H, d, J=8.5 Hz), 7.43-7.45 (2H, m), 7.89 (3H, brs).

Example 14

Phosphoric Acid mono[2-amino-4-(4-heptyloxy-3-trifluoromethylphenyl)-2-methylbutyl]ester

(14-1) Synthesis of [3-(4-heptyloxy-3-trifluoromethylphenyl)-1-hydroxymethyl-1-methylpropyl]carbamic Acid t-butyl Ester (Compound 14-1)

To a solution of compound 13-6 (841 mg) in methanol (25 ml) were added N,N-diisopropylethylamine (1.10 ml) and di-t-butyl dicarbonate (692 mg), and the mixture was stirred at room temperature for 24 hr. The reaction mixture was concentrated under reduced pressure. Saturated sodium hydrogencarbonate was added, and the mixture was extracted with ethyl acetate. The organic layer was washed with saturated brine, and dried over anhydrous magnesium sulfate. The solvent was evaporated under reduced pressure and the obtained residue was purified by silica gel column chromatography to give the object product (880 mg) as a colorless oil.

$^1$H-NMR (CDCl$_3$) δ (ppm): 0.89 (3H, t, J=6.8 Hz), 1.22 (3H, s), 1.28-1.39 (6H, m), 1.44-1.49 (11H, m), 1.79 (2H, quint, J=6.9 Hz), 1.83-1.90 (1H, m), 1.99-2.07 (1H, m), 2.50-2.58 (1H, m), 2.61-2.68 (1H, m), 3.63-3.72 (2H, m), 4.00 (2H, t, J=6.5 Hz), 4.06 (1H, brs), 4.63 (1H, brs), 6.89 (1H, d, J=8.5 Hz), 7.28 (1H, dd, J=1.7, 8.5 Hz), 7.36 (1H, d, J=1.7 Hz).

(14-2) Synthesis of [1-di(t-butyl)phosphoryloxymethyl-3-(4-heptyloxy-3-trifluoromethylphenyl)-1-methylpropyl]carbamic Acid t-butyl Ester (Compound 14-2)

To a solution of compound 14-1 (870 mg) in methylene chloride (15 ml) was added a solution of 1H-tetrazole (158 mg) in acetonitrile (15 ml). Di-t-butyl diisopropylphosphoramidite (0.713 ml) was added to the mixture at 0° C., and the mixture was stirred for 1.5 hr under ice-cooling. A solution of 1H-tetrazole (158 mg) in acetonitrile (15 ml) and di-t-butyl diisopropylphosphoramidite (0.713 ml) were added, and the mixture was further stirred for 2 hr under ice-cooling. m-Chloroperbenzoic acid (25% water containing product, 600 mg) was added, and the mixture was stirred for 40 min under ice-cooling. Saturated aqueous sodium hydrogencarbonate solution was added to the reaction mixture, and the mixture was extracted with chloroform. The organic layer was washed with saturated aqueous sodium hydrogencarbonate solution and saturated brine, and dried over anhydrous magnesium sulfate. The solvent was evaporated under reduced pressure and the obtained residue was purified by silica gel column chromatography to give the object product (1.26 g) as a colorless oil.

$^1$H-NMR (CDCl$_3$) δ (ppm): 0.89 (3H, t, J=6.8 Hz), 1.28-1.35 (6H, m), 1.35 (3H, s), 1.43 (9H, s), 1.49 (18H, s), 1.51-1.53 (2H, m), 1.79 (2H, quint, J=6.9 Hz), 1.86-1.94 (1H, m), 2.03-2.11 (1H, m), 2.52-2.62 (2H, m), 3.86 (1H, dd, J=5.6, 10.2 Hz), 4.00 (2H, t, J=6.4 Hz), 4.04 (1H, dd, J=5.5, 10.2 Hz), 4.85 (1H, brs), 6.88 (1H, d, J=8.5 Hz), 7.27 (1H, dd, J=1.8, 8.5 Hz), 7.35 (1H, d, J=1.8 Hz).

(14-3) Synthesis of Phosphoric Acid mono[2-amino-4-(4-heptyloxy-3-trifluoromethylphenyl)-2-methylbutyl]ester (Compound 14-3)

Compound 14-2 (1.24 g) was dissolved in ethanol (5 ml), concentrated hydrochloric acid (1 ml) was added, and the mixture was stirred at 50° C. for 1 hr. The reaction mixture was added to water (30 ml), and the precipitated powder was collected by filtration and washed with water and diethyl ether to give the object product (648 mg) as a white solid.

MS (ESI) m/z: 442[M+H]

$^1$H-NMR (CD$_3$OD) δ (ppm): 0.91 (3H, t, J=6.8 Hz), 1.29-1.41 (6H, m), 1.38 (3H, s), 1.46-1.53 (2H, m), 1.75-1.81 (2H, m), 1.83-1.90 (1H, m), 1.97-2.05 (1H, m), 2.60-2.68 (1H, m), 2.70-2.76 (1H, m), 3.85 (1H, dd, J=5.4, 11.4 Hz), 3.94 (1H, dd, J=5.9, 11.4 Hz), 4.04 (2H, t, J=6.2 Hz), 7.07 (1H, d, J=8.2 Hz), 7.42-7.44 (2H, m).

Example 15

(R)-2-amino-4-(4-heptyloxy-3-trifluoromethylphenyl)-2-methylbutanol Hydrochloride (15-1) Synthesis of 2-amino-4-(4-heptyloxy-3-trifluoromethylphenyl)-2-methylbutanol (Compound 15-1)

A saturated aqueous sodium hydrogencarbonate solution (100 ml) was added to compound 13-6 (1.30 g) and the mixture was extracted with ethyl acetate. The organic layer was washed with saturated brine, and dried over anhydrous magnesium sulfate. The solvent was evaporated under reduced pressure to give the object product (1.16 g) as a white waxy solid.

$^1$H-NMR (DMSO-d$_6$) δ (ppm): 0.86 (3H, t, J=6.7 Hz), 1.08 (3H, s), 1.23-1.35 (6H, m), 1.38-1.45 (2H, m), 1.58-1.74 (4H, m), 2.55-2.65 (2H, m), 3.28 (1H, d, J=10.9 Hz), 3.32 (1H, d, J=10.9 Hz), 4.05 (2H, t, J=6.2 Hz), 5.09 (1H, brs), 5.52 (2H, brs), 7.16 (1H, d, J=9.0 Hz), 7.41-7.44 (2H, m).

(15-2) Synthesis of (R)-2-amino-4-(4-heptyloxy-3-trifluoromethylphenyl)-2-methylbutanol (Compound 15-2-1) and (S)-2-amino-4-(4-heptyloxy-3-trifluoromethylphenyl)-2-methylbutanol (Compound 15-2-2)

Compound 15-1 (2.63 g) was separated by supercritical fluid chromatography (SFC) using a CHIRALPAK (registered trade mark) AD-H (carbon dioxide/ethanol/diethylamine) to give both enantiomers as white waxy solids. The first peak with short retention time was R form (0.91 g, compound 15-2-1) and the second peak with long retention time was S form (0.95 g, compound 15-2-2).

(15-3) Synthesis of (R)-2-amino-4-(4-heptyloxy-3-trifluoromethylphenyl)-2-methylbutanol Hydrochloride (Compound 15-3)

Compound 15-2-1 (745 mg) was suspended in ethyl acetate (5 ml), and a solution of 4M hydrogen chloride in ethyl acetate (2 ml) was added. Hexane (10 ml) was further added and the mixture was stood for 1 hr. The precipitated solid was collected by filtration to give the object product (753 mg) as a white powder.

MS (ESI) m/z: 362[M+H]

$^1$H-NMR (DMSO-d$_6$) δ (ppm): 0.86 (3H, t, J=6.7 Hz), 1.19 (3H, s), 1.25-1.35 (6H, m), 1.37-1.45 (2H, m), 1.67-1.83 (4H, m), 2.60 (2H, t, J=8.7 Hz), 3.41-3.49 (2H, m), 4.06 (2H, t, J=6.2 Hz), 5.53 (1H, t, J=5.1 Hz), 7.18 (1H, d, J=8.4 Hz), 7.43-7.45 (2H, m), 7.78 (3H, brs).

Example 16

(R)-phosphoric Acid mono[2-amino-4-(4-heptyloxy-3-trifluoromethylphenyl)-2-methylbutyl]ester (16-1) Synthesis of (R)-[3-(4-heptyloxy-3-trifluoromethylphenyl)-1-hydroxymethyl-1-methylpropyl]carbamic Acid t-butyl Ester (Compound 16-1)

To a solution of compound 15-2-1 (120 mg) in methanol (10 ml) were added N,N-diisopropylethylamine (0.117 ml) and di-t-butyl dicarbonate (109 mg), and the mixture was stirred at room temperature for 24 hr. Saturated sodium hydrogencarbonate was added to the reaction mixture, and methanol was evaporated under reduced pressure. The obtained residue was diluted with water and extracted with ethyl acetate. The organic layer was washed with saturated brine, and dried over anhydrous magnesium sulfate. The solvent was evaporated under reduced pressure and the obtained residue was purified by silica gel column chromatography to give the object product (159 mg) as a colorless oil.

$^1$H-NMR (CDCl$_3$) δ (ppm): 0.89 (3H, t, J=6.7 Hz), 1.22 (3H, s), 1.28-1.38 (6H, m), 1.42-1.50 (11H, m), 1.79 (2H, quint, J=6.9 Hz), 1.83-1.90 (1H, m), 1.99-2.07 (1H, m), 2.50-2.58 (1H, m), 2.61-2.68 (1H, m), 3.63-3.72 (2H, m), 4.00 (2H, t, J=6.4 Hz), 4.03 (1H, brs), 4.62 (1H, brs), 6.89 (1H, d, J=8.5 Hz), 7.28 (1H, dd, J=1.6, 8.5 Hz), 7.36 (1H, d, J=1.6 Hz).

(16-2) (R)-phosphoric Acid mono[2-amino-4-(4-heptyloxy-3-trifluoromethylphenyl)-2-methylbutyl] ester (Compound 16-2)

To a solution of compound 16-1 (159 mg) in methylene chloride (5 ml) was added a solution of acetonitrile (5 ml) in 1H-tetrazole (27.9 mg). Di-t-butyl diisopropylphosphoramidite (0.126 ml) was added to the mixture at 0° C., and the mixture was stirred for 1 hr under ice-cooling. 1H-tetrazole (27.9 mg) and di-t-butyl diisopropylphosphoramidite (0.126 ml) were added, and the mixture was further stirred for 1 hr under ice-cooling. 1H-tetrazole (55.8 mg) and di-t-butyl diisopropylphosphoramidite (0.252 ml) were added, and the mixture was further stirred for 1 hr under ice-cooling. m-Chloroperbenzoic acid (25% water containing product, 106 mg) was added, and the mixture was stirred for 20 min under ice-cooling. M-chloroperbenzoic acid (25% water containing product, 106 mg) was added, and the mixture was further stirred for 30 min under ice-cooling. An aqueous sodium hydrogencarbonate solution was added to the reaction mixture, and the mixture was extracted with methylene chloride. The organic layer was washed with saturated aqueous sodium hydrogencarbonate solution and saturated brine, and dried over anhydrous magnesium sulfate. The solvent was evaporated under reduced pressure and the obtained residue was purified by silica gel column chromatography to give a colorless oil (271 mg) mainly containing (R)-[1-di(t-butyl)phosphoryloxymethyl-3-(4-heptyloxy-3-trifluoromethylphenyl)-1-methylpropyl]carbamic acid t-butyl ester. The oil was dissolved in ethanol (10 ml), concentrated hydrochloric acid (3 ml) was added, and the mixture was stirred at 50° C. for 3 hr. Water (50 ml) was added to the reaction mixture, and the precipitated powder was collected by filtration, and washed with water and diethyl ether to give the object product (81.9 mg) as a white powder.

MS (ESI) m/z: 442[M+H]

$^1$H-NMR (CD$_3$OD) δ (ppm): 0.91 (3H, t, J=6.8 Hz), 1.29-1.41 (6H, m), 1.37 (3H, s), 1.45-1.53 (2H, m), 1.75-1.81 (2H, m), 1.82-1.90 (1H, m), 1.96-2.04 (1H, m), 2.60-2.67 (1H, m), 2.69-2.77 (1H, m), 3.85 (1H, dd, J=5.3, 11.4 Hz), 3.94 (1H, dd, J=5.9, 11.4 Hz), 4.04 (2H, t, J=6.2 Hz), 7.07 (1H, d, J=8.1 Hz), 7.42-7.44 (2H, m).

Example 17

(S)-2-Amino-4-(4-heptyloxy-3-trifluoromethylphenyl)-2-methylbutanol Hydrochloride (17-1) Synthesis of (S)-2-amino-4-(4-heptyloxy-3-trifluoromethylphenyl)-2-methylbutanol Hydrochloride (Compound 17-1)

Compound 15-2-2 (785 mg) was suspended in ethyl acetate (5 ml), and a solution of 4M hydrogen chloride in ethyl acetate (2 ml) was added. Hexane (10 ml) was further added and stood for 1 hr. The precipitated solid was collected by filtration to give the object product (833 mg) as a white powder.

MS (ESI) m/z: 362[M+H]

$^1$H-NMR (DMSO-d$_6$) δ (ppm): 0.86 (3H, t, J=6.7 Hz), 1.20 (3H, s), 1.25-1.35 (6H, m), 1.37-1.45 (2H, m), 1.67-1.83 (4H, m), 2.60 (2H, t, J=8.7 Hz), 3.41-3.49 (2H, m), 4.06 (2H, t, J=6.2 Hz), 5.53 (1H, t, J=5.0 Hz), 7.18 (1H, d, J=8.5 Hz), 7.44-7.46 (2H, m), 7.84 (3H, brs).

Example 18

(S)-phosphoric Acid mono[2-amino-4-(4-heptyloxy-3-trifluoromethylphenyl)-2-methylbutyl]ester (18-1) Synthesis of (S)-[3-(4-heptyloxy-3-trifluoromethylphenyl)-1-hydroxymethyl-1-methylpropyl] carbamic Acid t-butyl Ester (Compound 18-1)

To a solution of compound 15-2-2 (120 mg) in methanol (10 ml) were added N,N-diisopropylethylamine (0.117 ml) and di-t-butyl dicarbonate (109 mg), and the mixture was stirred at room temperature for 24 hr. Saturated sodium hydrogencarbonate was added to the reaction mixture, and methanol was evaporated under reduced pressure. The obtained residue was diluted with water and extracted with ethyl acetate. The organic layer was washed with saturated brine, and dried over anhydrous magnesium sulfate. The solvent was evaporated under reduced pressure and the obtained residue was purified by silica gel column chromatography to give the object product (139 mg) as a colorless oil.

$^1$H-NMR (CDCl$_3$) δ (ppm): 0.89 (3H, t, J=6.7 Hz), 1.22 (3H, s), 1.28-1.38 (6H, m), 1.42-1.50 (11H, m), 1.79 (2H, quint, J=6.9 Hz), 1.83-1.90 (1H, m), 1.99-2.07 (1H, m), 2.51-2.58 (1H, m), 2.61-2.69 (1H, m), 3.63-3.72 (2H, m), 4.00 (2H, t, J=6.3 Hz), 4.02 (1H, brs), 4.63 (1H, brs), 6.89 (1H, d, J=8.4 Hz), 7.28 (1H, dd, J=1.7, 8.4 Hz), 7.36 (1H, d, J=1.7 Hz).

(18-2) (R)-phosphoric Acid mono[2-amino-4-(4-heptyloxy-3-trifluoromethylphenyl)-2-methylbutyl] ester (Compound 18-2)

To a solution of compound 18-1 (139 mg) in methylene chloride (5 ml) was added a solution of 1H-tetrazole (27.9 mg) in acetonitrile (5 ml). Di-t-butyl diisopropylphosphoramidite (0.126 ml) was added to the mixture at 0° C., and the mixture was stirred for 1 hr under ice-cooling. 1H-tetrazole (27.9 mg) and di-t-butyl diisopropylphosphoramidite (0.126 ml) were added, and the mixture was further stirred for 40 min under ice-cooling. 1H-tetrazole (55.8 mg) and di-t-butyl diisopropylphosphoramidite (0.252 ml) were added, and the mixture was further stirred for 50 min under ice-cooling. m-Chloroperbenzoic acid (25% water containing product, 106 mg) was added, and the mixture was stirred for 20 min under ice-cooling. m-Chloroperbenzoic acid (25% water containing product, 106 mg) was added, and the mixture was further stirred for 50 min under ice-cooling. An aqueous sodium hydrogencarbonate solution was added to the reaction mixture, and the mixture was extracted with methylene chloride. The organic layer was washed with saturated aqueous sodium hydrogencarbonate solution and saturated brine, and dried over anhydrous magnesium sulfate. The solvent was evaporated under reduced pressure and the obtained residue was purified by silica gel column chromatography to give a colorless oil (260 mg) mainly containing (S)-[1-di(t-butyl)phosphoryloxymethyl-3-(4-heptyloxy-3-trifluoromethylphenyl)-1-methylpropyl]carbamic acid t-butylester. The oil was dissolved in ethanol (10 ml), concentrated hydrochloric acid (3 ml) was added, and the mixture was stirred at 50° C. for 3 hr. Water (50 ml) was added to the reaction mixture, and the precipitated powder was collected by filtration and washed with water and diethyl ether to give the object product (63.0 mg) as a white powder.

MS (ESI) m/z: 442[M+H]

¹H-NMR (CD₃OD) (ppm): 0.91 (3H, t, J=6.8 Hz), 1.29-1.41 (6H, m), 1.37 (3H, s), 1.45-1.53 (2H, m), 1.75-1.81 (2H, m), 1.82-1.90 (1H, m), 1.96-2.04 (1H, m), 2.60-2.76 (2H, m), 3.85 (1H, dd, J=5.3, 11.4 Hz), 3.94 (1H, dd, J=5.9, 11.4 Hz), 4.04 (2H, t, J=6.2 Hz), 7.07 (1H, d, J=8.1 Hz), 7.42-7.44 (2H, m).

Example 19

2-Amino-2-ethyl-4-(4-heptyloxy-3-trifluoromethylphenyl)butanol Hydrochloride (19-1) Synthesis of [1,1-bis(hydroxymethyl)propyl]carbamic Acid t-butyl Ester (Compound 19-1)

To a solution of 2-amino-2-ethyl-1,3-propanediol (22.0 g) in methanol (500 ml) and N,N-diisopropylethylamine (64.3 ml) was added di-t-butyl dicarbonate (60.5 g) under ice-cooling, and the mixture was stirred for 40 min under ice-cooling and further at room temperature for 16 hr. 1M aqueous sodium hydroxide solution (184 ml) was added to the reaction mixture under ice-cooling and the mixture was stirred for 40 min. Methanol was removed under reduced pressure. Water was added and the mixture was extracted with ethyl acetate. The organic layer was washed with saturated brine, and dried over anhydrous magnesium sulfate. The solvent was evaporated under reduced pressure to give the object product (41.0 g) as a colorless oil.

¹H-NMR (CDCl₃) δ (ppm): 0.90<(3H, t, J=7.5 Hz) 1.45 (9H, s), 1.59 (2H, q, J=7.5 Hz), 3.45 (2H, brs), 3.60 (2H, dd, J=6.9, 11.6 Hz), 3.84 (2H, dd, J=4.8, 11.6 Hz), 4.89 (1H, brs).

(19-2) Synthesis of [1-hydroxymethyl-1-(methoxymethoxy)methyl]propylcarbamic Acid t-butyl Ester (Compound 19-2)

To a solution of compound 19-1 (41.0 g) in methylene chloride (400 ml) were added N,N-diisopropylethylamine (40.7 ml) and methoxymethyl chloride (17.6 ml) under ice-cooling, and the mixture was stirred for 40 min under ice-cooling and further at room temperature for 4 hr. Water was added to the reaction mixture, and the mixture was extracted with methylene chloride. The organic layer was washed with saturated brine, and dried over anhydrous magnesium sulfate. The solvent was evaporated under reduced pressure and the obtained residue was purified by silica gel chromatography to give the object product (21.3 g) as a colorless oil.

¹H-NMR (CDCl₃) δ (ppm): 0.89 (3H, t, J=7.5 Hz), 1.44 (9H, s), 1.55-1.62 (1H, m), 1.75-1.84 (1H, m), 3.38 (3H, s), 3.49 (1H, d, J=9.8 Hz), 3.68 (2H, d, J=6.6 Hz), 3.74 (1H, d, J=9.8 Hz), 4.04 (1H, brs), 4.63 (2H, s), 5.05 (1H, brs).

(19-3) Synthesis of [1-formyl-1-(methoxymethoxy)methyl]propylcarbamic Acid t-butyl Ester (Compound 19-3)

To a mixed solution of compound 19-2 (21.3 g) and sodium bromide (8.32 g) in toluene (170 ml), ethyl acetate (170 ml) and water (30 ml) were added 2,2,6,6-tetramethylpiperidine 1-oxyl, free radical (253 mg) under ice-cooling. Then, 10% aqueous sodium hypochlorite solution (66.3 g) and a solution of sodium hydrogencarbonate (19.6 g) in water (200 ml) were added dropwise over 1.5 hr. The mixture was further stirred for 1.5 hr under ice-cooling, 10% aqueous sodium hypochlorite solution (22.1 g) and a solution of sodium hydrogencarbonate (6.53 g) in water (67 ml) were added dropwise over 30 min, and the mixture was further stirred for 30 min. The organic layer was partitioned and diluted with ethyl acetate (200 ml). The organic layer was washed with saturated brine, and dried over anhydrous magnesium sulfate. The solvent was evaporated under reduced pressure to give the object product (22.0 g) as a pale-brown oil.

¹H-NMR (CDCl₃) δ (ppm): 0.81 (3H, t, J=7.5 Hz), 1.45 (9H, s), 1.74-1.83 (1H, m), 2.04-2.11 (1H, m), 3.32 (3H, s), 3.81 (1H, d, J=10.0 Hz), 4.03 (1H, d, J=10.0 Hz), 4.59 (2H, s), 5.37 (1H, brs), 9.39 (1H, s).

(19-4) Synthesis of [1-ethyl-3-(4-hydroxy-3-trifluoromethylphenyl)-1-(methoxymethoxy)methyl]propylcarbamic acid t-butyl ester (compound 19-4)

Reference Example compound 2-5 (26.3 g) was suspended in tetrahydrofuran (120 ml), potassium t-butoxide (5.24 g) was added under ice-cooling, and the mixture was stirred for 50 min. A solution of compound 19-3 (6.10 g) in tetrahydrofuran (80 ml) was added to the mixed solution, and the mixture was stirred for 2 hr under ice-cooling, and at room temperature for 4 hr. The reaction mixture was added to brine, and extracted with ethyl acetate. The organic layer was washed with saturated brine, and dried over anhydrous magnesium sulfate. The solvent was evaporated under reduced pressure and the obtained residue was purified by silica gel column chromatography to give [1-ethyl-3-(4-benzyloxy-3-trifluoromethylphenyl)-1-(methoxymethoxy)methyl]allylcarbamic acid t-butyl ester (10.3 g) as a colorless oil. The geometric isomer ratio of the obtained compound was E:Z=1:2.8. 10% Palladium carbon (about 50% water containing, 2 g) was added to a solution of this oil in 1,4-dioxane (200 ml), and the mixture was stirred at room temperature for 9 hr under a hydrogen atmosphere. The reaction mixture was filtered through celite and concentrated to give the object product (8.67 g) as a white powder.

¹H-NMR (CDCl₃) δ (ppm): 0.89 (3H, t, J=7.5 Hz), 1.45 (9H, s), 1.65-1.74 (1H, m), 1.76-1.86 (1H, m), 1.93-1.97 (2H, m), 2.52-2.56 (2H, m), 3.39 (3H, s), 3.57 (1H, d, J=9.7 Hz), 3.63 (1H, d, J=9.7 Hz), 4.64 (3H, m), 5.85 (1H, brs), 6.85 (1H, d, J=8.3 Hz), 7.20 (1H, brd, J=8.3 Hz), 7.29 (1H, d, J=1.4 Hz).

(19-5) Synthesis of [1-ethyl-3-(4-heptyloxy-3-trifluoromethylphenyl)-1-(methoxymethoxy)methyl] propylcarbamic Acid t-butyl Ester (Compound 19-5)

To a solution of compound 19-4 (1.5 g) in N,N-dimethylformamide (15 ml) were added potassium carbonate (1.48 g) and n-heptylbromide (0.61 ml), and the mixture was stirred at 50° C. for 6 hr. The reaction mixture was added to water, and extracted with ethyl acetate. The organic layer was washed with saturated brine and dried over anhydrous magnesium sulfate. The solvent was evaporated under reduced pressure to give the object product (1.83 g) as a colorless oil.

¹H-NMR (CDCl₃) δ (ppm): 0.89 (3H, t, J=6.4 Hz), 0.89 (3H, t, J=7.6 Hz), 1.28-1.38 (6H, m), 1.42-1.49 (11H, m), 1.68-1.88 (4H, m), 1.92-1.97 (2H, m), 2.52-2.57 (2H, m), 3.38 (3H, s), 3.57 (1H, d, J=9.7 Hz), 3.63 (1H, d, J=9.7 Hz), 4.00 (2H, t, J=6.4 Hz), 4.60 (1H, brs), 4.64 (2H, s), 6.88 (1H, d, J=8.5 Hz), 7.27 (1H, dd, J=1.6, 8.5 Hz), 7.35 (1H, d, J=1.6 Hz).

(19-6) Synthesis of 2-amino-2-ethyl-4-(4-heptyloxy-3-trifluoromethylphenyl)butanol Hydrochloride (Compound 19-6)

To a solution of compound 19-5 (1.83 g) in ethanol (15 ml) was added concentrated hydrochloric acid (3 ml), and the mixture was stirred at 50° C. for 4 hr. 1M aqueous sodium hydroxide solution (100 ml) was added to the reaction mixture and the mixture was extracted with ethyl acetate. The organic layer was washed with saturated brine, and dried over anhydrous magnesium sulfate. The solvent was evaporated under reduced pressure. The obtained residue was dissolved in ethyl acetate (30 ml), 1M hydrogen chloride ether solution (10 ml) was added, and the solvent was evaporated. Diethyl ether and hexane were added to the residue, and the precipitated solid was collected by filtration and dried to give the object product (1.22 g) as a white powder.

MS (ESI) m/z: 376[M+H]

$^1$H-NMR (DMSO-$d_6$) δ (ppm): 0.86 (3H, t, J=6.4 Hz), 0.90 (3H, t, J=7.4 Hz), 1.25-1.35 (6H, m), 1.37-1.45 (2H, m), 1.57-1.65 (2H, m), 1.67-1.77 (4H, m), 2.56-2.61 (2H, m), 3.43-3.51 (2H, m), 4.06 (2H, t, J=6.2 Hz), 5.49 (1H, t, J=5.0 Hz), 7.18 (1H, d, J=9.2 Hz), 7.45-7.46 (2H, m), 7.90 (3H, brs).

Example 20

Phosphoric Acid mono[2-amino-2-ethyl-4-(4-heptyloxy-3-trifluoromethylphenyl)butyl]ester (20-1) Synthesis of [1-ethyl-3-(4-heptyloxy-3-trifluoromethylphenyl)-1-hydroxymethylpropyl]carbamic Acid t-butyl Ester (Compound 20-1)

To a solution of compound 19-6 (1.04 g) in methanol (25 ml) were added N,N-diisopropylethylamine (1.32 ml) and di-t-butyl dicarbonate (825 mg), and the mixture was stirred at room temperature for 13 hr. The reaction mixture was concentrated under reduced pressure, saturated sodium hydrogencarbonate was added and the mixture was extracted with ethyl acetate. The organic layer was washed with saturated brine, and dried over anhydrous magnesium sulfate. The solvent was evaporated under reduced pressure. The obtained residue was purified by silica gel column chromatography to give the object product (1.21 g) as a colorless oil.

$^1$H-NMR (CDCl$_3$) δ (ppm): 0.89 (3H, t, J=6.8 Hz), 0.93 (3H, t, J=7.5 Hz), 1.28-1.39 (6H, m), 1.42-1.49 (11H, m), 1.64 (2H, q, J=7.5 Hz), 1.79 (2H, quint, J=7.0 Hz), 1.82-1.94 (2H, m), 2.46-2.54 (1H, m), 2.56-2.64 (1H, m), 3.72 (2H, d, J=6.3 Hz), 4.00 (2H, t, J=6.5 Hz), 4.09 (1H, brs), 4.57 (1H, brs), 6.89 (1H, d, J=8.5 Hz), 7.28 (1H, dd, J=1.7, 8.5 Hz), 7.35 (1H, d, J=1.7 Hz).

(20-2) Synthesis of [1-di(t-butyl)phosphoryloxymethyl-1-ethyl-3-(4-heptyloxy-3-trifluoromethylphenyl)propyl]carbamic Acid t-butyl Ester (Compound 20-2)

To a solution of compound 20-1 (1.20 g) in methylene chloride (15 ml) was added a solution of 1H-tetrazole (212 mg) in acetonitrile (15 ml). Di-t-butyl diisopropylphosphoramidite (0.956 ml) was added to this mixture at 0° C., and the mixture was stirred for 1 hr under ice-cooling. A solution of 1H-tetrazole (106 mg) in acetonitrile (15 ml) and di-t-butyl diisopropylphosphoramidite (0.478 ml) were added, and the mixture was further stirred for 1 hr under ice-cooling. m-Chloroperbenzoic acid (25% water containing product, 804 mg) was added and the mixture was stirred for 50 min under ice-cooling. A saturated aqueous sodium hydrogencarbonate solution was added to the reaction mixture, and the mixture was extracted with chloroform. The organic layer was washed with aqueous saturated sodium hydrogencarbonate and saturated brine, and dried over anhydrous magnesium sulfate. The solvent was evaporated under reduced pressure. The obtained residue was purified by silica gel column chromatography to give the object product (1.56 g) as a colorless oil.

$^1$H-NMR (CDCl$_3$) δ (ppm): 0.89 (3H, t, J=6.8 Hz), 0.90 (3H, t, J=7.3 Hz), 1.28-1.38 (6H, m), 1.43 (9H, s), 1.47-1.51 (2H, m), 1.49 (18H, s), 1.70-1.82 (4H, m), 1.86-2.01 (2H, m), 2.53-2.59 (2H, m), 3.95-4.06 (4H, m), 4.67 (1H, brs), 6.88 (1H, d, J=8.5 Hz), 7.28 (1H, dd, J=1.7, 8.5 Hz), 7.35 (1H, brs).

(20-3) Synthesis of Phosphoric Acid mono[2-amino-2-ethyl-4-(4-heptyloxy-3-trifluoromethylphenyl)butyl]ester (Compound 20-3)

Compound 20-2 (1.55 g) was dissolved in ethanol (5 ml), concentrated hydrochloric acid (1 ml) was added and the mixture was stirred at 50° C. for 1 hr. Water (50 ml) was added to the reaction mixture, and the precipitated powder was collected by filtration and washed with water and diethyl ether to give the object product (907 mg) as a white powder.

MS (ESI) m/z: 456[M+H]

$^1$H-NMR (CD$_3$OD) δ (ppm): 0.91 (3H, t, J=6.7 Hz), 1.03 (3H, t, J=7.5 Hz), 1.30-1.40 (6H, m), 1.49 (2H, quint, J=7.5 Hz), 1.73-2.01 (6H, m), 2.57-2.74 (2H, m), 3.88-3.96 (2H, m), 4.05 (2H, t, J=6.2 Hz), 7.08 (1H, d, J=8.9 Hz), 7.42-7.44 (2H, m).

Example 21

Diethyl 2-amino-2-[2-(4-heptyloxy-3-trifluoromethylphenyl)ethyl]butane-1,4-diol Hydrochloride (21-1) Synthesis of 2-[(t-butyloxycarbonyl)amino]-2-[2-(tetrahydro-2H-pyran-2-yloxy)ethyl]malonic Acid Diethyl Ester (Compound 21-1)

Diethyl (t-butyloxycarbonyl)aminomalonate (52.3 g) was dissolved in tetrahydrofuran (400 ml), sodium t-butoxide (19.2 g) was added thereto, a solution of 2-(2-bromoethoxy)tetrahydro-2H-pyran (40.4 g) in tetrahydrofuran (100 ml) was added to the reaction mixture at 70° C., and the mixture was stirred with heating for 10 hr. After cooling, the reaction mixture was poured into saturated brine. The mixture was extracted with ethyl acetate, and the organic layer was washed with saturated brine and dried over anhydrous magnesium sulfate. The solvent was evaporated under reduced pressure, and the obtained residue was purified by silica gel column chromatography to give the object product (50.0 g) as a colorless oil.

$^1$H-NMR (CDCl$_3$) (ppm): 1.30 (6H, t, J=7.1 Hz), 1.45 (9H, s), 1.45-1.55 (4H, m), 1.58-1.78 (2H, m), 2.60-2.64 (2H, m), 3.35-3.41 (1H, m), 3.46-3.50 (1H, m), 3.77-3.84 (2H, m), 4.12-4.28 (4H, m), 4.49-4.51 (1H, m), 6.08 (1H, brs).

(21-2) Synthesis of 1,1-bis(hydroxymethyl)-3-(tetrahydro-2H-pyran-2-yloxy)propylcarbamic Acid t-butyl Ester (Compound 21-2)

Compound 21-1 (50.0 g) was dissolved in a mixture of ethanol (530 ml), tetrahydrofuran (130 ml) and water (260 ml). Calcium chloride (27.5 g) was added to this solution at 0° C., sodium borohydride (18.8 g) was subsequently added in portions, and the mixture was stirred at the same temperature for 2 hr, and further at room temperature for 18 hr. The reaction mixture was concentrated under reduced pressure, added to saturated aqueous ammonium chloride solution (31), and extracted with ethyl acetate. The organic layer was washed with saturated brine and dried over anhydrous magnesium sulfate. The solvent was evaporated under reduced pressure and the obtained residue was purified by silica gel chromatography to give the object product (21.6 g) as a colorless oil.

¹H-NMR (CDCl₃) δ (ppm): 1.43 (9H, s), 1.53-1.62 (4H, m), 1.71-1.83 (2H, m), 1.95 (1H, ddd, J=15.3, 8.0, 2.8 Hz), 2.02 (1H, ddd, J=15.3, 7.4, 2.8 Hz), 3.46-3.59 (4H, m), 3.69-3.73 (2H, m), 3.82-3.88 (1H, m), 3.91-3.96 (1H, m), 4.13 (2H, brs), 4.60-4.62 (1H, m), 5.79 (1H, brs).

(21-3) Synthesis of 1-hydroxymethyl-1-(methoxymethoxy)methyl-3-(tetrahydro-2H-pyran-2-yloxy)propylcarbamic Acid t-butyl Ester (Compound 21-3)

To a solution of compound 21-2 (21.6 g) in methylene chloride (250 ml) were added N,N-diisopropylethylamine (14.7 ml) and methoxymethyl chloride (6.37 ml) under ice-cooling, and the mixture was stirred for 1.5 hr under ice-cooling, and further at room temperature for 17 hr. Water was added to the reaction mixture, and the mixture was extracted with methylene chloride. The organic layer was washed with saturated brine, and dried over anhydrous magnesium sulfate. The solvent was evaporated under reduced pressure. The obtained residue was purified by silica gel chromatography to give the object product (9.61 g) as a colorless oil.

¹H-NMR (CDCl₃) δ (ppm): 1.42 (9H, s), 1.51-1.63 (4H, m), 1.68-1.93 (3H, m), 2.03-2.10 (1H, m), 3.37 (3H, s), 3.51-3.60 (3H, m), 3.69-4.00 (5H, m), 4.26, 4.35 (1H, 2×brs), 4.61-4.66 (3H, m), 5.61, 5.75 (1H, 2×brs).

(21-4) Synthesis of 1-formyl-1-(methoxymethoxy)methyl-3-(tetrahydro-2H-pyran-2-yloxy)propylcarbamic Acid t-butyl Ester (Compound 21-4)

To a mixed solution of compound 21-3 (9.59 g) and sodium bromide (2.72 g) in toluene (50 ml), ethyl acetate (50 ml) and water (9 ml) was added 2,2,6,6-tetramethylpiperidine 1-oxyl, free radical (82.5 mg) under ice-cooling, then a solution of 10% aqueous sodium hypochlorite solution (21.7 g) and sodium hydrogencarbonate (3.19 g) in water (75 ml) were added dropwise over 2 hr. The mixture was further stirred for 2 hr under ice-cooling, a solution of 10% aqueous sodium hypochlorite solution (10.9 g) and sodium hydrogencarbonate (3.19 g) in water (35 ml) was added dropwise over 20 min, and the mixture was further stirred for 20 min. The organic layer was partitioned and diluted with ethyl acetate (200 ml), washed with saturated brine, and dried over anhydrous magnesium sulfate. The solvent was evaporated under reduced pressure to give the object product (8.54 g) as a brown oil.

¹H-NMR (CDCl₃) δ (ppm): 1.44 (9H, s), 1.45-1.78 (6H, m), 2.10-2.18 (1H, m), 2.35-2.46 (1H, m), 3.31, 3.32 (3H, 2×s), 3.33-3.41 (1H, m), 3.47-3.51 (1H, m), 3.67-3.74 (1H, m), 3.77-3.84 (2H, m), 4.05-4.13 (1H, m), 4.43-4.45, 4.56-4.58 (1H, 2×m), 4.58, 4.58 (2H, 2×s), 5.72, 5.74 (1H, 2×brs), 9.40, 9.44 (1H, 2×s).

(21-5) Synthesis of 3-(4-benzyloxy-3-trifluoromethylphenyl)-1-(methoxymethoxy)methyl-1-[2-(tetrahydro-2H-pyran-2-yloxy)ethyl]propylcarbamic Acid t-butyl Ester (Compound 21-5)

Reference Example compound 2-5 (10.9 g) was suspended in tetrahydrofuran (80 ml), potassium t-butoxide (2.17 g) was added under ice-cooling and the mixture was stirred for 30 min. A solution of compound 21-4 (3.50 g) in tetrahydrofuran (25 ml) was added to the mixed solution and the mixture was stirred for 20 min under ice-cooling, and further at room temperature for 5 hr. The reaction mixture was added to brine, and the mixture was extracted with ethyl acetate. The organic layer was washed with saturated brine, and dried over anhydrous magnesium sulfate. The solvent was evaporated under reduced pressure. The obtained residue was purified by silica gel column chromatography to give 3-(4-benzyloxy-3-trifluoromethylphenyl)-1-(methoxymethoxy)methyl-1-[2-(tetrahydro-2H-pyran-2-yloxy)ethyl]allylcarbamic acid t-butyl ester (4.95 g) as a pale-yellow oil. The geometric isomer ratio of the obtained compound was E:Z=1:3. To a solution of this oil in toluene (200 ml) was added chlorotris(triphenylphosphine)rhodium(I) (5.0 g), and the mixture was stirred at 60° C. for 19 hr. Chlorotris(triphenylphosphine)rhodium(I) (2.5 g) was added and the mixture was stirred at 60° C. for 10 hr under a hydrogen atmosphere. The reaction mixture was filtered through celite and concentrated. The obtained residue was purified by silica gel column chromatography to give the object product (4.95 g) as a yellow oil.

¹H-NMR (CDCl₃) δ (ppm): 1.43 (9H, s), 1.51-1.64 (4H, m), 1.67-1.75 (1H, m), 1.79-1.88 (1H, m), 1.92-2.28 (4H, m), 2.54-2.62 (2H, m), 3.36, 3.37 (3H, 2×s), 3.46-3.59 (2H, m), 3.71-3.78 (2H, m), 3.82-4.03 (2H, m), 4.60-4.64 (3H, m), 5.15 (2H, s), 5.41, 5.55 (1H, 2×brs), 6.93 (1H, d, J=8.5 Hz), 7.26-7.32 (2H, m), 7.36-7.44 (5H, m).

(21-6) Synthesis of 3-(4-hydroxy-3-trifluoromethylphenyl)-1-(methoxymethoxy)methyl-1-[2-(tetrahydro-2H-pyran-2-yloxy)ethyl]propylcarbamic Acid t-butyl Ester (Compound 21-6)

To a solution of compound 21-5 (4.94 g) in 1,4-dioxane (150 ml) was added 10% palladium carbon (about 50% water containing, 2 g), and the mixture was stirred for 22 hr under a hydrogen atmosphere. The reaction mixture was filtered through celite, and concentrated to give the object product (4.07 g) as a colorless oil.

¹H-NMR (CDCl₃) δ (ppm): 1.43 (9H, s), 1.52-1.64 (4H, m), 1.68-1.75 (1H, m), 1.79-1.88 (1H, m), 1.92-2.27 (4H, m), 2.55-2.61 (2H, m), 3.36, 3.37 (3H, 2×s), 3.46-3.60 (2H, m), 3.71-4.03 (4H, m), 4.61-4.63 (3H, m), 5.45, 5.59 (1H, 2×brs), 5.54 (1H, brs), 6.85 (1H, d, J=8.4 Hz), 7.21-7.23 (1H, m), 7.30 (1H, brs).

(21-7) Synthesis of 3-(4-heptyloxy-3-trifluoromethylphenyl)-1-(methoxymethoxy)methyl-1-[2-(tetrahydro-2H-pyran-2-yloxy)ethyl]propylcarbamic Acid t-butyl Ester (Compound 21-7)

Compound 21-6 (1.24 g) was dissolved in N,N-dimethylformamide (20 ml), potassium carbonate (986 mg) and n-heptyl bromide (0.458 ml) were added, and the mixture was stirred at 80° C. for 2.5 hr. Water was added to the reaction mixture, and the mixture was extracted with ethyl acetate, washed with water and saturated brine, and dried over anhydrous magnesium sulfate. The solvent was evaporated under reduced pressure to give the object product (1.49 g) as a pale-yellow oil.

¹H-NMR (CDCl₃) δ (ppm): 0.89 (3H, t, J=6.8 Hz), 1.25-1.40 (7H, m), 1.40-1.49 (2H, m), 1.43 (9H, s), 1.50-1.68 (3H, m), 1.69-1.90 (4H, m), 1.91-2.00 (2H, m), 2.00-2.20 (2H, m), 2.56-2.61 (2H, m), 3.36, 3.37 (3H, 2×s), 3.45-3.60 (2H, m), 3.71-3.96 (4H, m), 4.00 (2H, t, J=6.4 Hz), 4.61-4.63 (3H, m), 5.40, 5.57 (1H, 2×brs), 6.88 (1H, d, J=8.5 Hz), 7.28 (1H, brs), 7.36 (1H, brs).

(21-8) Synthesis of 2-amino-2-[2-(4-heptyloxy-3-trifluoromethylphenyl)ethyl]butane-1,4-diol Hydrochloride (Compound 21-8)

Compound 21-7 (1.49 g) was dissolved in ethanol (20 ml), concentrated hydrochloric acid (3 ml) was added, and the mixture was stirred at 80° C. for 1.5 hr. The reaction mixture was concentrated, and the residue was washed with diethyl ether to give the object product (915 mg) as a white powder.
MS (ESI) m/z: 392[M+H]
$^1$H-NMR (DMSO-$d_6$) δ (ppm): 0.86 (3H, t, J=6.8 Hz), 1.25-1.34 (6H, m), 1.35-1.45 (2H, m), 1.68-1.78 (2H, m), 1.79-1.83 (4H, m), 2.59-2.65 (2H, m), 3.51 (2H, d, J=4.4 Hz), 3.60 (2H, t, J=6.4 Hz), 4.05 (2H, t, J=6.2 Hz), 5.45 (1H, t, J=4.8 Hz), 7.18 (1H, d, J=9.2 Hz), 7.43-7.46 (2H, m), 7.75 (3H, brs).

Example 22

2-Amino-4-fluoro-2-[2-(4-heptyloxy-3-trifluoromethylphenyl)ethyl]butanol Hydrochloride

(22-1) Synthesis of 4-(2-fluoroethyl)-4-[2-(4-heptyloxy-3-trifluoromethylphenyl)ethyl]-2-methyl-2-oxazoline (Compound 22-1)

To a solution of compound 21-8 (830 mg) in N,N-dimethylformamide (20 ml) were added N,N-diisopropylethylamine (1.04 ml) and trimethyl orthoacetate (0.368 ml), and the mixture was stirred at 120° C. for 5 hr. Water was added to the reaction mixture, and the mixture was extracted with ethyl acetate, washed with water and saturated brine, and dried over anhydrous magnesium sulfate. The solvent was evaporated under reduced pressure to give 840 mg of a brown oil. Molecular sieves 4 Å (8.4 g), p-toluenesulfonyl fluoride (690 mg) and 1M-tetrabutylammonium fluoride/tetrahydrofuran solution (5.82 ml) were added to a solution of the brown oil in tetrahydrofuran (30 ml) and the mixture was heated under reflux for one day. The reaction mixture was filtrated, and 1M aqueous hydrochloric acid solution was added to the filtrate. The mixture was extracted with ethyl acetate, washed with saturated aqueous sodium hydrogencarbonate solution and saturated brine, and dried over anhydrous sodium sulfate. The solvent was evaporated under reduced pressure. The obtained residue was purified by silica gel column chromatography (hexane:ethyl acetate=1:2-1:3) to give the object product (400 mg) as a brown oil.
$^1$H-NMR (DMSO-$d_6$) δ (ppm): 0.86-0.94 (3H, m), 1.25-1.40 (6H, m), 1.41-1.51 (2H, m), 1.76-1.95 (4H, m), 1.97-2.08 (2H, m), 2.01 (3H, s), 2.50-2.66 (2H, m), 4.00 (2H, t, J=6.2 Hz), 4.06 (1H, d, J=8.8 Hz), 4.14 (1H, d, J=8.8 Hz), 4.53 (1H, dd, J=48, 3.8 Hz), 4.65 (1H, dd, J=48, 3.8 Hz), 6.89 (1H, d, J=8.4 Hz), 7.26 (1H, brs), 7.36 (1H, brs).

(22-2) Synthesis of 2-amino-4-fluoro-2-[2-(4-heptyloxy-3-trifluoromethylphenyl)ethyl]butanol Hydrochloride (Compound 22-2)

Compound 22-1 (400 mg) was dissolved in ethanol (10 ml), concentrated hydrochloric acid (2 ml) was added, and the mixture was stirred at 70° C. for 4.5 hr. The reaction mixture was concentrated, and the residue was washed with diisopropyl ether to give the object product (360 mg) as a white powder.
MS (ESI) m/z: 394[M+H]
$^1$H-NMR (DMSO-$d_6$) δ (ppm): 0.86 (3H, t, J=6.7 Hz), 1.24-1.38 (6H, m), 1.39-1.46 (2H, m), 1.68-1.78 (2H, m), 1.79-1.86 (2H, m), 2.04 (1H, t, J=6.0 Hz), 2.10 (1H, t, J=6.0 Hz), 2.59-2.66 (2H, m), 3.53 (2H, d, J=5.0 Hz), 4.06 (2H, t, J=6.2 Hz), 4.61 (1H, dt, J=47, 6.0 Hz), 4.73 (1H, dt, J=47, 6.0 Hz), 5.56 (1H, t, J=5.0 Hz), 7.18 (1H, d, J=8.4 Hz), 7.42-7.45 (2H, m), 8.09 (3H, brs).

Example 23

Phosphoric Acid mono[2-amino-2-(2-fluoroethyl)-4-(4-heptyloxy-3-trifluoromethylphenyl)butyl]ester

(23-1) Synthesis of [1-di(t-butyl)phosphoryloxymethyl-1-(2-fluoroethyl)-3-(4-heptyloxy-3-trifluoromethylphenyl)propyl]carbamic Acid t-butyl Ester (Compound 23-1)

To a solution of compound 22-2 (290 mg) in methanol (15 ml) were added triethylamine (0.284 ml) and di-t-butyl dicarbonate (220 mg), and the mixture was stirred at room temperature for 18 hr. Further, di-t-butyl dicarbonate (220 mg) was added, and the mixture was stirred at room temperature for 5 hr. The reaction mixture was concentrated under reduced pressure, water was added to the residue and the mixture was extracted with ethyl acetate. The organic layer was washed with saturated brine and dried over anhydrous magnesium sulfate. The solvent was evaporated under reduced pressure to give 400 mg of a pale-yellow oil. To a solution of the pale-yellow oil (400 mg) in methylene chloride (5 ml) and acetonitrile (2 ml) were added 1H-tetrazole (94 mg) and di-t-butyl diethylphosphoramidite (0.401 ml), and the mixture was stirred at room temperature for 2 hr. The reaction solution was ice-cooled, a decane solution containing t-butyl hydroperoxide (5-6M, 0.402 ml) was added and the mixture was stirred at room temperature for 30 min. A saturated aqueous sodium hydrogencarbonate solution was added to the reaction mixture, and the mixture was extracted with chloroform. The organic layer was dried over anhydrous magnesium sulfate. The solvent was evaporated under reduced pressure. The obtained residue was purified by silica gel column chromatography (hexane:ethyl acetate=1:1-1:2) to give the object product (530 mg) as a colorless oil.
$^1$H-NMR (CDCl$_3$) δ (ppm): 0.89 (3H, t, J=6.8 Hz), 1.29-1.40 (6H, m), 1.41-1.50 (2H, m), 1.43 (9H, s), 1.49 (18H, s), 1.75-1.81 (2H, m), 1.90-2.01 (2H, m), 2.10-2.25 (2H, m), 2.61 (2H, t, J=8.6 Hz), 4.03 (2H, t, J=6.2 Hz), 4.04-4.18 (2H, m), 4.55 (1H, dt, J=47, 5.8 Hz), 4.66 (1H, dt, J=47, 5.8 Hz), 7.37 (1H, d, J=8.4 Hz), 7.34-7.37 (2H, m).

(23-2) Synthesis of Phosphoric Acid mono[2-amino-2-(2-fluoroethyl)-4-(4-heptyloxy-3-trifluoromethylphenyl)butyl]ester (Compound 23-2)

Compound 23-1 (530 mg) was dissolved in methylene chloride (5 ml), dioxane containing hydrogen chloride (4 mol/l, 2 ml) was added, and the mixture was stirred at room temperature for 3.5 hr. The solvent was concentrated under reduced pressure, and methanol (3 ml), diethyl ether (7 ml) and propyleneoxide (7 ml) were added to the residue. The precipitated powder was collected by filtration and washed with ethyl acetate and diethyl ether to give the object product (182 mg) as a white solid.
MS (ESI) m/z: 474[M+H]
$^1$H-NMR (CD$_3$OD) δ (ppm): 0.91 (3H, t, J=6.4 Hz), 1.29-1.44 (6H, m), 1.45-1.52 (2H, m), 1.73-1.82 (2H, m), 1.92-2.10 (2H, m), 2.12-2.20 (1H, m), 2.21-2.26 (1H, m), 2.60-

2.79 (2H, m), 3.99 (2H, d, J=5.6 Hz), 4.05 (2H, t, J=6.2 Hz), 4.68 (1H, t, J=5.4 Hz), 4.79-4.81 (1H, m), 7.07 (1H, d, J=8.3 Hz), 7.41-7.44 (2H, m).

Example 24

2-Amino-2-[2-(4-heptylthio-3-trifluoromethylphenyl)ethyl]propane-1,3-diol Hydrochloride (24-1) Synthesis of [1,1-bis(hydroxymethyl)-3-(4-heptylthio-3-trifluoromethylphenyl)propyl]carbamic Acid t-butyl Ester (Compound 24-1)

To a solution of compound 1-1 (1.00 g) in methylene chloride (30 ml) were added under ice-cooling triethylamine (0.503 ml), anhydrous trifluoromethanesulfonic acid (0.607 ml), the mixture was stirred for 1 hr under ice-cooling. Water was added to the reaction mixture, and the mixture was extracted with methylene chloride, washed with water and saturated brine, and dried over anhydrous sodium sulfate. The solvent was evaporated under reduced pressure. The obtained residue was purified by silica gel column chromatography (hexane:ethyl acetate=1:2-1:4) to give acetonide deprotected compound with the protected phenolic hydroxyl group by a triflate (500 mg) as a colorless oil. Diisopropylamine (0.377 ml), heptanethiol (0.204 ml), 4,5-bis(diphenylphosphino)-9,9-dimethylxanthene (Xantphos) (31 mg) and tris(dibenzylideneacetone)palladium(0)-chloroform adduct (27 mg) were added to a solution of the colorless oil in dioxane (10 ml), and the mixture was stirred at 120° C. for 4 hr. Water was added to the reaction mixture, and the mixture was extracted with ethyl acetate, washed with saturated brine, and dried over anhydrous magnesium sulfate. The solvent was evaporated under reduced pressure. The obtained residue was purified by silica gel column chromatography (hexane:ethyl acetate=1:2-1:3) to give the object product (390 mg) as a pale-yellow oil.

$^1$H-NMR (CDCl$_3$) δ (ppm): 0.88 (3H, t, J=6.8 Hz), 1.23-1.38 (6H, m), 1.39-1.50 (2H, m), 1.46 (9H, s), 1.60-1.68 (2H, m), 1.86-1.91 (2H, m), 2.61-2.66 (2H, m), 2.92 (2H, t, J=7.4 Hz), 3.20 (2H, brs), 3.63-3.68 (2H, m), 3.85-3.90 (2H, m), 5.05 (1H, brs), 7.25-7.30 (1H, m), 7.39 (1H, d, J=8.0 Hz), 7.45 (1H, brs).

(24-2) Synthesis of 2-amino-2-[2-(4-heptylthio-3-trifluoromethylphenyl)ethyl]propane-1,3-diol Hydrochloride (Compound 24-2)

Compound 24-1 (390 mg) was dissolved in methylene chloride (5 ml), dioxane containing hydrogen chloride (4 mol/l, 5 ml) was added, and the mixture was stirred at room temperature for 4 hr. The reaction mixture was concentrated, and the residue was washed with diethyl ether to give a white powder. The white powder was purified by preparative HPLC, ether containing hydrogen chloride (1 mol/l, 15 ml) was added to the obtained residue to give a hydrochloride. The precipitate was collected by filtration and dried to give the object product (200 mg) as a white powder.

MS (ESI) m/z: 394[M+H]

$^1$H-NMR (DMSO-d$_6$) δ (ppm): 0.84 (3H, t, J=6.8 Hz), 1.19-1.31 (6H, m), 1.32-1.42 (2H, m), 1.51-1.60 (2H, m), 1.75-1.80 (2H, m), 2.63-2.68 (2H, m), 3.02 (2H, t, J=7.2 Hz), 3.52 (4H, d, J=4.0 Hz), 5.36 (2H, brs), 7.47 (1H, d, J=8.4 Hz), 7.56-7.59 (2H, m), 7.74 (3H, brs).

Example 25

2-Amino-2-[2-(4-octylthio-3-trifluoromethylphenyl)ethyl]propane-1,3-diol Hydrochloride (25-1) Synthesis of {2,2-dimethyl-5-[2-(4-octylthio-3-trifluoromethylphenyl)ethyl]-1,3-dioxan-5-yl}carbamic Acid t-butyl Ester (Compound 25-1)

To a solution of compound 1-1 (1.00 g) in methylene chloride (30 ml) was added pyridine (0.926 ml), a solution of anhydrous trifluoromethanesulfonic acid (0.480 ml) in methylene chloride (5 ml) was added dropwise under ice-cooling and the mixture was stirred for 2.5 hr under ice-cooling. A saturated aqueous sodium hydrogencarbonate solution was added to the reaction mixture, and the mixture was extracted with methylene chloride, washed with saturated brine, and dried over anhydrous sodium sulfate. The solvent was evaporated under reduced pressure. The obtained residue was purified by silica gel column chromatography (hexane:ethyl acetate=3:1-2:1) to give a compound (970 mg), wherein the phenolic hydroxyl group is protected by triflate, as a white solid. To a solution of the white solid in dioxane (20 ml) were added diisopropylamine (0.631 ml), octanethiol (0.375 ml) 4,5-bis(diphenylphosphino)-9,9-dimethylxanthene (Xantphos) (53 mg) and tris(dibenzylideneacetone)palladium(0)-chloroform adduct (46 mg), and the mixture was stirred at 120° C. for 2 days. Further, diisopropylamine (0.631 ml), octanethiol (0.375 ml), 4,5-bis(diphenylphosphino)-9,9-dimethylxanthene (Xantphos) (53 mg) and tris(dibenzylideneacetone)palladium(0)-chloroform adduct (46 mg) were added to the reaction solution and the mixture was stirred at 120° C. for 1 day. Water was added to the reaction mixture, and the mixture was extracted with ethyl acetate, washed with saturated brine, and dried over anhydrous magnesium sulfate. The solvent was evaporated under reduced pressure. The obtained residue was purified by silica gel column chromatography (hexane:ethyl acetate=5:1-2:1) to give the object product (910 mg) as a pale-yellow solid.

$^1$H-NMR (CDCl$_3$) δ (ppm): 0.88 (3H, t, J=6.8 Hz), 1.24-1.36 (8H, m), 1.42-1.50 (2H, m), 1.43 (3H, s), 1.44 (3H, s), 1.47 (9H, s), 1.60-1.70 (2H, m), 1.96-2.00 (2H, m), 2.55-2.60 (2H, m), 2.91 (2H, t, J=7.4 Hz), 3.69 (2H, d, J=11.7 Hz), 3.89 (2H, d, J=11.7 Hz), 4.98 (1H, brs), 7.25-7.29 (1H, m), 7.38 (1H, d, J=8.2 Hz), 7.44 (1H, d, J=1.0 Hz).

(25-2) Synthesis of 2-amino-2-[2-(4-octylthio-3-trifluoromethylphenyl)ethyl]propane-1,3-diol Hydrochloride (Compound 25-2)

Compound 25-1 (910 mg) was dissolved in ethanol (20 ml), concentrated hydrochloric acid (2 ml) was added, and the mixture was stirred at 80° C. for 2 hr. The reaction mixture was concentrated, and the residue was washed with diethyl ether to give the object product (630 mg) as a white powder.

MS (ESI) m/z: 408[M+H]

$^1$H-NMR (DMSO-d$_6$) δ (ppm): 0.85 (3H, t, J=6.8 Hz), 1.19-1.32 (8H, m), 1.33-1.43 (2H, m), 1.51-1.60 (2H, m), 1.76-1.81 (2-H, m), 2.64-2.69 (2H, m), 3.02 (2H, t, J=7.2 Hz), 3.52 (4H, d, J=4.8 Hz), 5.38 (2H, t, J=5.0 Hz), 7.47 (1H, d, J=8.3 Hz), 7.56-7.59 (2H, m), 7.83 (3H, brs).

Example 26

2-Amino-4-(4-octylthio-3-trifluoromethylphenyl)-2-(phosphoryloxymethyl)butanol

(26-1) Synthesis of [1-hydroxymethyl-3-(4-octylthio-3-trifluoromethylphenyl)-1-(methoxymethoxy)methyl]propylcarbamic Acid t-butyl Ester (Compound 26-1)

Compound 25-2 (560 mg) was dissolved in methanol (10 ml), triethylamine (0.531 ml) and di-t-butyl dicarbonate (412 mg) were added, and the mixture was stirred at room temperature for 12 hr. Further, di-t-butyl dicarbonate (300 mg) was added to the reaction mixture and the mixture was stirred at room temperature for 12 hr. Water was added and the mixture was extracted with ethyl acetate. The organic layer was washed with saturated brine, and dried over anhydrous magnesium sulfate. The solvent was evaporated under reduced pressure to give a pale-yellow oil. To a solution of the oil in methylene chloride (20 ml) were added N,N-diisopropylethylamine (0.285 ml) and methoxymethyl chloride (0.121 ml) under ice-cooling, and the mixture was stirred for 10 min under ice-cooling and further at room temperature for 14 hr. Water was added to the reaction mixture, and the mixture was extracted with methylene chloride. The organic layer was washed with saturated brine, and dried over anhydrous magnesium sulfate. The solvent was evaporated under reduced pressure. The obtained residue was purified by silica gel chromatography to give the object product (290 mg) and [1,1-bis(hydroxymethyl)-3-(4-octylthio-3-trifluoromethylphenyl)]propylcarbamic acid t-butyl ester (280 mg) each as a colorless oil. To a solution of [1,1-bis(hydroxymethyl)-3-(4-octylthio-3-trifluoromethylphenyl)]propylcarbamic acid t-butyl ester recovered above in methylene chloride (15 ml) were added N,N-diisopropylethylamine (0.129 ml) and methoxymethyl chloride (0.063 ml) under ice-cooling, and the mixture was stirred for 5 min under ice-cooling and further at room temperature for 14 hr. Water was added to the reaction mixture, and the mixture was extracted with methylene chloride. The organic layer was washed with saturated brine, and dried over anhydrous magnesium sulfate. The solvent was evaporated under reduced pressure. The obtained residue was purified by silica gel chromatography to give the object product (210 mg) as a colorless oil. The total weight of the object product including the object product obtained by the first reaction was 500 mg.

$^1$H-NMR (CDCl$_3$) δ (ppm): 0.87 (3H, t, J=6.8 Hz), 1.25-1.38 (8H, m), 1.39-1.49 (2H, m), 1.45 (9H, s), 1.59-1.70 (2H, m), 1.85-1.93 (1H, m), 2.04-2.12 (1H, m), 2.54-2.64 (1H, m), 2.66-2.76 (1H, m), 2.91 (2H, t, 7.4 Hz), 3.39 (3H, s), 3.51 (1H, d, J=9.6 Hz), 3.70-3.79 (3H, m), 3.94 (1H, brs), 4.65 (2H, s), 5.17 (1H, brs), 7.27-7.30 (1H, m), 7.39 (1H, d, J=8.1 Hz), 7.45 (1H, d, J=1.3 Hz).

(26-2) Synthesis of [1-dimethylphosphoryloxymethyl-3-(4-octylthio-3-trifluoromethylphenyl)-1-(methoxymethoxy)methylpropyl]carbamic Acid t-butyl Ester (Compound 26-2)

To a solution of compound 26-1 (500 mg) in methylene chloride (3 ml) were added pyridine (2 ml), carbon tetrabromide (334 mg) and trimethyl phosphite (0.161 ml), and the mixture was stirred at room temperature for 4.5 hr. Further, trimethyl phosphite (0.080 ml) was added to the reaction mixture, and the mixture was stirred at room temperature for 2.5 hr. Water was added to the reaction mixture, and the mixture was extracted with chloroform. The organic layer was washed with water and saturated brine, and dried over anhydrous magnesium sulfate. The solvent was evaporated under reduced pressure. The obtained residue was purified by silica gel column chromatography (hexane:ethyl acetate=1:3-1:4) to give the object product (490 mg) as a brown oil.

$^1$H-NMR (CD$_3$OD) δ (ppm): 0.89 (3H, t, J=6.7 Hz), 1.26-1.38 (8H, m), 1.39-1.51 (2H, m), 1.45 (9H, s), 1.55-1.68 (2H, m), 1.88-1.97 (1H, m), 2.05-2.16 (1H, m), 2.68 (2H, t, J=8.5 Hz), 2.96 (2H, t, J=7.3 Hz), 3.60 (1H, d, J=9.7 Hz), 3.69 (1H, d, J=9.7 Hz), 3.77 (3H, s), 3.80 (3H, s), 4.14-4.18 (1H, m), 4.30-4.34 (1H, m), 4.64 (2H, s), 7.37-7.39 (1H, m), 7.49-7.52 (2H, m).

(26-3) Synthesis of 2-amino-4-(4-octylthio-3-trifluoromethylphenyl)-2-(phosphoryloxymethyl)butanol (Compound 26-3)

Compound 26-2 (490 mg) was dissolved in ethanol (5 ml), concentrated hydrochloric acid (1 ml) was added, and the mixture was stirred at 50° C. for 2 hr. The solvent was concentrated under reduced pressure. To a solution of the residue in methylene chloride (7 ml) was added trimethylsilyl iodide (0.527 ml) under ice-cooling, and the mixture was stirred under ice-cooling for 1 hr. The solvent was concentrated under reduced pressure to half, and acetonitrile (15 ml) was added. Precipitated powder was collected by filtration, washed with acetonitrile and diethyl ether to give the object product (245 mg) as a pale-yellow solid.

MS (ESI) m/z: 488[M+H]

$^1$H-NMR (CD$_3$OD) δ (ppm): 0.89 (3H, t, J=6.8 Hz), 1.24-1.38 (8H, m), 1.39-1.50 (2H, m), 1.56-1.68 (2H, m), 1.95-2.01 (2H, m), 2.68-2.80 (2H, m), 2.97 (2H, t, J=7.3 Hz), 3.71 (2H, brs), 3.98-4.04 (2H, m), 7.46 (1H, d, J=8.0 Hz), 7.53 (1H, d, J=8.2 Hz), 7.57 (1H, brs).

Example 27

2-Amino-2-[2-(4-hexylthio-3-trifluoromethylphenyl)ethyl]propane-1,3-diol Hydrochloride

(27-1) Synthesis of {2,2-dimethyl-5-[2-(4-hexylthio-3-trifluoromethylphenyl)ethyl]-1,3-dioxan-5-yl}carbamic Acid t-butyl Ester (Compound 27-1)

To a solution of compound 1-1 (1.00 g) in methylene chloride (30 ml) was added pyridine (0.926 ml) under ice-cooling, a solution of anhydrous trifluoromethanesulfonic acid (0.480 ml) in methylene chloride (5 ml) was added dropwise, and the mixture was stirred for 2.5 hr under ice-cooling. A saturated aqueous sodium hydrogencarbonate solution was added to the reaction mixture, and the mixture was extracted with methylene chloride, washed with saturated brine, and dried over anhydrous sodium sulfate. The solvent was evaporated under reduced pressure. The obtained residue was purified by silica gel column chromatography (hexane:ethyl acetate=3:1-2:1) to give a compound (980 mg), wherein the phenolic hydroxyl group is protected by triflate, as a white solid. To a solution of the white solid in dioxane (20 ml) were added diisopropylamine (0.638 ml), hexanethiol (0.301 ml), 4,5-bis(diphenylphosphino)-9,9-dimethylxanthene (Xantphos) (53 mg) and tris(dibenzylideneacetone)palladium(0)-chloroform adduct (46 mg), and the mixture was stirred at 120° C. for 2 days. Further, diisopropylamine (0.631 ml), octanethiol (0.375 ml), 4,5-bis(diphenylphosphino)-9,9-dimethylxanthene (Xantphos) (53 mg) and tris(dibenzylideneacetone)palladium(0)-chloroform adduct (46 mg) were added to the reaction solution, and the mixture was stirred at 120° C. for 1 day. Water was added to the reaction mixture, and the mixture was extracted with ethyl acetate, washed with saturated brine, and dried over anhydrous magnesium sulfate. The solvent was evaporated under reduced pressure, and the obtained residue was purified by silica gel column chromatography (hexane: ethyl acetate=5:1-3:1) to give {2,2-di-methyl-5-[2-(4-hexylthio-3-trifluoromethylphenyl)ethyl]-1,3-dioxan-5-yl}carbamic acid t-butyl ester as a pale-yellow solid. The pale-yellow solid obtained above was dissolved in ethanol (15 ml), concentrated hydrochloric acid (1.5 ml) was added, and the mixture was stirred at 80° C. for 2 hr. The reaction mixture was concentrated and the residue was washed with diethyl ether to give a white solid. The white solid was purified by preparative HPLC, ether containing hydrogen chloride (1 mol/l, 15 ml) was added to the obtained residue to give a hydrochloride salt. The precipitate was collected by filtration, and dried to give the object product (132 mg) as a white powder.

MS (ESI) m/z: 380[M+H]
$^1$H-NMR (DMSO-d$_6$) δ (ppm): 0.85 (3H, t, J=6.6 Hz), 1.20-1.31 (4H, m), 1.32-1.43 (2H, m), 1.51-1.60 (2H, m), 1.75-1.81 (2H, m), 2.63-2.69 (2H, m), 3.03 (2H, t, J=7.2 Hz), 3.52 (4H, d, J=5.0 Hz), 5.41 (2H, t, J=5.1 Hz), 7.47 (1H, d, J=8.7 Hz), 7.57-7.59 (2H, m), 7.84 (3H, brs).

Example 28

(E)-2-amino-2-[2-(4-heptyloxy-3-trifluoromethylphenyl)vinyl]propane-1,3-diol (28-1) Synthesis of 4-heptyloxy-3-trifluoromethylbenzoic Acid (Compound 28-1)

To a suspension of potassium t-butoxide (20.7 g) in N,N-dimethylformamide (120 ml) was added n-heptanol (15.6 ml), and the mixture was stirred at room temperature for 30 min. A solution of 4-fluoro-3-trifluoromethylbenzoic acid (16.7 g) in N,N-dimethylformamide (60 ml) was added dropwise to the reaction mixture at 0° C., and the mixture was stirred at 70° C. for 1 hr. The reaction mixture was ice-cooled, water (320 ml) was added, and 6M-hydrochloric acid (40 ml) was added at room temperature. The mixture was stirred at room temperature for 30 min and precipitated crystals were collected by filtration. The crystals were dissolved in ethanol (60 ml) at 70° C., water (96 ml) was added dropwise at the same temperature and the mixture was stirred for 30 min. The mixture was allowed to cool to room temperature, and stirred for 30 min under ice-cooling. The precipitated crystals were collected by filtration to give the object product (24.1 g) as pale-brown crystals.

$^1$H-NMR (CDCl$_3$) δ (ppm): 0.90 (3H, t, J=6.6 Hz), 1.28-1.49 (8H, m), 1.80-1.90 (2H, m), 4.13 (2H, t, J=6.3 Hz), 7.04 (1H, d, J=8.7 Hz), 8.24 (1H, dd, J=2.1 Hz, 9.0 Hz), 8.33 (1H, d, J=1.8 Hz).

(28-2) Synthesis of 4-heptyloxy-3-trifluoromethylbenzyl Alcohol (Compound 28-2)

To a solution of compound 28-1 (30.0 g) in N,N-dimethylformamide (240 ml) was added dropwise a solution of bis(2-methoxyethoxy)aluminum hydride/toluene solution (65 wt %) (20.0 g) in toluene (80 ml) at 0° C. under a nitrogen atmosphere, and a solution of bis(2-methoxyethoxy)aluminum hydride/toluene solution (65 wt %) (80.0 g) in toluene (80 ml) was added dropwise. The mixture was stirred at room temperature for 2 hr and ice-cooled. 5N-aqueous sodium hydroxide solution (200 ml) was added dropwise, and the mixture was stirred at room temperature for 30 min. The organic layer was partitioned and extracted, washed with 5N-aqueous sodium hydroxide solution (100 ml), and dried over anhydrous magnesium sulfate. The solvent was evaporated under reduced pressure to give the object product (28.3 g) as white crystals.

$^1$H-NMR (CDCl$_3$) δ (ppm): 0.89 (3H, t, J=6.6 Hz), 1.26-1.56 (8H, m), 1.65 (1H, t, J=5.7 Hz), 1.77-1.85 (2H, m), 4.04 (2H, t, J=6.3 Hz), 4.65 (2H, d, J=5.7 Hz), 6.97 (1H, d, J=8.4 Hz), 7.47 (1H, dd, J=1.5 Hz, 8.4 Hz), 7.57 (1H, d, J=1.8 Hz).

(28-3) Synthesis of 4-heptyloxy-3-trifluoromethylbenzyl Chloride (Compound 28-3)

To a solution of compound 28-2 (26.8 g) in methylene chloride (107 ml) was added several drops of N,N-dimethylformamide, and thionyl chloride (8.09 ml) was added dropwise at 0° C. The mixture was stirred at the same temperature for 2 hr, and water (50 ml) was added to the reaction mixture. The organic layer was partitioned and extracted, washed with water (50 ml) and saturated aqueous sodium hydrogencarbonate (70 ml), and dried over anhydrous magnesium sulfate. The solvent was evaporated under reduced pressure to give the object product (28.3 g) as white crystals.

$^1$H-NMR (CDCl$_3$) δ (ppm): 0.89 (3H, t, J=6.5 Hz), 1.26-1.54 (8H, m), 1.77-1.86 (2H, m), 4.04 (2H, t, J=6.4 Hz), 4.56 (2H, s), 6.96 (1H, d, J=8.6 Hz), 7.49 (1H, dd, J=2.0 Hz, 8.5 Hz), 7.58 (1H, d, J=1.9 Hz).

(28-4) Synthesis of Diethyl (4-heptyloxy-3-trifluoromethylbenzyl)phosphonate (Compound 28-4)

A solution of compound 28-3 (27.3 g) in triethyl phosphite (29.3 g) was heated under reflux for 4 hr under a nitrogen atmosphere. The triethyl phosphite was evaporated under reduced pressure to give the object product (36.1 g) as a pale-yellow oil.

$^1$H-NMR (CDCl$_3$) δ (ppm): 0.89 (3H, t, J=6.6 Hz), 1.23-1.54 (14H, m), 1.77-1.86 (2H, m), 3.10 (2H, d, J=21.3 Hz), 3.98-4.08 (4H, m), 6.93 (1H, d, J=8.4 Hz), 7.42 (1H, dd, J=2.4 Hz, 8.4 Hz), 7.45 (1H, d, J=2.1 Hz).

(28-5) Synthesis of (E)-{2,2-dimethyl-5-[2-(4-heptyloxy-3-trifluoromethylphenyl)vinyl]-1,3-dioxan-5-yl}carbamic Acid t-butyl Ester (Compound 28-5)

To a solution of potassium t-butoxide (24.9 g) in tetrahydrofuran (177 ml) were added dropwise under ice-cooling a solution of Reference Example compound 1-2 (28.8 g) and compound 28-4 (35.1 g) in tetrahydrofuran (203 ml), and the mixture was stirred at 0° C. for 5 hr. Heptane (203 ml) and then water (203 ml) were added to the reaction mixture. The organic layer was partitioned and extracted, washed with water, and dried over anhydrous magnesium sulfate. The solvent was evaporated under reduced pressure. The residue was suspended in hexane (50 ml) and collected by filtration to give the object product (32.6 g) as white crystals.

$^1$H-NMR (CDCl$_3$) δ (ppm): 0.89 (3H, t, J=6.6 Hz), 1.30-1.57 (8H, m), 1.44 (9H, s), 1.47 (3H, s), 1.49 (3H, s), 1.76-1.84 (2H, m), 3.90 (2H, d, J=11.4 Hz), 3.94 (2H, d, J=13.8 Hz), 4.03 (2H, t, J=6.3 Hz), 5.21 (1H, brs), 6.10 (1H, d, J=16.5

Hz), 6.48 (1H, d, J=16.5 Hz), 6.91 (1H, d, J=8.4 Hz), 7.43-7.46 (1H, m), 7.55 (1H, d, J=1.8 Hz).

(28-6) Synthesis of (E)-2-amino-2-[2-(4-heptyloxy-3-trifluoromethylphenyl)vinyl]propane-1,3-diol Hydrochloride (Compound 28-6)

Compound 28-5 (500 mg) was dissolved in ethanol (15 ml), concentrated hydrochloric acid (1.5 ml) was added, and the mixture was stirred at 80° C. for 1.5 hr. The reaction mixture was concentrated, and the residue was washed with diethyl ether to give the object product (330 mg) as a white powder.
MS (ESI) m/z: 359
$^1$H-NMR (DMSO-$d_6$) δ (ppm): 0.86 (3H, t, J=6.8 Hz), 1.25-1.39 (6H, m), 1.40-1.46 (2H, m), 1.69-1.77 (2H, m), 3.59-3.67 (4H, m), 4.11 (2H, t, J=6.2 Hz), 5.48 (2H, t, J=5.3 Hz), 6.24 (1H, d, J=16.8 Hz), 6.71 (1H, d, J=16.8 Hz), 7.27 (1H, d, J=9.3 Hz), 7.25-7.28 (2H, m), 8.12 (3H, brs).

Example 29

(E)-2-amino-4-(4-heptyloxy-3-trifluoromethylphenyl)-2-(phosphoryloxymethyl)-3-buten-1-ol (29-1) Synthesis of (E)-{4-di(t-butyl)phosphoryloxymethyl-2-methyl-4-[2-(4-heptyloxy-3-trifluoromethylphenyl)ethenyl]-2-oxazoline} (Compound 29-1)

To a solution of compound 28-6 (280 mg) in N,N-dimethylformamide (10 ml) were added N,N-diisopropylethylamine (0.366 ml) and trimethyl orthoacetate (0.129 ml), and the mixture was stirred at 120° C. for 5 hr. Water was added to the reaction mixture, the mixture was extracted with ethyl acetate, and the extract was washed with water and saturated brine, and dried over anhydrous magnesium sulfate. The solvent was evaporated under reduced pressure to give 270 mg of a brown oil. To a solution of the brown oil (270 mg) in methylene chloride (5 ml) and acetonitrile (2 ml) were added 1H-tetrazole (95 mg) and di-t-butyl diethylphosphoramidite (0.407 ml), and the mixture was stirred at room temperature for 2 hr. The reaction solution was ice-cooled, a decane solution containing t-butyl hydroperoxide (5-6M, 0.408 ml) was added, and the mixture was stirred at room temperature for 30 min. Saturated aqueous sodium hydrogencarbonate solution was added to the reaction mixture, and the mixture was extracted with chloroform. The organic layer was dried over anhydrous magnesium sulfate, and the solvent was evaporated under reduced pressure. The obtained residue was purified by silica gel column chromatography (hexane:ethyl acetate=1:3-ethyl acetate alone) to give the object product (200 mg) as a yellow oil.
$^1$H-NMR (CD$_3$OD) δ (ppm): 0.90 (3H, t, J=6.9 Hz), 1.29-1.45 (6H, m), 1.47-1.53 (2H, m), 1.49 (9H, s), 1.50 (9H, s), 1.75-1.83 (2H, m), 2.05 (3H, s), 3.94-3.98 (1H, m), 4.00-4.05 (1H, m), 4.08 (2H, t, J=6.2 Hz), 4.23 (1H, d, J=8.7 Hz), 4.50 (1H, d, J=8.7 Hz), 6.30 (1H, d, J=16.2 Hz), 6.64 (1H, d, J=16.2 Hz), 7.11 (1H, d, J=8.4 Hz), 7.59-7.62 (2H, m).

(29-2) E-[2-amino-4-(4-heptyloxy-3-trifluoromethylphenyl)-2'-(phosphoryloxymethyl)-3-buten-1-ol] (Compound 29-2)

Compound 29-1 (200 mg) was dissolved in ethanol (5 ml), concentrated hydrochloric acid (1 ml) was added, and the mixture was stirred at 50° C. for 3 hr. The solvent was concentrated under reduced pressure, and methanol (3 ml), diethyl ether (3 ml) and propylene oxide (5 ml) were added to the residue. The precipitated powder was collected by filtration, and washed with ethyl acetate and diethyl ether to give the object product (45 mg) as a white solid.
MS (ESI) m/z: 456[M+H]
$^1$H-NMR (CD$_3$OD) δ (ppm): 0.91 (3H, t, J=6.9 Hz), 1.27-1.47 (6H, m), 1.45-1.54 (2H, m), 1.76-1.83 (2H, m), 3.75 (1H, d, J=11.6 Hz), 3.83 (1H, d, J=11.6 Hz), 3.98-4.04 (1H, m), 4.07-4.15 (1H, m), 4.09 (2H, t, J=6.3 Hz), 6.22 (1H, d, J=16.7 Hz), 6.76 (1H, d, J=16.7 Hz), 7.14 (1H, d, J=9.3 Hz), 7.65-7.67 (2H, m).

Example 30

2-Amino-2-[2-(3-difluoromethyl-4-heptyloxyphenyl)ethyl]propane-1,3-diol Hydrochloride (30-1) Synthesis of 2-benzyloxy-5-bromobenzaldehyde (Compound 30-1)

To a suspension of 5-bromosalicylaldehyde (25.0 g) and potassium carbonate (51.4 g) in N,N-dimethylformamide (250 ml) was added benzyl bromide (15.4 ml) under ice-cooling, and the mixture was stirred for 40 min under ice-cooling, and further at room temperature for 15 hr. Water was added to the reaction mixture, the mixture was extracted with ethyl acetate, and the extract was washed successively with 0.1M aqueous sodium hydroxide solution and saturated brine, and dried over anhydrous magnesium sulfate. The solvent was evaporated under reduced pressure and the obtained residue was suspended in hexane (200 ml) and collected by filtration to give the object product (32.7 g) as a pale-yellow powder.
$^1$H-NMR (CDCl$_3$) δ (ppm): 5.19 (2H, s), 6.95 (1H, d, J=8.8 Hz), 7.34-7.43 (5H, m), 7.61 (1H, dd, J=2.8, 8.8 Hz), 7.95 (1H, d, J=2.8 Hz), 10.46 (1H, s).

(30-2) Synthesis of 1-benzyloxy-4-bromo-2-difluoromethylbenzene (Compound 30-2)

To a solution of compound 30-1 (2.70 g) in methylene chloride (5 ml) was added a solution of (diethylamino)sulfur trifluoride (DAST, 1.66 g) in methylene chloride (5 ml), and the mixture was stirred at room temperature for 21 hr. Water was added to the reaction mixture, and the mixture was extracted with methylene chloride. The organic layer was washed with saturated brine, and dried over anhydrous magnesium sulfate. The solvent was evaporated under reduced pressure and the obtained residue was purified by silica gel chromatography to give the object product (2.16 g) as a colorless oil.
$^1$H-NMR (CDCl$_3$) δ (ppm): 5.11 (2H, s), 6.86 (1H, d, J=9.1 Hz), 6.95 (1H, t, J=55.3 Hz), 7.33-7.42 (5H, m), 7.49 (1H, dd, J=1.6, 9.8 Hz), 7.69 (1H, d, J=1.9 Hz).

(30-3) Synthesis of {5-[(4-benzyloxy-3-difluoromethylphenyl)ethynyl]-2,2-dimethyl-1,3-dioxan-5-yl}carbamic Acid t-butyl Ester (Compound 30-3)

Compound 30-2 (9.48 g), (2,2-dimethyl-5-ethynyl-1,3-dioxan-5-yl)carbamic acid t-butyl ester (7.34 g) synthesized by a known method (for example, Tetrahedron vol. 57 (2001) 6531-6538), 2-dicyclohexylphosphino-2',4',6'-triisopropylbiphenyl (868 mg), bis(acetonitrile)palladium(II) dichloride (157 mg) and cesium carbonate (25.6 g) in acetonitrile (200 ml) were stirred at 80° C. for 8 hr. Water was added to the reaction mixture, the mixture was extracted with ethyl acetate, and the extract was washed with saturated brine, and dried over anhydrous sodium sulfate. The solvent was evaporated under reduced pressure. The residue was purified by silica gel column chromatography to give the object product (11.1 g) as a pale-brown oil.

$^1$H-NMR (CDCl$_3$) δ (ppm): 1.45 (3H, s), 1.48 (9H, s), 1.50 (3H, s), 4.03 (2H, d, J=11.2 Hz), 4.10 (2H, d, J=11.2 Hz), 5.13 (2H, s), 5.20 (1H, brs), 6.91 (1H, d, J=8.6 Hz), 6.94 (1H, t, J=55.4 Hz), 7.33-7.40 (5H, m), 7.46 (1H, d, J=8.6 Hz), 7.65 (1H, s)

(30-4) Synthesis of {5-[2-(3-difluoromethyl-4-hydroxyphenyl)ethyl]-2,2-dimethyl-1,3-dioxan-5-yl}carbamic Acid t-butyl Ester (Compound 30-4)

Compound 30-3 (11.1 g) was dissolved in 1,4-dioxane (250 ml), 10% palladium carbon (3.5 g) was added, and the mixture was stirred at room temperature for 3.5 hr under a hydrogen atmosphere. The inside of the reaction container was displaced with nitrogen, the solution was filtrated, and the filtrate was concentrated. The residue was suspended in a mixed solution of diisopropyl ether and hexane, and collected by filtration to give the object product (8.17 g) as a white powder.

$^1$H-NMR (CDCl$_3$) (ppm): 1.43 (3H, s), 1.44 (3H, s), 1.48 (9H, s), 1.92-1.96 (2H, m), 2.50-2.54 (2H, m), 3.69 (2H, d, J=11.7 Hz), 3.89 (2H, d, J=11.7 Hz), 5.03 (1H, brs), 5.57 (1H, brs), 6.77 (1H, d, J=8.4 Hz), 6.84 (1H, t, J=55.5 Hz), 7.12 (1H, d, J=8.4 Hz), 7.23 (1H, s).

(30-5) Synthesis of 2-amino-2-[2-(3-difluoromethyl-4-heptyloxyphenyl)ethyl]propane-1,3-diol Hydrochloride (Compound 30-5)

Compound 30-4 (500 mg) was dissolved in N,N-dimethylformamide (10 ml), potassium carbonate (516 mg) and n-heptyl bromide (0.240 ml) were added, and the mixture was stirred at room temperature for 15 hr. Water was added to the reaction mixture, the mixture was extracted with ethyl acetate, and the extract was washed with water and saturated brine, and dried over anhydrous magnesium sulfate. The solvent was evaporated under reduced pressure to give 620 mg of a colorless oil. The colorless oil was dissolved in ethanol (15 ml), concentrated hydrochloric acid (1.5 ml) was added, and the mixture was stirred at 80° C. for 1 hr. The reaction mixture was concentrated, and the residue was washed with diethyl ether to give a white powder. The white powder was purified by preparative HPLC, ether containing hydrogen chloride (1 mol/l, 15 ml) was added to the obtained residue to give hydrochloride. The precipitate was collected by filtration, and dried to give the object product (160 mg) as a white powder.

MS (ESI) m/z: 360[M+H]

$^1$H-NMR (DMSO-d$_6$) δ (ppm): 0.87 (3H, t, J=6.8 Hz), 1.25-1.37 (6H, m), 1.38-1.45 (2H, m), 1.68-1.79 (4H, m), 2.56-2.62 (2H, m), 3.52 (4H, d, J=4.0 Hz), 4.02 (2H, t, J=6.4 Hz), 5.40 (2H, t, J=4.5 Hz), 7.05 (1H, t, J=55.4 Hz), 7.07 (1H, d, J=8.6 Hz), 7.32 (1H, d, J=8.6 Hz), 7.36 (1H, s), 7.80 (3H, brs).

Example 31

2-Amino-4-(3-difluoromethyl-4-heptyloxyphenyl)-2-(phosphoryloxymethyl)butanol

(31-1) Synthesis of 4-di(t-butyl)phosphoryloxymethyl-2-methyl-4-[2-(3-difluoromethyl-4-heptyloxyphenyl)ethyl]-2-oxazoline (Compound 31-1)

To a solution of compound 30-5 (115 mg) in N,N-dimethylformamide (5 ml) were added N,N-diisopropylethylamine (0.156 ml) and trimethyl orthoacetate (0.055 ml), and the mixture was stirred at 120° C. for 12.5 hr. To the reaction mixture were added N,N-diisopropylethylamine (0.156 ml) and trimethyl orthoacetate (0.055 ml) again, and the mixture was stirred at 120° C. for 3.5 hr. Water was added to the reaction mixture, the mixture was extracted with ethyl acetate, and the extract was washed with water and saturated brine, and dried over anhydrous magnesium sulfate. The solvent was evaporated under reduced pressure to give 140 mg of a brown oil. To a solution of the brown oil (140 mg) in methylene chloride (3 ml) and acetonitrile (1 ml) were added 1H-tetrazole (41 mg) and di-t-butyl diethylphosphoramidite (0.174 ml), and the mixture was stirred at room temperature for 2 hr. The reaction solution was ice-cooled, a decane solution containing t-butyl hydroperoxide (5-6M, 0.174 ml) was added, and the mixture was stirred at room temperature for 20 min. Saturated aqueous sodium hydrogencarbonate solution was added to the reaction mixture, and the mixture was extracted with chloroform. The organic layer was dried over anhydrous magnesium sulfate, and the solvent was evaporated under reduced pressure. The obtained residue was purified by silica gel column chromatography (hexane:ethyl acetate=1:4-ethyl acetate alone) to give the object product (110 mg) as a yellow oil.

$^1$H-NMR (CD$_3$OD) δ (ppm): 0.91 (3H, t, J=6.7 Hz), 1.30-1.42 (6H, m), 1.43-1.53 (2H, m), 1.48 (18H, 2×s), 1.70-1.90 (4H, m), 2.01 (3H, s), 2.51-2.69 (2H, m), 3.87-3.92 (2H, m), 4.02 (2H, t, J=6.4 Hz), 4.17 (1H, d, J=9.0 Hz), 4.32 (1H, d, J=9.0 Hz), 6.91 (1H, t, J=55.8 Hz), 6.97 (1H, d, J=8.5 Hz), 7.29 (1H, d, J=8.5 Hz), 7.36 (1H, s).

(31-2) Synthesis of 2-amino-4-(3-difluoromethyl-4-heptyloxyphenyl)-2-(phosphoryloxymethyl)butanol (Compound 31-2)

Compound 31-1 (110 mg) was dissolved in ethanol (5 ml), concentrated hydrochloric acid (1 ml) was added, and the mixture was stirred at 50° C. for 4 hr. The solvent was concentrated under reduced pressure, methanol (1 ml), diethyl ether (1 ml) and propylene oxide (2 ml) were added to the residue. The precipitated powder was collected by filtration, and washed with ethyl acetate and diethyl ether to give the object product (60 mg) as a pale-yellow solid.

MS (ESI) m/z: 440[M+H]

$^1$H-NMR (CD$_3$OD) δ (ppm): 0.91 (3H, t, J=6.8 Hz), 1.26-1.43 (6H, m), 1.44-1.52 (2H, m), 1.74-1.82 (2H, m), 1.92-2.00 (2H, m), 2.59-2.71 (2H, m), 3.70 (2H, brs), 3.91-4.04 (4H, m), 6.92 (1H, t, J=55.8 Hz), 6.98 (1H, d, J=8.5 Hz), 7.33 (1H, d, J=8.3 Hz), 7.40 (1H, brs).

Example 32

2-Amino-2-[2-(3-difluoromethyl-4-octyloxyphenyl)ethyl]propane-1,3-diol Hydrochloride

(32-1) Synthesis of {2,2-dimethyl-5-[2-(3-difluoromethyl-4-octyloxyphenyl)ethyl]-1,3-dioxan-5-yl}carbamic Acid t-butyl Ester (Compound 32-1)

Compound 30-4 (600 mg) was dissolved in N,N-dimethylformamide (10 ml), potassium carbonate (412 mg) and 1-bromooctane (0.311 ml) were added, and the mixture was stirred at room temperature for 2 hr. Water was added to the reaction mixture, the mixture was extracted with ethyl acetate, and the extract was washed with water and saturated brine, and dried over anhydrous magnesium sulfate. The solvent was evaporated under reduced pressure, and the obtained residue was purified by silica gel column chromatography (hexane:ethyl acetate=50:1-3:1) to give the object product (230 mg) as a colorless oil.

$^1$H-NMR (CDCl$_3$) δ (ppm): 0.89 (3H, t, J=6.8 Hz), 1.25-1.49 (8H, m), 1.40-1.50 (2H, m), 1.42 (3H, s), 1.44 (3H, s), 1.47 (9H, s), 1.75-1.81 (2H, m), 1.91-1.98 (2H, m), 2.50-2.57 (2H, m), 3.68 (2H, d, J=11.8 Hz), 3.89 (2H, d, J=11.7 Hz), 3.97 (2H, t, J=6.4 Hz), 4.98 (1H, brs), 6.82 (1H, d, J=8.4 Hz), 6.93 (1H, t, J=55.8 Hz), 7.21 (1H, d, J=8.0 Hz), 7.35 (1H, brs).

(32-2) Synthesis of 2-amino-2-[2-(3-difluoromethyl-4-octyloxyphenyl)ethyl]propane-1,3-diol Hydrochloride (Compound 32-2)

Compound 32-1 (230 mg) was dissolved in ethanol (10 ml), concentrated hydrochloric acid (1 ml) was added, and the mixture was stirred at 80° C. for 2 hr. The reaction mixture was concentrated, and the residue was washed with diethyl ether to give the object product (105 mg) as a white powder.

MS (ESI) m/z: 374[M+H]

$^1$H-NMR (DMSO-d$_6$) δ (ppm): 0.86 (3H, t, J=6.8 Hz), 1.24-1.38 (8H, m), 1.39-1.44 (2H, m), 1.68-1.80 (4H, m), 2.55-2.62 (2H, m), 3.52 (4H, d, J=4.6 Hz), 4.01 (2H, t, J=6.4 Hz), 5.39 (2H, brt, J=4.8 Hz), 7.05 (1H, t, J=55.4 Hz), 7.07 (1H, d, J=8.5 Hz), 7.32 (1H, d, J=8.5 Hz), 7.36 (1H, s), 7.79 (3H, brs).

Example 33

2-Amino-4-(3-difluoromethyl-4-octyloxyphenyl)-2-(phosphoryloxymethyl)butanol

(33-1) Synthesis of 4-di(t-butyl)phosphoryloxymethyl-2-methyl-4-[2-(3-difluoromethyl-4-octyloxyphenyl)ethyl]-2-oxazoline (Compound 33-1)

To a solution of compound 32-2 (226 mg) in N,N-dimethylformamide (10 ml), N,N-diisopropylethylamine (0.296 ml) and trimethyl orthoacetate (0.139 ml) were added, and the mixture was stirred at 120° C. for 2.5 hr. Water was added to the reaction mixture, the mixture was extracted with ethyl acetate, and the extract was washed with water and saturated brine, and dried over anhydrous magnesium sulfate. The solvent was evaporated under reduced pressure to give 220 mg of a brown oil. To a solution of the brown oil (220 mg) in methylene chloride (5 ml) and acetonitrile (2 ml) were added 1H-tetrazole (77 mg) and di-t-butyl diethylphosphoramidite (0.329 ml), and the mixture was stirred at room temperature for 2 hr. The reaction solution was ice-cooled, a decane solution containing t-butyl hydroperoxide (5-6M, 0.330 ml) was added, and the mixture was stirred at room temperature for 20 min. Saturated aqueous sodium hydrogencarbonate solution was added to the reaction mixture, and the mixture was extracted with chloroform. The organic layer was dried over anhydrous magnesium sulfate, and the solvent was evaporated under reduced pressure. The obtained residue was purified by silica gel column chromatography (hexane:ethyl acetate=1:4-ethyl acetate alone) to give the object product (280 mg) as a yellow oil.

$^1$H-NMR (CD$_3$OD) δ (ppm): 0.90 (3H, t, J=7.0 Hz), 1.28-1.41 (8H, m), 1.45-1.52 (2H, m), 1.48 (18H, 2×s), 1.75-1.90 (4H, m), 2.01 (3H, s), 2.51-2.70 (2H, m), 3.87-3.92 (2H, m), 4.02 (2H, t, J=6.3 Hz), 4.17 (1H, d, J=9.0 Hz), 4.32 (1H, d, J=9.0 Hz), 6.92 (1H, t, J=55.7 Hz), 6.97 (1H, d, J=8.4 Hz), 7.29 (1H, d, J=8.9 Hz), 7.36 (1H, brs).

(33-2) Synthesis of 2-amino-4-(3-difluoromethyl-4-octyloxyphenyl)-2-(phosphoryloxymethyl)butanol (Compound 33-2)

Compound 33-1 (280 mg) was dissolved in ethanol (5 ml), concentrated hydrochloric acid (1 ml) was added, and the mixture was stirred at 50° C. for 3.5 hr. The solvent was concentrated under reduced pressure, methanol (2 ml), diethyl ether (2 ml) and propylene oxide (5 ml) were added to the residue. The precipitated powder was collected by filtration, and washed with methanol and diethyl ether to give the object product (175 mg) as a pale-yellow solid.

MS (ESI) m/z: 454[M+H]

$^1$H-NMR (CD$_3$OD) δ (ppm): 0.90 (3H, t, J=6.9 Hz), 1.26-1.42 (8H, m), 1.44-1.52 (2H, m), 1.75-1.82 (2H, m), 1.92-1.99 (2H, m), 2.62-2.72 (2H, m), 3.67-3.74 (2H, m), 3.94-4.04 (4H, m), 6.92 (1H, t, J=55.8 Hz), 6.98 (1H, d, J=8.5 Hz), 7.33 (1H, d, J=8.5 Hz), 7.40 (1H, brs).

Example 34

2-Amino-2-[2-(3-fluoromethyl-4-heptyloxyphenyl)ethyl]propane-1,3-diol Hydrochloride

(34-1) Synthesis of 5-bromo-2-heptyloxybenzaldehyde (Compound 34-1)

To a suspension of 5-bromosalicylaldehyde (5.00 g) and potassium carbonate (10.3 g) in N,N-dimethylformamide (50 ml) was added heptyl bromide (4.10 ml), and the mixture was stirred at room temperature for 1.5 hr, and further at 50° C. for 5 hr. Water was added to the reaction mixture, and the mixture was extracted with ethyl acetate. The organic layer was washed successively with 1M aqueous sodium hydroxide solution and saturated brine, and dried over anhydrous magnesium sulfate. The solvent was evaporated under reduced pressure to give the object product (7.61 g) as a yellow oil.

$^1$H-NMR (CDCl$_3$) δ (ppm): 0.90 (3H, t, J=6.8 Hz), 1.28-1.40 (6H, m), 1.44-1.51 (2H, m), 1.85 (2H, quint, J=7.0 Hz), 4.06 (2H, t, J=6.5 Hz), 6.88 (1H, d, J=8.9 Hz), 7.60 (1H, dd, J=2.8, 8.9 Hz), 7.92 (1H, d, J=2.8 Hz), 10.42 (1H, s).

(34-2) Synthesis of 5-bromo-2-heptyloxybenzyl Alcohol (Compound 34-2)

To a solution of compound 34-1 (7.60 g) in ethanol (80 ml) was added sodium borohydride (0.48 g) under ice-cooling, and the mixture was stirred for 1.5 hr under ice-cooling. 1M hydrochloric acid (50 ml) was added to the reaction mixture, and ethanol was evaporated under reduced pressure. The obtained residue was diluted with water, and the mixture was extracted with ethyl acetate. The organic layer was washed with saturated brine, and dried over anhydrous magnesium sulfate. The solvent was evaporated under reduced pressure to give the object product (7.66 g) as a pale-yellow oil.

$^1$H-NMR (CDCl$_3$) δ (ppm): 0.89 (3H, t, J=6.8 Hz), 1.28-1.39 (6H, m), 1.41-1.48 (2H, m), 1.80 (2H, quint, J=7.0 Hz), 2.26 (1H, t, J=6.3 Hz), 3.98 (2H, t, J=6.5 Hz), 4.65 (2H, d, J=5.9 Hz), 6.74 (1H, d, J=8.6 Hz), 7.34 (1H, dd, J=2.4, 8.6 Hz), 7.41 (1H, d, J=2.4 Hz).

(34-3) Synthesis of (5-bromo-2-heptyloxybenzyl) oxy-t-butyldimethylsilane (Compound 34-3)

To a solution of compound 34-2 (7.66 g) and imidazole (4.32 g) in N,N-dimethylformamide (30 ml) was added t-butyldimethylchlorosilane (4.59 g), and the mixture was stirred for 14 hr. Saturated aqueous sodium hydrogencarbonate solution was added to the reaction mixture, and the mixture was extracted with ethyl acetate. The organic layer was washed successively with saturated aqueous sodium hydrogencarbonate solution and saturated brine, and dried over anhydrous magnesium sulfate. The solvent was evaporated under reduced pressure to give the object product (10.6 g) as a yellow oil.

$^1$H-NMR (CDCl$_3$) δ (ppm): 0.12 (6H, s), 0.89 (3H, t, J=6.8 Hz), 0.96 (9H, s), 1.28-1.38 (6H, m), 1.40-1.47 (2H, m), 1.77 (2H, quint, J=7.0 Hz), 3.92 (2H, t, J=6.5 Hz), 4.71 (2H, s), 6.67 (1H, d, J=8.7 Hz), 7.27 (1H, dd, J=2.4, 8.7 Hz), 7.55 (1H, d, J=2.4 Hz).

(34-4) Synthesis of {5-[3-(t-butyldimethylsilyloxymethyl)-4-heptyloxyphenylethynyl]-2,2-dimethyl-1,3-dioxan-5-yl}carbamic Acid t-butyl Ester (Compound 34-4)

Compound 34-3 (10.5 g), (2,2-dimethyl-5-ethynyl-1,3-dioxan-5-yl)carbamic acid t-butyl ester (6.46 g) synthesized by a known method (for example, Tetrahedron vol. 57 (2001) 6531-6538), 2-dicyclohexylphosphino-2',4',6'-triisopropylbiphenyl (725 mg), bis(acetonitrile)palladium(II) dichloride (131 mg) and cesium carbonate (21.4 g) in acetonitrile (150 ml) was stirred at 80° C. for 12 hr. Water was added to the reaction mixture, the mixture was extracted with ethyl acetate, and the extract was washed with saturated brine, and dried over anhydrous sodium sulfate. The solvent was evaporated under reduced pressure. The residue was purified by silica gel column chromatography to give the object (11.7 g) as a brown oil.

$^1$H-NMR (CDCl$_3$) δ (ppm): 0.11 (6H, s), 0.89 (3H, t, J=6.8 Hz), 0.95 (9H, s), 1.28-1.38 (6H, m), 1.40-1.47 (2H, m), 1.45 (3H, s), 1.48 (9H, s), 1.50 (3H, s), 1.77 (2H, quint, J=6.9 Hz), 3.95 (2H, t, J=6.4 Hz), 4.03 (2H, d, J=11.5 Hz), 4.09 (2H, d, J=11.5 Hz), 4.69 (2H, s), 5.19 (1H, brs), 6.71 (1H, d, J=8.5 Hz), 7.27 (1H, dd, J=1.9, 8.5 Hz), 7.49 (1H, s).

(34-5) Synthesis of {2,2-dimethyl-5-[2-(4-heptyloxy-3-hydroxymethylphenyl)ethyl]-1,3-dioxan-5-yl}carbamic Acid t-butyl Ester (Compound 34-5)

Compound 34-4 (11.7 g) was dissolved in 1,4-dioxane (150 ml), 10% palladium carbon (12.0 g) was added, and the mixture was stirred at room temperature for 16 hr under a hydrogen atmosphere. The inside of the reaction container was displaced with nitrogen, the solution was filtrated, and the filtrate was concentrated. To a solution of the obtained residue in tetrahydrofuran (100 ml) was added 1M tetrabutylammonium fluoride-tetrahydrofuran solution (20 ml) under ice-cooling, and the mixture was stirred for 1.5 hr under ice-cooling. A solution of 1M tetrabutylammonium fluoride-tetrahydrofuran solution (10 ml) was added, and the mixture was further stirred for 4 hr under ice-cooling. Water was added to the reaction mixture, the mixture extracted with ethyl acetate, washed successively with water saturated brine, and dried over anhydrous sodium sulfate. The solvent was evaporated under reduced pressure. The residue was purified by silica gel column chromatography to give the object product (5.99 g) as a pale-brown oil.

$^1$H-NMR (CDCl$_3$) δ (ppm): 0.89 (3H, t, J=6.8 Hz), 1.28-1.39 (6H, m), 1.42-1.47 (2H, m), 1.42 (3H, s), 1.43 (3H, s), 1.47 (9H, s), 1.79 (2H, quint, J=7.0 Hz), 1.92-1.96 (2H, m), 2.40 (1H, t, J=6.5 Hz), 2.48-2.53 (2H, m), 3.67 (2H, d, J=11.7 Hz), 3.89 (2H, d, J=11.7 Hz), 3.98 (2H, t, J=6.5 Hz), 4.65 (2H, d, J=6.8 Hz), 4.97 (1H, brs), 6.77 (1H, d, J=8.0 Hz), 7.04-7.07 (2H, m).

(34-6) Synthesis of {2,2-dimethyl-5-[2-(3-fluoromethyl-4-heptyloxyphenyl)ethyl]-1,3-dioxan-5-yl}carbamic acid t-butyl ester (compound 34-6)

A mixture of compound 34-5 (3.74 g), p-toluenesulfonyl fluoride (4.08 g), molecular sieves 4 A (3.74 g) and 1M tetrabutylammonium fluoride-tetrahydrofuran solution (46.8 ml) was stirred for 12 hr under reflux. Celite was added to the reaction mixture, and the mixture was filtrated. Ethyl acetate (200 ml) and water (200 ml) were added to the filtrate, and the mixture was filtrated with celite. The organic layer of the filtrate was washed with saturated brine and dried over anhydrous sodium sulfate. The solvent was evaporated under reduced pressure. The residue was purified by silica gel column chromatography to give the object product (0.92 g) as a colorless oil.

$^1$H-NMR (CDCl$_3$) δ (ppm): 0.89 (3H, t, J=6.7 Hz), 1.26-1.38 (6H, m), 1.40-1.47 (2H, m), 1.42 (3H, s), 1.43 (3H, s), 1.47 (9H, s), 1.77 (2H, quint, J=6.9 Hz), 1.93-1.97 (2H, m), 2.50-2.54 (2H, m), 3.68 (2H, d, J=11.7 Hz), 3.88 (2H, d, J=11.7 Hz), 3.95 (2H, t, J=6.4 Hz), 4.98 (1H, brs), 5.42 (2H, d, J=47.9 Hz), 6.78 (1H, d, J=8.5 Hz), 7.11 (1H, d, J=8.5 Hz), 7.17 (1H, m).

(34-7) Synthesis of 2-amino-2-[2-(3-fluoromethyl-4-heptyloxyphenyl)ethyl]propane-1,3-diol Hydrochloride (Compound 34-7)

Compound 34-6 (0.92 g) was dissolved in methanol (30 ml), p-toluenesulfonic acid (15 mg) was added, and the mixture was stirred at room temperature for 3 hr. Saturated aqueous sodium hydrogencarbonate solution (10 ml) and saturated brine (100 ml) were added to the reaction mixture, the mixture was extracted with ethyl acetate, and the extract was washed with saturated brine, and dried over anhydrous sodium sulfate. The solvent was evaporated under reduced pressure. Ethyl acetate (1 ml) and in 4M hydrogen chloride-ethyl acetate solution (1 ml) were added to the obtained residue under ice-cooling, and the mixture was stirred for 30 min under ice-cooling. The precipitated solid was collected by filtration, and washed with diisopropyl ether to give the object product (44.4 mg) as a white powder.

MS (ESI) m/z: 342[M+H]

$^1$H-NMR (DMSO-d$_6$) δ (ppm): 0.87 (3H, t, J=6.7 Hz), 1.26-1.36 (6H, m), 1.37-1.44 (2H, m); 1.71 (2H, quint, J=6.9 Hz), 1.74-1.79 (2H, m), 2.53-2.57 (2H, m), 3.52 (4H, d, J=5.2 Hz), 3.97 (2H, t, J=6.3 Hz), 5.38 (2H, d, J=48.0 Hz), 5.40 (2H, t, J=5.1 Hz), 6.97 (1H, d, J=8.3 Hz), 7.17-7.20 (2H, m), 7.85 (3H, brs).

Example 35

2-Amino-2-[2-(3-fluoromethyl-4-heptyloxyphenyl)ethyl]propane-1,3-diol Hydrochloride (35-1) Synthesis of 5-bromo-2-octyloxybenzaldehyde (Compound 35-1)

To a suspension of 5-bromosalicylaldehyde (5.00 g) and potassium carbonate (10.3 g) in N,N-dimethylformamide (50 ml) was added octyl bromide (4.52 ml), and the mixture was stirred at room temperature for 1.5 hr, and further at 50° C. for 3.5 hr. Water was added to the reaction mixture, and the mixture was extracted with ethyl acetate. The organic layer was washed with saturated brine 3 times, and dried over anhydrous magnesium sulfate, and the solvent was evaporated under reduced pressure to give the object product (7.72 g) as a white solid.

$^1$H-NMR (CDCl$_3$) δ (ppm): 0.89 (3H, t, J=6.3 Hz), 1.25-1.38 (8H, m), 1.44-1.51 (2H, m), 1.84 (2H, quint, J=6.8 Hz), 4.06 (2H, t, J=6.4 Hz), 6.88 (1H, d, J=8.9 Hz), 7.61 (1H, d, J=8.9 Hz), 7.92 (1H, s), 10.42 (1H, s).

(35-2) Synthesis of 5-bromo-2-octyloxybenzyl alcohol (compound 35-2)

To a solution of compound 35-1 (7.72 g) in ethanol (80 ml) was added sodium borohydride (0.47 g) under ice-cooling, and the mixture was stirred for 30 min under ice-cooling. Water (100 ml) and 1M hydrochloric acid (30 ml) were added to the reaction mixture, and ethanol was evaporated under reduced pressure. The obtained residue was diluted with 0.1M hydrochloric acid, and the mixture was extracted with ethyl acetate. The organic layer was washed with saturated brine, and dried over anhydrous magnesium sulfate, and the solvent was evaporated under reduced pressure to give the object product (7.95 g) as a pale-brown oil.

$^1$H-NMR (CDCl$_3$) δ (ppm): 0.89 (3H, t, J=6.7 Hz), 1.25-1.38 (8H, m), 1.41-1.48 (2H, m), 1.80 (2H, quint, J=7.0 Hz), 2.25 (1H, t, J=6.3 Hz), 3.98 (2H, t, J=6.4 Hz), 4.65 (2H, d, J=6.0 Hz), 6.74 (1H, d, J=8.6 Hz), 7.34 (1H, dd, J=2.4, 8.6 Hz), 7.41 (1H, d, J=2.4 Hz).

(35-3) Synthesis of (5-bromo-2-octyloxybenzyl)oxy-t-butyldimethylsilane (Compound 35-3)

To a solution of compound 35-2 (7.95 g) and imidazole (4.19 g) in N,N-dimethylformamide (35 ml) was added t-butyldimethylchlorosilane (4.45 g) under ice-cooling, and the mixture was stirred for 20 min under ice-cooling, and further at room temperature for 18 hr. Saturated aqueous sodium hydrogencarbonate solution was added to the reaction mixture, and the mixture was extracted with ethyl acetate. The organic layer was washed successively with saturated aqueous sodium hydrogencarbonate solution and saturated brine, and dried over anhydrous magnesium sulfate. The solvent was evaporated under reduced pressure to give the object product (11.1 g) as a pale-brown oil.

$^1$H-NMR (CDCl$_3$) δ (ppm): 0.12 (6H, s), 0.89 (3H, t, J=6.9 Hz), 0.96 (9H, s), 1.24-1.38 (8H, m), 1.40-1.47 (2H, m), 1.76 (2H, quint, J=7.0 Hz), 3.92 (2H, t, J=6.5 Hz), 4.71 (2H, s), 6.67 (1H, d, J=8.7 Hz), 7.27 (1H, dd, J=2.5, 8.7 Hz), 7.55 (1H, d, J=2.5 Hz).

(35-4) Synthesis of {5-[3-(t-butyldimethylsilyloxymethyl)-4-octyloxyphenylethynyl]-2,2-dimethyl-1,3-dioxan-5-yl}carbamic acid t-butyl ester (compound 35-4)

Compound 35-3 (11.1 g), (2,2-dimethyl-5-ethynyl-1,3-dioxan-5-yl)carbamic acid t-butyl ester (6.28 g) synthesized by a known method (for example, Tetrahedron vol. 57 (2001) 6531-6538), 2-dicyclohexylphosphino-2',4',6'-triisopropyl-biphenyl (706 mg), bis(acetonitrile)palladium(II) dichloride (128 mg) and cesium carbonate (20.8 g) in acetonitrile (150 ml) were stirred at 80° C. for 10 hr. Brine was added to the reaction mixture, the mixture was extracted with ethyl acetate, and the extract was washed with saturated brine, and dried over anhydrous sodium sulfate. The solvent was evaporated under reduced pressure. The residue was purified by silica gel column chromatography to give the object product (12.4 g) as a brown oil.

$^1$H-NMR (CDCl$_3$) δ (ppm): 0.11 (6H, s), 0.89 (3H, t, J=6.8 Hz), 0.95 (9H, s), 1.24-1.37 (8H, m), 1.40-1.47 (2H, m), 1.45 (3H, s), 1.48 (9H, s), 1.50 (3H, s), 1.77 (2H, quint, J=6.9 Hz), 3.95 (2H, t, J=6.5 Hz), 4.03 (2H, d, J=11.6 Hz), 4.09 (2H, d, J=11.6 Hz), 4.69 (2H, s), 5.19 (1H, brs), 6.71 (1H, d, J=8.4 Hz), 7.27 (1H, dd, J=1.9, 8.4 Hz), 7.49 (1H, s).

(35-5) Synthesis of {2,2-dimethyl-5-[2-(4-octyloxy-3-hydroxymethylphenyl)ethyl]-1,3-dioxan-5-yl}carbamic Acid t-butyl Ester (Compound 35-5)

Compound 35-4 (12.4 g) was dissolved in 1,4-dioxane (100 ml), 10% palladium carbon (3.0 g) was added, and the mixture was stirred at room temperature for 5.5 hr under a hydrogen atmosphere. The inside of the reaction container was displaced with nitrogen, the solution was filtrated, and the filtrate was concentrated. To a solution of the obtained residue in tetrahydrofuran (100 ml) was added 1M tetrabutylammonium fluoride-tetrahydrofuran solution (30 ml), and the mixture was stirred for 3 hr. The reaction mixture was diluted with ethyl acetate (200 ml), and the extract was washed with water and saturated brine, and dried over anhydrous magnesium sulfate. The solvent was evaporated under reduced pressure. The residue was purified by silica gel column chromatography to give the object product (9.61 g) as a pale-brown oil.

$^1$H-NMR (CDCl$_3$) δ (ppm): 0.89 (3H, t, J=6.7 Hz), 1.24-1.38 (8H, m), 1.41-1.47 (2H, m), 1.42 (3H, s), 1.43 (3H, s), 1.47 (9H, s), 1.79 (2H, quint, J=7.0 Hz), 1.92-1.96 (2H, m), 2.41 (1Ht, J=6.6 Hz), 2.48-2.53 (2H, m), 3.67 (2H, d, J=11.7 Hz), 3.89 (2H, d, J=11.7 Hz), 3.98 (2H, t, J=6.5 Hz), 4.65 (2H, d, J=6.8 Hz), 4.98 (1H, brs), 6.77 (1H, d, J=8.0 Hz), 7.04-7.07 (2H, m).

(35-6) Synthesis of {2,2-dimethyl-5-[2-(3-fluoromethyl-4-octyloxyphenyl)ethyl]-1,3-dioxan-5-yl}carbamic acid t-butyl ester (compound 35-6)

A mixture of compound 35-5 (9.61 g), p-toluenesulfonyl fluoride (10.2 g), molecular sieves 4 A (9.61 g) and 1M tetrabutylammonium fluoride-tetrahydrofuran solution (117 ml) was stirred for 13 hr under reflux. The reaction mixture was added to a mixture of water and ethyl acetate, and the mixture was stirred for 5 hr. The organic layer was washed with water and saturated brine, and dried over anhydrous magnesium sulfate. The solvent was evaporated under reduced pressure. The residue was purified by silica gel column chromatography to give the object product (1.91 g) as a colorless oil.

$^1$H-NMR (CDCl$_3$) δ (ppm): 0.89 (3H, t, J=6.7 Hz), 1.24-1.38 (8H, m), 1.40-1.47 (2H, m), 1.42 (3H, s), 1.43 (3H, s), 1.47 (9H, s), 1.77 (2H, quint, J=7.0 Hz), 1.93-1.97 (2H, m), 2.50-2.55 (2H, m), 3.68 (2H, d, J=11.7 Hz), 3.89 (2H, d, J=11.7 Hz), 3.95 (2H, t, J=6.5 Hz), 4.98 (1H, brs), 5.42 (2H, d, J=47.9 Hz), 6.78 (1H, d, J=8.4 Hz), 7.11 (1H, d, J=8.4 Hz), 7.17 (1H, s).

(35-7) Synthesis of 2-amino-2-[2-(3-fluoromethyl-4-heptyloxyphenyl)ethyl]propane-1,3-diol Hydrochloride (Compound 35-7)

Compound 35-6 (1.91 g) was dissolved in methanol (60 ml), p-toluenesulfonic acid monohydrate (20 mg) was added, and the mixture was stirred at room temperature for 9 hr.

Saturated aqueous sodium hydrogencarbonate solution (200 ml) and saturated brine (100 ml) were added to the reaction mixture, and the mixture was extracted with ethyl acetate. The organic layer was washed with saturated brine, and dried over anhydrous sodium sulfate, and the solvent was evaporated under reduced pressure. Ethyl acetate (3 ml) and 4M hydrogen chloride-ethyl acetate solution (3 ml) were added to the obtained residue under ice-cooling, and the mixture was stirred for 40 min under ice-cooling. The precipitated solid was collected by filtration, and washed with ethyl acetate to give the object product (158 mg) as a white powder.

MS (ESI) m/z: 356[M+H]

$^1$H-NMR (DMSO-$d_6$) δ (ppm): 0.86 (3H, t, J=6.8 Hz), 1.23-1.35 (8H, m), 1.37-1.44 (2H, m), 1.67-1.78 (4H, m), 2.52-2.56 (2H, m), 3.51 (4H, d, J=4.6 Hz), 3.97 (2H, t, J=6.4 Hz), 5.38 (2H, d, J=48.0 Hz), 5.38 (2H, brs), 6.97 (1H, d, J=8.3 Hz), 7.17-7.20 (2H, m), 7.75 (3H, brs).

Example 36

2-Dimethylamino-2-[2-(4-heptyloxy-3-trifluoromethylphenyl)ethyl]propane-1,3-diol Hydrochloride (36-1) Synthesis of 2-dimethylamino-2-[2-(4-heptyloxy-3-trifluoromethylphenyl)ethyl]propane-1,3-diol Hydrochloride (Compound 36-1)

To a solution of compound 1-3 (1.24 g), 37% formaldehyde (20 ml) and 30% aqueous acetic acid solution (3 ml) in acetonitrile (30 ml) was added sodium cyanoborohydride (0.817 g) under ice-cooling, and the mixture was stirred for 1 hr. Saturated aqueous sodium hydrogencarbonate solution (50 ml) was added to the reaction mixture, and acetonitrile was evaporated under reduced pressure. Saturated aqueous sodium hydrogencarbonate solution was added to the obtained concentration, the mixture was extracted with ethyl acetate, and the extract was washed with saturated brine, and dried over anhydrous magnesium sulfate. The solvent was evaporated under reduced pressure. Ethyl acetate (10 ml) and 4M hydrogen chloride-ethyl acetate solution (5 ml) were added to the residue, and the solvent was evaporated under reduced pressure. Diisopropyl ether was added to the residue, and the resulting solid was collected by filtration to give the object product (0.808 g) as a white solid.

MS (ESI) m/z: 406[M+H]

$^1$H-NMR (DMSO-$d_6$) δ (ppm): 0.86 (3H, t, J=6.7 Hz), 1.24-1.35 (6H, m), 1.38-1.45 (2H, m), 1.71 (2H, quint, J=6.8 Hz), 1.87-1.91 (2H, m), 2.60-2.67 (2H, m), 2.80 (6H, d, J=4.8 Hz), 3.70 (2H, dd, J=4.9, 12.9 Hz), 3.76 (2H, dd, J=4.8, 12.8 Hz), 4.06 (2H, t, J=6.2 Hz), 5.71 (2H, t, J=4.6 Hz), 7.18 (1H, d, J=8.2 Hz), 7.49-7.51 (2H, m).

Synthetic Example 1 of Comparison Compound
2-Amino-2-[2-(4-heptyloxy-3-methylphenyl)ethyl]propane-1,3-diol Hydrochloride (1-1) Synthesis of 4'-methoxy-3'-methylacetophenone (Comparison Compound 1-1)

To a solution of 4'-hydroxy-3'-methylacetophenone (25.0 g) in N,N-dimethylformamide (120 ml) were added potassium carbonate (69.1 g) and methyl iodide (11.4 ml) under ice-cooling, and the mixture was stirred for 2 hr under ice-cooling and further at room temperature for 2 hr. Water was added to the reaction mixture, and the mixture was extracted with ethyl acetate. The organic layer was washed with saturated brine, and dried over anhydrous magnesium sulfate. The solvent was evaporated under reduced pressure to give the object product (27.5 g) as a yellow oil.

$^1$H-NMR (CDCl$_3$) δ (ppm): 2.25 (3H, s), 2.55 (3H, s), 3.89 (3H, s), 6.85 (1H, d, J=8.6 Hz), 7.77 (1H, d, J=1.7 Hz), 7.82 (1H, dd, J=2.2, 8.6 Hz).

(1-2) Synthesis of 4'-methoxy-3'-methylphenacyl Bromide (Comparison Compound 1-2)

To a solution of comparison compound 1-1 (27.2 g) in acetic acid (170 ml) was added pyridinium tribromide (90%, 59.0 g), and the mixture was stirred at 50° C. for 1 hr. Water was added to the reaction mixture, and the mixture was extracted with ethyl acetate. The organic layer was washed successively with water, 1M aqueous sodium hydroxide solution, saturated ammonium chloride and saturated brine. The organic layer was dried over anhydrous magnesium sulfate, and the solvent was evaporated under reduced pressure to give the object product (40.3 g) as a brown solid.

$^1$H-NMR (CDCl$_3$) δ (ppm): 2.26 (3H, s), 3.91 (3H, s), 4.40 (2H, s), 6.87 (1H, d, J=8.6 Hz), 7.80 (1H, d, J=1.5 Hz), 7.86 (1H, dd, J=2.2, 8.6 Hz).

(1-3) Synthesis of 2-acetamido-2-[2-(4-methoxy-3-methylphenyl)-2-oxoethyl]malonic Acid Diethyl Ester (Comparison Compound 1-3)

To a solution of diethyl 2-acetamidomalonate (29.1 g) in N,N-dimethylformamide (140 ml) was added sodium hydride (60%, 5.63 g) in four portions under ice-cooling, and the mixture was stirred for 1 hr. To this solution was added a solution of comparison compound 1-2 (39.1 g) in N,N-dimethylformamide (50 ml), and the mixture was stirred for 3 hr under ice-cooling. The reaction mixture was added to ice water, and the mixture was extracted with ethyl acetate. The organic layer was washed with saturated brine, and dried over anhydrous magnesium sulfate. The solvent was evaporated under reduced pressure. The obtained residue was purified by silica gel chromatography to give the object product (45.0 g) as a brown oil.

$^1$H-NMR (CDCl$_3$) δ (ppm): 1.24 (6H, t, J=7.0 Hz), 1.96 (3H, s), 2.23 (3H, s), 3.89 (3H, s), 4.20 (2H, s), 4.26 (4H, dq, J=1.4, 7.0 Hz), 6.84 (1H, d, J=8.6 Hz), 7.10 (1H, brs), 7.77 (1H, d, J=1.8 Hz), 7.83 (1H, dd, J=2.2, 8.6 Hz).

(1-4) Synthesis of 2-acetamido-2-[2-(4-methoxy-3-methylphenyl)ethyl]malonic Acid Diethyl Ester (Comparison Compound 1-4)

To a solution of comparison compound 1-3 (45.0 g) in trifluoroacetic acid (260 ml) was added triethylsilane (133 ml), and the mixture was stirred at 70° C. for 24 hr. The reaction mixture was concentrated under reduced pressure, water was added, and the mixture was extracted with ethyl acetate. The organic layer was washed successively with water, 1M aqueous sodium hydroxide solution and saturated brine, and dried over anhydrous magnesium sulfate. The solvent was evaporated under reduced pressure. Diethyl ether and hexane were added to the obtained residue, and the precipitated solid was collected by filtration, and dried to give the object product (31.3 g) as a white powder.

$^1$H-NMR (CDCl$_3$) δ (ppm): 1.25 (6H, t, J=7.0 Hz), 2.00 (3H, s), 2.18 (3H, s), 2.37-2.41 (2H, m), 2.62-2.67 (2H, m), 3.79 (3H, s), 4.15-4.27 (4H, m), 6.70-6.73 (1H, m), 6.75 (1H, brs), 6.90-6.93 (2H, m).

(1-5) Synthesis of N-[1,1-bis(hydroxymethyl)-3-(4-methoxy-3-methylphenyl)propyl]acetamide (Comparison Compound 1-5)

To a solution of comparison compound 1-4 (31.3 g) in ethanol (300 ml) and water (60 ml) was added calcium chloride (19.0 g), and the solid was dissolved. Sodium borohydride (13.0 g) was added to this mixture in five portions under ice-cooling, and the mixture was stirred for 3 hr under ice-cooling, and further at room temperature for 19 hr. 1M hydrochloric acid (300 ml) was added to the reaction mixture under ice-cooling, and the mixture was concentrated under reduced pressure. 0.5M hydrochloric acid (700 ml) was added, and the mixture was extracted with ethyl acetate. The organic layer was washed with saturated brine, and dried over anhydrous magnesium sulfate, and the solvent was evaporated under reduced pressure to give a white solid. The object product (22.8 g) was obtained as a colorless oil by operation in the same manner mentioned above to this white solid.

$^1$H-NMR (CDCl$_3$) δ (ppm): 1.91-1.95 (2H, m), 1.95 (3H, s), 2.19 (3H, s), 2.55-2.59 (2H, m), 3.62 (2H, d, J=11.6 Hz), 3.80 (3H, s), 3.87 (2H, d, J=11.6 Hz), 5.84 (1H, brs), 6.74 (1H, d, J=8.8 Hz), 6.97-6.98 (2H, m).

(1-6) Synthesis of [1,1-bis(hydroxymethyl)-3-(4-hydroxy-3-methylphenyl)propyl]carbamaic Acid t-butyl Ester (Comparison Compound 1-6)

To a solution of comparison compound 1-5 (22.5 g) in methylene chloride (200 ml) was added dropwise 1M boron tribromide-methylene chloride solution (320 ml) at −70° C. The mixture was stirred over 1 hr until the temperature rose to 0° C., and further stirred for 1.5 hr under ice-cooling. Methanol (300 ml) was gradually added to the reaction mixture under ice-cooling, and the mixture was concentrated under reduced pressure. To a solution of the obtained residue in ethanol (100 ml) was added concentrated hydrochloric acid (100 ml), and the mixture was stirred at 80° C. for 4 hr. The reaction mixture was concentrated under reduced pressure. To a solution of the obtained residue and N,N-diisopropylethylamine (34.8 ml) in methanol (150 ml) was added di-t-butyl dicarbonate (19.2 g) under ice-cooling, and the mixture was stirred for 1 hr under ice-cooling, and further at room temperature for 4 hr. The reaction mixture was concentrated under reduced pressure, saturated aqueous sodium hydrogencarbonate solution (500 ml) was added, and the mixture was extracted with ethyl acetate. The organic layer was washed successively with saturated aqueous sodium hydrogencarbonate solution and saturated brine, and dried over anhydrous magnesium sulfate. The solvent was evaporated under reduced pressure. The obtained residue was washed with diethyl ether to give the object product (15.1 g) as a white powder.

$^1$H-NMR (CDCl$_3$) δ (ppm): 1.45 (9H, s), 1.82-1.86 (2H, m), 2.21 (3H, s), 2.50-2.54 (2H, m), 3.39 (2H, brs), 3.64 (2H, dd, J=6.8, 11.5 Hz), 3.88 (2H, dd, J=5.5, 11.5 Hz), 4.83 (1H, brs), 4.99 (1H, brs), 6.68 (1H, d, J=8.1 Hz), 6.88 (1H, dd, J=1.9, 8.1 Hz), 6.94 (1H, d, J=1.9 Hz).

(1-7) Synthesis of 2-amino-2-[2-(4-heptyloxy-3-methylphenyl)ethyl]propane-1,3-diol Hydrochloride (Comparison Compound 1-7)

Comparison compound 1-6 (500 mg) was dissolved in N,N-dimethylformamide (10 ml), potassium carbonate (425 mg) and n-heptyl bromide (0.296 ml) were added, and the mixture was stirred at 80° C. for 6 hr. Water was added to the reaction mixture, the mixture was extracted with ethyl acetate, and the extract was washed with water and saturated brine, and dried over anhydrous magnesium sulfate. The solvent was evaporated under reduced pressure to give 640 mg of a colorless oil. The colorless oil (640 mg) was dissolved in methylene chloride (5 ml), dioxane containing hydrogen chloride (4 mol/l, 5 ml) was added, and the mixture was stirred at room temperature for 15 hr. The reaction mixture was concentrated, and the residue was washed with diethyl ether to give a white powder. The white powder was purified by preparative HPLC, ether containing hydrogen chloride (1 mol/l, 15 ml) was added to the obtained residue to give hydrochloride. The precipitate was collected by filtration, and dried to give the object product (320 mg) as a white powder.

MS (ESI) m/z: 324[M+H]

$^1$H-NMR (CD$_3$OD) δ (ppm): 0.91 (3H, t, J=6.6 Hz), 1.30-1.42 (6H, m), 1.43-1.52 (2H, m), 1.74-1.81 (2H, m), 1.88-1.94 (2H, m), 2.16 (3H, s), 2.53-2.58 (2H, m), 3.64-3.71 (4H, m), 3.94 (2H, t, J=6.4 Hz), 6.77 (1H, d, J=8.0 Hz), 6.96-6.98 (2H, m).

The structures of the synthesized compounds are shown below.

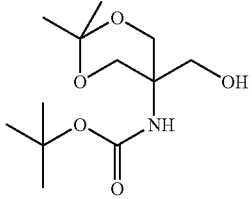

(Reference Example Compound 1-1)

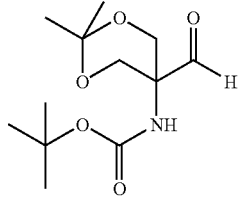

(Reference Example Compound 1-2)

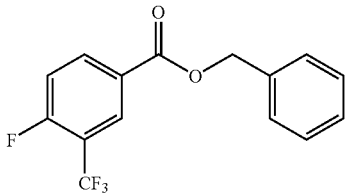

(Reference Example Compound 2-1)

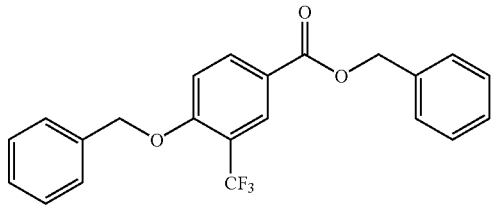

(Reference Example Compound 2-2)

-continued
(Reference Example Compound 2-3)
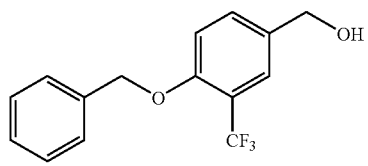
(Reference Example Compound 2-4)
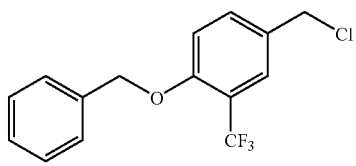
(Reference Example Compound 2-5)
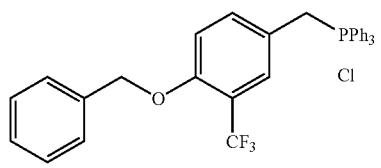
(Reference Example Compound 3-1)
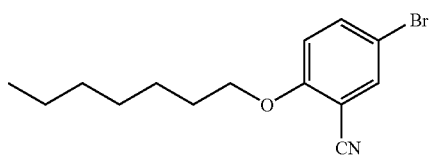
(Compound 1-1)
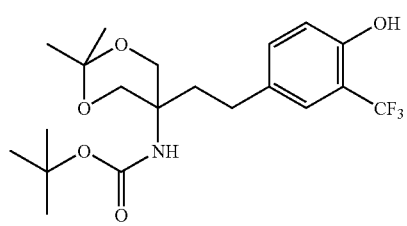
(Compound 1-2)
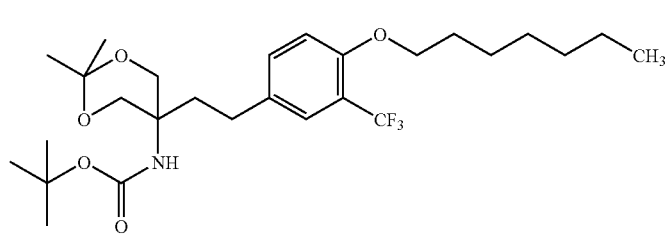
(Compound 1-3)
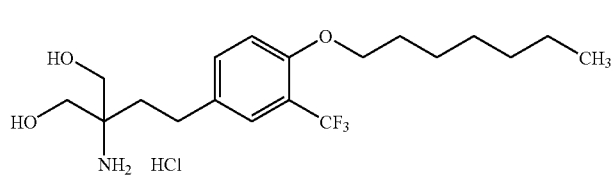
(Compound 2-1)
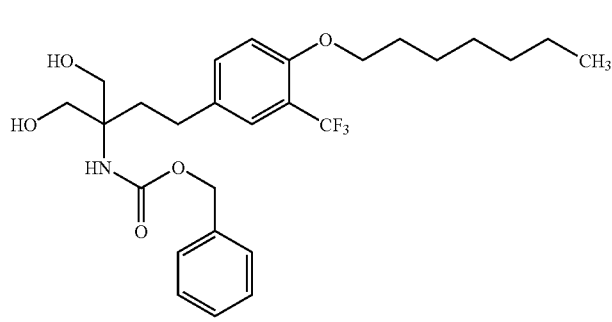

-continued
(Compound 2-2)
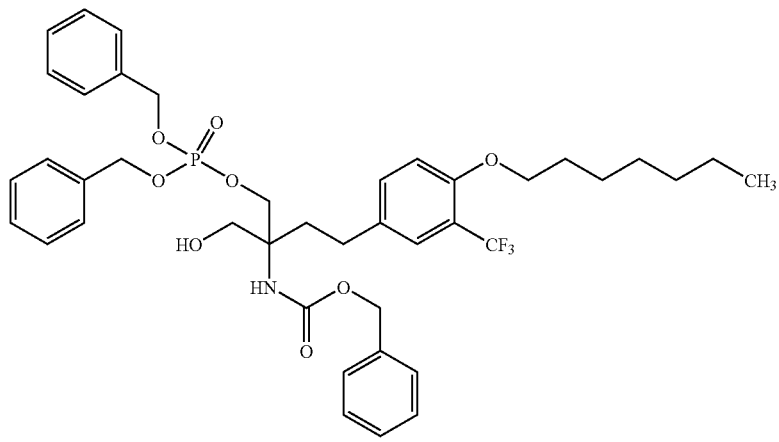
(Compound 2-3)
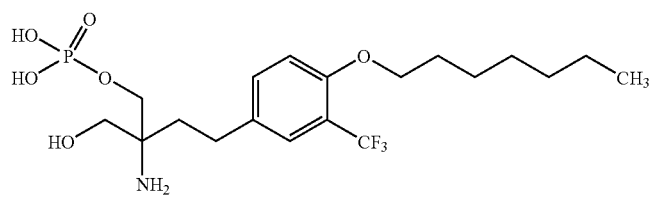
(Compound 3-1)
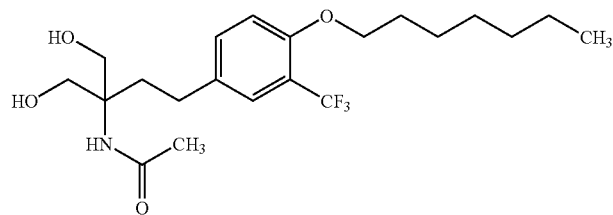
(Compound 3-2)
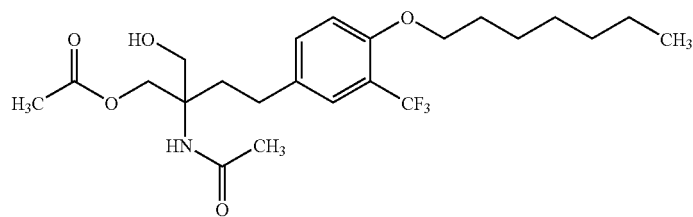
(Compound 3-3)
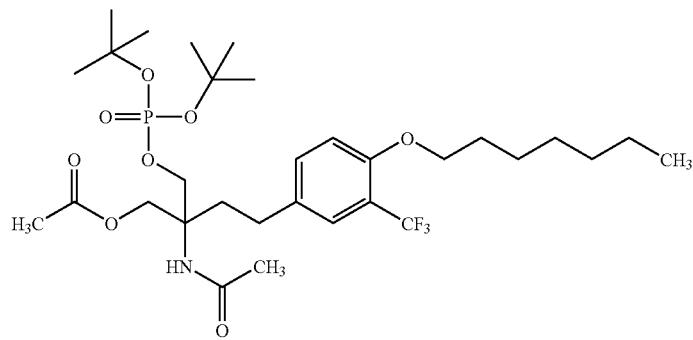

-continued
(Compound 3-4-1)
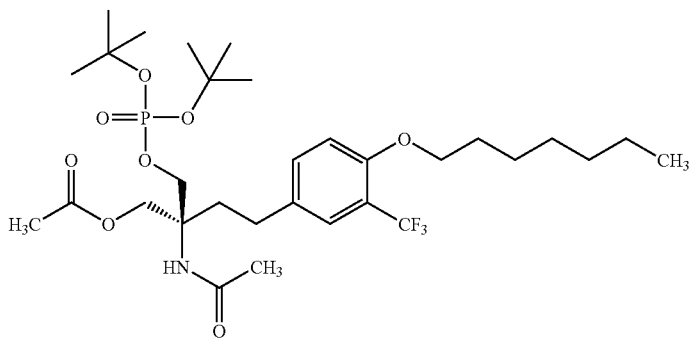
(Compound 3-4-2)
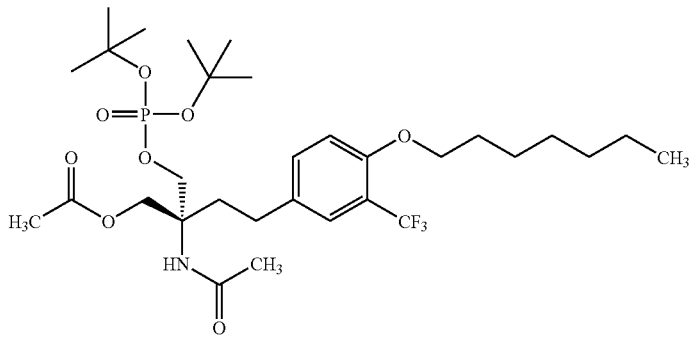
(Compound 3-5)
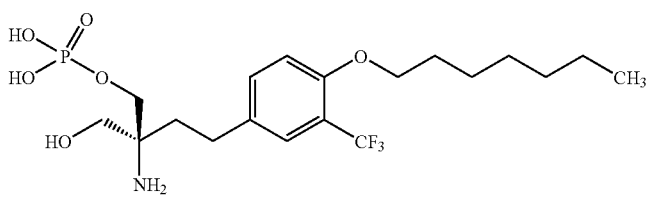
(Compound 4-1)
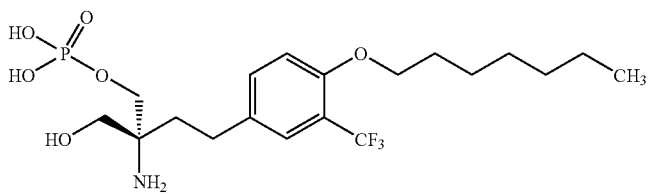
(Compound 5-1)
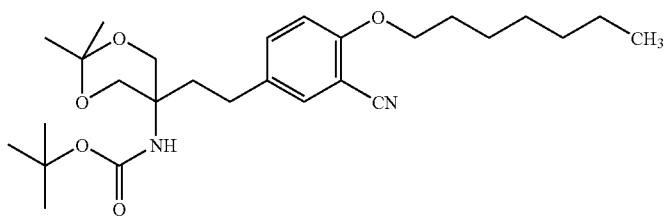
(Compound 5-2)
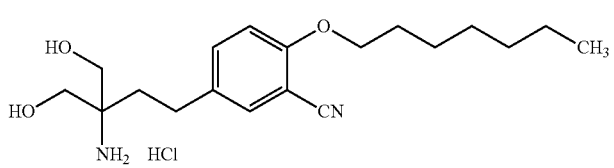

(Compound 6-1)
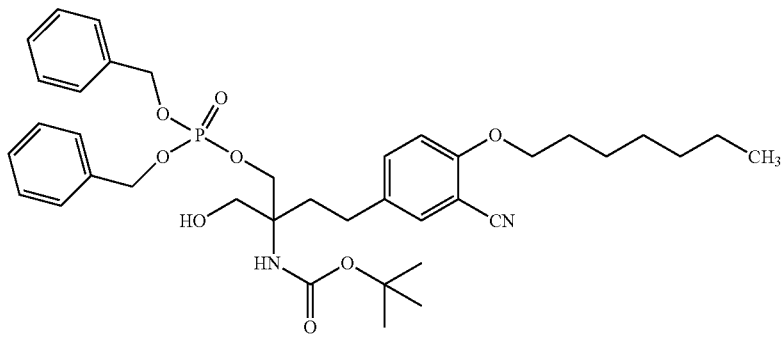
(Compound 6-2)
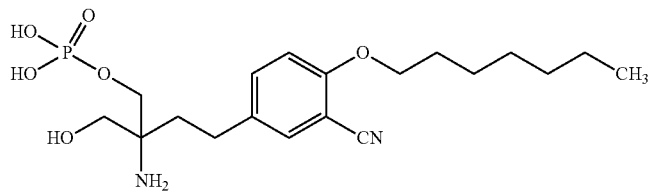
(Compound 7-1)
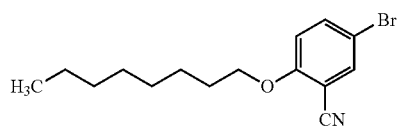
(Compound 7-2)
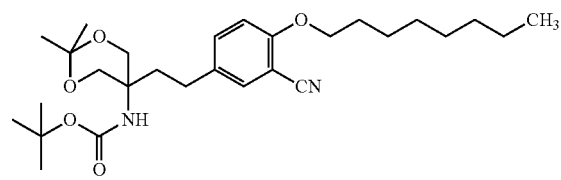
(Compound 7-3)
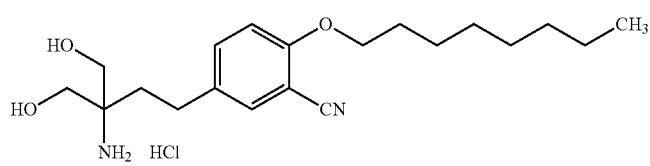
(Compound 8-1)
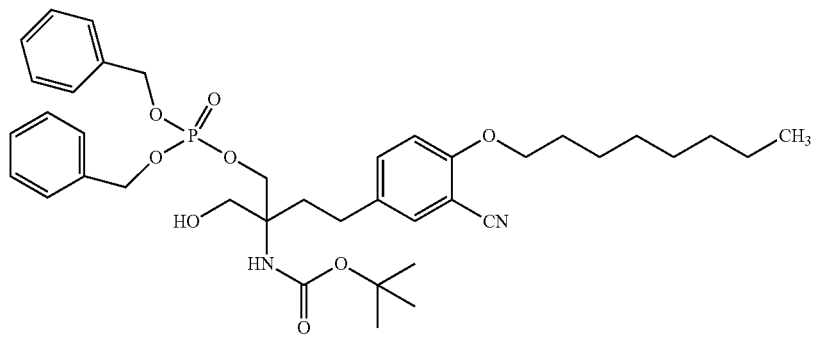
(Compound 8-2)
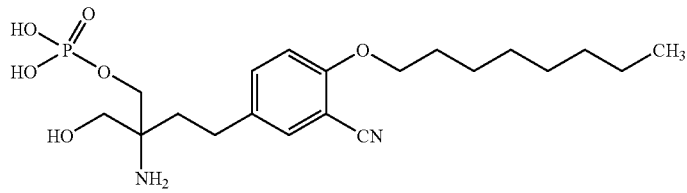

-continued
(Compound 9-1)
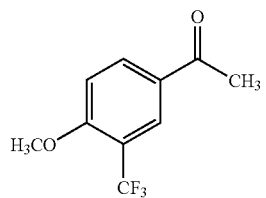
(Compound 9-2)
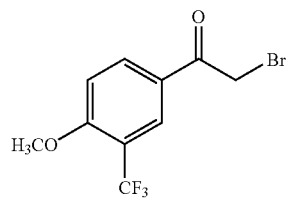
(Compound 9-3)
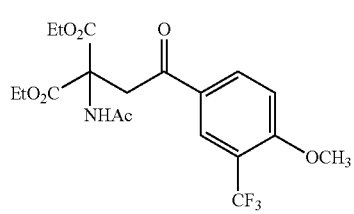
(Compound 9-4)
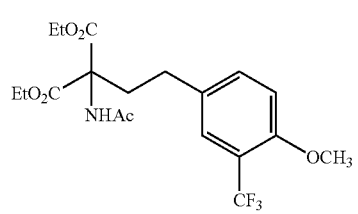
(Compound 9-5)
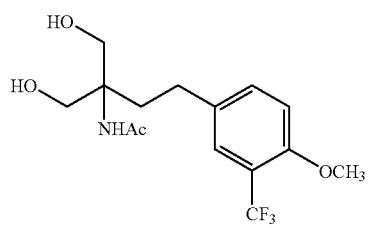
(Compound 9-6)
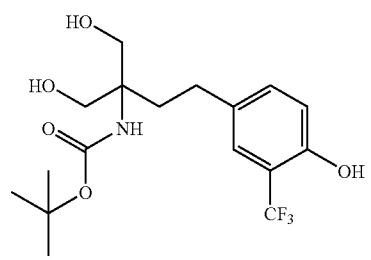
(Compound 9-7)
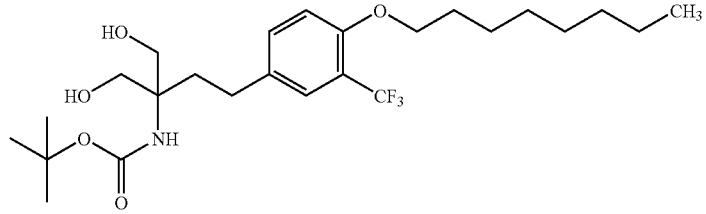
(Compound 9-8)
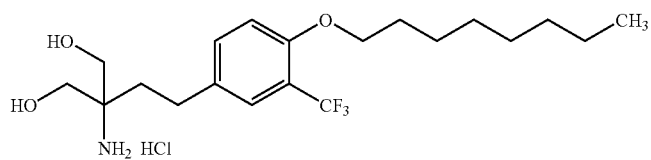
(Compound 10-1)
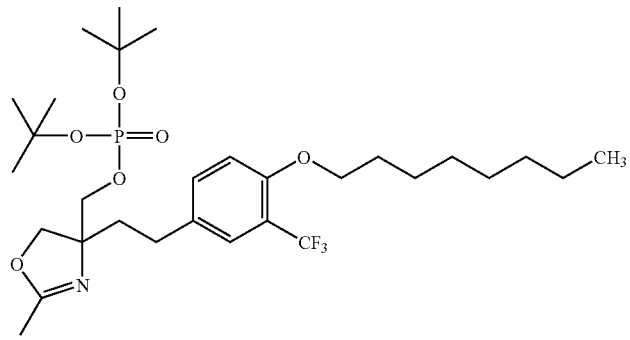
(Compound 10-2)
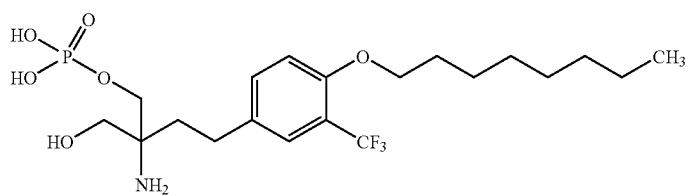

(Compound 11-1)
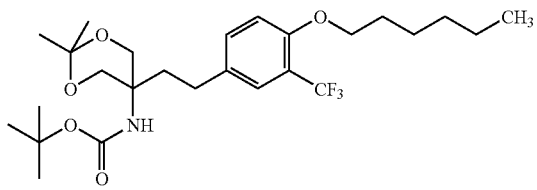
(Compound 11-2)
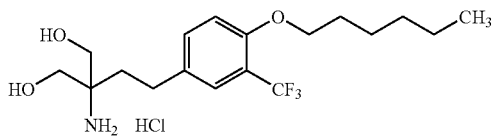
(Compound 12-1)
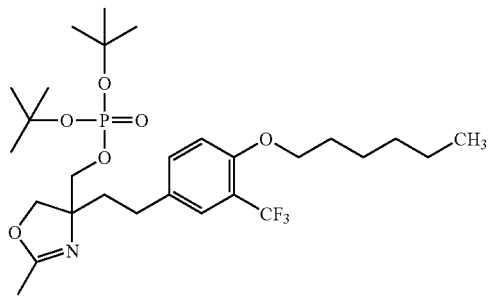
(Compound 12-2)
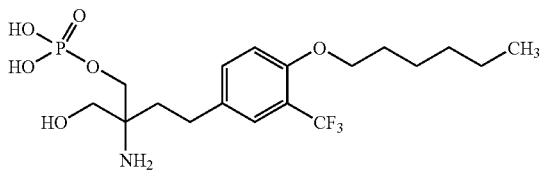
(Compound 13-1)
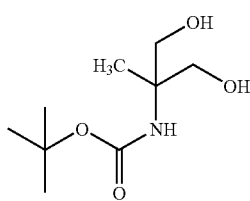
(Compound 13-2)
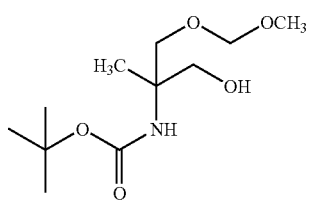
(Compound 13-3)
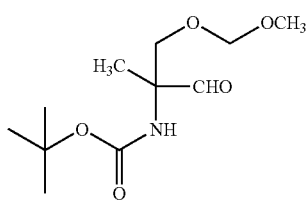
(Compound 13-4)
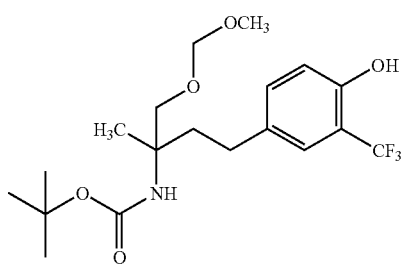
(Compound 13-5)
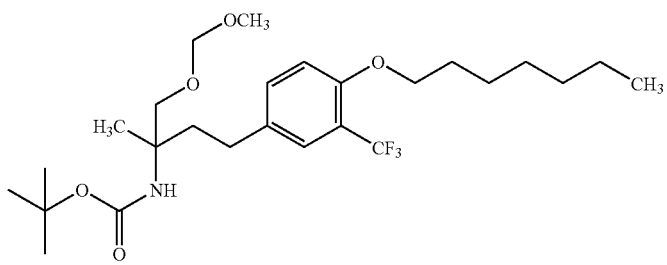
(Compound 13-6)
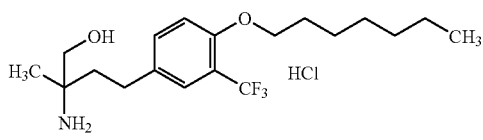
(Compound 14-1)
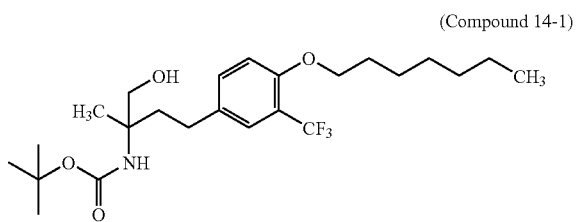

-continued
(Compound 14-2)
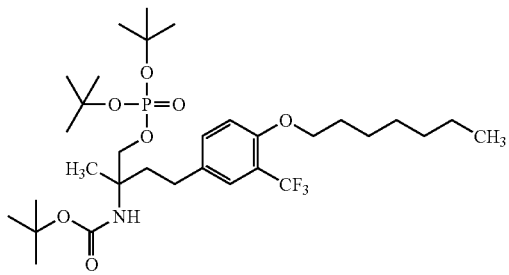
(Compound 14-3)
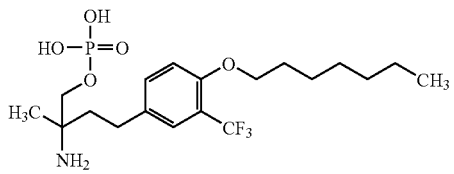
(Compound 15-1)
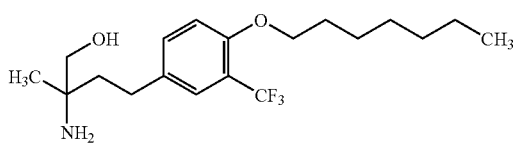
(Compound 15-2-1)
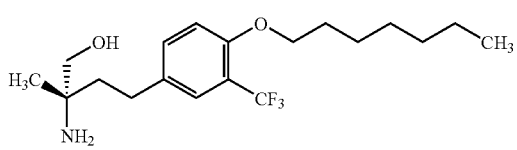
(Compound 15-2-2)
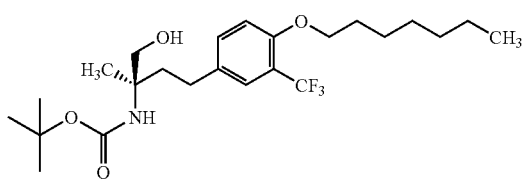
(Compound 15-3)
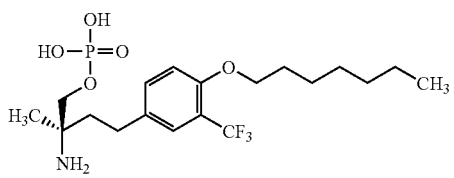
(Compound 16-1)
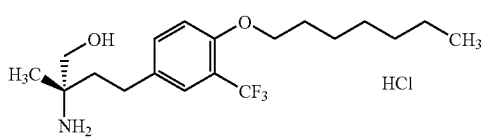
(Compound 16-2)
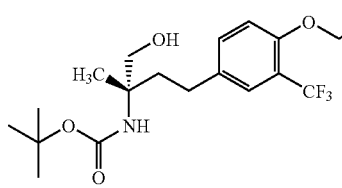
(Compound 17-1)
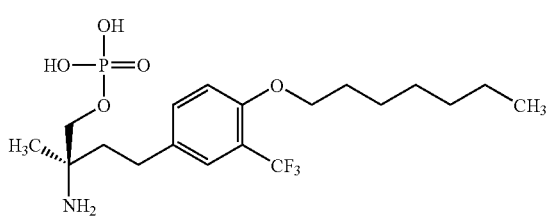
(Compound 18-1)
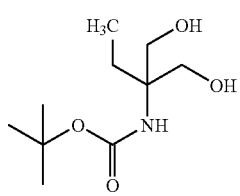
(Compound 18-2)
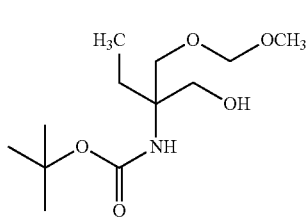
(Compound 19-1)
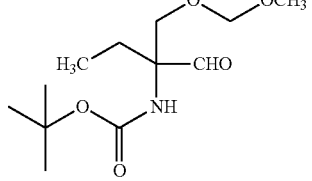
(Compound 19-2)
(Compound 19-3)

-continued
(Compound 19-4)
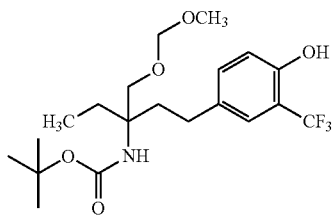
(Compound 19-5)
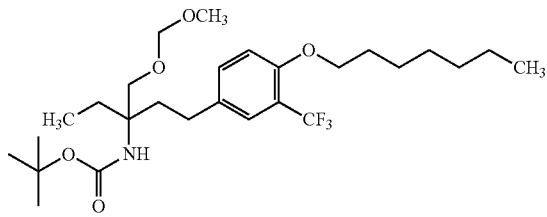
(Compound 19-6)
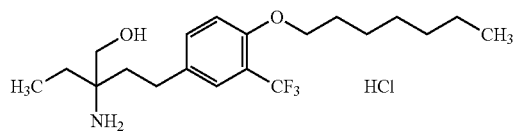
(Compound 20-1)
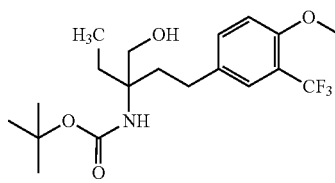
(Compound 20-2)
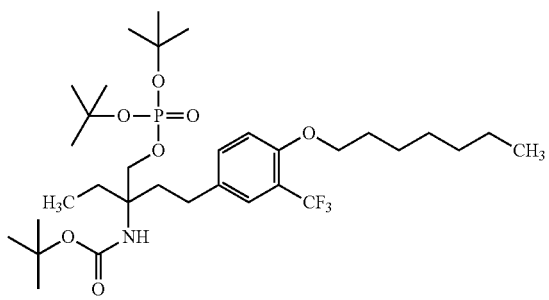
(Compound 20-3)
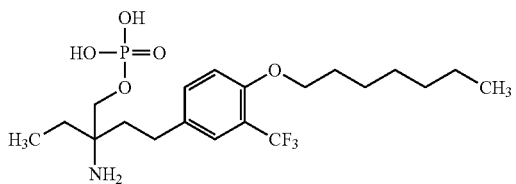
(Compound 21-1)
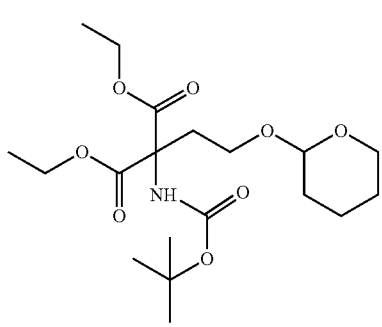
(Compound 21-2)
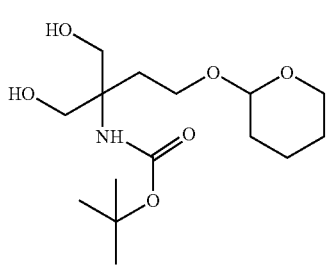
(Compound 21-3)
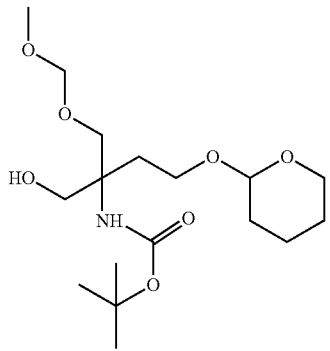
(Compound 21-4)
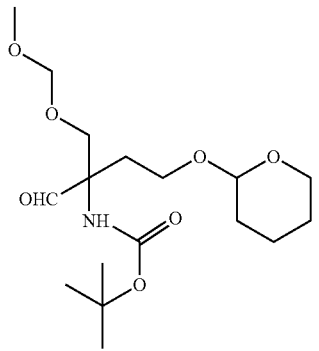

-continued
(Compound 21-5)
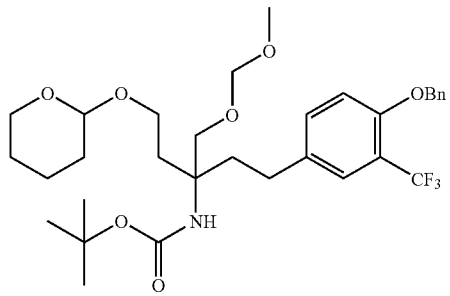
(Compound 21-6)
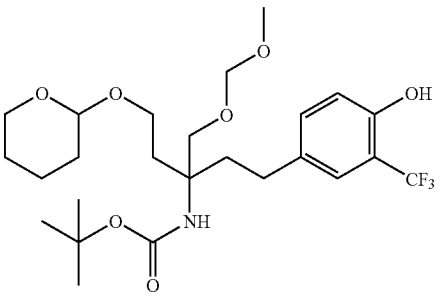
(Compound 21-7)
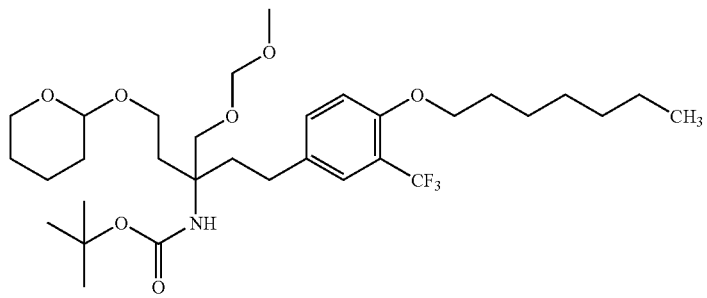
(Compound 21-8)
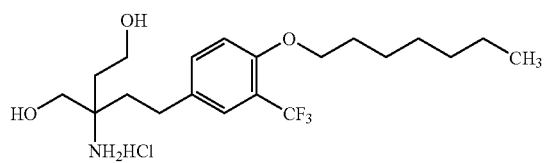
(Compound 22-1)
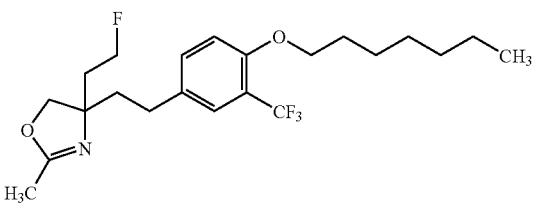
(Compound 22-2)
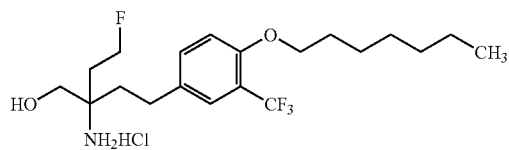
(Compound 23-1)
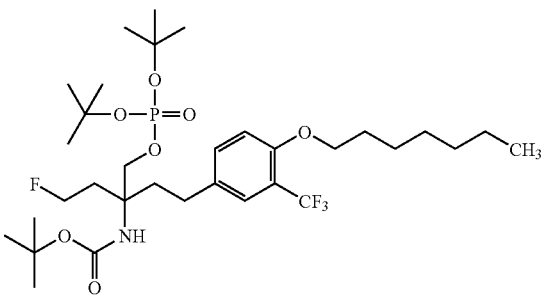
(Compound 23-2)
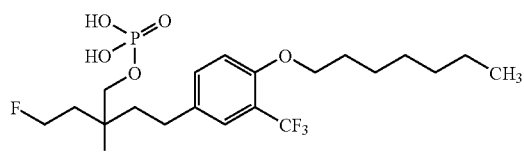
(Compound 24-1)
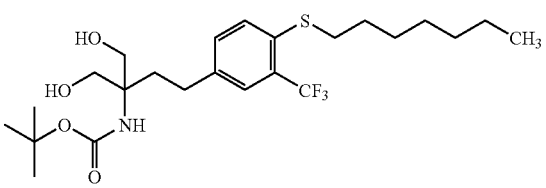
(Compound 24-2)
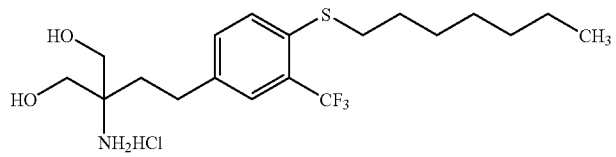

-continued
(Compound 25-1)
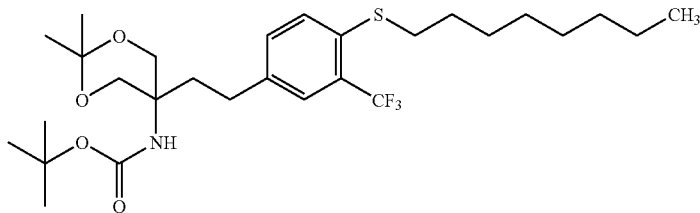
(Compound 25-2)
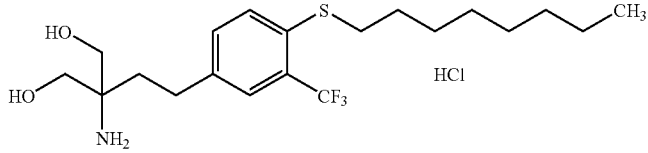
(Compound 26-1)
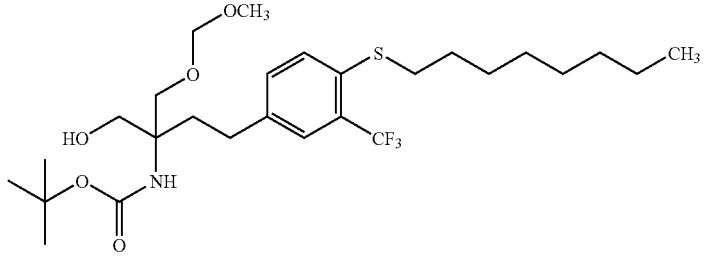
(Compound 26-2)
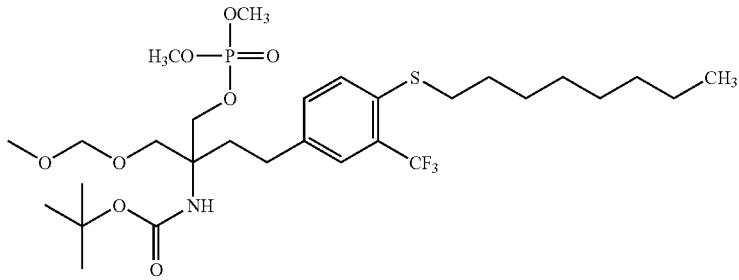
(Compound 26-3)
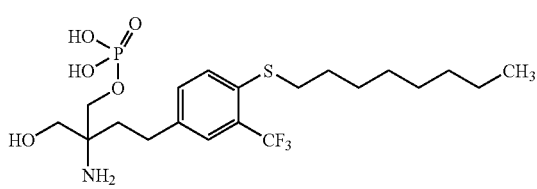
(Compound 27-1)
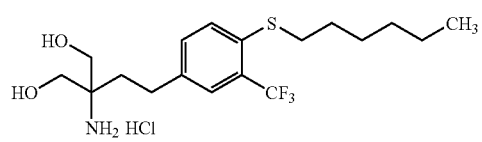
(Compound 28-1)
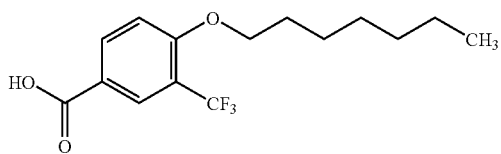
(Compound 28-2)
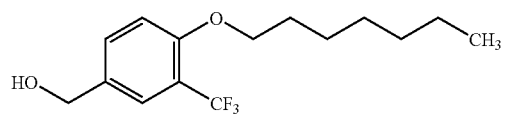
(Compound 28-3)
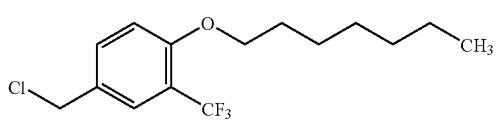
(Compound 28-4)
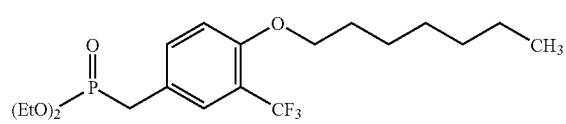

-continued
(Compound 28-5)
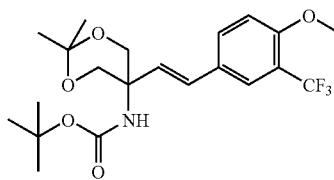
(Compound 28-6)
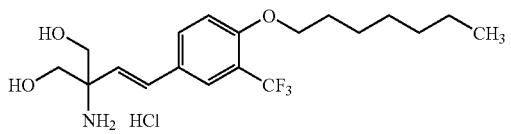
(Compound 29-1)
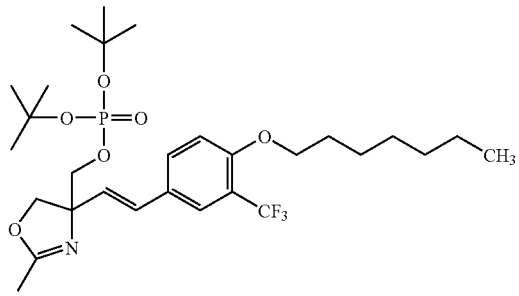
(Compound 29-2)
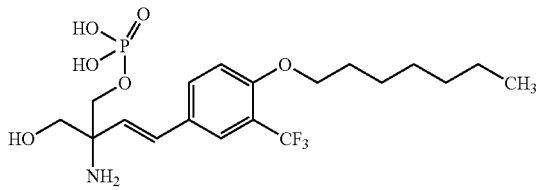
(Compound 30-1)
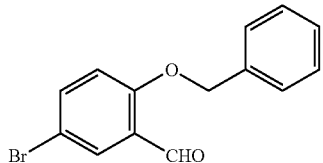
(Compound 30-2)
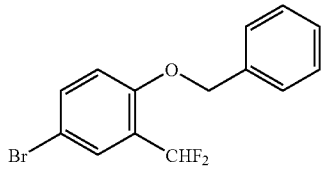
(Compound 30-3)
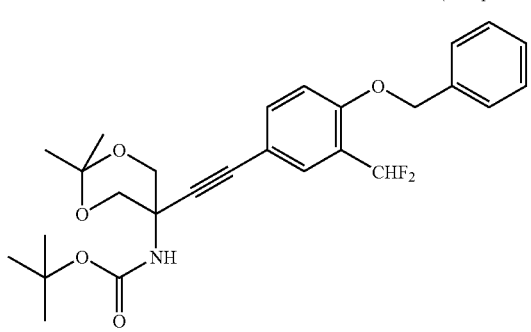
(Compound 30-4)
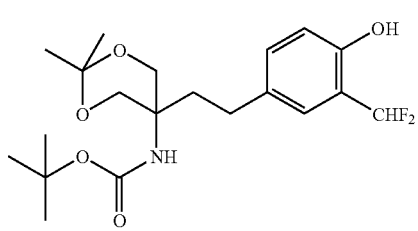
(Compound 30-5)
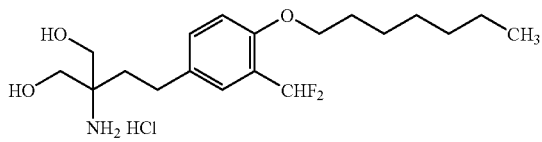
(Compound 31-1)
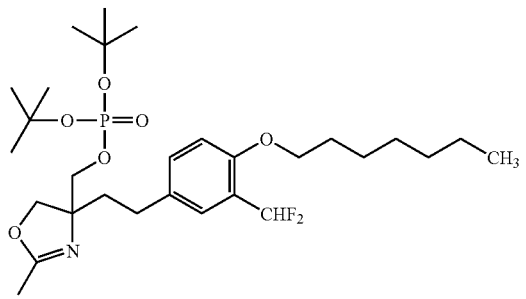
(Compound 31-2)
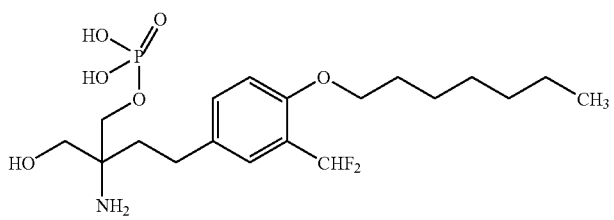

-continued
(Compound 32-1)
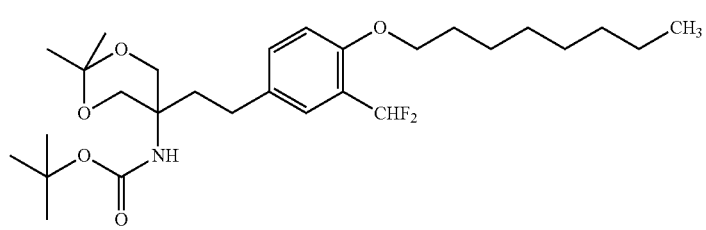
(Compound 32-2)
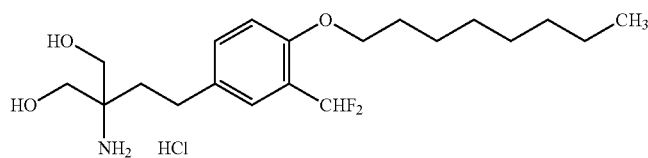
(Compound 33-1)
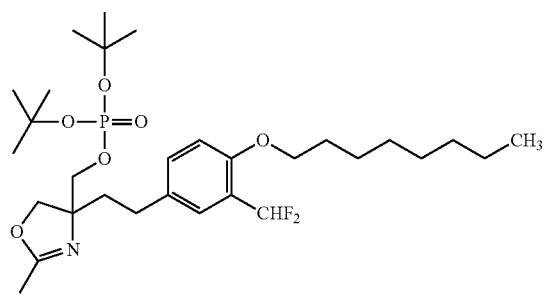
(Compound 33-2)
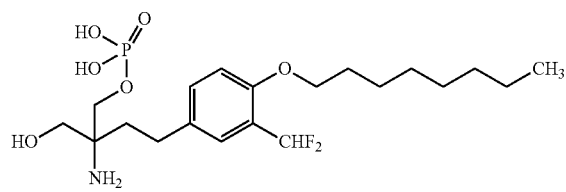
(Compound 34-1)
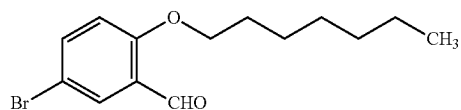
(Compound 34-2)
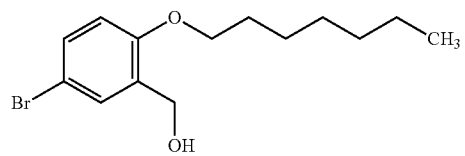
(Compound 34-3)
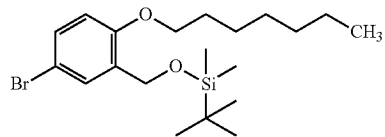
(Compound 34-4)
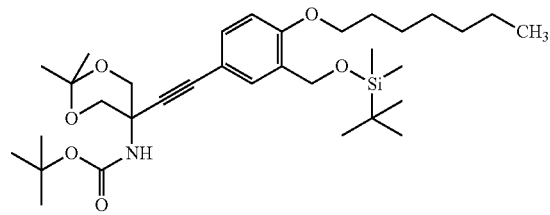
(Compound 34-5)
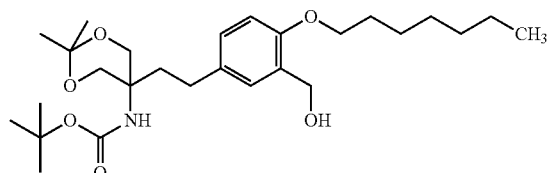
(Compound 34-6)
(Compound 34-7)
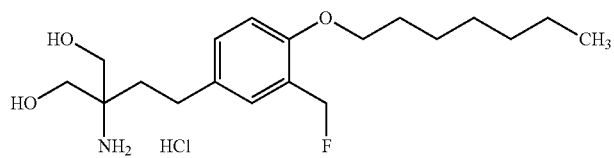
(Compound 35-1)
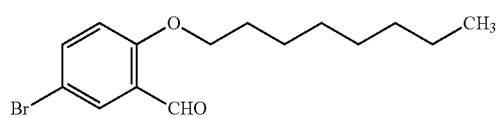
(Compound 35-2)
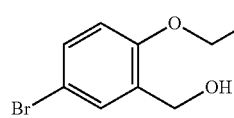

(Compound 35-3)
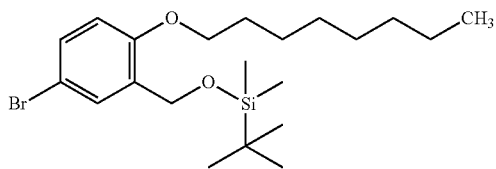
(Compound 35-4)
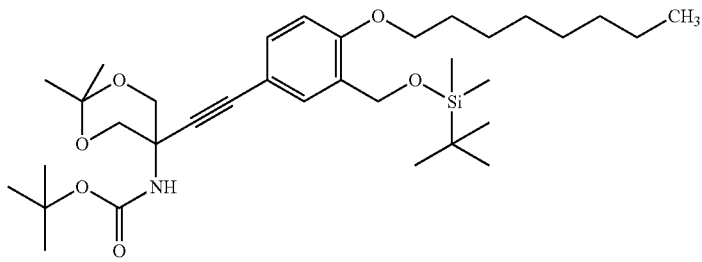
(Compound 35-5)
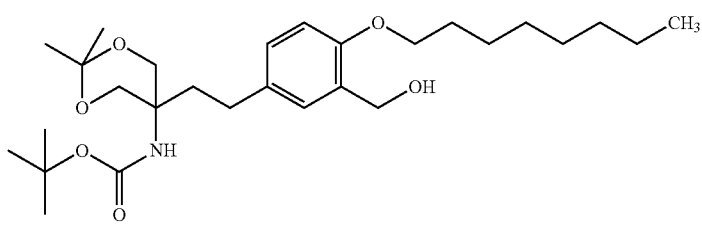
(Compound 35-6)
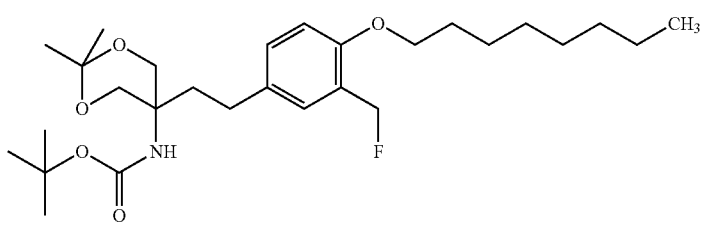
(Compound 35-7)
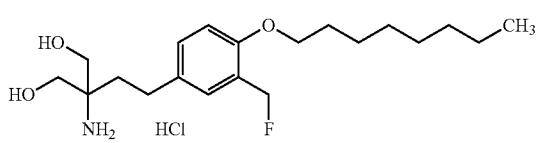
(Compound 36-1)
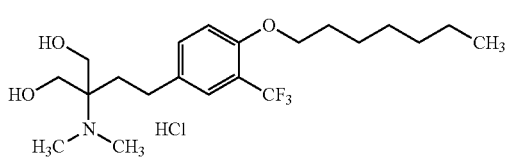
(Reference Example Compound 1-1)
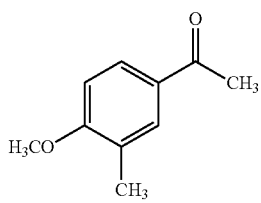
(Reference Example Compound 1-2)
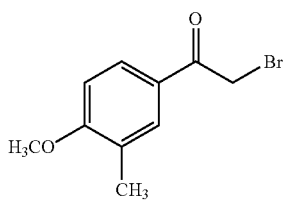
(Reference Example Compound 1-3)
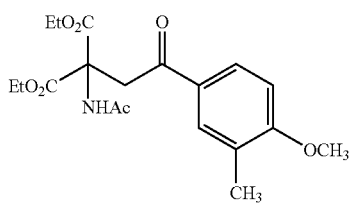
(Reference Example Compound 1-4)
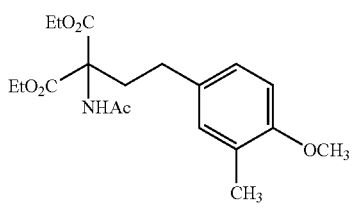

(Reference Example Compound 1-5)

(Reference Example Compound 1-6)

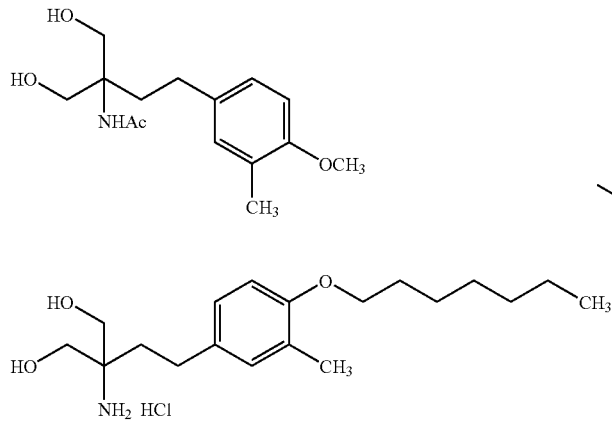

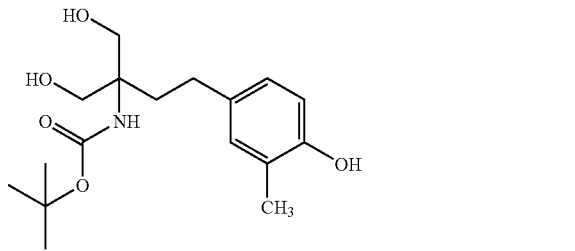

(Reference Example Compound 1-7)

Experimental Example 1

Evaluation of Peripheral Blood Lymphocyte Count-Decreasing Effect in Mice

The compound of the present invention was dissolved or suspended in 20% cyclodextrin (manufactured by NIHON SHOKUHIN KAKO CO., LTD), and intraperitoneally administered to a 7- to 10-week-old male BALB/cAnNCrj mice (CHARLES RIVER LABORATORIES, JAPAN INC.) at a dose of 0.001-10 mg/kg body weight. After 24 hr from the administration of the compound of the present invention, peripheral blood (about 0.3 ml) was drawn from the postcava of the mouse with a heparin sodium (manufactured by NovoNordisk)-treated tuberculin syringe (manufactured by TERUMO CORPORATION) under ether anesthesia. The blood (0.1 ml) was hemolysed with an automatic hemolysis treatment apparatus (TQ-Prep, manufactured by BECK-MAN-COULTER), and the number of lymphocytes was counted with a Flow Cytometer (CYTOMICS FC 500, manufactured by BECKMAN-COULTER) by a gating method using scattering at the front and the side of the laser beam as indices and using Flow-Count™ Fluorospheres (manufactured by BECKMAN-COULTER), whose standard particle count is known, as internal standard. A dose necessary for 50% reduction of the lymphocyte count of vehicle group as 100% was calculated and used as $ED_{50}$ value (mg/kg body weight). The mouse peripheral blood lymphocyte count-decreasing effect of the comparison compound 1-7 was 0.64 mg/kg body weight in $ED_{50}$ value, the mouse peripheral blood lymphocyte count-decreasing effect of compound 1-3, compound 13-6, compound 15-3 and compound 28-6 were 0.04, 0.02, 0.02 and 0.03 mg/kg body weight, respectively, in $ED_{50}$ value.

Experimental Example 2

Effect on Heart Rate in Rat Telemetry

Male Sprague-Dawley (IGS) rats were anesthetized by intraperitoneal administration of Nembutal (manufactured by DAINIPPON PHARMACEUTICAL CO., LTD.), a pressure sensor connected to a telemetry transmitter (TL11M2-C50-PTX, manufactured by Data Sciences International) was inserted into the abdominal artery, and the transmitter was subcutaneously dwelled in the abdomen. The data of blood pressure and heart rate were recorded by an analysis soft (Dataquest A.R.T., Data Science) via a receiver (RPC-1, manufactured by Data Sciences International). When 10 days to 2 weeks elapsed from the surgery, recovery of heart rate circadian rhythm was confirmed, and the rats were subjected to the experiment. The compound of the present invention was suspended in 0.5% hydroxypropylmethylcellulose (manufactured by Shin-Etsu Chemical Co., Ltd.) and orally administered. The heart rate was measured from 24 hr before the administration to 72 hr after the administration. Compound 1-3 did not affect the heart rate of the rat up to the dose of 30 mg/kg body weight.

Experimental Example 3

Effect on Heart Rate of Rat Under Anesthesia

Male Sprague-Dawley (IGS) rats are anesthetized by intraperitoneal administration of Nembutal (manufactured by DAINIPPON PHARMACEUTICAL CO., LTD.), and fixed at the dorsal position. Electrodes are mounted on four limbs, electrocardiogram is recorded by a standard limb lead II using an electrocardiogram amplifier (AC-601G, manufactured by NIHON KOHDEN CORPORATION). The heart rate is counted using an instant heart rate meter unit (AT-601G, manufactured by NIHON KOHDEN CORPORATION) and an electrocardiographic wave as a trigger. The test compound is dissolved in 20% cyclodextrin (manufactured by NIHON SHOKUHIN KAKO CO., LTD) and intravenously administered over 30 seconds at a dose of 0.001-10 mg/kg body weight. The heart rate is measured before the administration, and 1, 2, 3, 4, 5, 10 and 15 min after the administration.

From the results of the above-mentioned Experimental Example 1, since the compound of the present invention has a superior peripheral blood lymphocyte decreasing action, it can be expected to show a superior immunosuppressive action, rejection suppressive action and allergy suppressive action, and is considered to be effective for the treatment or prophylaxis of autoimmune diseases; prophylaxis or suppression of resistance or acute rejection or chronic rejection of organ or tissue transplantation; treatment or prophylaxis of graft-versus-host (GvH) disease due to bone marrow transplantation; or treatment or prophylaxis of allergic diseases. Moreover, from the results of the above-mentioned Experimental Example 2, the compound of the present invention is considered to be a compound showing reduced side effects such as bradycardia and the like.

This application is based on a patent application No. 2005-361363 filed in Japan, the contents of which are incorporated in full herein by this reference.

The invention claimed is:

1. A compound represented by the following formula (I)

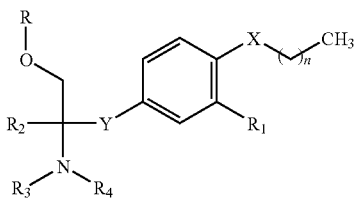

(I)

or a pharmaceutically acceptable acid addition salt thereof, wherein

R is a hydrogen atom or $P(=O)(OH)_2$,

X is an oxygen atom or a sulfur atom,

Y is $CH_2CH_2$ or $CH=CH$, and wherein $R_1$ is cyano, $R_2$ is alkyl having a carbon number of 1 to 4 and optionally substituted by a hydroxyl group(s) or a halogen atom(s), $R_3$ and $R_4$ may be the same or different and each is a hydrogen atom or alkyl having a carbon number of 1 to 4, and n is 5-8, or wherein $R_1$ is difluoromethyl or trifluoromethyl, $R_2$ is methyl optionally substituted by a hydroxyl group(s) or ethyl optionally substituted by a hydroxyl group(s), $R_3$ and $R_4$ each is a hydrogen atom and n is 6 or 7.

2. The compound of claim 1, wherein $R_3$ and $R_4$ are each a hydrogen atom, or a pharmaceutically acceptable acid addition salt thereof.

3. The compound of claim 1, having the following formula (Ia) or (Ib)

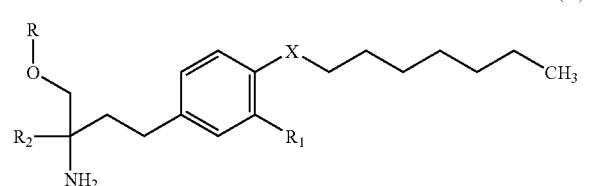

(Ia)

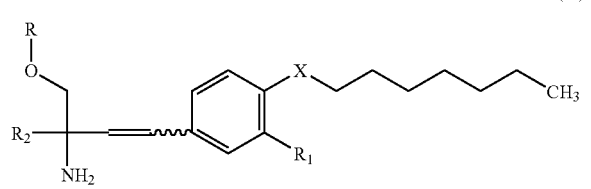

(Ib)

or a pharmaceutically acceptable acid addition salt thereof, wherein

R is a hydrogen atom or $P(=O)(OH)_2$,

X is an oxygen atom or a sulfur atom, and wherein $R_1$ is cyano, and $R_2$ is alkyl having a carbon number of 1 to 4 and optionally substituted by a hydroxyl group(s) or a halogen atom(s), or wherein $R_1$ is difluoromethyl or trifluoromethyl, and $R_2$ is methyl optionally substituted by a hydroxyl group(s) or ethyl optionally substituted by a hydroxyl group(s).

4. The compound of claim 1, wherein X is an oxygen atom, or a pharmaceutically acceptable acid addition salt thereof.

5. The compound of claim 1, wherein Y is $CH_2CH_2$, or a pharmaceutically acceptable acid addition salt thereof.

6. The compound of claim 1, wherein $R_1$ is trifluoromethyl, or a pharmaceutically acceptable acid addition salt thereof.

7. The compound of claim 1, wherein $R_2$ is methyl optionally substituted by a hydroxyl group(s), or a pharmaceutically acceptable acid addition salt thereof.

8. The compound of claim 1, wherein $R_2$ is hydroxymethyl, or a pharmaceutically acceptable acid addition salt thereof.

9. The compound of claim 1, wherein R is a hydrogen atom, or a pharmaceutically acceptable acid addition salt thereof.

10. The compound of claim 1, wherein the compound of the formula (I) is any of the following a-e, or a pharmaceutically acceptable acid addition salt thereof
   a. 2-amino-2-[2-(4-heptyloxy-3-trifluoromethylphenyl)ethyl]propane-1,3-diol, or a pharmaceutically acceptable acid addition salt thereof
   b. (E)-2-amino-2-[2-(4-heptyloxy-3-trifluoromethylphenyl)vinyl]propane-1,3-diol, or a pharmaceutically acceptable acid addition salt thereof
   c. 2-amino-4-(4-heptyloxy-3-trifluoromethylphenyl)-2-methylbutanol, or a pharmaceutically acceptable acid addition salt thereof
   d. (R)-2-amino-4-(4-heptyloxy-3-trifluoromethylphenyl)-2-methylbutanol, or a pharmaceutically acceptable acid addition salt thereof
   e. 2-amino-2-[2-(3-cyano-4-heptyloxyphenyl)ethyl]propane-1,3-diol, or a pharmaceutically acceptable acid addition salt thereof.

11. The compound of claim 1, wherein the compound of the formula (I) is any of the following f-j, or a pharmaceutically acceptable acid addition salt thereof
   f. 2-amino-4-(4-heptyloxy-3 -trifluoromethylphenyl)-2-(phosphoryloxymethyl)butanol, or a pharmaceutically acceptable acid addition salt thereof
   g. (E)-2-amino-4-(4-heptyloxy-3-trifluoromethylphenyl)-2-(phosphoryloxymethyl)-3-buten- 1 -ol, or a pharmaceutically acceptable acid addition salt thereof
   h. phosphoric acid mono[2-amino-4-(4-heptyloxy-3-trifluoromethylphenyl)-2-methylbutyl] ester, or a pharmaceutically acceptable acid addition salt thereof
   i. (R)-phosphoric acid mono[2-amino-4-(4-heptyloxy-3-trifluoromethylphenyl)-2-methylbutyl] ester, or a pharmaceutically acceptable acid addition salt thereof
   j. 2-amino-4-(3-cyano-4-heptyloxyphenyl)-2-(phosphoryloxymethyl)butanol, or a pharmaceutically acceptable acid addition salt thereof.

12. 2-Amino-2-[2-(4-heptyloxy-3-trifluoromethylphenyl)ethyl]propane-1,3-diol, or a hydrochloride thereof.

13. A phaiinaceutical composition comprising the compound of claim 1 or 12 and a pharmaceutically acceptable carrier.

* * * * *

UNITED STATES PATENT AND TRADEMARK OFFICE
CERTIFICATE OF CORRECTION

PATENT NO. : 8,809,304 B2  
APPLICATION NO. : 12/086419  
DATED : August 19, 2014  
INVENTOR(S) : Kiuchi et al.

Page 1 of 1

It is certified that error appears in the above-identified patent and that said Letters Patent is hereby corrected as shown below:

Title Page, Item (75) Inventors:

should read

-- (75) Inventors: Masatoshi Kiuchi, Osaka (JP);  
Kaoru Marukawa, Osaka (JP);  
Nobutaka Kobayashi, Osaka (JP) --.

Signed and Sealed this  
Twenty-eighth Day of July, 2015

Michelle K. Lee  
*Director of the United States Patent and Trademark Office*